(12) United States Patent
Khan

(10) Patent No.: US 9,994,614 B2
(45) Date of Patent: Jun. 12, 2018

(54) N-METHYL-D-ASPARTATE RECEPTOR MODULATORS AND METHODS OF MAKING AND USING SAME

(71) Applicant: Naurex, Inc., Parsippany, NJ (US)

(72) Inventor: M. Amin Khan, Evanston, IL (US)

(73) Assignee: Naurex, Inc., Parsippany, NJ (US)

( * ) Notice: Subject to any disclaimer, the term of this patent is extended or adjusted under 35 U.S.C. 154(b) by 0 days. days.

(21) Appl. No.: 15/328,341

(22) PCT Filed: Jul. 24, 2015

(86) PCT No.: PCT/US2015/042070
§ 371 (c)(1),
(2) Date: Jan. 23, 2017

(87) PCT Pub. No.: WO2016/014982
PCT Pub. Date: Jan. 28, 2016

(65) Prior Publication Data
US 2017/0210779 A1    Jul. 27, 2017

Related U.S. Application Data

(60) Provisional application No. 62/129,388, filed on Mar. 6, 2015, provisional application No. 62/028,512, filed on Jul. 24, 2014.

(51) Int. Cl.
*C07D 207/08* (2006.01)
*A61K 38/00* (2006.01)
*C07K 5/103* (2006.01)
*A61K 9/00* (2006.01)
*C07K 5/097* (2006.01)

(52) U.S. Cl.
CPC .......... *C07K 5/1013* (2013.01); *A61K 9/0019* (2013.01); *C07K 5/0823* (2013.01); *A61K 38/00* (2013.01)

(58) Field of Classification Search
CPC ..... C07D 207/08; C07K 5/1016; A61K 38/00
See application file for complete search history.

(56) References Cited

U.S. PATENT DOCUMENTS

2011/0306586 A1* 12/2011 Khan ................... C07D 487/10
514/210.02

* cited by examiner

*Primary Examiner* — Rebecca L Anderson
*Assistant Examiner* — Karen Cheng

(57) ABSTRACT

Disclosed are compounds having enhanced potency in the modulation of NMDA receptor activity. Such compounds are contemplated for use in the treatment of diseases and disorders, such as learning, cognitive activities, and analgesia, particularly in alleviating and/or reducing neuropathic pain. Orally available formulations and other pharmaceutically acceptable delivery forms of the compounds, including intravenous formulations, are also disclosed.

9 Claims, 21 Drawing Sheets

Exemplary compound of formula (III).

(III-A)

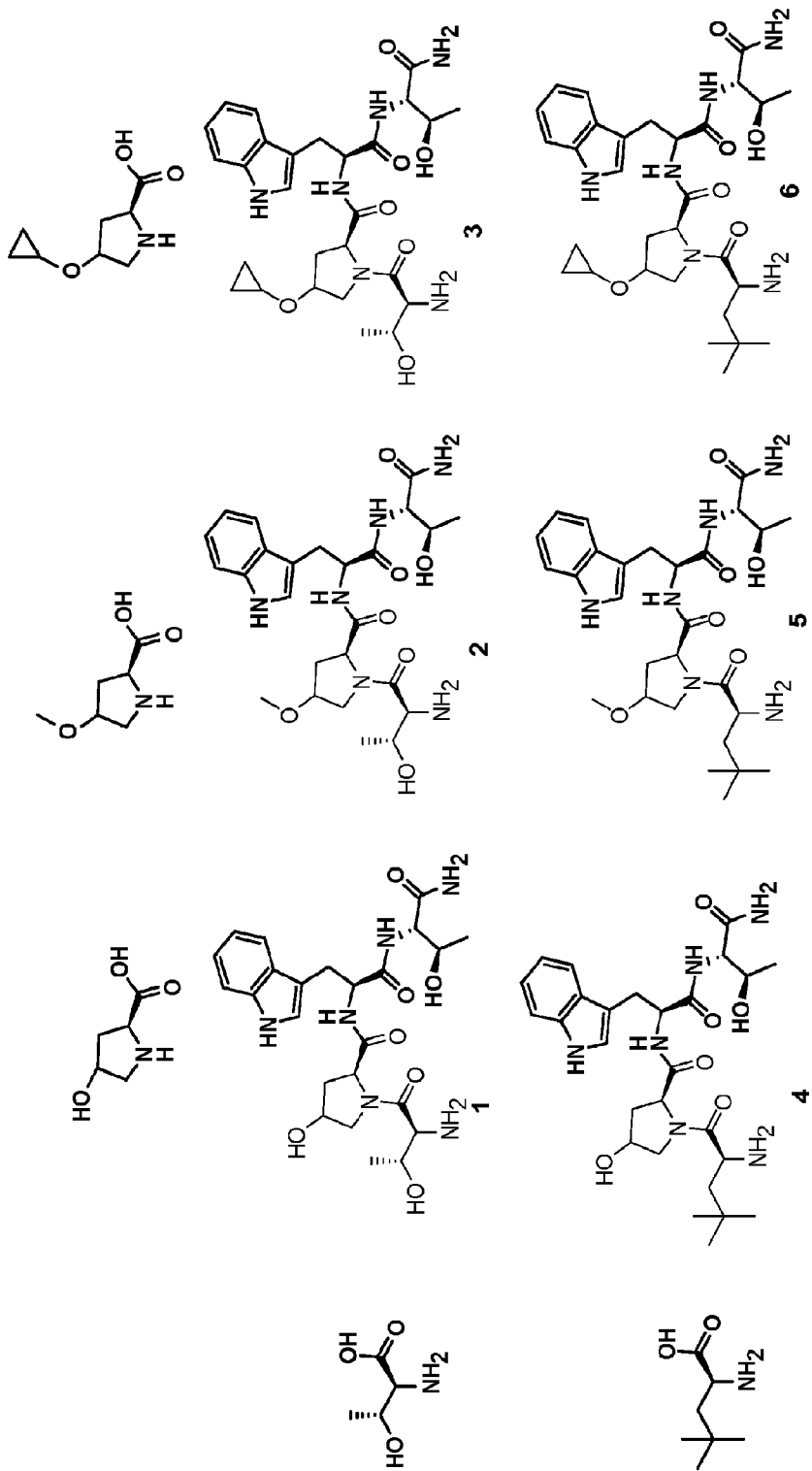
FIG. 2  Exemplary compounds of formula (III) and (IV) and corresponding starting materials.

16

17

18

36

35

34

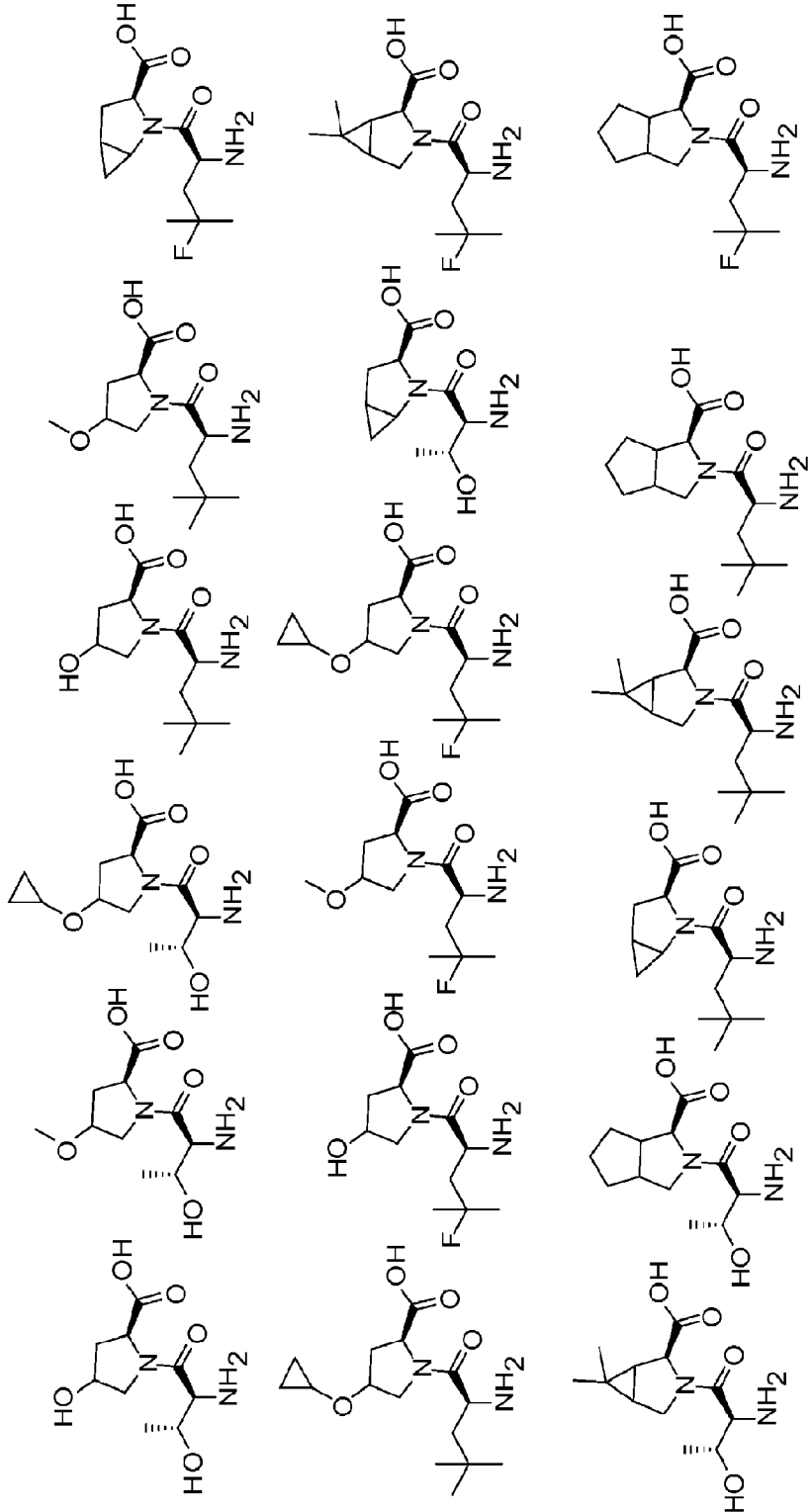
FIG. 3  Exemplary starting materials for compounds of formula (III) and (IV).

Glycine dose response in the presence of 50μM glutamate.

Transformation of the glycine dose response.

FIG. 7 Glyx-13 dose response.
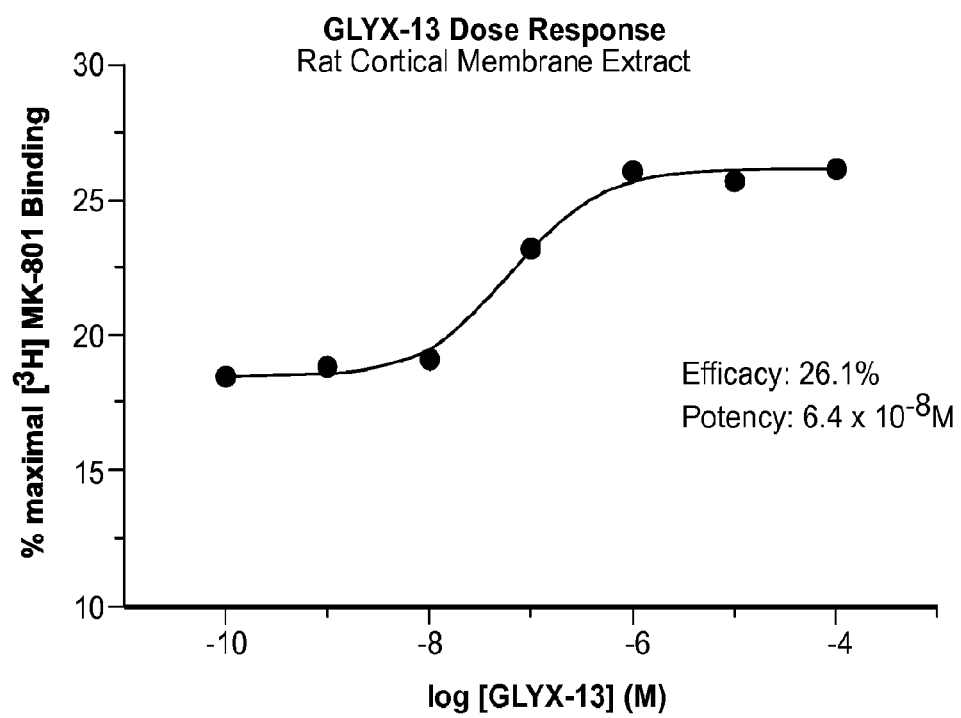

N-METHYL-D-ASPARTATE RECEPTOR MODULATORS AND METHODS OF MAKING AND USING SAME

CROSS REFERENCE TO RELATED APPLICATIONS

This application is a national stage application under 35 U.S.C. § 371 PCT patent application PCT/US2015/042070, filed on Jul. 24, 2015, which claims priority to and the benefit of U.S. Patent Application No. 62/129,388, filed Mar. 6, 2015, and U.S. Patent Application No. 62/028,512, filed Jul. 24, 2014, the disclosures of which are hereby incorporated herein by reference in their entireties.

BACKGROUND

An N-methyl-d-aspartate (NMDA) receptor is a postsynaptic, ionotropic receptor that is responsive to, inter alia, the excitatory amino acids glutamate and glycine and the synthetic compound NMDA. The NMDA receptor controls the flow of both divalent and monovalent ions into the postsynaptic neural cell through a receptor associated channel (Foster et al., Nature 1987, 329:395-396; Mayer et al., Trends in Pharmacol. Sci. 1990, 11:254-260). The NMDA receptor has been implicated during development in specifying neuronal architecture and synaptic connectivity, and may be involved in experience-dependent synaptic modifications. In addition, NMDA receptors are also thought to be involved in long term potentiation and central nervous system disorders.

The NMDA receptor plays a major role in the synaptic plasticity that underlies many higher cognitive functions, such as memory acquisition, retention and learning, as well as in certain cognitive pathways and in the perception of pain (Collingridge et al., The NMDA Receptor, Oxford University Press, 1994). In addition, certain properties of NMDA receptors suggest that they may be involved in the information-processing in the brain that underlies consciousness itself.

The NMDA receptor has drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptors which opens their ligand-gated ion channels; in turn the calcium influx produces a high level of intracellular calcium which activates a biochemical cascade resulting in protein degradation and cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's, and Alzheimer's diseases. Activation of the NMDA receptor has been shown to be responsible for post-stroke convulsions, and, in certain models of epilepsy, activation of the NMDA receptor has been shown to be necessary for the generation of seizures. Neuropsychiatric involvement of the NMDA receptor has also been recognized since blockage of the NMDA receptor $Ca^{++}$ channel by the animal anesthetic PCP (phencyclidine) produces a psychotic state in humans similar to schizophrenia (reviewed in Johnson, K. and Jones, S., 1990). Further, NMDA receptors have also been implicated in certain types of spatial learning.

The NMDA receptor is believed to consist of several protein chains embedded in the postsynaptic membrane. The first two types of subunits discovered so far form a large extracellular region, which probably contains most of the allosteric binding sites, several transmembrane regions looped and folded so as to form a pore or channel, which is permeable to $Ca^{++}$, and a carboxyl terminal region. The opening and closing of the channel is regulated by the binding of various ligands to domains (allosteric sites) of the protein residing on the extracellular surface. The binding of the ligands is thought to affect a conformational change in the overall structure of the protein which is ultimately reflected in the channel opening, partially opening, partially closing, or closing.

NMDA receptor compounds may exert dual (agonist/antagonist) effect on the NMDA receptor through the allosteric sites. These compounds are typically termed "partial agonists". In the presence of the principal site ligand, a partial agonist will displace some of the ligand and thus decrease $Ca^{++}$ flow through the receptor. In the absence of or lowered level of the principal site ligand, the partial agonist acts to increase $Ca^{++}$ flow through the receptor channel.

A need continues to exist in the art for novel and more specific/potent compounds that are capable of binding the glycine binding site of NMDA receptors, and provide pharmaceutical benefits. In addition, a need continues to exist in the medical arts for an orally deliverable forms of such compounds.

SUMMARY

Provided herein, at least in part, are compounds that are NMDA modulators, for example, partial agonists of NMDA. For example, disclosed herein are compounds having formula (I):

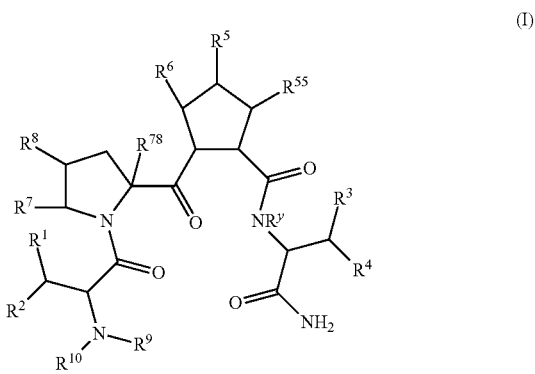

and pharmaceutically acceptable salts, stereoisomers, metabolites, and hydrates thereof, wherein:

$R^1$, $R^2$, $R^3$, $R^4$, $R^5$, $R^6$, $R^7$, $R^8$, $R^9$, $R^{10}$, $R^{55}$, $R^{78}$, and $R^y$ are as defined below.

In another aspect, a compound of formula (I) is provided, in which one or more (e.g., one, two, three, or four) of the four constituent amino acids is replaced with a beta-amino acid (e.g., the C-terminal and/or the N-terminal is/are replaced with a beta-amino acid(s); e.g., one or both of the proline moieties is/are replaced with a beta-amino acid(s); e.g., the C-terminal and/or the N-terminal is/are replaced with a beta-amino acid(s), and one or both of the proline moieties is/are replaced with a beta-amino acid(s)). In some embodiments, the constituent amino acid is replaced with its corresponding beta-amino acid (e.g., proline replaced with beta-proline). By way of example, such compounds can have formula (I-A), in which formula (I) is modified such that the left-most proline moiety is replaced with:

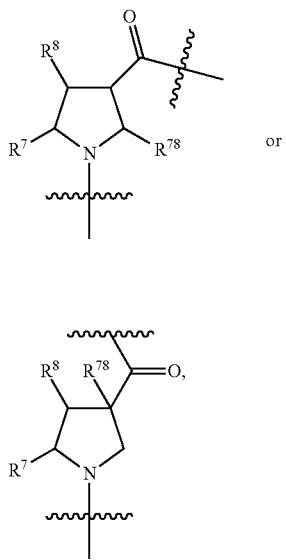

in which $R^7$, $R^8$, and $R^{78}$ are as defined below. As another example, such compounds can have formula (I-B), in which formula (I) is modified such that the right-most proline moiety is replaced with:

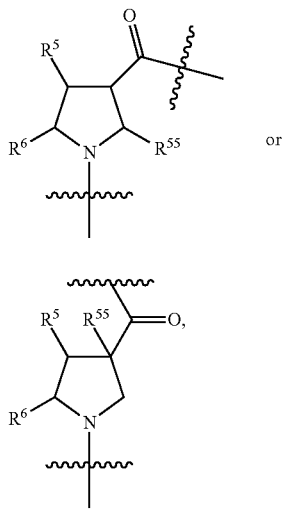

in which $R^5$, $R^6$, and $R^{55}$ are as defined below. In still another embodiment, compounds are provided, in which any one or more of compounds of formula (I), (I-A), and (I-B) are modified such that the left-most (N-terminal) amino acid is replaced with hydrogen, thereby providing a tripeptide wherein the ring nitrogen of left-most proline moiety is bonded to hydrogen.

In another aspect, a compound is provided having formula (II):

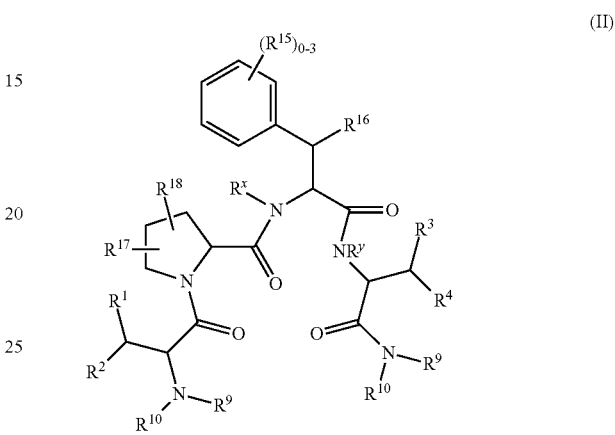

and pharmaceutically acceptable salts, stereoisomers, metabolites, and hydrates thereof, wherein:

$R^1$, $R^2$, $R^3$, $R^4$, $R^9$, $R^{10}$, $R^{15}$, $R^{16}$, $R^{17}$, $R^{18}$, $R^x$, and $R^y$ are as defined below.

In another aspect, a compound of formula (II) is provided, in which one or more (e.g., one, two, three, or four) of the four constituent amino acids is replaced with a beta-amino acid (e.g., the C-terminal and/or the N-terminal is/are replaced with a beta-amino acid(s); e.g., the proline and/or phenyl alanine moieties is/are replaced with a beta-amino acid(s); e.g., the C-terminal and/or the N-terminal is/are replaced with a beta-amino acid(s), and the proline and/or phenyl alanine moieties is/are replaced with a beta-amino acid(s)). In some embodiments, the constituent amino acid is replaced with its corresponding beta-amino acid (e.g., proline replaced with beta-proline). By way of example, such compounds can have formula (II-A), in which formula (II) is modified such that the proline moiety is replaced with:

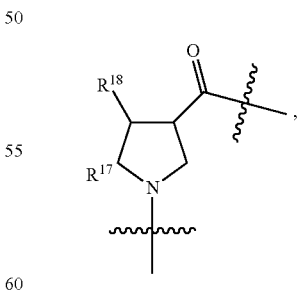

in which $R^{17}$ and $R^{18}$ are as defined below. In still another embodiment, compounds are provided, in which any one or more of compounds of formula (II) and (II-A) are modified such that the left-most (N-terminal) amino acid is replaced with hydrogen, thereby providing a tripeptide wherein the ring nitrogen of proline moiety is bonded to hydrogen.

In yet another aspect, a compound is provided having formula (III):

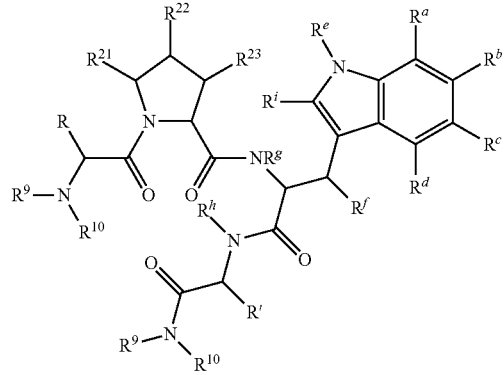

(III)

and pharmaceutically acceptable salts, stereoisomers, metabolites, and hydrates thereof,
wherein:
R, R$^t$, R$^9$, R$^{10}$, R$^{21}$, R$^{22}$, R$^{23}$, R$^a$, R$^b$, R$^c$, R$^d$, R$^e$, R$^f$, R$^g$, R$^h$ and R$^i$ are as defined below.

In another aspect, a compound of formula (III) is provided, in which one or more (e.g., one, two, three, or four) of the four constituent amino acids is replaced with a beta-amino acid (e.g., the C-terminal and/or the N-terminal is/are replaced with a beta-amino acid(s); e.g., the proline and/or trytophan moieties is/are replaced with a beta-amino acid(s); e.g., the C-terminal and/or the N-terminal is/are replaced with a beta-amino acid(s), and the proline and/or tryptophan moieties is/are replaced with a beta-amino acid(s)). In some embodiments, the constituent amino acid is replaced with its corresponding beta-amino acid (e.g., proline replaced with beta-proline). By way of example, such compounds can have formula (III-A), in which formula (III) is modified such that the proline moiety is replaced with:

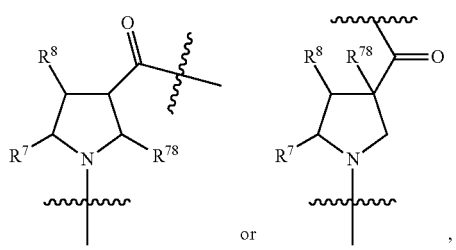

in which R$^{21}$, R$^{22}$, and R$^{23}$ are as defined below. In still another embodiment, compounds are provided, in which any one or more of compounds of formula (III) and (III-A) are modified such that the left-most (N-terminal) amino acid is replaced with hydrogen, thereby providing a tripeptide wherein the ring nitrogen of proline moiety is bonded to hydrogen.

In yet another aspect, a compound is provided having formula (IV):

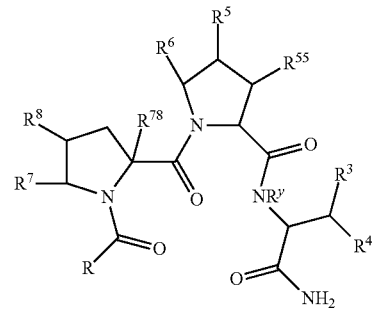

(IV)

and pharmaceutically acceptable salts, stereoisomers, metabolites, and hydrates thereof,
wherein:
R$^3$, R$^4$, R$^5$, R$^6$, R$^7$, R$^8$, R$^{55}$, R$^{78}$, and R$^y$ are as defined below.

In another aspect, a compound of formula (IV) is provided, in which one or more (e.g., one, two, three, or four) of the four constituent amino acids is replaced with a beta-amino acid (e.g., the C-terminal and/or the N-terminal is/are replaced with a beta-amino acid(s); e.g., one or both of the proline moieties is/are replaced with a beta-amino acid(s); e.g., the C-terminal and/or the N-terminal is/are replaced with a beta-amino acid(s), and one or both of the proline moieties is/are replaced with a beta-amino acid(s)). In some embodiments, the constituent amino acid is replaced with its corresponding beta-amino acid (e.g., proline replaced with beta-proline). By way of example, such compounds can have formula (IV-A), in which formula (IV) is modified such that the left-most proline moiety is replaced with:

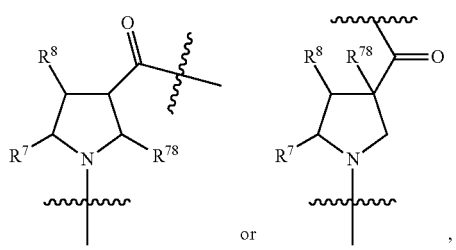

in which R$^7$, R$^8$, and R$^{78}$ are as defined below. As another example, such compounds can have formula (IV-B), in which formula (IV) is modified such that the right-most proline moiety is replaced with:

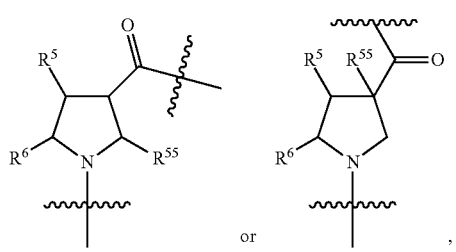

in which R$^5$, R$^6$, and R$^{55}$ are as defined below. In still another embodiment, compounds are provided, in which any one or more of compounds of formula (IV), (IV-A), and (IV-B) are modified such that the left-most (N-terminal) amino acid is replaced with hydrogen, thereby providing a tripeptide wherein the ring nitrogen of left-most proline moiety is bonded to hydrogen.

In a further aspect, a compound is provided having formula (V):

and pharmaceutically acceptable salts, stereoisomers, metabolites, and hydrates thereof, wherein $T^1$, $P^1$, $P^2$, and $T^2$ are as defined below.

Also provided herein are compounds that are useful, e.g., as synthetic intermediates, e.g.,

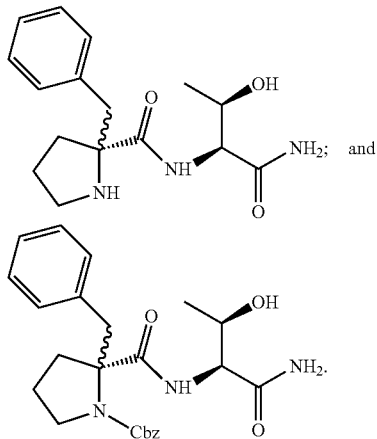

In some embodiments, protecting groups other than Cbz can be employed for compounds of formula (V) e.g., 9-fluorenylmethyloxycarbonyl (Fmoc), tert-butoxycarbonyl (Boc), p-methoxybenzyloxycarbonyl, acetyl, trifluoroacetyl, benzoyl, phthalimido, benzyl (Bn), p-methoxybenzyl, p-methoxyphenyl, 3,4-dimethoxybenzyl, triphenylmethyl, benzylidene, and p-toluenesulfonyl (Ts). In some embodiments, the hydroxyl group of the compounds shown above can also be protected, e.g., with an alkyl or silyl group (thereby forming the corresponding alkyl or silyl ether) or acyl (e.g., $CH_3C(O)$—, thereby forming an ester).

In certain embodiments, protecting groups employed in the compounds of formula (V) can have the following formula: —C(O)OR$_{PG1}$, wherein R$_{PG1}$ is selected from the group consisting of: $C_1$-$C_6$ alkyl; $C_1$-$C_6$ haloalkyl; $C_2$-$C_6$ alkenyl; $C_2$-$C_6$ alkynyl; $C_3$-$C_{10}$ cycloalkyl, wherein the $C_3$-$C_{10}$ cycloalkyl is optionally substituted with from 1-3 independently selected $C_1$-$C_3$ alkyl; —CH$_2$—$C_3$-$C_{10}$ cycloalkyl wherein the $C_3$-$C_{10}$ cycloalkyl is optionally substituted with from 1-3 independently selected $C_1$-$C_3$ alkyl; —CH$_2$-phenyl, wherein the phenyl is optionally substituted with from 1-2 substituents independently selected from $C_1$-$C_3$ alkyl, $C_1$-$C_3$ haloalkyl, $C_1$-$C_3$ alkoxy, $C_1$-$C_3$ haloalkoxy, nitro, halo, SO$_2$Me, cyano, and —OC(O)CH$_3$; and —CH$_2$-pyridyl.

In other embodiments, protecting groups employed in the compounds of formula (V) can have the following formula: —C(O)R$_{PG2}$, wherein R$_{32}$ is selected from the group consisting of: H; $C_1$-$C_6$ alkyl; $C_1$-$C_6$ haloalkyl; phenyl, wherein the phenyl is optionally substituted with from 1-2 substituents independently selected from $C_1$-$C_3$ alkyl; $C_1$-$C_3$ haloalkyl; $C_1$-$C_3$ alkoxy; $C_1$-$C_3$ haloalkoxy; nitro; halo; SO$_2$Me, cyano; and —OC(O)CH$_3$; and pyridyl.

Also provided herein are pharmaceutically acceptable compositions comprising a disclosed compound, and a pharmaceutically acceptable excipient. For example, such compositions may be suitable for oral administration to a patient. In other embodiments, such compositions may be suitable for injection. Compounds can also include any compound disclosed in the schemes, tables, and figures provided herein.

In another aspect, a method of treating autism, in a patient in need thereof, is provided comprising administering to the patient a pharmaceutically effective amount of a contemplated compound.

In yet another aspect, a method of treating a condition selected from the group consisting of epilepsy, AIDS dementia, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, peripheral neuropathy, myelopathy, ischemic retinopathy, diabetic retinopathy, glaucoma, cardiac arrest, behavior disorders, and impulse control disorders, in a patient in need thereof, is provided comprising administering to the patient a pharmaceutically effective amount of a contemplated compound.

In still another aspect, a method of treating a condition selected from the group consisting of attention deficit disorder, ADHD, schizophrenia, depression, anxiety, amelioration of opiate, nicotine, and/or ethanol addiction, traumatic brain injury, spinal cord injury, post-traumatic stress syndrome, and Huntington's chorea, in a patient in need thereof, is provided comprising administering to the patient a pharmaceutically effective amount of a contemplated compound.

In yet another aspect, a method of treating Alzheimer's disease, or memory loss that accompanies early stage Alzheimer's disease in a patient in need thereof, is provided comprising administering to the patient a pharmaceutically effective amount of a contemplated compound.

In still another aspect, a method of treating Huntington's disease, in a patient in need thereof, is provided comprising administering to the patient a pharmaceutically effective amount of a contemplated compound.

In some embodiments, a contemplated compound may be administered to a patient in need thereof intravenously, intraperitoneally, intranasally, orally, intramuscularly, or subcutaneously.

BRIEF DESCRIPTION OF THE DRAWINGS

FIG. 7 shows a compound dose response performed using the [³H]MK-801 assay described herein.

DETAILED DESCRIPTION

Figure 1:
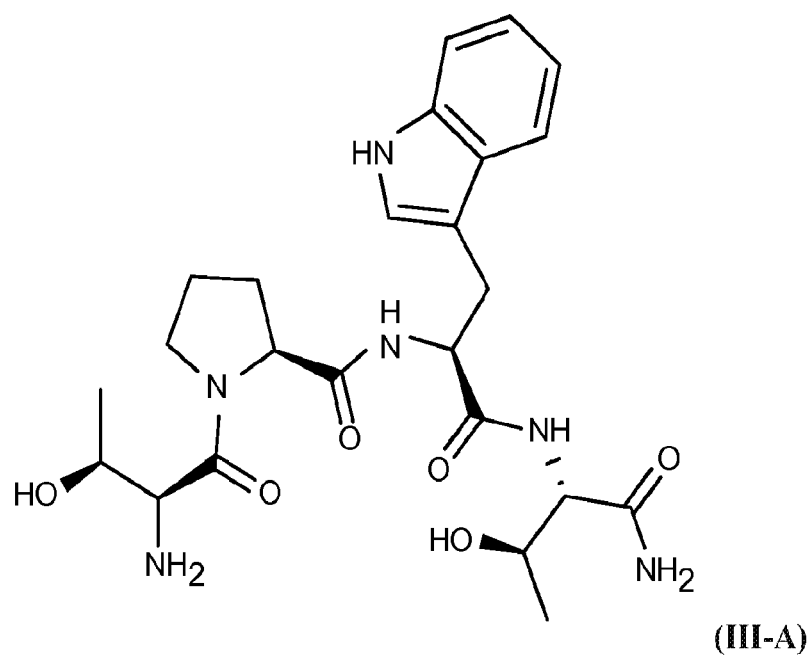
FIG. 1 shows the chemical structure of an exemplary formula (III) compound.

This disclosure is generally directed to compounds that are capable of modulating NMDA, e.g., NMDA antagonists or partial agonists, and compositions and/or methods of using the disclosed compounds.

Definitions

In some embodiments, the compounds, as described herein, may be substituted with any number of substituents or functional moieties. In general, the term "substituted" whether preceded by the term "optionally" or not, and substituents contained in formulas, refer to the replacement of hydrogen radicals in a given structure with the radical of a specified substituent.

In some instances, when more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. In some embodiments, heteroatoms such as nitrogen may have hydrogen substituents and/or any permissible substituents of organic compounds described herein which satisfy the valencies of the heteroatoms. Non-limiting examples of substituents include acyl; aliphatic; heteroaliphatic; aryl (e.g., phenyl); heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroarylthio; oxo; —F; —Cl; —Br; —I; —OH; —NO₂; —N₃; —CN; —SCN; —SR$^x$; —CF₃; —CH₂CF₃; —CHCl₂; —CH₂OH; —CH₂CH₂OH; —CH₂NH₂; —CH₂SO₂CH₃; —OR$^x$, —C(O)R$^x$; —CO₂(R$^x$); —C(O)N(R$^x$)₂; —C(NR$^x$)N(R$^x$)₂; —OC(O)R$^x$; —OCO₂R$^x$; —OC(O)N(R$^x$)₂; —N(R$^x$)₂; —SOR$^x$; —S(O)₂R$^x$; —NR$^x$C(O)R$^x$; —NR$^x$C(O)N(R$^x$)₂; —NR$^x$C(O)OR$^x$; —NR$^x$C(NR$^x$)N(R$^x$)₂; and —C(R$^x$)₃; wherein each occurrence of R$^x$ independently includes, but is not limited to, hydrogen, halogen, acyl, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Furthermore, the compounds described herein are not intended to be limited in any manner by the permissible substituents of organic compounds. In some embodiments, combinations of substituents and variables described herein may be preferably those that result in the formation of stable compounds. The term "stable," as used herein, refers to compounds which possess stability sufficient to allow manufacture and which maintain the integrity of the compound for a sufficient period of time to be detected and preferably for a sufficient period of time to be useful for the purposes detailed herein.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties.

The terms "aryl" and "heteroaryl," as used herein, refer to mono- or polycyclic unsaturated moieties having preferably 3-14 carbon atoms, each of which may be substituted or unsubstituted. In certain embodiments, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments, "heteroaryl" refers to a mono- or bicyclic heterocyclic ring system having one or two aromatic rings in which one, two, or three ring atoms are heteroatoms independently selected from the group consisting of S, O, and N and the remaining ring atoms are carbon. Non-limiting examples of heteroaryl groups include pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group attached to an oxygen (—O-alkyl). Exemplary alkoxy groups include, but are not limited to, groups with an alkyl group of 1-12, 1-8, or 1-6 carbon atoms, referred to herein as $C_1$-$C_{12}$alkoxy, $C_1$-$C_8$alkoxy, and $C_1$-$C_6$alkoxy, respectively. Exemplary alkoxy groups include, but are not limited to methoxy, ethoxy, etc. Similarly, exemplary "alkenoxy" groups include, but are not limited to vinyloxy, allyloxy, butenoxy, etc. The term "cycloalkoxy" as used herein refers to an cycloalkyl group attached to an oxygen (—O-cycloalkyl).

The term "alkoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkynyloxy" used herein refers to a straight or branched alkynyl group attached to an oxygen (alkynyl-O)). Exemplary alkynyloxy groups include, but are not limited to, propynyloxy.

The term "alkyl" as used herein refers to a saturated straight or branched hydrocarbon, for example, such as a straight or branched group of 1-6, 1-4, or 1-3 carbon atom, referred to herein as $C_1$-$C_6$alkyl, $C_1$-$C_4$alkyl, and $C_1$-$C_3$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_1$-$C_6$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond, such as a straight or branched group of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

Alkyl, alkenyl and alkynyl groups can optionally be substituted, if not indicated otherwise, with one or more groups selected from alkoxy, alkyl, cycloalkyl, amino, halogen, and —C(O)alkyl. In certain embodiments, the alkyl, alkenyl, and alkynyl groups are not substituted, i.e., they are unsubstituted.

The term "amide" or "amido" as used herein refers to a radical of the form —$R^aC(O)N(R^b)$—, —$R^aC(O)N(R^b)R^e$—, or —$C(O)NR^bR^e$, wherein $R^a$, $R^b$, and $R^e$ are each independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amide can be attached to another group through the carbon, the nitrogen, $R^b$, $R^e$, or $R^a$. The amide also may be cyclic, for example $R^b$ and $R^e$, $R^a$ and $R^b$, or $R^a$ and $R^e$ may be joined to form a 3- to 12-membered ring, such as a 3- to 10-membered ring or a 5- to 6-membered ring. The term "carboxamido" refers to the structure —$C(O)NR^bR^e$.

The term "amine" or "amino" as used herein refers to a radical of the form —$NR^dR^e$, where $R^d$ and $R^e$ are independently selected from hydrogen, alkyl, alkenyl, alkynyl, aryl, arylalkyl, cycloalkyl, haloalkyl, heteroaryl, and heterocyclyl. The amino also may be cyclic, for example, $R^d$ and $R^e$ are joined together with the N to form a 3- to 12-membered ring, e.g., morpholino or piperidinyl. The term amino also includes the corresponding quaternary ammonium salt of any amino group, e.g., —$[N(R^d)(R^e)(R^f)]+$. Exemplary amino groups include aminoalkyl groups, wherein at least one of $R^d$, $R^e$, or $R^f$ is an alkyl group. In certain embodiment, $R^d$ and $R^e$ are hydrogen or alkyl.

The term "cycloalkyl" as used herein refers to a monocyclic saturated or partially unsaturated hydrocarbon group of for example 3-6, or 4-6 carbons, referred to herein, e.g., as $C_{3-6}$cycloalkyl or $C_{4-6}$cycloalkyl and derived from a cycloalkane. Exemplary cycloalkyl groups include, but are not limited to, cyclohexyl, cyclohexenyl, cyclopentyl, cyclobutyl or, cyclopropyl.

The terms "halo" or "halogen" or "Hal" as used herein refer to F, Cl, Br, or I. The term "haloalkyl" as used herein refers to an alkyl group substituted with one or more halogen atoms. Perfluoroakly refers to an alkyl group in which all of the constituent hydrogen atoms of the alkyl group have been replaced with fluorine atoms.

The terms "heterocyclyl" or "heterocyclic group" are art-recognized and refer to saturated or partially unsaturated 3- to 10-membered ring structures, alternatively 3- to 7-membered rings, whose ring structures include one to four heteroatoms, such as nitrogen, oxygen, and sulfur. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. The heterocyclic ring may be substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocyclic group is not substituted, i.e., the heterocyclic group is unsubstituted.

The term "heterocyclylalkoxy" as used herein refers to a heterocyclyl-alkyl-O— group.

The term "heterocyclyloxy" refers to a heterocyclyl-O— group.

The term "heterocyclyloxyalkyl" refers to a heterocyclyl-O-alkyl-group.

The terms "hydroxy" and "hydroxyl" as used herein refers to the radical —OH.

The term "oxo" as used herein refers to the radical =O.

The term "cyano" as used herein refers to the radical CN.

The term "beta amino acid" refers to an amino acid, which have their amino group bonded to the beta (β) carbon rather than the alpha ("α") carbon. Non-limiting examples include, without limitation, β-proline and β-phenylalanine:

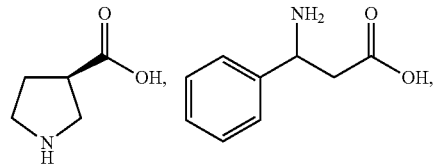

"Pharmaceutically or pharmacologically acceptable" include molecular entities and compositions that do not produce an adverse, allergic or other untoward reaction when administered to an animal, or a human, as appropriate. "For human administration, preparations should meet sterility, pyrogenicity, general safety and purity standards as required by FDA Office of Biologics standards.

As used in the present disclosure, the term "partial NMDA receptor agonist" is defined as a compound that is capable of binding to a glycine binding site of an NMDA receptor; at low concentrations a NMDA receptor agonist acts substantially as agonist and at high concentrations it acts substantially as an antagonist. These concentrations are experimentally determined for each and every "partial agonist.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The symbol  denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

As used in the present disclosure, "NMDA" is defined as N-methyl-d-aspartate.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in defined as that amount needed to give maximal enhancement of a behavior (for example, learning), physiological response (for example, LTP induction), or inhibition of neuropathic pain.

Compounds

Disclosed compounds include those having formula (I):

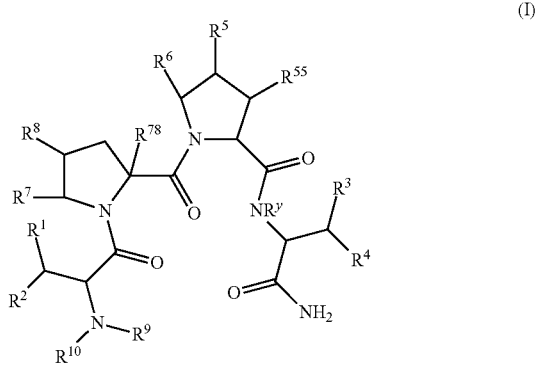

(I)

and pharmaceutically acceptable salts, stereoisomers, metabolites, and hydrates thereof (e.g., salts),
wherein:

$R^1$, $R^2$, $R^3$, and $R^4$ are each independently selected from the group consisting of hydrogen; halogen; $C_{1-6}$alkyl; $C_{1-6}$ perfluoroalkyl; $C_{2-6}$alkenyl; $C_{2-6}$alkynyl; $C_{3-6}$cycloalkyl; phenyl; heteroaryl including from 5 to 6 ring atoms wherein 1, 2, or 3 of the ring atoms are independently selected from the group consisting of N, NH, N(C1-C3 alkyl), O, and S; —$OR^x$; —$C(O)R^x$; —$CO_2(R^x)$; —$C(O)N(R^x)_2$; —$C(NR^x)N(R^x)_2$; —$OC(O)R^x$; —$OCO_2R^x$; —$OC(O)N(R^x)_2$; —$N(R^x)_2$; —$NR^xC(O)R^x$; —$NR^xC(O)N(R^x)_2$; —$NR^xC(O)OR^x$; and —$NR^xC(NR^x)N(R^x)_2$; wherein $C_{1-6}$alkyl is optionally substituted by one, two, or three substituents independently selected from the group consisting of halogen; hydroxyl; phenyl; heteroaryl including from 5 to 6 ring atoms wherein 1, 2, or 3 of the ring atoms are independently selected from the group consisting of N, NH, N(C1-C3 alkyl), O, and S; and $N(R^x)_2$;

$R^5$ and $R^6$ are independently selected from the group consisting of hydrogen; $C_1$-$C_6$ alkyl, optionally substituted by one, two or three substituents independently selected from the group consisting of halogen, hydroxyl, and $N(R^x)_2$; $C_{1-6}$ perfluoroalkyl; $C_1$-$C_6$ alkoxy, optionally substituted by one, two, or three substituents independently selected from the group consisting of halogen, hydroxyl, phenyl, and $N(R^x)_2$; and -Q-Ar, wherein Q is a bond or $C_1$-$C_6$ alkylene, optionally substituted by one, two, or three independently selected halogens, and Ar is selected from the group consisting of phenyl and heteroaryl including from 5 to 6 ring atoms wherein 1, 2, or 3 of the ring atoms are independently selected from the group consisting of N, NH, N(C1-C3 alkyl), O, and S, wherein phenyl and heteroaryl are each optionally substituted by one, two, or three substituents independently selected from the group consisting of halogen, hydroxyl, phenyl, and $N(R^x)_2$; or $R^5$ and $R^6$, together with the atoms to which they are attached, form a C3-C6 cycloalkyl or heterocyclyl including from 3 to 6 ring atoms wherein 1, 2, or 3 of the ring atoms are independently selected from the group consisting of N, NH, N(C1-C3 alkyl), O, and S; wherein the C3-C6 cycloalkyl and heterocyclyl are each optionally substituted by one, two, or three substituents independently selected from the group consisting of halogen, hydroxyl, phenyl, and $N(R^x)_2$;

$R^{55}$ is H, or $R^{55}$ and $R^5$, together with the atoms to which they are attached, form a C3-C6 cycloalkyl or heterocyclyl including from 3 to 6 ring atoms wherein 1, 2, or 3 of the ring atoms are independently selected from the group consisting of N, NH, N(C1-C3 alkyl), O, and S; wherein the C3-C6 cycloalkyl and heterocyclyl are each optionally substituted by one, two, or three substituents independently selected from the group consisting of halogen, hydroxyl, phenyl, and $N(R^x)_2$;

$R^7$ and $R^{78}$ are each independently selected from the group consisting of hydrogen; $C_1$-$C_6$ alkyl; $C_{1-6}$ perfluoroalkyl; $C_1$-$C_6$ alkoxy; $C_3$-$C_6$ cycloalkoxy; heteroaryl including from 5 to 6 ring atoms wherein 1, 2, or 3 of the ring atoms are independently selected from the group consisting of N, NH, N(C1-C3 alkyl), O, and S; heterocyclyl including from 3 to 6 ring atoms wherein 1, 2, or 3 of the ring atoms are independently selected from the group consisting of N, NH, N(C1-C3 alkyl), O, and S; and phenyl; wherein $C_1$-$C_6$ alkyl; $C_1$-$C_6$ alkoxy; $C_3$-$C_6$ cycloalkoxy; heteroaryl; heterocyclyl; phenyl are each optionally substituted by one, two, or three substituents independently selected from the group consisting of halogen; hydroxyl; phenyl; heteroaryl including from 5 to 6 ring atoms wherein 1, 2, or 3 of the ring atoms are independently selected from the group consisting of N, NH, N(C1-C3 alkyl), O, and S; and $N(R^x)_2$;

$R^8$ is selected from the group consisting of hydrogen; halogen; hydroxyl; $C_1$-$C_6$ alkyl; $C_{1-6}$ perfluoroalkyl; $C_1$-$C_6$ alkoxy; $C_3$-$C_6$ cycloalkoxy; heteroaryl including from 5 to 6 ring atoms wherein 1, 2, or 3 of the ring atoms are independently selected from the group consisting of N, NH, N(C1-C3 alkyl), O, and S; heterocyclyl including from 3 to 6 ring atoms wherein 1, 2, or 3 of the ring atoms are independently selected from the group consisting of N, NH, N(C1-C3 alkyl), O, and S; and phenyl; wherein $C_1$-$C_6$ alkyl; $C_1$-$C_6$ alkoxy; $C_3$-$C_6$ cycloalkoxy; heteroaryl; heterocyclyl; and phenyl are each optionally substituted by one, two, or three substituents independently selected from the group consisting of halogen, hydroxyl, phenyl, and $N(R^x)_2$; or $R^7$ and $R^8$, together with the atoms to which they are attached, form C3-C6 cycloalkyl or heterocyclyl including from 3 to 6 ring atoms wherein 1, 2, or 3 of the ring atoms are independently selected from the group consisting of N, NH, N(C1-C3 alkyl), O, and S; wherein the C3-C6 cycloalkyl and heterocyclyl are each optionally substituted by one, two, or three substituents independently selected from the group consisting of halogen, hydroxyl, phenyl, and $N(R^x)_2$;

with the proviso that at least one of $R^7$, $R^{78}$, $R^5$, and $R^6$ is not H;

$R^9$ and $R^{16}$ are independently selected, for each occurrence, from the group consisting of hydrogen; $C_1$-$C_6$ alkyl, optionally substituted by one, two, or three substituents substituents independently selected from the group consisting of halogen, oxo, hydroxyl, phenyl, and heteroaryl including from 5 to 6 ring atoms wherein 1, 2, or 3 of the ring atoms are independently selected from the group consisting of N, NH, N(C1-C3 alkyl), O, and S; $C_{1-6}$ perfluoroalkyl; $C_{2-6}$alkenyl, optionally substituted by one, two, or three substituents substituents independently selected from the group consisting of halogen, oxo, and hydroxyl; $C_{2-6}$alkynyl, optionally substituted by one, two, or three substituents substituents independently selected from the group consisting of halogen, oxo, and hydroxyl; $C_{3-6}$cycloalkyl, optionally substituted by one, two, or three substituents substituents independently selected from the group consisting of $C_{1-6}$alkyl, $C_{1-6}$ perfluoroalkyl; halogen, oxo, and hydroxyl; phenyl, optionally substituted by one, two, or three substituents substituents independently selected from the group consisting of $C_{1-6}$alkyl; $C_{1-6}$ perfluoroalkyl; $C_{1-6}$alkoxy; halogen; hydroxyl; —C(O)$R^x$; —CO$_2$($R^x$); —C(O)N($R^x$)$_2$; —C(N$R^x$)N($R^x$)$_2$; and —C($R^x$)$_3$;

or $R^9$ and $R^{10}$, together with the nitrogen atom to which each is attached, form a heterocyclyl including from 3 to 6 ring atoms, which is optionally substituted by one, two, or three substituents substituents independently selected from the group consisting of $C_{1-6}$alkyl, $C_{1-6}$ perfluoroalkyl; halogen, oxo, and hydroxyl; wherein when $R^9$ and $R^{16}$ form a heterocyclyl including 6 ring atoms, the heterocyclyl optionally includes, in addition to the nitrogen atom attached to $R^9$ and $R^{10}$, a second ring heteroatom selected from the group consisting of N, NH, N(C1-C3 alkyl), O, and S;

$R^x$ is independently selected, for each occurrence, from the group consisting of hydrogen; halogen; acyl; $C_{1-6}$alkyl; $C_{1-6}$ perfluoroalkyl; and phenyl; and $R^y$ is hydrogen or $C_{1-3}$alkyl.

In another aspect, a compound of formula (I) is provided, in which one or more (e.g., one, two, three, or four) of the four constituent amino acids is replaced with a beta-amino acid (e.g., the C-terminal and/or the N-terminal is/are replaced with a beta-amino acid(s); e.g., one or both of the proline moieties is/are replaced with a beta-amino acid(s); e.g., the C-terminal and/or the N-terminal is/are replaced with a beta-amino acid(s), and one or both of the proline moieties is/are replaced with a beta-amino acid(s)). In some embodiments, the constituent amino acid is replaced with its corresponding beta-amino acid (e.g., proline replaced with beta-proline). By way of example, such compounds can have formula (I-A), in which formula (I) is modified such that the left-most proline moiety is replaced with:

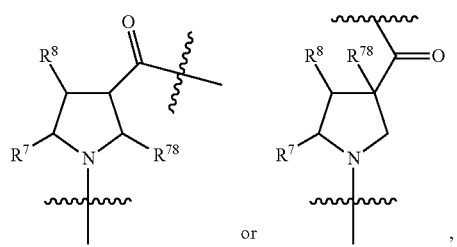

or in which $R^7$, $R^8$, and $R^{78}$ are as defined anywhere herein. As another example, such compounds can have formula (I-B), in which formula (I) is modified such that the right-most proline moiety is replaced with:

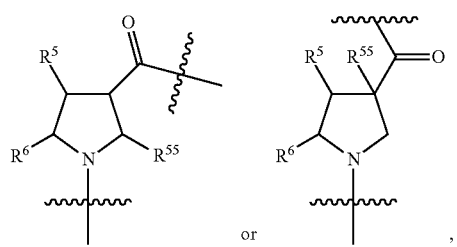

or in which $R^5$, $R^6$, and $R^{55}$ are as defined anywhere herein. In still another embodiment, compounds are provided, in which any one or more of compounds of formula (I), (I-A), and (I-B) are modified such that the left-most (N-terminal) amino acid is replaced with hydrogen, thereby providing a tripeptide wherein the ring nitrogen of left-most proline moiety is bonded to hydrogen.

Embodiments of formula (I), (I-A), and (I-B) tetra- and tripeptide compounds can include one or more of the following features and/or combinations of the following features.

In certain embodiments, $R^1$ is hydrogen, $C_1$-$C_6$ alkyl (e.g., methyl), $C_{1-6}$ perfluoroalkyl; or OH.

In certain embodiments, $R^2$ is $C_{1-6}$alkyl, optionally substituted; or phenyl optionally substituted.

In certain embodiments, $R^1$ is as defined above, and $R^2$ is as defined above. In certain embodiments, $R^1$ is —OH. In certain embodiments, $R^2$ is $C_1$-$C_6$ alkyl (e.g., methyl). In certain embodiments, $R^1$ is —OH, and $R^2$ is $C_1$-$C_6$ alkyl (e.g., methyl).

In certain embodiments, $R^3$ is —OH. In certain embodiments, $R^4$ is $C_1$-$C_6$ alkyl (e.g., methyl). In certain embodiments, $R^3$ is —OH, and $R^4$ is $C_1$-$C_6$ alkyl (e.g., methyl).

In certain embodiments, $R^5$ and/or $R^8$ (e.g., $R^8$) is independently selected from the group consisting of hydroxyl; $C_1$-$C_6$ alkoxy (e.g., methoxy); and $C_3$-$C_6$ cycloalkoxy (e.g., cyclopropoxy); wherein $C_1$-$C_6$ alkoxy and $C_3$-$C_6$ cycloalkoxy are each optionally and independently substituted by one, two or three substituents independently selected from the group consisting of halogen, hydroxyl, $C_1$-$C_6$ alkyl, $C_{1-6}$ perfluoroalkyl; phenyl, and N($R^x$)$_2$, and the other pyrrolidine substituents are hydrogen. In other embodiments, $R^5$ and $R^6$ or $R^7$ and $R^8$ or $R^5$ and $R^{55}$ forms a ring as defined herein.

In certain embodiments, each occurrence of $R^9$ and $R^{10}$ is hydrogen.

In certain embodiments, $R^x$ is hydrogen. In other embodiments, $R^x$ is CH$_3$.

Disclosed compounds include those having formula (II):

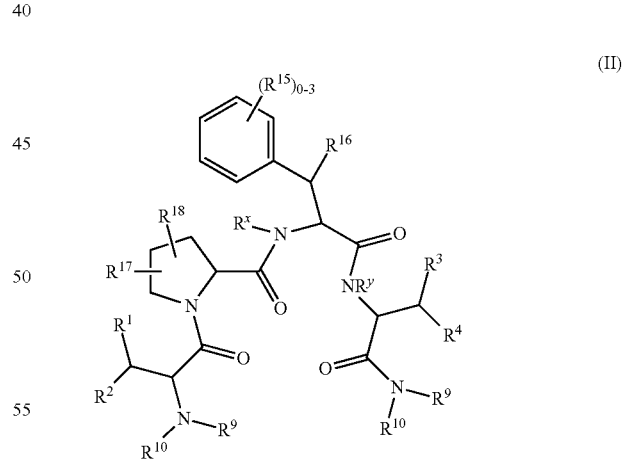

and pharmaceutically acceptable salts, stereoisomers, metabolites, and hydrates thereof,
wherein:
$R^1$, $R^2$, $R^3$, and $R^4$ are independently selected from the group consisting of hydrogen; halogen; $C_{1-6}$alkyl, optionally substituted by one, two, or three substituents independently selected from the group consisting of halogen, hydroxyl, phenyl, heteroaryl including from 5 to 6 ring atoms wherein 1, 2, or 3 of the ring atoms are independently selected from the group consisting of N, NH, N(C1-C3 alkyl), O, and S; and N($R^x$)$_2$; $C_{1-6}$ perfluoroalkyl; $C_{2-6}$alkenyl; $C_{2-6}$alkynyl; $C_{3-6}$cycloalkyl; phenyl; heteroaryl including from 5 to 6 ring atoms wherein 1, 2, or 3 of the ring atoms are independently selected from the group consisting of N, NH, N(C1-C3 alkyl), O, and S; —O$R^x$; —C(O)$R^x$; —CO$_2$($R^x$); —C(O)N($R^x$)$_2$; —C(N$R^x$)N($R^x$)$_2$; —OC(O)$R^x$; —OCO$_2R^x$; —OC(O)N($R^x$)$_2$; —N($R^x$)$_2$; —N$R^x$C(O)$R^x$; —N$R^x$C(O)N($R^x$)$_2$; —N$R^x$C(O)O$R^x$; and —N$R^x$C(N$R^x$)N($R^x$)$_2$;

when present, $R^{15}$ replaces a hydrogen atom attached to the phenyl ring and, and each occurrence of $R^{15}$ is independently selected from the group consisting of hydrogen; halogen; hydroxyl; $C_1$-$C_6$ alkyl; $C_{1-6}$ perfluoroalkyl; $C_1$-$C_6$ alkoxy; heteroaryl including from 5 to 6 ring atoms wherein 1, 2, or 3 of the ring atoms are independently selected from the group consisting of N, NH, N(C1-C3 alkyl), O, and S; heterocyclyl including from 3 to 6 ring atoms wherein 1, 2, or 3 of the ring atoms are independently selected from the group consisting of N, NH, N(C1-C3 alkyl), O, and S; and phenyl; wherein $C_1$-$C_6$ alkyl, $C_1$-$C_6$ alkoxy, heteroaryl, heterocyclyl, and phenyl are optionally substituted by one, two, or three substituents independently selected from halogen; hydroxyl; phenyl; heteroaryl including from 5 to 6 ring atoms wherein 1, 2, or 3 of the ring atoms are independently selected from the group consisting of N, NH, N(C1-C3 alkyl), O, and S; and N($R^x$)$_2$;

$R^{16}$ is selected from the group consisting of hydrogen; halogen; $C_{1-6}$alkyl; $C_{1-6}$ perfluoroalkyl; and phenyl;

$R^{17}$ and $R^{18}$ are each independently selected from the group consisting of hydrogen; halogen; hydroxyl; $C_1$-$C_6$ alkyl; $C_{1-6}$ perfluoroalkyl; $C_1$-$C_6$ alkoxy; $C_3$-$C_6$ cycloalkoxy; heteroaryl including from 5 to 6 ring atoms wherein 1, 2, or 3 of the ring atoms are independently selected from the group consisting of N, NH, N(C1-C3 alkyl), O, and S; heterocyclyl including from 3 to 6 ring atoms wherein 1, 2, or 3 of the ring atoms are independently selected from the group consisting of N, NH, N(C1-C3 alkyl), O, and S; and phenyl; wherein $C_1$-$C_6$ alkyl, $C_1$-$C_6$ alkoxy, $C_3$-$C_6$ cycloalkoxy; heteroaryl, heterocyclyl, and phenyl are optionally substituted by one, two, or three substituents independently selected from halogen; hydroxyl; phenyl; heteroaryl including from 5 to 6 ring atoms wherein 1, 2, or 3 of the ring atoms are independently selected from the group consisting of N, NH, N(C1-C3 alkyl), O, and S; and N($R^x$)$_2$; provided that $R^{17}$ cannot be halogen or hydroxyl when $R^{17}$ is a to the pyrrolidine nitrogen, and $R^{18}$ cannot be halogen or hydroxyl when $R^{18}$ is a to the pyrrolidine nitrogen; or $R^{17}$ and $R^{18}$, together with the atoms to which they are attached, form C3-C6 cycloalkyl or heterocyclyl including from 3 to 6 ring atoms wherein 1, 2, or 3 of the ring atoms are independently selected from the group consisting of N, NH, N(C1-C3 alkyl), O, and S; wherein the C3-C6 cycloalkyl and heterocyclyl are each optionally substituted by one, two, or three substituents independently selected from the group consisting of halogen, hydroxyl, phenyl, and N($R^x$)$_2$;

$R^9$ and $R^{10}$ are independently selected, for each occurrence, from the group consisting of hydrogen; $C_1$-$C_6$ alkyl, optionally substituted by one, two, or three substituents independently selected from the group consisting of halogen, oxo, hydroxyl, phenyl, and heteroaryl including from 5 to 6 ring atoms wherein 1, 2, or 3 of the ring atoms are independently selected from the group consisting of N, NH, N(C1-C3 alkyl), O, and S; $C_{1-6}$ perfluoroalkyl; $C_{2-6}$alkenyl, optionally substituted by one, two, or three substituents independently selected from the group consisting of halogen, oxo, and hydroxyl; $C_{2-6}$alkynyl, optionally substituted by one, two, or three substituents independently selected from the group consisting of halogen, oxo, and hydroxyl; $C_{3-6}$cycloalkyl, optionally substituted by one, two, or three substituents independently selected from the group consisting of $C_{1-6}$alkyl, $C_{1-6}$ perfluoroalkyl; halogen, oxo, and hydroxyl; phenyl, optionally substituted by one, two, or three substituents independently selected from the group consisting of $C_{1-6}$alkyl; $C_{1-6}$ perfluoroalkyl; $C_{1-6}$alkoxy; halogen; hydroxyl; —C(O)$R^x$; —CO$_2$($R^x$); —C(O)N($R^x$)$_2$; —C(N$R^x$)N($R^x$)$_2$; and —C($R^x$)$_3$;

or $R^9$ and $R^{10}$, together with the nitrogen atom to which each is attached, form a heterocyclyl including from 3 to 6 ring atoms, which is optionally substituted by one, two, or three substituents substituents independently selected from the group consisting of $C_{1-6}$alkyl, halogen, oxo, and hydroxyl; wherein when $R^9$ and $R^{10}$ form a heterocyclyl including 6 ring atoms, the heterocyclyl optionally includes, in addition to the nitrogen atom attached to $R^9$ and $R^{10}$, a second ring heteroatom selected from the group consisting of N, NH, N(C1-C3 alkyl), O, and S;

$R^x$ is independently selected, for each occurrence, from the group consisting of hydrogen; halogen; acyl; $C_{1-6}$alkyl; $C_{1-6}$ perfluoroalkyl; and phenyl; and $R^y$ is hydrogen or $C_{1-3}$alkyl.

In another aspect, a compound of formula (II) is provided, in which one or more (e.g., one, two, three, or four) of the four constituent amino acids is replaced with a beta-amino acid (e.g., the C-terminal and/or the N-terminal is/are replaced with a beta-amino acid(s); e.g., the proline and/or phenyl alanine moieties is/are replaced with a beta-amino acid(s); e.g., the C-terminal and/or the N-terminal is/are replaced with a beta-amino acid(s), and the proline and/or phenyl alanine moieties is/are replaced with a beta-amino acid(s)). In some embodiments, the constituent amino acid is replaced with its corresponding beta-amino acid (e.g., proline replaced with beta-proline). By way of example, such compounds can have formula (II-A), in which formula (II) is modified such that the proline moiety is replaced with:

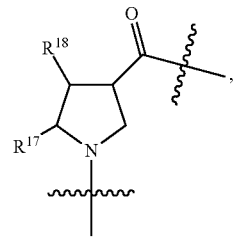

in which $R^{17}$ and $R^{18}$ are as defined anywhere herein. In still another embodiment, compounds are provided, in which any one or more of compounds of formula (II) and (II-A) are modified such that the left-most (N-terminal) amino acid is replaced with hydrogen, thereby providing a tripeptide wherein the ring nitrogen of proline moiety is bonded to hydrogen.

Embodiments of formula (II) and (II-A) tetra- and tripeptide compounds can include one or more of the following features and/or combinations of the following features.

In certain embodiments, $R^1$ is hydrogen, $C_1$-$C_6$ alkyl (e.g., methyl), $C_{1-6}$ perfluoroalkyl; or —OH.

In certain embodiments, $R^2$ is $C_{1-6}$alkyl, optionally substituted; or phenyl optionally substituted.

In certain embodiments, $R^1$ is as defined above, and $R^2$ is as defined above. In certain embodiments, $R^1$ is —OH. In certain embodiments, $R^2$ is $C_1$-$C_6$ alkyl (e.g., methyl). In certain embodiments, $R^1$ is —OH, and $R^2$ is $C_1$-$C_6$ alkyl (e.g., methyl).

In certain embodiments, $R^3$ is —OH. In certain embodiments, $R^4$ is $C_1$-$C_6$ alkyl (e.g., methyl). In certain embodiments, $R^3$ is —OH, and $R^4$ is $C_1$-$C_6$ alkyl (e.g., methyl).

In certain embodiments, one of $R^{17}$ and $R^{18}$ is independently selected from the group consisting of hydroxyl; $C_1$-$C_6$ alkoxy (e.g., methoxy); and $C_3$-$C_6$ cycloalkoxy (e.g., cyclopropoxy); wherein $C_1$-$C_6$ alkoxy and $C_3$-$C_6$ cycloalkoxy are each optionally and independently substituted by one, two or three substituents independently selected from the group consisting of halogen, hydroxyl, $C_1$-$C_6$ alkyl, $C_{1-6}$ perfluoroalkyl; phenyl, and $N(R^x)_2$, and the other is hydrogen. In other embodiments, $R^{17}$ and $R^{18}$ form a ring.

In certain embodiments, each occurrence of $R^9$ and $R^{10}$ is hydrogen.

In certain embodiments, $R^{16}$ is hydrogen.

In certain embodiments, at least one $R^{15}$ is present.

In certain embodiments, $R^x$ is hydrogen. In other embodiments, $R^x$ is $CH_3$.

In certain embodiments, $R^y$ is hydrogen. In other embodiments, $R^y$ is $CH_3$.

Disclosed compounds include those having formula (III):

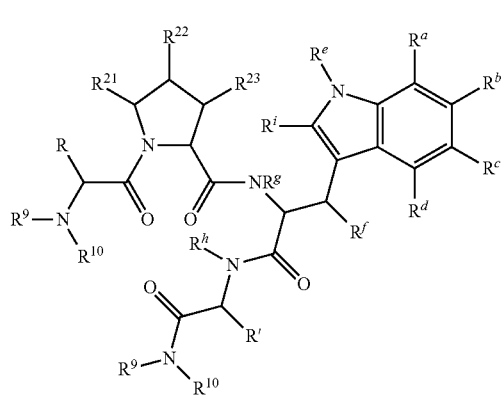

(III)

and pharmaceutically acceptable salts, stereoisomers, metabolites, and hydrates thereof,
wherein:
R is —$C(R^1)(R^{11})(R^2)$;
R' is —$C(R^3)(R^{31})(R^4)$;
each of $R^1$ and $R^2$ is independently selected from the group consisting of:
hydrogen;
halogen;
$C_{1-6}$alkyl, optionally substituted by one, two or three substituents independently selected from the group consisting of halogen; hydroxyl; $C_{1-6}$alkoxy; phenyl; $N(R^x)_2$; $C_3$-$C_6$ cycloalkyl; heteroaryl including from 5 to 6 ring atoms wherein 1, 2, or 3 of the ring atoms are independently selected from the group consisting of N, NH, N(C1-C3 alkyl), O, and S; and heterocyclyl including from 3 to 6 ring atoms wherein 1, 2, or 3 of the ring atoms are independently selected from the group consisting of N, NH, N(C1-C3 alkyl), O, and S; wherein the phenyl, cycloakyl, heteroaryl, and heterocyclyl are each optionally substituted with one, two, or three substituents that are independently selected from the group consisting of halogen, hydroxyl, $C_1$-$C_6$ alkyl, $C_{1-6}$ perfluoroalkyl; and $N(R^x)_2$;
$C_{1-6}$ perfluoroalkyl;
$C_{2-6}$alkenyl;
$C_{2-6}$alkynyl;
$C_{3-6}$cycloalkyl optionally substituted by one, two or three independently selected $C_{1-3}$alkyl;
phenyl optionally substituted with one, two, or three substituents that are independently selected from the group consisting of halogen, hydroxyl, $C_1$-$C_6$ alkyl, $C_{1-6}$ perfluoroalkyl; and $N(R^x)_2$;
heteroaryl including from 5 to 6 ring atoms wherein 1, 2, or 3 of the ring atoms are independently selected from the group consisting of N, NH, N(C1-C3 alkyl), O, and S; which is optionally substituted with one, two, or three substituents independently selected from the group consisting of halogen, hydroxyl, $C_1$-$C_6$ alkyl, $C_{1-6}$ perfluoroalkyl; and $N(R^x)_2$;
—$OR^x$;
—$C(O)R^x$;
—$CO_2(R^x)$;
—$C(O)N(R^x)_2$;
—$C(NR^x)N(R^x)_2$;
—$OC(O)R^x$;
—$OCO_2R^x$;
—$OC(O)N(R^x)_2$;
—$N(R^x)_2$;
—$NR^xC(O)R^x$;
—$NR^xC(O)N(R^x)_2$;
—$NR^xC(O)OR^x$; and
—$NR^xC(NR^x)N(R^x)_2$; or
$R^1$ and $R^2$ together with the carbon atom to which each is attached form a ring selected from the group consisting of (i) phenyl and (ii) heteroaryl including from 5 to 6 ring atoms wherein 1, 2, or 3 of the ring atoms are independently selected from N, NH, N($C_1$-$C_3$ alkyl), O, and S; each of which is optionally substituted with one, two, or three substituents independently selected from the group consisting of halogen, hydroxyl, $C_1$-$C_6$ alkyl, $C_{1-6}$ perfluoroalkyl; phenyl, and $N(R^x)_2$;
each of $R^3$ and $R^4$ is independently selected from the group consisting of:
hydrogen;
halogen;
$C_{1-6}$alkyl, optionally substituted with one, two or three substituents independently selected from the group consisting of halogen; hydroxyl; $C_{1-6}$alkoxy; phenyl; $N(R^x)_2$; $C_3$-$C_6$ cycloalkyl; heteroaryl including from 5 to 6 ring atoms wherein 1, 2, or 3 of the ring atoms are independently selected from the group consisting of N, NH, N($C_1$-$C_3$ alkyl), O, and S; and heterocyclyl including from 3 to 6 ring atoms wherein 1, 2, or 3 of the ring atoms are independently selected from the group consisting of N, NH, N($C_1$-$C_3$ alkyl), O, and S; wherein the phenyl, cycloakyl, heteroaryl, and heterocyclyl are each optionally substituted with one, two, or three substituents independently selected from the group consisting of halogen, hydroxyl, $C_1$-$C_6$ alkyl, $C_{1-6}$ perfluoroalkyl; and $N(R^x)_2$;
$C_{1-6}$ perfluoroalkyl;
$C_{2-6}$alkenyl;
$C_{2-6}$alkynyl;
$C_{3-6}$cycloalkyl optionally substituted with one, two or three independently selected $C_{1-3}$alkyl;
phenyl optionally substituted with one, two, or three substituents that are independently selected from the group consisting of halogen, hydroxyl, $C_1$-$C_6$ alkyl, $C_{1-6}$ perfluoroalkyl; and $N(R^x)_2$;

heteroaryl including from 5 to 6 ring atoms wherein 1, 2, or 3 of the ring atoms are independently selected from the group consisting of N, NH, N($C_1$-$C_3$ alkyl), O, and S; which is optionally substituted with one, two, or three substituents independently selected from the group consisting of halogen, hydroxyl, $C_1$-$C_6$ alkyl, $C_{1-6}$ perfluoroalkyl; and N($R^x$)$_2$,
—O$R^x$;
—C(O)$R^x$;
—CO$_2$($R^x$);
—C(O)N($R^x$)$_2$;
—C(N$R^x$)N($R^x$)$_2$;
—OC(O)$R^x$;
—OCO$_2R^x$;
—OC(O)N($R^x$)$_2$;
—N($R^x$)$_2$;
—N$R^x$C(O)$R^x$;
—N$R^x$C(O)N($R^x$)$_2$;
—N$R^x$C(O)O$R^x$; and
—N$R^x$C(N$R^x$)N($R^x$)$_2$; or $R^3$ and $R^4$ together with the carbon atom to which each is attached form a ring selected from the group consisting of (i) phenyl and (ii) heteroaryl including from 5 to 6 ring atoms wherein 1, 2, or 3 of the ring atoms are independently selected from N, NH, N($C_1$-$C_3$ alkyl), O, and S; each of which is optionally substituted with one, two, or three substituents independently selected from the group consisting of halogen, hydroxyl, $C_1$-$C_6$ alkyl, $C_{1-6}$ perfluoroalkyl; phenyl, and N($R^x$)$_2$;

each of $R^{11}$ and $R^{31}$ is, independently, hydrogen, $C_1$-$C_6$ alkyl, or $C_{1-6}$ perfluoroalkyl; or $R^{11}$ is absent when $R^1$ and $R^2$ together form phenyl or heteroaryl;

$R^{31}$ is absent when $R^3$ and $R^4$ together form phenyl or heteroaryl;

each of $R^a$, $R^b$, $R^c$, and $R^d$ is independently selected from the group consisting of hydrogen; halogen; hydroxyl; $C_1$-$C_6$ alkyl; $C_{1-6}$ perfluoroalkyl; $C_1$-$C_6$ alkoxy; heteroaryl including from 5 to 6 ring atoms wherein 1, 2, or 3 of the ring atoms are independently selected from the group consisting of N, NH, N($C_1$-$C_3$ alkyl), O, and S; heterocyclyl including from 3 to 6 ring atoms wherein 1, 2, or 3 of the ring atoms are independently selected from the group consisting of N, NH, N($C_1$-$C_3$ alkyl), O, and S; and phenyl; wherein $C_1$-$C_6$ alkyl, $C_1$-$C_6$ alkoxy, heteroaryl, heterocyclyl, and phenyl are each optionally substituted by one, two, or three substituents independently selected from the group consisting of halogen, hydroxyl, phenyl, and N($R^x$)$_2$;

each of $R^e$ and $R^g$ is independently selected from the group consisting of hydrogen; acyl; $C_{1-6}$alkyl; $C_{1-6}$ perfluoroalkyl; and phenyl;

$R^f$ is selected from the group consisting of hydrogen; halogen; acyl; $C_{1-6}$alkyl; $C_{1-6}$ perfluoroalkyl; and phenyl;

$R^h$ is hydrogen or $C_{1-3}$alkyl;

$R^i$ is selected from the group consisting of hydrogen; halogen; cyano, CH$_3$, and CF$_3$;

$R^{21}$ is selected from the group consisting of hydrogen; $C_1$-$C_6$ alkyl; $C_{1-6}$ perfluoroalkyl; $C_1$-$C_6$ alkoxy; $C_3$-$C_6$ cycloalkoxy; $C_2$-$C_6$ acyloxy, heteroaryl including from 5 to 6 ring atoms wherein 1, 2, or 3 of the ring atoms are independently selected from the group consisting of N, NH, N($C_1$-$C_3$ alkyl), O, and S; heterocyclyl including from 3 to 6 ring atoms wherein 1, 2, or 3 of the ring atoms are independently selected from the group consisting of N, NH, N($C_1$-$C_3$ alkyl), O, and S; and phenyl; wherein $C_1$-$C_6$ alkyl, $C_1$-$C_6$ alkoxy, $C_3$-$C_6$ cycloalkoxy, heteroaryl, heterocyclyl, and phenyl are each optionally and independently substituted by one, two or three substituents that are independently selected from the group consisting of halogen, hydroxyl, $C_1$-$C_6$ alkyl, $C_{1-6}$ perfluoroalkyl, phenyl, and N($R^x$)$_2$;

each of $R^{22}$ and $R^{23}$ is independently selected from the group consisting of hydrogen; halogen; hydroxyl; $C_1$-$C_6$ alkyl; $C_{1-6}$ perfluoroalkyl; $C_1$-$C_6$ alkoxy; $C_3$-$C_6$ cycloalkoxy; $C_2$-$C_6$ acyloxy, heteroaryl including from 5 to 6 ring atoms wherein 1, 2, or 3 of the ring atoms are independently selected from the group consisting of N, NH, N($C_1$-$C_3$ alkyl), O, and S; heterocyclyl including from 3 to 6 ring atoms wherein 1, 2, or 3 of the ring atoms are independently selected from the group consisting of N, NH, N($C_1$-$C_3$ alkyl), O, and S; and phenyl; wherein $C_1$-$C_6$ alkyl, $C_1$-$C_6$ alkoxy, $C_3$-$C_6$ cycloalkoxy, heteroaryl, heterocyclyl, and phenyl are each optionally and independently substituted by one, two or three substituents that are independently selected from the group consisting of halogen, hydroxyl, $C_1$-$C_6$ alkyl, $C_{1-6}$ perfluoroalkyl; phenyl, and N($R^x$)$_2$; or $R^{21}$ and $R^{22}$, together with the carbon atoms to which each is attached, form a ring selected from the group consisting of (i) 3-6 membered heterocyclyl wherein 1, 2, or 3 of the ring atoms are independently selected from N, NH, N($C_1$-$C_3$ alkyl), O, and S; (ii) $C_3$-$C_6$ cycloalkyl; (iii) phenyl; and (iv) heteroaryl including from 5 to 6 ring atoms wherein 1, 2, or 3 of the ring atoms are independently selected from N, NH, N($C_1$-$C_3$ alkyl), O, and S; wherein each of (i)-(iv) is optionally substituted by one, two, or three substituents that are independently selected from the group consisting of halogen, hydroxyl, $C_1$-$C_6$ alkyl, $C_{1-6}$ perfluoroalkyl; phenyl, and N($R^x$)$_2$; and $R^{23}$ is as defined above; or $R^{22}$ and $R^{23}$, together with the carbon atoms to which each is attached, form a ring selected from the group consisting of (i) 3-6 membered heterocyclyl wherein 1, 2, or 3 of the ring atoms are independently selected from N, NH, N($C_1$-$C_3$ alkyl), O, and S; (ii) $C_3$-$C_6$ cycloalkyl; (iii) phenyl; and (iv) heteroaryl including from 5 to 6 ring atoms wherein 1, 2, or 3 of the ring atoms are independently selected from N, NH, N($C_1$-$C_3$ alkyl), O, and S; wherein each of (i)-(iv) is optionally substituted by one, two, or three substituents that are independently selected from the group consisting of halogen, hydroxyl, $C_1$-$C_6$ alkyl, $C_{1-6}$ perfluoroalkyl; phenyl, and N($R^x$)$_2$; and $R^{21}$ is as defined above;

each occurrence of $R^9$ and $R^{10}$ is independently selected from the group consisting of hydrogen; $C_1$-$C_6$ alkyl, optionally substituted by one, two, or three substituents each independently selected from the group consisting of halogen, oxo, and hydroxyl; $C_{1-6}$ perfluoroalkyl; $C_{2-6}$alkenyl, optionally substituted by one, two, or three substituents each independently selected from the group consisting of halogen, oxo, and hydroxyl; $C_{2-6}$alkynyl, optionally substituted by one, two, or three substituents each independently selected from the group consisting of halogen, oxo, and hydroxyl; $C_{3-6}$cycloalkyl, optionally substituted by one, two, or three substituents each independently selected from the group consisting of $C_{1-6}$alkyl, $C_{1-6}$ perfluoroalkyl; halogen, oxo, and hydroxyl; and phenyl, optionally substituted by one, two, or three substituents each independently selected from the group consisting of $C_{1-6}$alkyl; $C_{1-6}$ perfluoroalkyl; $C_{1-6}$alkoxy; halogen; hydroxyl; —C(O)$R^x$; —CO$_2$($R^x$); —C(O)N($R^x$)$_2$; —C(N$R^x$)N($R^x$)$_2$; and —C($R^x$)$_3$;

or $R^9$ and $R^{10}$, together with the nitrogen atom to which each is attached, form heterocyclyl including from 3 to 6 ring atoms wherein 1, 2, or 3 of the ring atoms are independently selected from the group consisting of N, NH, N(C1-C3 alkyl), O, and S; which is optionally substituted by one, two, or three substituents each independently selected from the group consisting of $C_{1-6}$alkyl, $C_{1-6}$ perfluoroalkyl;

halogen, oxo, and hydroxyl; wherein when $R^9$ and $R^{10}$ form a heterocyclyl including 6 ring atoms, the heterocyclyl optionally includes, in addition to the nitrogen atom attached to $R^9$ and $R^{10}$, a second ring heteroatom selected from the group consisting of N, NH, N(C1-C3 alkyl), O, and S; and $R^x$ is independently selected, for each occurrence, from the group consisting of hydrogen; halogen; acyl; $C_{1-6}$alkyl; $C_{1-6}$ perfluoroalkyl; and phenyl.

In another aspect, a compound of formula (III) is provided, in which one or more (e.g., one, two, three, or four) of the four constituent amino acids is replaced with a beta-amino acid (e.g., the C-terminal and/or the N-terminal is/are replaced with a beta-amino acid(s); e.g., the proline and/or trytophan moieties is/are replaced with a beta-amino acid(s); e.g., the C-terminal and/or the N-terminal is/are replaced with a beta-amino acid(s), and the proline and/or tryptophan moieties is/are replaced with a beta-amino acid(s)). In some embodiments, the constituent amino acid is replaced with its corresponding beta-amino acid (e.g., proline replaced with beta-proline). By way of example, such compounds can have formula (III-A), in which formula (III) is modified such that the proline moiety is replaced with:

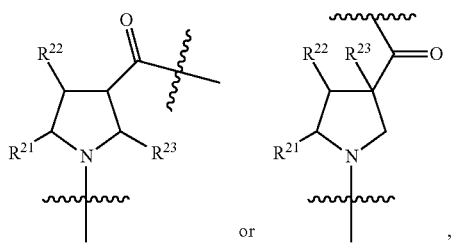

in which $R^{21}$, $R^{22}$, and $R^{23}$ are as defined anywhere herein. In still another embodiment, compounds are provided, in which any one or more of compounds of formula (III) and (III-A) are modified such that the left-most (N-terminal) amino acid is replaced with hydrogen, thereby providing a tripeptide wherein the ring nitrogen of proline moiety is bonded to hydrogen.

Embodiments of formula (III) and (III-A) tetra- and tripeptide compounds can include one or more of the following features and/or combinations of the following features.

In certain embodiments, $R^{21}$ and $R^{22}$ and $R^{22}$ and $R^{23}$ do not form a ring as defined herein.

For example, one of $R^{22}$ and $R^{23}$ (e.g., $R^{22}$) is selected from the group consisting of halogen; hydroxyl; $C_1$-$C_6$ alkyl; $C_{1-6}$ perfluoroalkyl; $C_1$-$C_6$ alkoxy; $C_3$-$C_6$ cycloalkoxy; $C_2$-$C_6$ acyloxy, heteroaryl including from 5 to 6 ring atoms wherein 1, 2, or 3 of the ring atoms are independently selected from the group consisting of N, NH, N($C_1$-$C_3$ alkyl), O, and S; heterocyclyl including from 3 to 6 ring atoms wherein 1, 2, or 3 of the ring atoms are independently selected from the group consisting of N, NH, N($C_1$-$C_3$ alkyl), O, and S; and phenyl; wherein $C_1$-$C_6$ alkyl, $C_1$-$C_6$ alkoxy, $C_3$-$C_6$ cycloalkoxy, heteroaryl, heterocyclyl, and phenyl are each optionally and independently substituted by one, two or three substituents that are independently selected from the group consisting of halogen, hydroxyl, $C_1$-$C_6$ alkyl, $C_{1-6}$ perfluoroalkyl; phenyl, and N($R^x$)$_2$, and the other is hydrogen.

As another example, one of $R^{22}$ and $R^{23}$ (e.g., $R^{22}$) is independently selected from the group consisting of hydroxyl; $C_1$-$C_6$ alkoxy (e.g., methoxy); and $C_3$-$C_6$ cycloalkoxy (e.g., cyclopropoxy); $C_2$-$C_6$ acyloxy (—OC(O)CH$_3$), wherein $C_1$-$C_6$ alkoxy and $C_3$-$C_6$ cycloalkoxy are each optionally and independently substituted by one, two or three substituents independently selected from the group consisting of halogen, hydroxyl, $C_1$-$C_6$ alkyl, $C_{1-6}$ perfluoroalkyl; phenyl, and N($R^x$)$_2$, and the other is hydrogen.

In certain of these embodiments, $R^{21}$ is hydrogen.

In other embodiments, $R^{21}$ and $R^{22}$ (together with the carbon atoms to which each is attached) or $R^{22}$ and $R^{23}$ (together with the carbon atoms to which each is attached) do form a ring as defined herein.

In certain embodiments, $R^{21}$ and $R^{22}$ form a ring as defined herein; e.g., a $C_3$-$C_6$ cycloalkyl ring (e.g., a $C_3$ or $C_5$), which is optionally substituted by one, two, or three substituents that are independently selected from the group consisting of halogen, hydroxyl, $C_1$-$C_6$ alkyl, $C_{1-6}$ perfluoroalkyl; phenyl, and N($R^x$)$_2$; or a phenyl ring, which is optionally substituted by one, two, or three substituents that are independently selected from the group consisting of halogen, hydroxyl, $C_1$-$C_6$ alkyl, $C_{1-6}$ perfluoroalkyl; phenyl, and N($R^x$)$_2$; or a heteroaryl ring including from 5 to 6 ring atoms wherein 1, 2, or 3 of the ring atoms are independently selected from N, NH, N($C_1$-$C_3$ alkyl), O, and S; each of which is optionally substituted by one, two, or three substituents that are independently selected from the group consisting of halogen, hydroxyl, $C_1$-$C_6$ alkyl, $C_{1-6}$ perfluoroalkyl; phenyl, and N($R^x$)$_2$.

In certain of these embodiments, $R^{23}$ is hydrogen.

In certain embodiments (e.g., when the proline is an α-proline), $R^{22}$ and $R^{23}$ form a ring as defined herein; e.g., a $C_3$-$C_6$ cycloalkyl ring (e.g., a $C_3$ or $C_5$), which is optionally substituted by one, two, or three substituents that are independently selected from the group consisting of halogen, hydroxyl, $C_1$-$C_6$ alkyl, $C_{1-6}$ perfluoroalkyl; phenyl, and N($R^x$)$_2$; or a phenyl ring, which is optionally substituted by one, two, or three substituents that are independently selected from the group consisting of halogen, hydroxyl, $C_1$-$C_6$ alkyl, $C_{1-6}$ perfluoroalkyl; phenyl, and N($R^x$)$_2$; or a heteroaryl ring including from 5 to 6 ring atoms wherein 1, 2, or 3 of the ring atoms are independently selected from N, NH, N($C_1$-$C_3$ alkyl), O, and S; each of which is optionally substituted by one, two, or three substituents that are independently selected from the group consisting of halogen, hydroxyl, $C_1$-$C_6$ alkyl, $C_{1-6}$ perfluoroalkyl; phenyl, and N($R^x$)$_2$.

In certain of these embodiments, $R^{21}$ is hydrogen.

In certain embodiments, $R^1$ and $R^2$ do not form a ring as defined herein.

In certain embodiments, $R^1$ is hydrogen, $C_1$-$C_6$ alkyl (e.g., methyl), $C_{1-6}$ perfluoroalkyl; or —OH (e.g., hydrogen, $C_1$-$C_6$ alkyl (e.g., methyl), or —OH).

In certain embodiments, $R^2$ is: $C_{1-6}$alkyl, optionally substituted by one, two or three substituents that are independently selected from the group consisting of halogen, hydroxyl, $C_{1-6}$alkoxy, phenyl, N($R^x$)$_2$, $C_3$-$C_6$ cycloalkyl, heteroaryl including from 5 to 6 ring atoms wherein 1, 2, or 3 of the ring atoms are independently selected from the group consisting of N, NH, N(C1-C3 alkyl), O, and S, and heterocyclyl including from 3 to 6 ring atoms wherein 1, 2, or 3 of the ring atoms are independently selected from the group consisting of N, NH, N(C1-C3 alkyl), O, and S; wherein the phenyl, cycloakyl, heteroaryl, and heterocyclyl are each optionally substituted with one, two, or three substituents that are independently selected from the group consisting of halogen, hydroxyl, $C_1$-$C_6$ alkyl, $C_{1-6}$ perfluoroalkyl; and N($R^x$)$_2$; $C_{1-4}$perhaloalkyl (e.g., CF$_3$); or phenyl optionally substituted with one, two, or three substituents that are independently selected from the group consisting of halogen, hydroxyl, $C_1$-$C_6$ alkyl, $C_{1-6}$ perfluoroalkyl; and $N(R^x)_2$. In certain embodiments, $R^2$ is unsubstituted $C_{1-6}$alkyl or substituted $C_1$ or $C_2$ (e.g., $C_1$) alkyl.

In certain embodiments, $R^1$ is as defined above, and $R^2$ is as defined above in the two preceding paragraphs. In certain embodiments, $R^1$ is —OH, and $R^2$ is as defined above . In certain embodiments, $R^1$ is hydrogen, and $R^2$ is as defined above. In certain embodiments, $R^1$ is $C_1$-$C_6$ alkyl (e.g., methyl), and $R^2$ is as defined above.

In certain embodiments, $R^{11}$ is hydrogen. In other embodiments, $R^{11}$ is $C_1$-$C_6$ alkyl (e.g., methyl); e.g., when $R^1$ and $R^2$ are also $C_1$-$C_6$ alkyl (e.g., methyl).

In other embodiments, $R^1$ and $R^2$ together with the carbon atoms to which each is attached form a ring as defined herein (e.g., a phenyl ring); and $R^{11}$ is absent.

In certain embodiments, $R^3$ is —OH. In certain embodiments, $R^4$ is $C_1$-$C_6$ alkyl (e.g., methyl). In certain embodiments, $R^3$ is —OH, and $R^4$ is $C_1$-$C_6$ alkyl (e.g., methyl). In certain embodiments, $R^{31}$ is hydrogen. In certain embodiments, $R^3$ is —OH, $R^4$ is $C_1$-$C_6$ alkyl (e.g., methyl), and $R^{31}$ is hydrogen.

In certain embodiments, each of $R^a$, $R^b$, $R^c$, $R^d$, $R^e$, and $R^f$ is hydrogen.

In certain embodiments, each occurrence of $R^9$ and $R^{10}$ is hydrogen.

In certain embodiments, $R^i$ is hydrogen.

In certain embodiments, each of $R^a$, $R^b$, $R^c$, $R^d$, $R^e$, $R^f$, $R^i$, $R^9$ and $R^{10}$ is hydrogen.

In certain embodiments, $R^g$ is hydrogen. In other embodiments, $R^g$ is $CH_3$.

In certain embodiments, $R^h$ is hydrogen. In other embodiments, $R^h$ is $CH_3$.

In certain embodiments, $R^1$ is —OH, and $R^2$ is as defined above (e.g., $R^2$ is $C_1$-$C_6$ alkyl (e.g., methyl)), or $R^1$ is hydrogen, and $R^2$ is as defined above, or $R^1$ is $C_1$-$C_6$ alkyl (e.g., methyl), and $R^2$ is as defined above, (e.g., $R^1$ is —OH, and $R^2$ is as defined above, e.g., $R^2$ is $C_1$-$C_6$ alkyl (e.g., methyl)); $R^{11}$ is hydrogen; $R^{21}$, $R^{22}$ and $R^{23}$ are hydrogen, or $R^{21}$ and $R^{23}$ are hydrogen, and $R^{22}$ is other than hydrogen as defined herein (e.g., hydroxyl; $C_1$-$C_6$ alkoxy (e.g., methoxy); and $C_3$-$C_6$ cycloalkoxy (e.g., cyclopropoxy); $C_2$-$C_6$ acyloxy (—OC(O)CH$_3$)); $R^3$ is —OH, $R^4$ is $C_1$-$C_6$ alkyl (e.g., methyl), $R^{31}$ is hydrogen; each of $R^a$, $R^b$, $R^e$, $R^d$, $R^e$, $R^f$, $R^i$, $R^9$ and $R^{10}$ is hydrogen; $R^g$ is hydrogen or $CH_3$; and $R^g$ is hydrogen or $CH_3$. In certain of these embodiments, the proline is an α-proline. In other of these embodiments, the proline is an β-proline.

Figure 2:
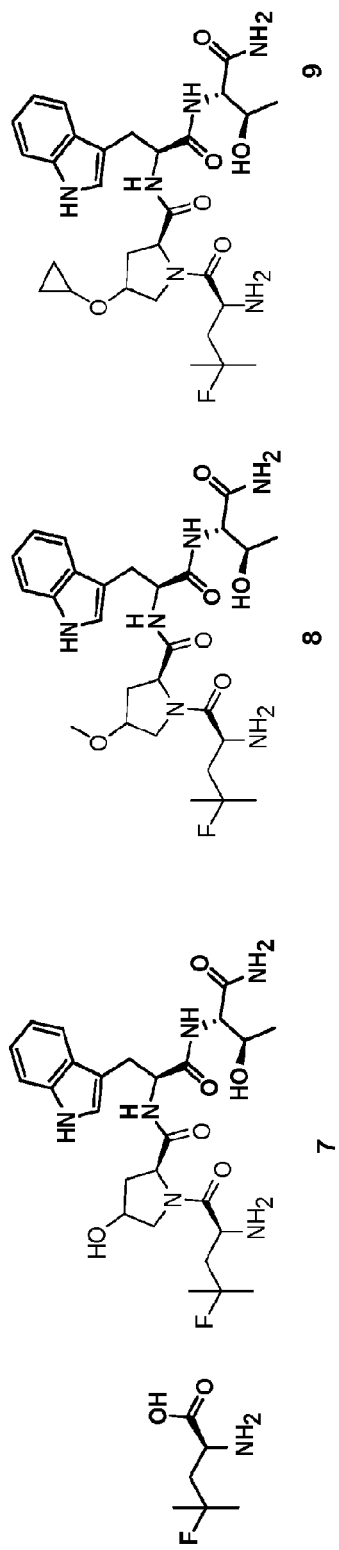
FIG. 2 is a series of matrices showing the chemical structures of 1 exemplary formula (III) compounds that contain unnatural amino acid precursors; the non-natural proline portion is shown in the top horizontal row of each matrix, and the non-natural proline portion is shown in the top horizontal row of each matrix.
Figure 2:
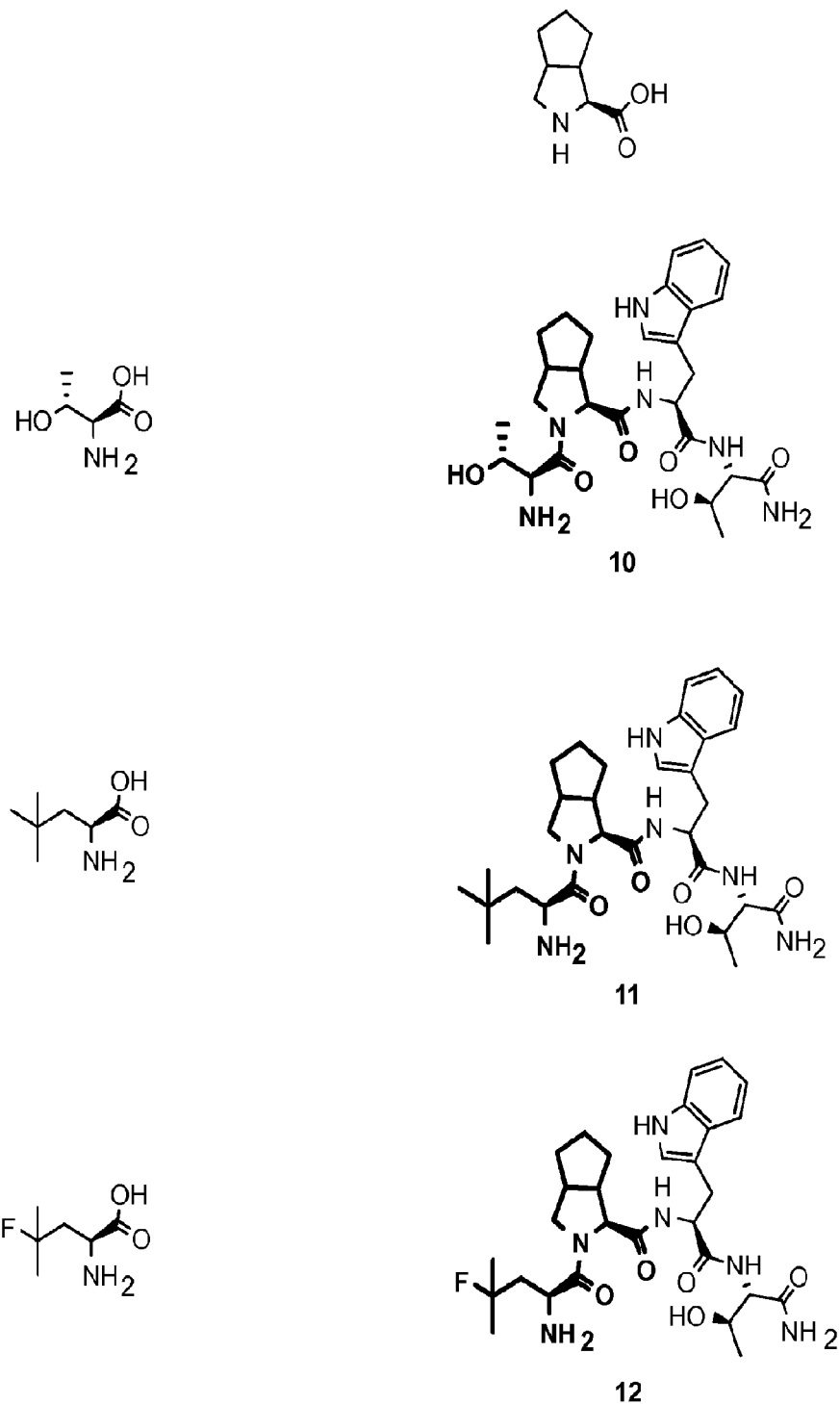
Figure 2:
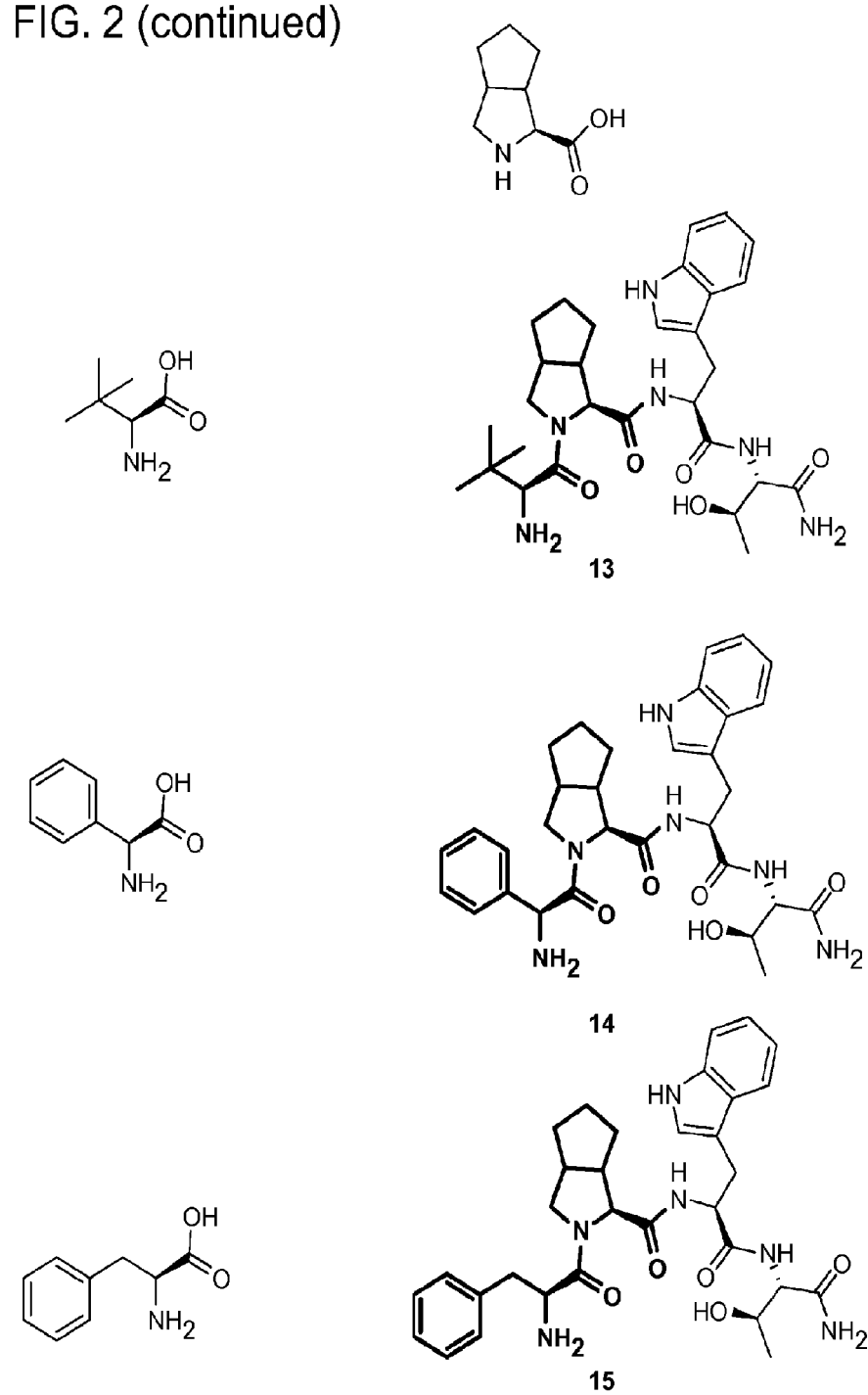
Figure 2:
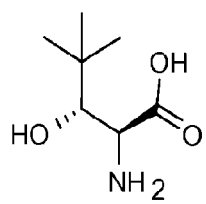
Figure 2:
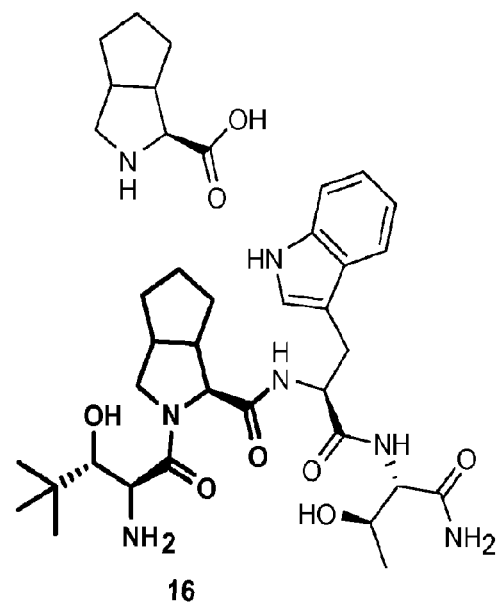
Figure 2:
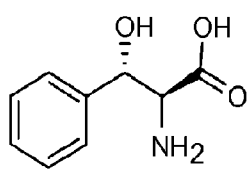
Figure 2:
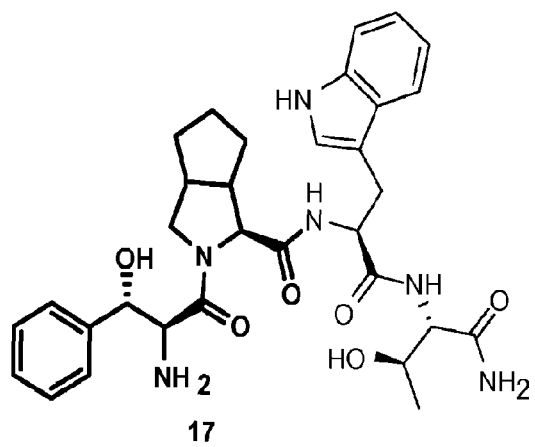
Figure 2:
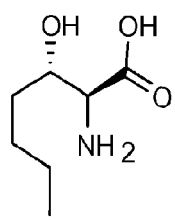
Figure 2:
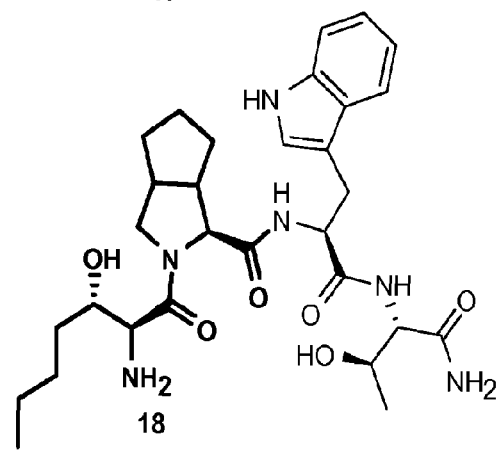
Figure 2:
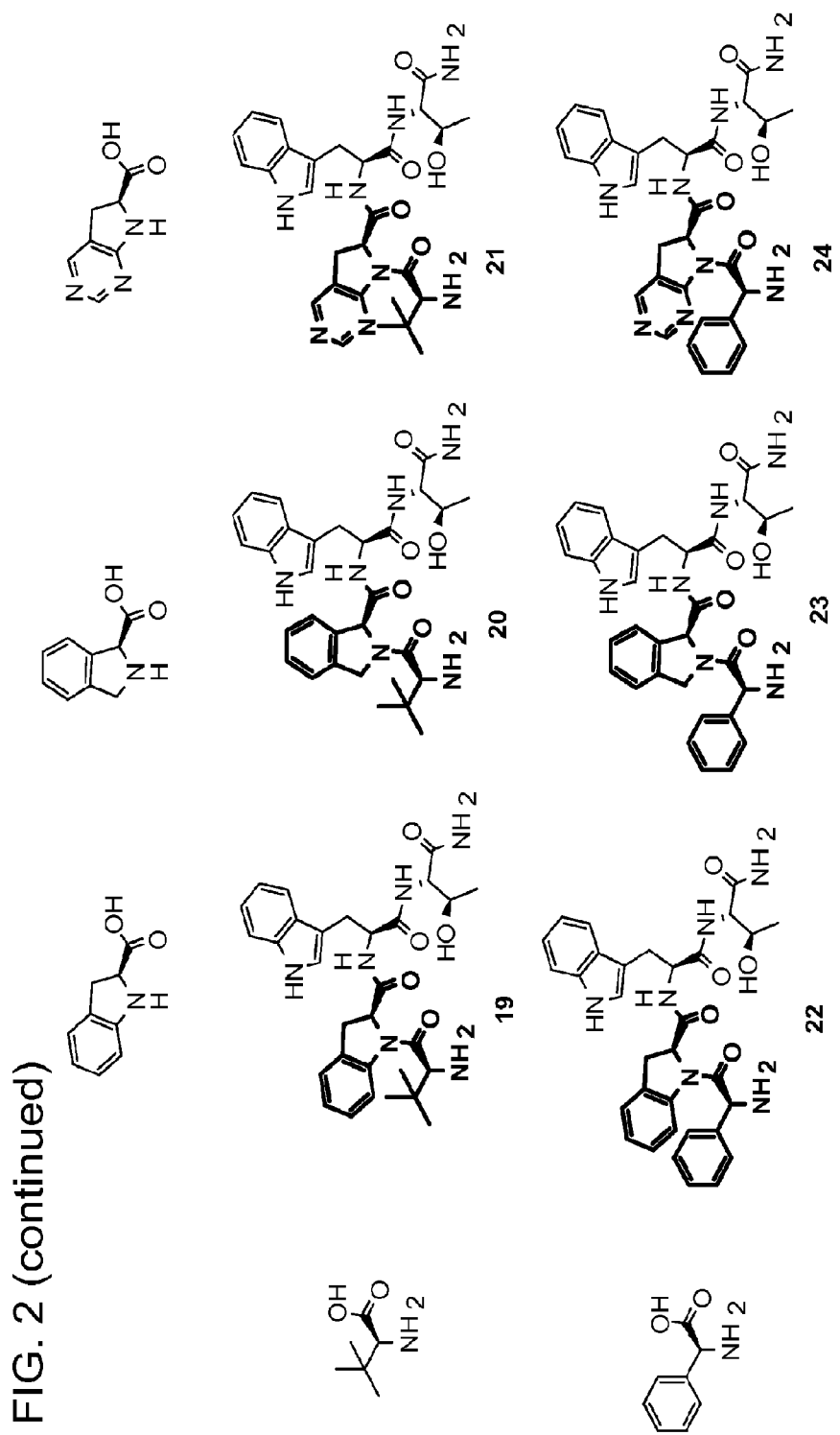
Figure 2:
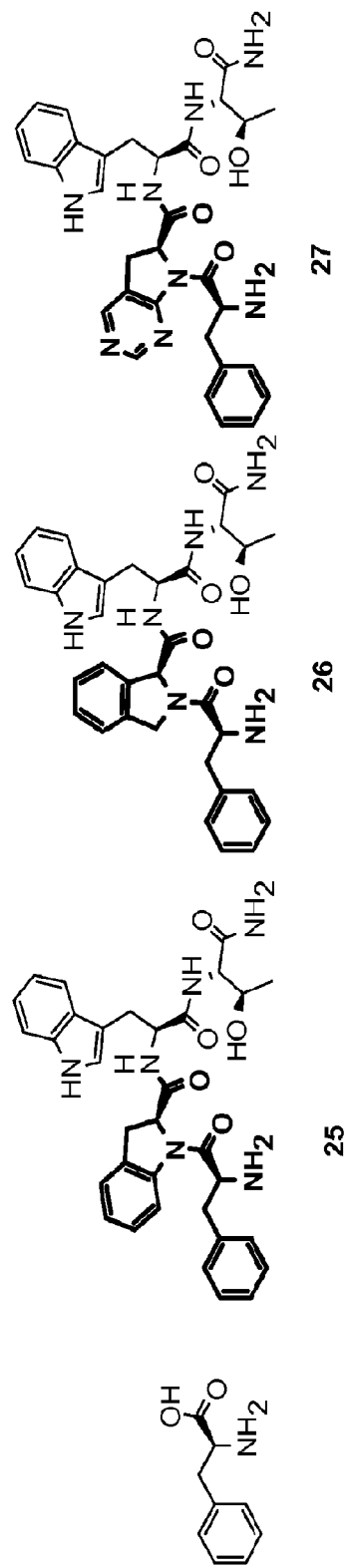
Figure 2:
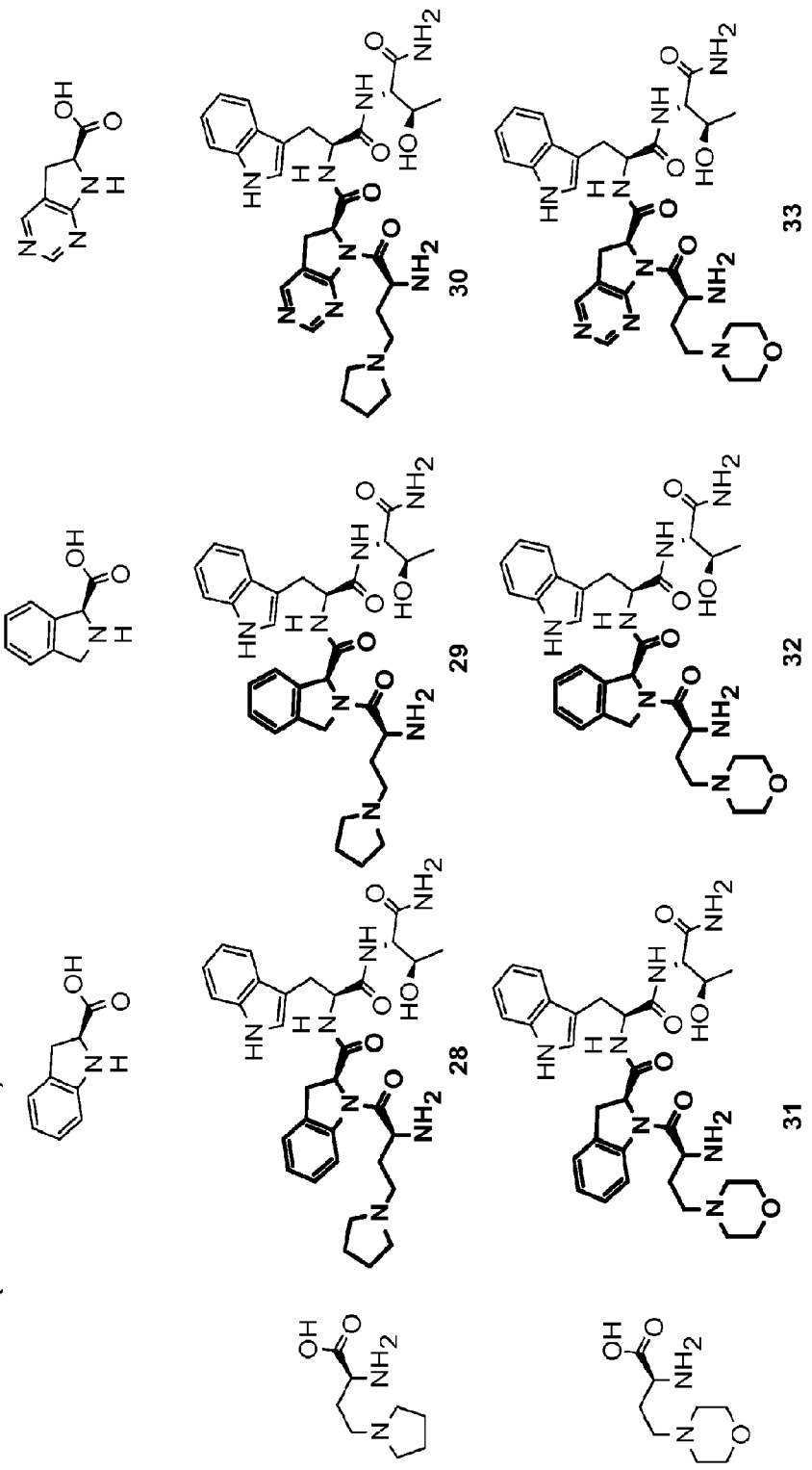
Figure 2:
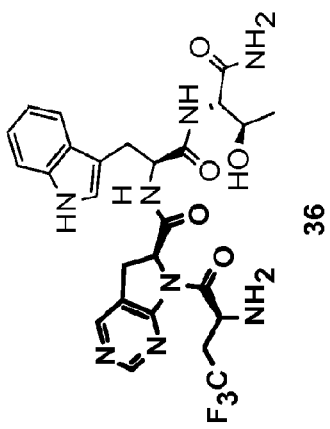
Figure 2:
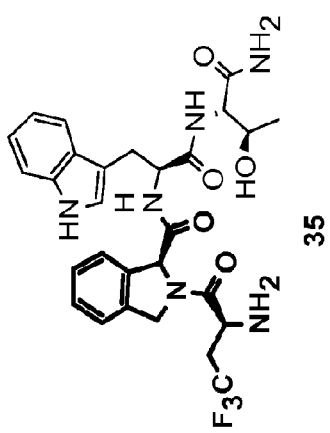
Figure 2:
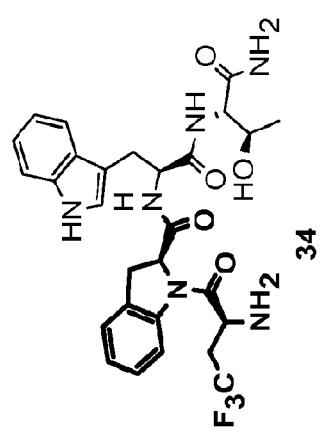
Figure 2:
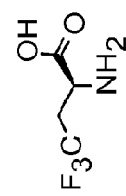
Figure 2:
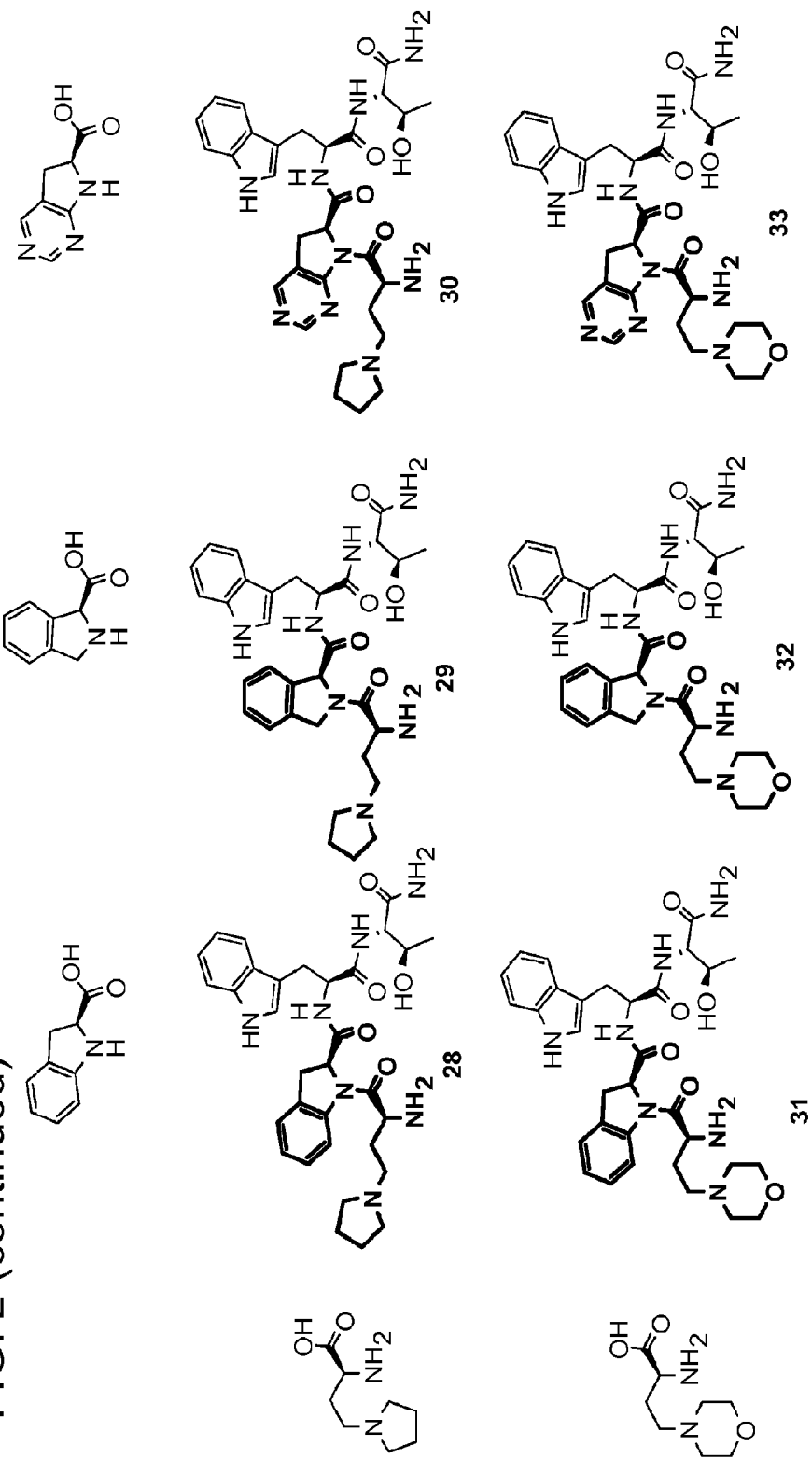
Figure 2:
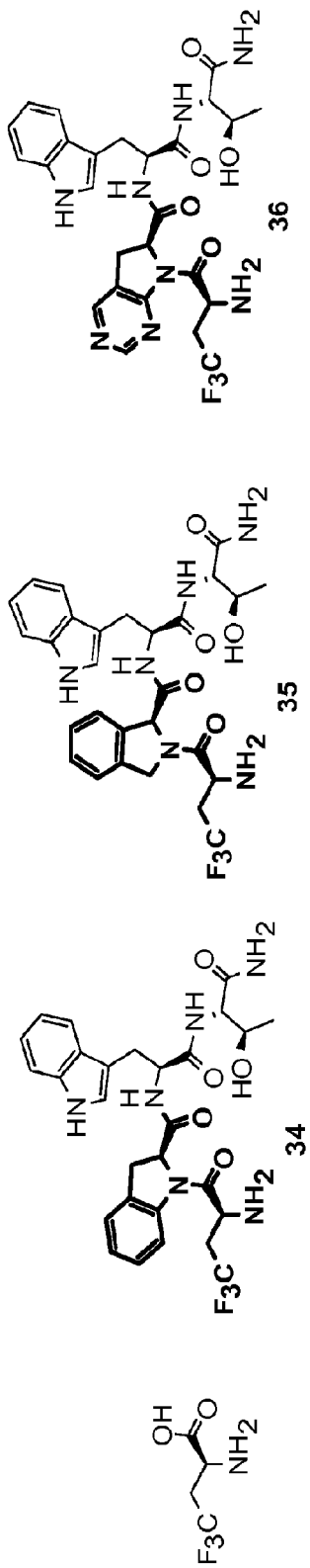

Non-limiting exemplary compounds include those delineated in Table 1, FIG. 1, and FIG. 2.

Disclosed compounds include those having formula (IV):

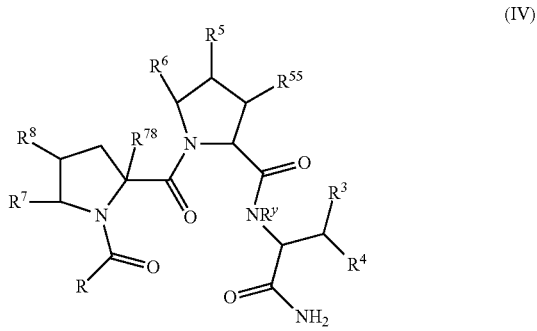

(IV)

and pharmaceutically acceptable salts, stereoisomers, metabolites, and hydrates thereof (e.g., salts), wherein:

R is selected from the group consisting of $C_{1-6}$alkyl; $C_{1-6}$ perfluoroalkyl; $C_{3-6}$cycloalkyl; phenyl; heteroaryl including from 5 to 6 ring atoms wherein 1, 2, or 3 of the ring atoms are independently selected from the group consisting of N, NH, N(C1-C3 alkyl), O, and S; —OR$^x$; —C(O)R$^x$; —CO$_2$(R$^x$); —C(O)N(R$^x$)$_2$; —C(NR$^x$)N(R$^x$)$_2$; —OC(O)R$^x$; —OCO$_2$R$^x$; —OC(O)N(R$^x$)$_2$; —N(R$^x$)$_2$; —NR$^x$C(O)R$^x$; —NR$^x$C(O)N(R$^x$)$_2$; —NR$^x$C(O)OR$^x$; and —NR$^x$C(NR$^x$)N(R$^x$)$_2$; wherein $C_{1-6}$alkyl is optionally substituted by one, two, or three substituents independently selected from the group consisting of halogen, hydroxyl, phenyl, heteroaryl including from 5 to 6 ring atoms wherein 1, 2, or 3 of the ring atoms are independently selected from the group consisting of N, NH, N(C1-C3 alkyl), O, and S; and N(R$^x$)$_2$;

$R^5$ and $R^6$ are independently selected from the group consisting of hydrogen; $C_1$-$C_6$ alkyl, optionally substituted by one, two or three substituents independently selected from the group consisting of halogen, hydroxyl, and N(R$^x$)$_2$; $C_{1-6}$ perfluoroalkyl; $C_1$-$C_6$ alkoxy, optionally substituted by one, two, or three substituents independently selected from the group consisting of halogen, hydroxyl, phenyl, and N(R$^x$)$_2$; and -Q-Ar, wherein Q is a bond or $C_1$-$C_6$ alkylene, optionally substituted by one, two, or three independently selected halogens, and Ar is selected from the group consisting of phenyl and heteroaryl including from 5 to 6 ring atoms wherein 1, 2, or 3 of the ring atoms are independently selected from the group consisting of N, NH, N(C1-C3 alkyl), O, and S, wherein phenyl and heteroaryl are each optionally substituted by one, two, or three substituents independently selected from the group consisting of halogen, hydroxyl, phenyl, and N(R$^x$)$_2$; or $R^5$ and $R^6$, together with the atoms to which they are attached, form a C3-C6 cycloalkyl or heterocyclyl including from 3 to 6 ring atoms wherein 1, 2, or 3 of the ring atoms are independently selected from the group consisting of N, NH, N(C1-C3 alkyl), O, and S; wherein the C3-C6 cycloalkyl and heterocyclyl are each optionally substituted by one, two, or three substituents independently selected from the group consisting of halogen, hydroxyl, phenyl, and N(R$^x$)$_2$;

$R^{55}$ is H, or $R^{55}$ and $R^5$, together with the atoms to which they are attached, form a C3-C6 cycloalkyl or heterocyclyl including from 3 to 6 ring atoms wherein 1, 2, or 3 of the ring atoms are independently selected from the group consisting of N, NH, N(C1-C3 alkyl), O, and S; wherein the C3-C6 cycloalkyl and heterocyclyl are each optionally substituted by one, two, or three substituents independently selected from the group consisting of halogen, hydroxyl, phenyl, and N(R$^x$)$_2$;

$R^7$ and $R^{78}$ are each independently selected from the group consisting of hydrogen; $C_1$-$C_6$ alkyl; $C_{1-6}$ perfluoroalkyl; $C_1$-$C_6$ alkoxy; $C_3$-$C_6$ cycloalkoxy; heteroaryl including from 5 to 6 ring atoms wherein 1, 2, or 3 of the ring atoms are independently selected from the group consisting of N, NH, N(C1-C3 alkyl), O, and S; heterocyclyl including from 3 to 6 ring atoms wherein 1, 2, or 3 of the ring atoms are independently selected from the group consisting of N, NH, N(C1-C3 alkyl), O, and S; and phenyl; wherein $C_1$-$C_6$ alkyl; $C_1$-$C_6$ alkoxy; $C_3$-$C_6$ cycloalkoxy; heteroaryl; heterocyclyl; phenyl are each optionally substituted by one, two, or three substituents independently selected from the group consisting of halogen, hydroxyl, phenyl, heteroaryl including from 5 to 6 ring atoms wherein 1, 2, or 3 of the ring atoms are independently selected from the group consisting of N, NH, N(C1-C3 alkyl), O, and S, and N(R$^x$)$_2$;

$R^8$ is selected from the group consisting of hydrogen; halogen; hydroxyl; $C_1$-$C_6$ alkyl; $C_{1-6}$ perfluoroalkyl; $C_1$-$C_6$ alkoxy; $C_3$-$C_6$ cycloalkoxy; heteroaryl including from 5 to 6 ring atoms wherein 1, 2, or 3 of the ring atoms are independently selected from the group consisting of N, NH, N(C1-C3 alkyl), O, and S; heterocyclyl including from 3 to 6 ring atoms wherein 1, 2, or 3 of the ring atoms are independently selected from the group consisting of N, NH, N(C1-C3 alkyl), O, and S; and phenyl; wherein $C_1$-$C_6$ alkyl; $C_1$-$C_6$ alkoxy; $C_3$-$C_6$ cycloalkoxy; heteroaryl; heterocyclyl; and phenyl are each optionally substituted by one, two, or three substituents independently selected from the group consisting of halogen, hydroxyl, phenyl, and $N(R^x)_2$; or $R^7$ and $R^8$, together with the atoms to which they are attached, form C3-C6 cycloalkyl or heterocyclyl including from 3 to 6 ring atoms wherein 1, 2, or 3 of the ring atoms are independently selected from the group consisting of N, NH, N(C1-C3 alkyl), O, and S; wherein the C3-C6 cycloalkyl and heterocyclyl are each optionally substituted by one, two, or three substituents independently selected from the group consisting of halogen, hydroxyl, phenyl, and $N(R^x)_2$;

$R^9$ and $R^{10}$ are independently selected, for each occurrence, from the group consisting of hydrogen; $C_1$-$C_6$ alkyl, optionally substituted by one, two, or three substituents substituents independently selected from the group consisting of halogen, oxo, hydroxyl, phenyl, and heteroaryl including from 5 to 6 ring atoms wherein 1, 2, or 3 of the ring atoms are independently selected from the group consisting of N, NH, N(C1-C3 alkyl), O, and S; $C_{1-6}$ perfluoroalkyl; $C_{2-6}$alkenyl, optionally substituted by one, two, or three substituents substituents independently selected from the group consisting of halogen, oxo, and hydroxyl; $C_{2-6}$alkynyl, optionally substituted by one, two, or three substituents substituents independently selected from the group consisting of halogen, oxo, and hydroxyl; $C_{3-6}$cycloalkyl, optionally substituted by one, two, or three substituents substituents independently selected from the group consisting of $C_{1-6}$alkyl, $C_{1-6}$ perfluoroalkyl; halogen, oxo, and hydroxyl; phenyl, optionally substituted by one, two, or three substituents substituents independently selected from the group consisting of $C_{1-6}$alkyl; $C_{1-6}$ perfluoroalkyl; $C_{1-6}$alkoxy; halogen; hydroxyl; —C(O)$R^x$; —CO$_2$($R^x$); —C(O)N($R^x$)$_2$; —C(N$R^x$)N($R^x$)$_2$; and —C($R^x$)$_3$;

or $R^9$ and $R^{10}$, together with the nitrogen atom to which each is attached, form a heterocyclyl including from 3 to 6 ring atoms, which is optionally substituted by one, two, or three substituents substituents independently selected from the group consisting of $C_{1-6}$alkyl, halogen, oxo, and hydroxyl; wherein when $R^9$ and $R^{10}$ form a heterocyclyl including 6 ring atoms, the heterocyclyl optionally includes, in addition to the nitrogen atom attached to $R^9$ and $R^{10}$, a second ring heteroatom selected from the group consisting of N, NH, N(C1-C3 alkyl), O, and S;

$R^x$ is independently selected, for each occurrence, from the group consisting of hydrogen; halogen; acyl; $C_{1-6}$alkyl; $C_{1-6}$ perfluoroalkyl; and phenyl; and $R^y$ is $C_{1-3}$alkyl.

In another aspect, a compound of formula (IV) is provided, in which one or more (e.g., one, two, three, or four) of the four constituent amino acids is replaced with a beta-amino acid (e.g., the C-terminal and/or the N-terminal is/are replaced with a beta-amino acid(s); e.g., one or both of the proline moieties is/are replaced with a beta-amino acid(s); e.g., the C-terminal and/or the N-terminal is/are replaced with a beta-amino acid(s), and one or both of the proline moieties is/are replaced with a beta-amino acid(s)). In some embodiments, the constituent amino acid is replaced with its corresponding beta-amino acid (e.g., proline replaced with beta-proline). By way of example, such compounds can have formula (IV-A), in which formula (IV) is modified such that the left-most proline moiety is replaced with:

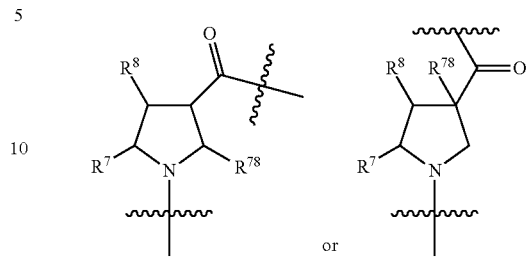

in which $R^7$, $R^8$, and $R^{78}$ are as defined anywhere herein. As another example, such compounds can have formula (IV-B), in which formula (IV) is modified such that the right-most proline moiety is replaced with:

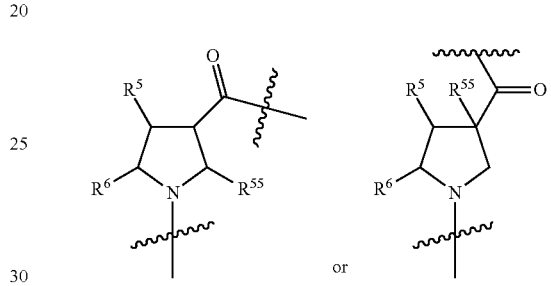

in which $R^5$, $R^6$, and $R^{55}$ are as defined anywhere herein. In still another embodiment, compounds are provided, in which any one or more of compounds of formula (IV), (IV-A), and (IV-B) are modified such that the left-most (N-terminal) amino acid is replaced with hydrogen, thereby providing a tripeptide wherein the ring nitrogen of left-most proline moiety is bonded to hydrogen.

Embodiments of formula (IV), (IV-A), and (IV-B) tetra- and tripeptide compounds can include one or more of the following features and/or combinations of the following features.

In certain embodiments, R is $C_{1-6}$alkyl (e.g., isopropyl).
In certain embodiments, $R^y$ is $CH_3$.
In certain embodiments, $R^3$ is —OH. In certain embodiments, $R^4$ is $C_1$-$C_6$ alkyl (e.g., methyl). In certain embodiments, $R^3$ is —OH, and $R^4$ is $C_1$-$C_6$ alkyl (e.g., methyl).

In certain embodiments, $R^5$, $R^6$, $R^7$, $R^8$, $R^{55}$, and $R^{78}$ are each hydrogen. In other embodiments, $R^5$ and $R^6$ or $R^7$ and $R^8$ or $R^5$ and $R^{55}$ forms a ring as defined herein, and the other pyrrolidine substituents are hydrogen.

Figure 4:
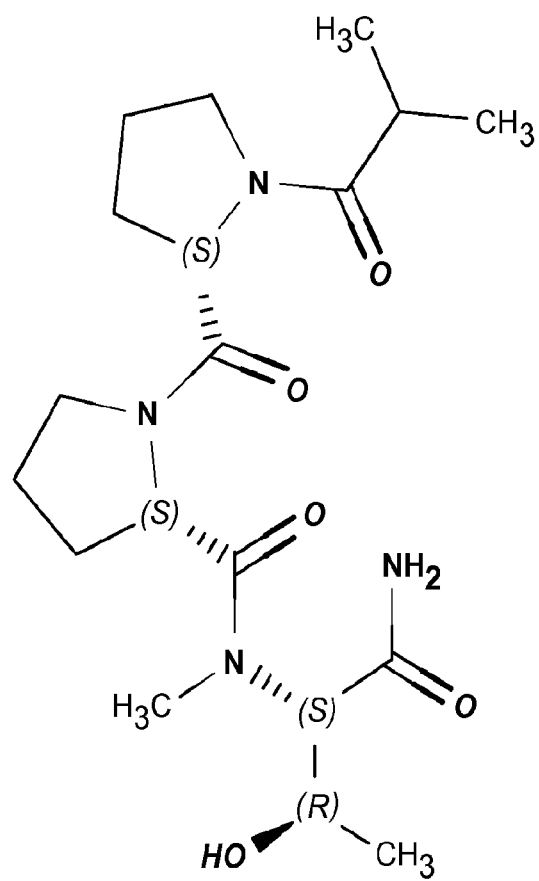
FIG. 4 shows the chemical structure of an exemplary formula (III) compound.

A non-limiting exemplary compound is delineated in FIG. 4.

Disclosed compounds include those having formula (V):

$$T^1\text{-}P^1\text{-}P^2\text{-}T^2 \tag{V}$$

or a pharmaceutically acceptable salt thereof, wherein:

$T^1$ is hydrogen or has formula (A):

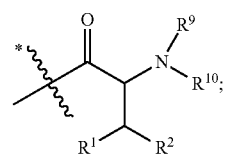

P¹ has formula (B) or formula (C):

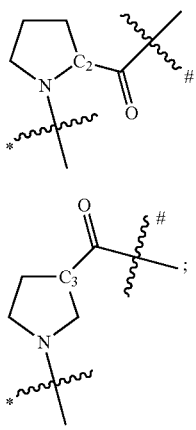

P² has formula (D) or formula (E):

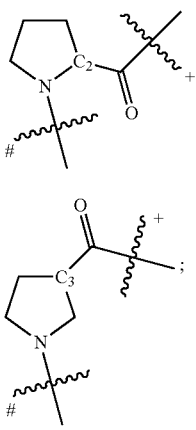

T² has formula (F):

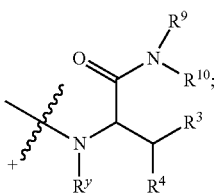

wherein: any line intersected by ⁎ represents the single bond connecting the carbonyl carbon of T¹ and the nitrogen atom of formula (B) or formula (C) in P¹; any line intersected by # represents the single bond connecting the carbonyl carbon of formula (B) or formula (C) in P¹ and the nitrogen atom of formula (D) or formula (E) in P²; and any line intersected by + represents the single bond connecting the carbonyl carbon of formula (D) or formula (E) in P² and the nitrogen atom of T²;

R¹, R², R³, and R⁴ are each independently selected from the group consisting of hydrogen; halogen; $C_{1-6}$alkyl; $C_{1-6}$ perfluoroalkyl; $C_{2-6}$alkenyl; $C_{2-6}$alkynyl; $C_{3-6}$cycloalkyl; phenyl; heteroaryl including from 5 to 6 ring atoms wherein 1, 2, or 3 of the ring atoms are independently selected from the group consisting of N, NH, N(C1-C3 alkyl), O, and S; —OR$^x$; —C(O)R$^x$; —CO₂(R$^x$); —C(O)N(R$^x$)₂; —C(NR$^x$)N(R$^x$)₂; —OC(O)R$^x$; —OCO₂R$^x$; —OC(O)N(R$^x$)₂; —N(R$^x$)₂; —NR$^x$C(O)R$^x$; —NR$^x$C(O)N(R$^x$)₂; —NR$^x$C(O)OR$^x$; and —NR$^x$C(NR$^x$)N(R$^x$)₂; wherein $C_{1-6}$alkyl is optionally substituted by one, two, or three substituents independently selected from the group consisting of halogen; hydroxyl; phenyl; heteroaryl including from 5 to 6 ring atoms wherein 1, 2, or 3 of the ring atoms are independently selected from the group consisting of N, NH, N(C1-C3 alkyl), O, and S; and N(R$^x$)₂;

R⁹ and R¹⁰ are independently selected, for each occurrence, from the group consisting of hydrogen; $C_1$-$C_6$ alkyl, optionally substituted by one, two, or three substituents substituents independently selected from the group consisting of halogen, oxo, hydroxyl, phenyl, and heteroaryl including from 5 to 6 ring atoms wherein 1, 2, or 3 of the ring atoms are independently selected from the group consisting of N, NH, N(C1-C3 alkyl), O, and S; $C_{1-6}$ perfluoroalkyl; $C_{2-6}$alkenyl, optionally substituted by one, two, or three substituents substituents independently selected from the group consisting of halogen, oxo, and hydroxyl; $C_{2-6}$alkynyl, optionally substituted by one, two, or three substituents substituents independently selected from the group consisting of halogen, oxo, and hydroxyl; $C_{3-6}$cycloalkyl, optionally substituted by one, two, or three substituents substituents independently selected from the group consisting of $C_{1-6}$alkyl, $C_{1-6}$ perfluoroalkyl; halogen, oxo, and hydroxyl; phenyl, optionally substituted by one, two, or three substituents substituents independently selected from the group consisting of $C_{1-6}$alkyl; $C_{1-6}$ perfluoroalkyl; $C_{1-6}$alkoxy; halogen; hydroxyl; —C(O)R$^x$; —CO₂(R$^x$); —C(O)N(R$^x$)₂; —C(NR$^x$)N(R$^x$)₂; and —C(R$^x$)₃;

or R⁹ and R¹⁰, together with the nitrogen atom to which each is attached, form a heterocyclyl including from 3 to 6 ring atoms, which is optionally substituted by one, two, or three substituents substituents independently selected from the group consisting of $C_{1-6}$alkyl, $C_{1-6}$ perfluoroalkyl; halogen, oxo, and hydroxyl; wherein when R⁹ and R¹⁰ form a heterocyclyl including 6 ring atoms, the heterocyclyl optionally includes, in addition to the nitrogen atom attached to R⁹ and R¹⁰, a second ring heteroatom selected from the group consisting of N, NH, N(C1-C3 alkyl), O, and S;

R$^x$ is independently selected, for each occurrence, from the group consisting of hydrogen; halogen; acyl; $C_{1-6}$alkyl; $C_{1-6}$ perfluoroalkyl; and phenyl; and R$^y$ is hydrogen or $C_{1-3}$alkyl. In some embodiments, it is provided that the compound is not GLYX-13.

In some embodiments, T¹ has formula (A). In other embodiments, T¹ is hydrogen. Embodiments in which T¹ has formula (A) or T¹ is hydrogen can include one or more of the following features and/or combinations of the following features.

P¹ can have formula (C). P² can have formula (D). In certain embodiments, C₃ in formula (C) has the R-configuration. In other embodiments, C₃ in formula (C) has the S-configuration. In certain embodiments, C₂ in formula (D) has the R-configuration. In other embodiments, C₂ in formula (D) has the S-configuration.

In certain embodiments, P¹ can have formula (C), and P² can have formula (D). For example, C₃ in formula (C) can have the R-configuration, and C₂ in formula (D) can have the R-configuration; or C₃ in formula (C) can have the R-configuration, and C₂ in formula (D) can have the S-configuration. As another example, C₃ in formula (C) can have the S-configuration, and C₂ in formula (D) can have the R-configuration; or C₃ in formula (C) can have the 5-configuration, and C₂ in formula (D) can have the S-configuration.

P¹ can have formula (B). P² can have formula (E). In certain embodiments, C₃ in formula (E) has the R-configuration. In other embodiments, C₃ in formula (E) has the S-configuration. In certain embodiments, C₂ in formula (B) has the R-configuration. In other embodiments, C₂ in formula (B) has the S-configuration.

In certain embodiments, P¹ can have formula (B), and P² can have formula (E). For example, C₃ in formula (E) can have the R-configuration, and C₂ in formula (B) can have the R-configuration; or C₃ in formula (E) can have the R-configuration, and C₂ in formula (B) can have the S-configuration. As another example, C₃ in formula (E) can have the S-configuration, and C₂ in formula (B) can have the R-configuration; or C₃ in formula (E) can have the 5-configuration, and C₂ in formula (B) can have the S-configuration.

In still other embodiments, P¹ has formula (B), P² has formula (D), and C₂ in either (or both) formula (B) or formula (D) has the R-configuration.

R$^y$ can be H.

R¹ can be —OR$^x$. In certain embodiments, R$^x$ is hydrogen or $C_{1-6}$alkyl. In certain embodiments, R$^x$ is hydrogen (i.e., R¹ is —OH).

R² can be $C_1$-$C_6$ alkyl optionally substituted by one, two, or three substituents independently selected from the group consisting of halogen; hydroxyl; phenyl; heteroaryl including from 5 to 6 ring atoms wherein 1, 2, or 3 of the ring atoms are independently selected from the group consisting of N, NH, N(C1-C3 alkyl), O, and S; and N(R$^x$)₂. In certain embodiments, R² is $C_1$-$C_6$ alkyl (e.g., CH₃).

R¹ can be —OR$^x$. In certain embodiments, R$^x$ is hydrogen or $C_{1-6}$alkyl. In certain embodiments, R$^x$ is hydrogen (i.e., R¹ is —OH).

R² can be $C_1$-$C_6$ alkyl optionally substituted by one, two, or three substituents independently selected from the group consisting of halogen; hydroxyl; phenyl; heteroaryl including from 5 to 6 ring atoms wherein 1, 2, or 3 of the ring atoms are independently selected from the group consisting of N, NH, N(C1-C3 alkyl), O, and S; and N(R$^x$)₂. In certain embodiments, R² is $C_1$-$C_6$ alkyl (e.g., CH₃).

R³ can be —OR$^x$. In certain embodiments, R$^x$ is hydrogen or $C_{1-6}$alkyl. In certain embodiments, R$^x$ is hydrogen (i.e., R³ is —OH).

R⁴ can be $C_1$-$C_6$ alkyl optionally substituted by one, two, or three substituents independently selected from the group consisting of halogen; hydroxyl; phenyl; heteroaryl including from 5 to 6 ring atoms wherein 1, 2, or 3 of the ring atoms are independently selected from the group consisting of N, NH, N(C1-C3 alkyl), O, and S; and N(R$^x$)₂. In certain embodiments, R⁴ is $C_1$-$C_6$ alkyl (e.g., CH₃).

Each occurrence of R⁹ and R¹⁰ can be hydrogen.

The compounds of the present disclosure and formulations thereof may have a plurality of chiral centers. Each chiral center may be independently R, S, or any mixture of R and S. For example, in some embodiments, a chiral center may have an R:S ratio of between about 100:0 and about 50:50, between about 100:0 and about 75:25, between about 100:0 and about 85:15, between about 100:0 and about 90:10, between about 100:0 and about 95:5, between about 100:0 and about 98:2, between about 100:0 and about 99:1, between about 0:100 and 50:50, between about 0:100 and about 25:75, between about 0:100 and about 15:85, between about 0:100 and about 10:90, between about 0:100 and about 5:95, between about 0:100 and about 2:98, between about 0:100 and about 1:99, between about 75:25 and 25:75, and about 50:50. Formulations of the disclosed compounds comprising a greater ratio of one or more isomers (i.e., R and/or S) may possess enhanced therapeutic characteristic relative to racemic formulations of a disclosed compounds or mixture of compounds.

Disclosed compounds may provide for efficient cation channel opening at the NMDA receptor, e.g. may bind or associate with the glutamate site of the NMDA receptor to assist in opening the cation channel. The disclosed compounds may be used to regulate (turn on or turn off) the NMDA receptor through action as an agonist.

The compounds as described herein may be glycine site NMDA receptor partial agonists. A partial agonist as used in this context will be understood to mean that at a low concentration, the analog acts as an agonist and at a high concentration, the analog acts as an antagonist. Glycine binding is not inhibited by glutamate or by competitive inhibitors of glutamate, and also does not bind at the same site as glutamate on the NMDA receptor. A second and separate binding site for glycine exists at the NMDA receptor. The ligand-gated ion channel of the NMDA receptor is, thus, under the control of at least these two distinct allosteric sites. Disclosed compounds may be capable of binding or associating with the glycine binding site of the NMDA receptor. In some embodiments, disclosed compounds may possess a potency that is 10-fold or greater than the activity of existing NMDA receptor glycine site partial agonists. For example, disclosed compounds may possess a 10-fold to 20-fold enhanced potency compared to GLYX-13. GLYX-13 is represented by:

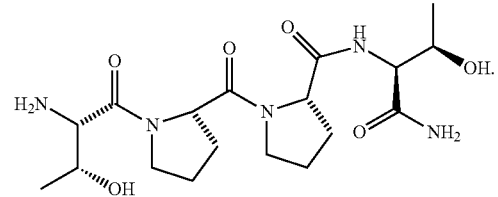

For example, provided herein are compounds that may be at least about 20-fold more potent as compared to GLYX-13, as measured by burst activated NMDA receptor-gated single neuron conductance ($I_{NMDA}$) in a culture of hippocampal CA1 pyramidal neurons at a concentration of 50 nM. In another embodiment, a provided compound may be capable of generating an enhanced single shock evoked NMDA receptor-gated single neuron conductance ($I_{NMDA}$) in hippocampal CA1 pyramidal neurons at concentrations of 100 nM to 1 μM. Disclosed compounds may have enhanced potency as compared to GLYX-13 as measured by magnitude of long term potentiation (LTP) at Schaffer collateral-CA-1 synapses in in vitro hippocampal slices.

The disclosed compounds may exhibit a high therapeutic index. The therapeutic index, as used herein, refers to the ratio of the dose that produces a toxicity in 50% of the population (i.e., $TD_{50}$) to the minimum effective dose for 50% of the population (i.e., $ED_{50}$) Thus, the therapeutic index=$(TD_{50}):(ED_{50})$. In some embodiments, a disclosed compound may have a therapeutic index of at least about 10:1, at least about 50:1, at least about 100:1, at least about 200:1, at least about 500:1, or at least about 1000:1.

Compositions

In other aspects, formulations and compositions comprising the disclosed compounds and optionally a pharmaceutically acceptable excipient are provided. In some embodiments, a contemplated formulation comprises a racemic mixture of one or more of the disclosed compounds.

Contemplated formulations may be prepared in any of a variety of forms for use. By way of example, and not limitation, the compounds may be prepared in a formulation suitable for oral administration, subcutaneous injection, or other methods for administering an active agent to an animal known in the pharmaceutical arts.

Amounts of a disclosed compound as described herein in a formulation may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

The specification for the dosage unit forms of the invention are dictated by and directly dependent on (a) the unique characteristics of the compound selected and the particular therapeutic effect to be achieved, and (b) the limitations inherent in the art of compounding such an active compound for the treatment of sensitivity in individuals.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

The compounds can be administered in a time release formulation, for example in a composition which includes a slow release polymer. The compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In some embodiments, certain disclosed compounds are capable of delivering an efficacious amount of compound when administered to a patient orally. For example, in certain embodiments, certain disclosed compounds are more efficacious when administered orally to a patient as compared to oral administration to a patient of a peptidyl compound represented by:

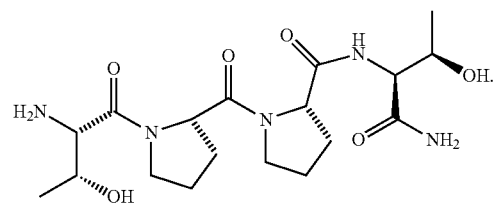

In accordance with an alternative aspect of the invention, a compound may be formulated with one or more additional compounds that enhance the solubility of the compound.

Methods

Methods for treating cognitive disorders and for enhancing learning are provided. Such methods include administering a pharmaceutically acceptable formulation of one or more of the disclosed compounds to a patient in need thereof. Also contemplated are methods of treating patients suffering from, memory deficits associated with aging, schizophrenia, special learning disorders, seizures, post-stroke convulsions, brain ischemia, ischemic stroke, transient ischemic attack, cardiac ischemia, myocardial infarction, hypoglycemia, cardiac arrest, epilepsy, migraine, as well as Huntington's, Parkinson's, and Alzheimer's disease.

Other methods contemplated include the treatment of cerebral ischemia, stroke, brain trauma, brain tumors, acute neuropathic pain, chronic neuropathic pain, sleep disorders, drug addiction, depression, certain vision disorders, ethanol withdrawal, anxiety, memory and learning disabilities, autism, epilepsy, AIDS dementia, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, peripheral neuropathy, myelopathy, ischemic retinopathy, diabetic retinopathy, glaucoma, cardiac arrest, behavior disorders, impulse control disorders, Alzheimer's disease, memory loss that accompanies early stage Alzheimer's disease, modulating an Alzheimer's amyloid protein (e.g., beta amyloid peptide, e.g. the isoform $A\beta_{1-42}$), in-vitro or in-vivo attention deficit disorder, ADHD (attention deficit hyperactivity disorder), schizophrenia, amelioration of opiate, nicotine addiction, ethanol addition, traumatic brain injury, spinal cord injury, post-traumatic stress syndrome, Huntington's disease, and Huntington's chorea.

For example, provided here are methods of treating benign Rolanic epilepsy, frontal lobe epilepsy, infantile spasms, juveline myoclonic epilepsy, Lennox-Gastaut syndrome, Landau-Kleffner syndrome, Dravet syndrome, progressive myoclonus epilepsies, reflex epilepsy, Rasmussen's syndrome, temporal lobe epilepsy, limbic epilepsy, status epilepticus, abdominal epilepsy, massive bilateral myoclonus, catamenial epilepsy, Jacksonian seizure disorder, Lafora disease, and/or photosensitive epilepsy comprising administering an effective amount of a disclosed compound.

For example, provided herein is a method of treating depression in a patient in need thereof, comprising administering a disclosed compound, e.g., by acutely administering a disclosed compound. In certain embodiments, the treatment-resistant patient is identified as one who has been treated with at least two types of antidepressant treatments prior to administration of a disclosed compound. In other embodiments, the treatment-resistant patient is one who is identified as unwilling or unable to tolerate a side effect of at least one type of antidepressant treatment.

The most common depression conditions include Major Depressive Disorder and Dysthymic Disorder. Other depression conditions develop under unique circumstances. Such depression conditions include but are not limited to Psychotic depression, Postpartum depression, Seasonal affective disorder (SAD), mood disorder, depressions caused by chronic medical conditions such as cancer or chronic pain, chemotherapy, chronic stress, post traumatic stress disorders, and Bipolar disorder (including bipolar I disorder, bipolar II disorder, cyclothymia, or manic depressive disorder).

Refractory depression occurs in patients suffering from depression who are resistant to standard pharmacological treatments, including tricyclic antidepressants, MAOIs, SSRIs, and double and triple uptake inhibitors and/or anxiolytic drugs, as well non-pharmacological treatments such as psychotherapy, electroconvulsive therapy, vagus nerve stimulation and/or transcranial magnetic stimulation. A treatment-resistant patient may be identified as one who fails to experience alleviation of one or more symptoms of depression (e.g., persistent anxious or sad feelings, feelings of helplessness, hopelessness, pessimism) despite undergoing one or more standard pharmacological or non-pharmacological treatment. In certain embodiments, a treatment-resistant patient is one who fails to experience alleviation of one or more symptoms of depression despite undergoing treatment with two different antidepressant drugs. In other embodiments, a treatment-resistant patient is one who fails to experience alleviation of one or more symptoms of depression despite undergoing treatment with four different antidepressant drugs. A treatment-resistant patient may also be identified as one who is unwilling or unable to tolerate the side effects of one or more standard pharmacological or non-pharmacological treatment.

In some embodiments, patients suffering from autism also suffer from another medical condition, such as Fragile X syndrome, tuberous sclerosis, congenital rubella syndrome, and untreated phenylketonuria.

In yet another aspect, a method for enhancing pain relief and for providing analgesia to an animal is provided.

In certain embodiments, methods for treating schizophrenia are provided. For example, paranoid type schizophrenia, disorganized type schizophrenia (i.e., hebephrenic schizophrenia), catatonic type schizophrenia, undifferentiated type schizophrenia, residual type schizophrenia, post-schizophrenic depression, and simple schizophrenia may be treated using the methods and compositions contemplated herein. Psychotic disorders such as schizoaffective disorders, delusional disorders, brief psychotic disorders, shared psychotic disorders, and psychotic disorders with delusions or hallucinations may also be treated using the compositions contemplated herein. Paranoid schizophrenia may be characterized where delusions or auditory hallucinations are present, but thought disorder, disorganized behavior, or affective flattening are not. Delusions may be persecutory and/or grandiose, but in addition to these, other themes such as jealousy, religiosity, or somatization may also be present. Disorganized type schizophrenia may be characterized where thought disorder and flat affect are present together. Catatonic type schizophrenia may be characterized where the subject may be almost immobile or exhibit agitated, purposeless movement. Symptoms can include catatonic stupor and waxy flexibility. Undifferentiated type schizophrenia may be characterized where psychotic symptoms are present but the criteria for paranoid, disorganized, or catatonic types have not been met. Residual type schizophrenia may be characterized where positive symptoms are present at a low intensity only. Post-schizophrenic depression may be characterized where a depressive episode arises in the aftermath of a schizophrenic illness where some low-level schizophrenic symptoms may still be present. Simple schizophrenia may be characterized by insidious and progressive development of prominent negative symptoms with no history of psychotic episodes.

In some embodiments, methods are provided for treating psychotic symptoms that may be present in other mental disorders, including, but not limited to, bipolar disorder, borderline personality disorder, drug intoxication, and drug-induced psychosis.

In another embodiment, methods for treating delusions (e.g., "non-bizarre") that may be present in, for example, delusional disorder are provided.

Also provided are methods for treating social withdrawal in conditions including, but not limited to, social anxiety disorder, avoidant personality disorder, and schizotypal personality disorder.

Additionally, methods are provided for treating obsessive-compulsive disorder (OCD).

In some embodiments, the patient is a mammal (e.g., a human). For example, the patient may be a human adult patient or a human pediatric patient.

In some embodiments, contemplated methods relate to use of a disclosed compound or compounds alone or in combination with one or more other agents for manufacturing a medicament for treating a contemplated indication.

For example, in a disclosed method, a contemplated compound, or a composition comprising a contemplated compound and, e.g., a pharmaceutically acceptable excipient, may be administered parenterally to a patient including, but not limited to, subcutaneously and intravenously. The compound or compositions contemplated herein may also be administered via slow controlled i.v. infusion or by release from an implant device. In an embodiment, a disclosed method for treating a contemplated indication includes administering one dose, or one or more doses, of a disclosed compound. In some embodiments, a patient may have substantial improvement in symptoms after 12 hours, after 1 day, after 1 week, after 2 days, after 3 days, after 4 days, after 5 days, after 6 days, or even after 8 days of a one (single) dose administration.

A therapeutically effective amount of a disclosed compound required for use in therapy varies with the nature of the condition being treated, the length of treatment time desired, the age and the condition of the patient, and is ultimately determined by the attending physician. In general, however, doses employed for adult human treatment typically are in the range of about 0.01 mg/kg to about 1000 mg/kg per day. The dose may be, for example, about 1 mg/kg to about 100 mg/kg per day. The desired dose may be conveniently administered in a single dose, or as multiple doses administered at appropriate intervals, for example as two, three, four or more sub-doses per day.

A number of factors may lead to the contemplated compounds being administered over a wide range of dosages. When given in combination with other therapeutic agents, the dosage of the contemplated compounds may be given at relatively lower dosages. As a result, the dosage of a contemplated compound may be from about 1 ng/kg to about 100 mg/kg. The dosage of a contemplated compound may be at any dosage including, but not limited to, about 1 ug/kg, 25 ug/kg, 50 ug/kg, 75 ug/kg, 100 u ug/kg, 125 ug/kg, 150 ug/kg, 175 ug/kg, 200 ug/kg, 225 ug/kg, 250 ug/kg, 275 ug/kg, 300 ug/kg, 325 ug/kg, 350 ug/kg, 375 ug/kg, 400 ug/kg, 425 ug/kg, 450 ug/kg, 475 ug/kg, 500 ug/kg, 525 ug/kg, 550 ug/kg, 575 ug/kg, 600 ug/kg, 625 ug/kg, 650 ug/kg, 675 ug/kg, 700 ug/kg, 725 ug/kg, 750 ug/kg, 775 ug/kg, 800 ug/kg, 825 ug/kg, 850 ug/kg, 875 ug/kg, 900 ug/kg, 925 ug/kg, 950 ug/kg, 975 ug/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, or 100 mg/kg.

In some embodiments, a disclosed compound may be dosed at an amount that produces antidepressive-like and/or anxiolytic-like effects.

Disclosed compounds may be provided as part of a liquid or solid formulation, for example, aqueous or oily suspensions, solutions, emulsions, syrups, and/or elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl hydroxybenzoate and sorbic acid. Contemplated compounds may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

EXAMPLES

The following examples are provided for illustrative purposes only, and are not intended to limit the scope of the disclosure.

Example 1—Synthesis of Compounds of Structure A

The following reaction sequence (Scheme 1) is used to synthesize compounds of structure A.

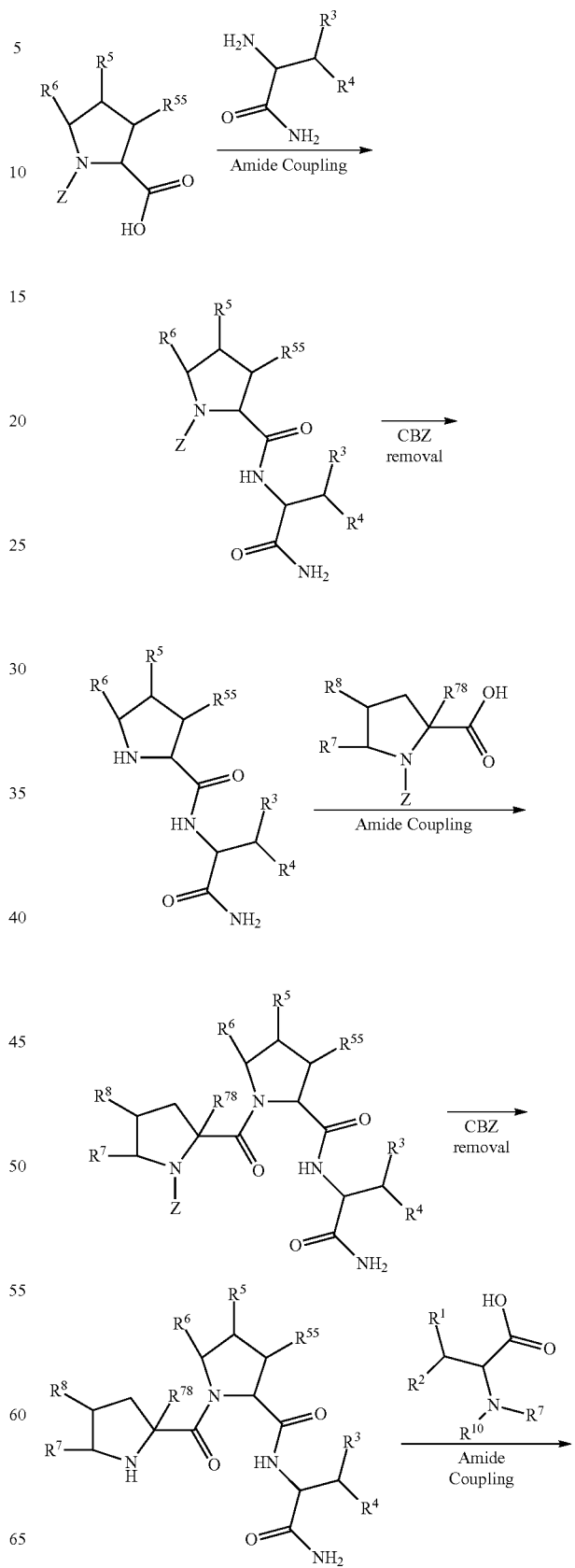

Scheme 1. Synthesis of compounds of structure A.

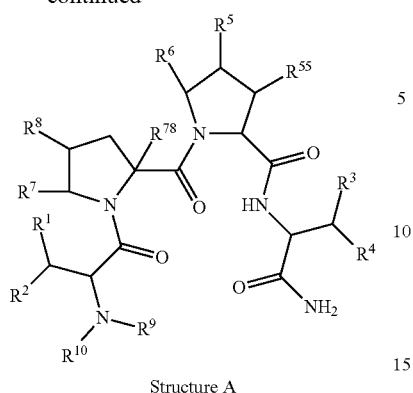
Structure A
Example 2—Synthesis of Compounds of Structure B
The following reaction sequence (Scheme 2) is used to synthesize compounds of structure B.
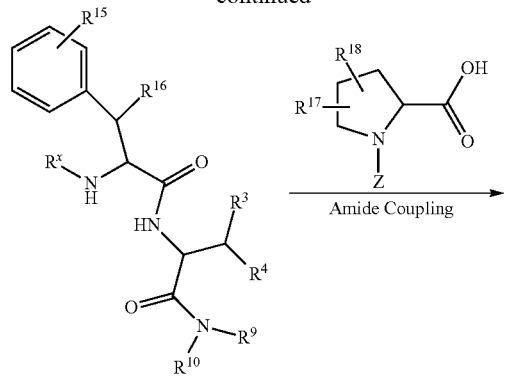
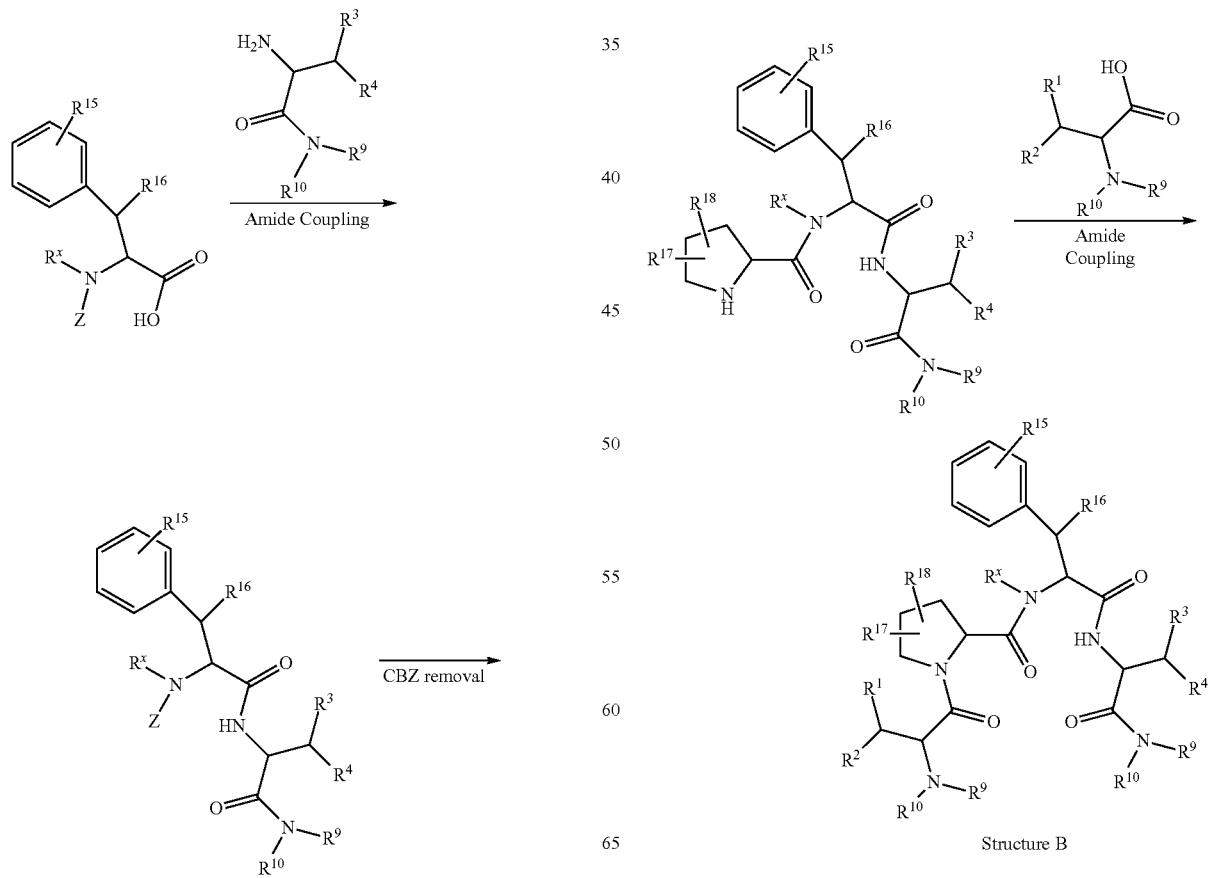
Structure B

Example 3—Synthesis of Compounds of Structure C

In some embodiments, the following reaction sequence (Scheme 3) can be used to synthesize compounds of formula (III), e.g., structure C below.

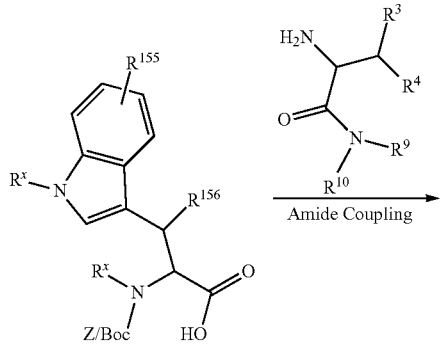
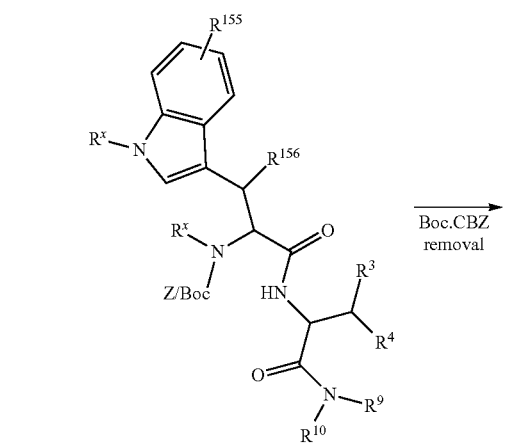
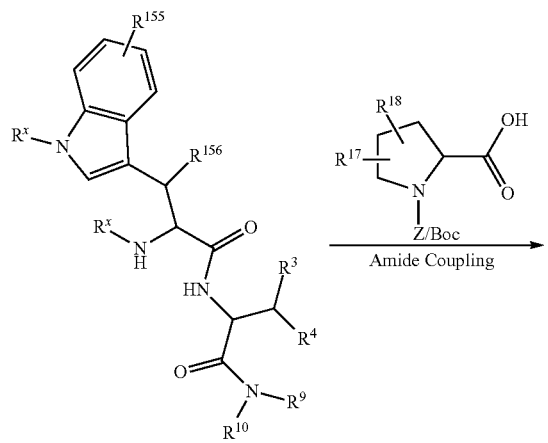
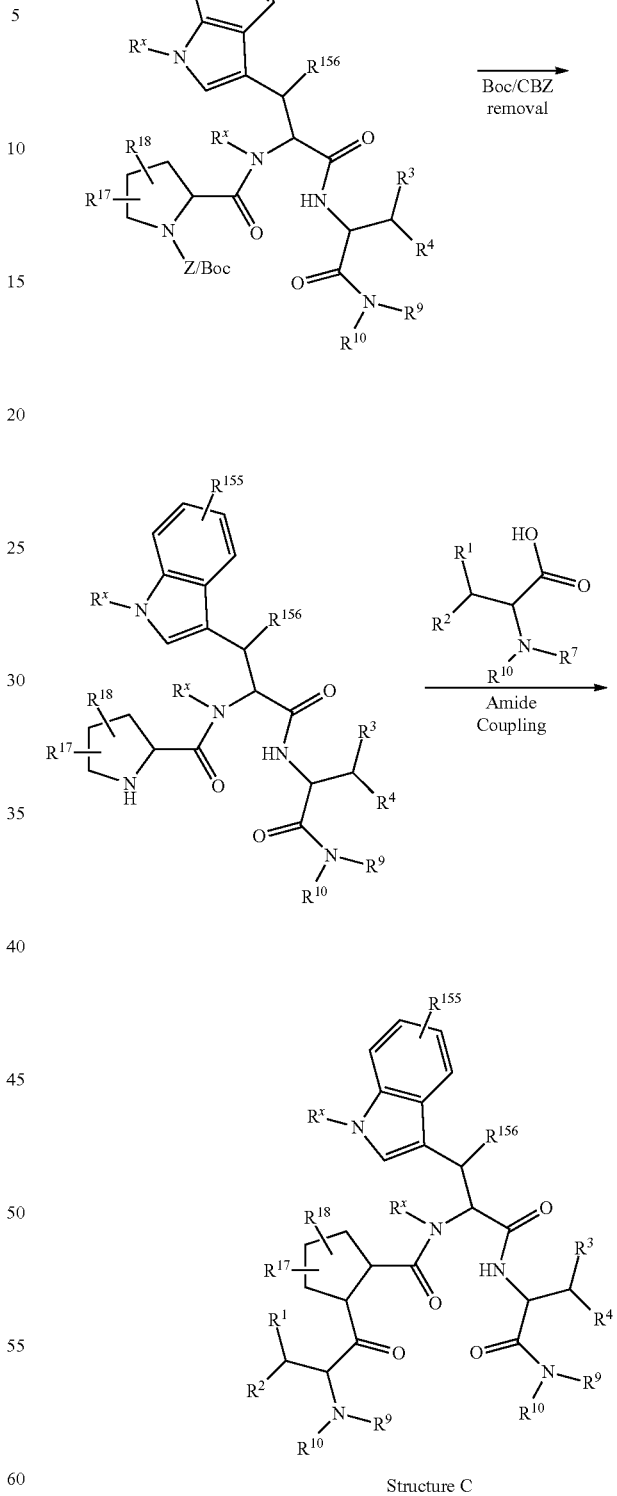

Structure C

In other embodiments, compounds of formula (III) can be prepared according to Scheme 4 below, in which the proline nitrogen atom of the left hand fragment is already substituted with the amino acid unit that is installed in the last step of Scheme 3 above.

Scheme 4

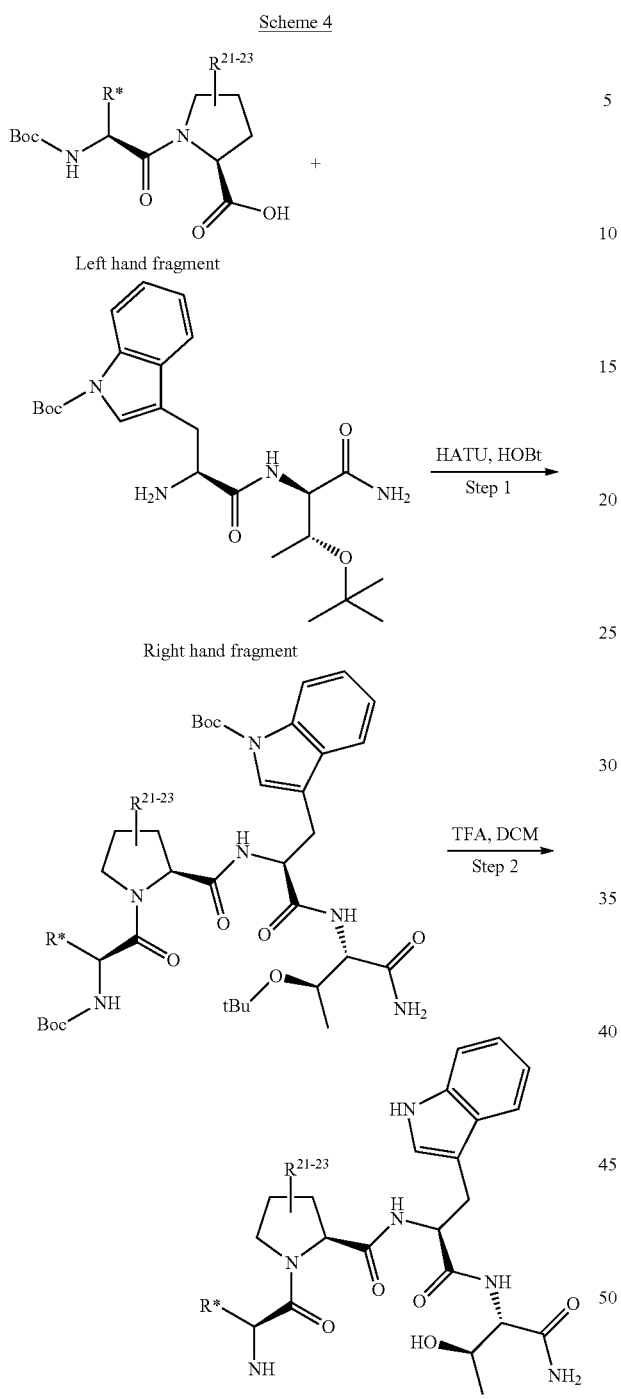

Left hand fragment

Right hand fragment

R* in Scheme 4 represents the C(R$^1$)(R$^2$)(R$^{11}$) portion of formula (III). R$^{21-23}$ in Scheme 4 represents any substitution pattern encompassed by the definitions of R$^{21}$, R$^{22}$, and R$^{23}$ provided herein. The left hand fragment and right hand fragment (Trp(Boc)-Thr(OtBu)-CONH$_2$) can be coupled using peptide coupling agents, such as HBTU, HATU, BOP or pyBOP, which have been shown to be suitable for amidation of conformationally constrained amino acids. Global deprotection of the side chain groups (Boc and tBu) can be achieved, e.g., by treatment of the product of step 1 with, e.g., trifluoroacetic acid in dichloromethane (DCM), to furnish the desired tetrapeptides.

In some embodiments, the right hand fragment can be prepared according to Scheme 5 below.

Scheme 5

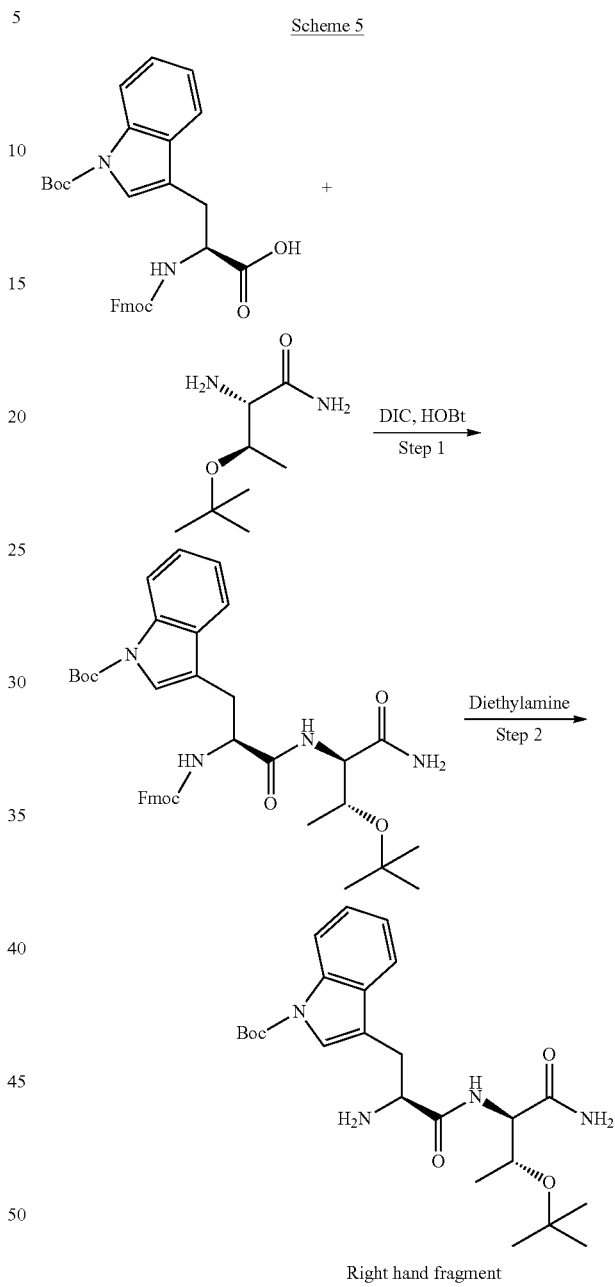

Right hand fragment

As shown in step 1 of Scheme 5, Fmoc-Trp-(Boc)-OH and Thr(O$^t$Bu)-CONH$_2$ can be coupled under conventional conditions using, e.g., DIC/HOBt or EDC/HOBt, to afford the protected dipeptide. Fmoc-Trp-(Boc)-OH can be prepared using conventional methods or obtained commercially; and Thr(OtBu)-CONH$_2$ can be prepared, e.g., in two steps from Z-Thr(OtBu)-OH. Fmoc deprotection under basic conditions (e.g., diethylamine/DCM at ambient temperature) can provide the desired dipeptide suitable for end-game coupling strategy.

In some embodiments, the left hand fragment can be prepared according to Scheme 6 below.

47
48

Scheme 6

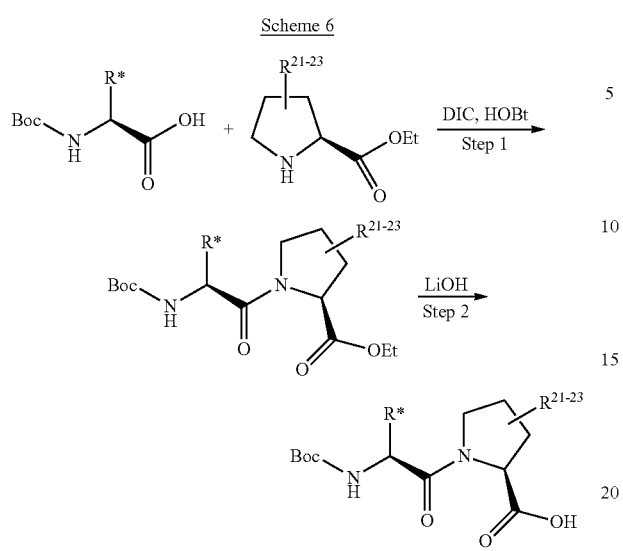

Figure 3:
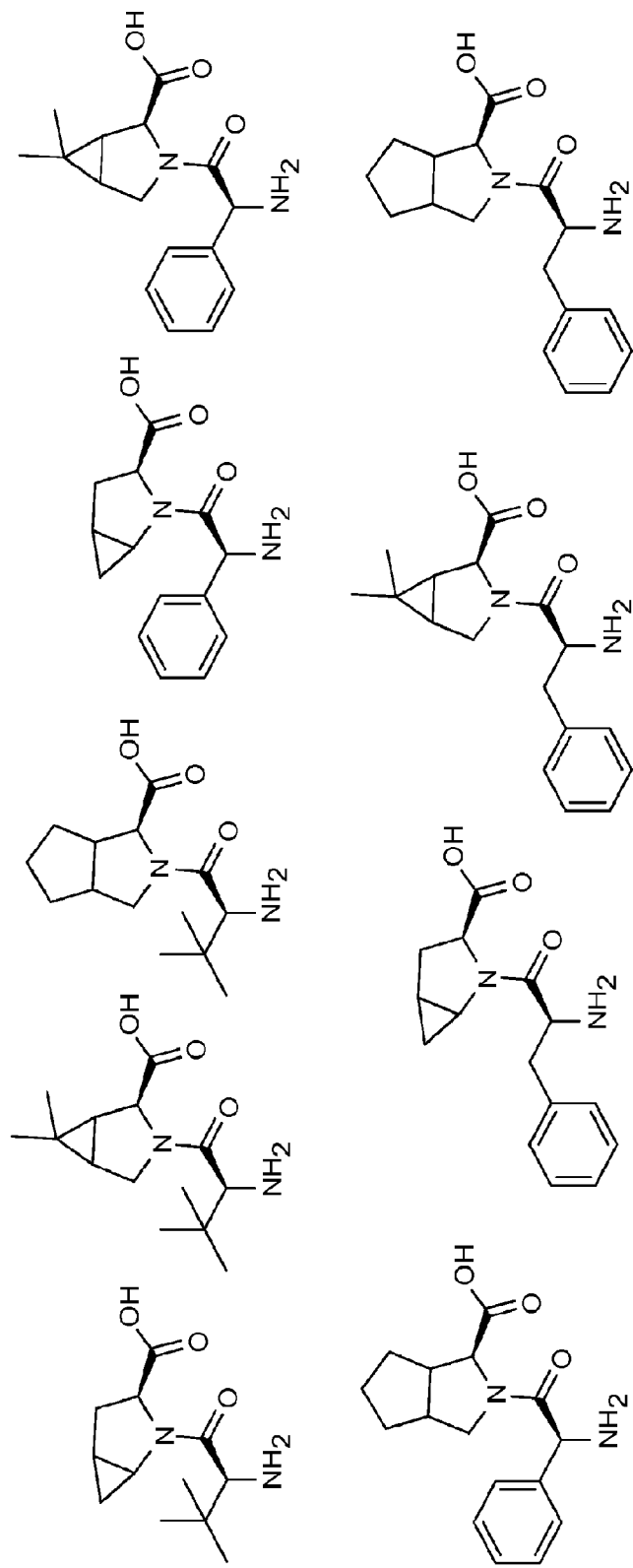
FIG. 3 shows the chemical structures of exemplary non-natural left-hand fragments that can be used to prepare the compounds described herein.
Figure 3:
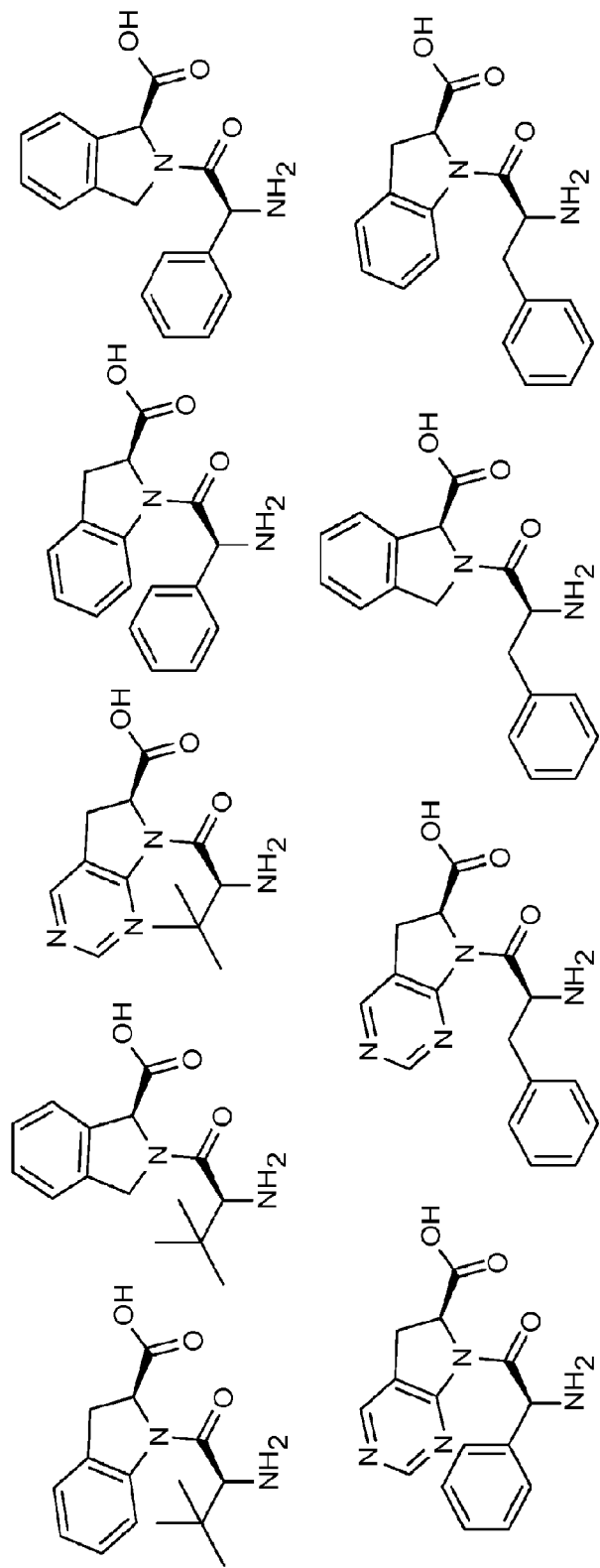
Figure 3:
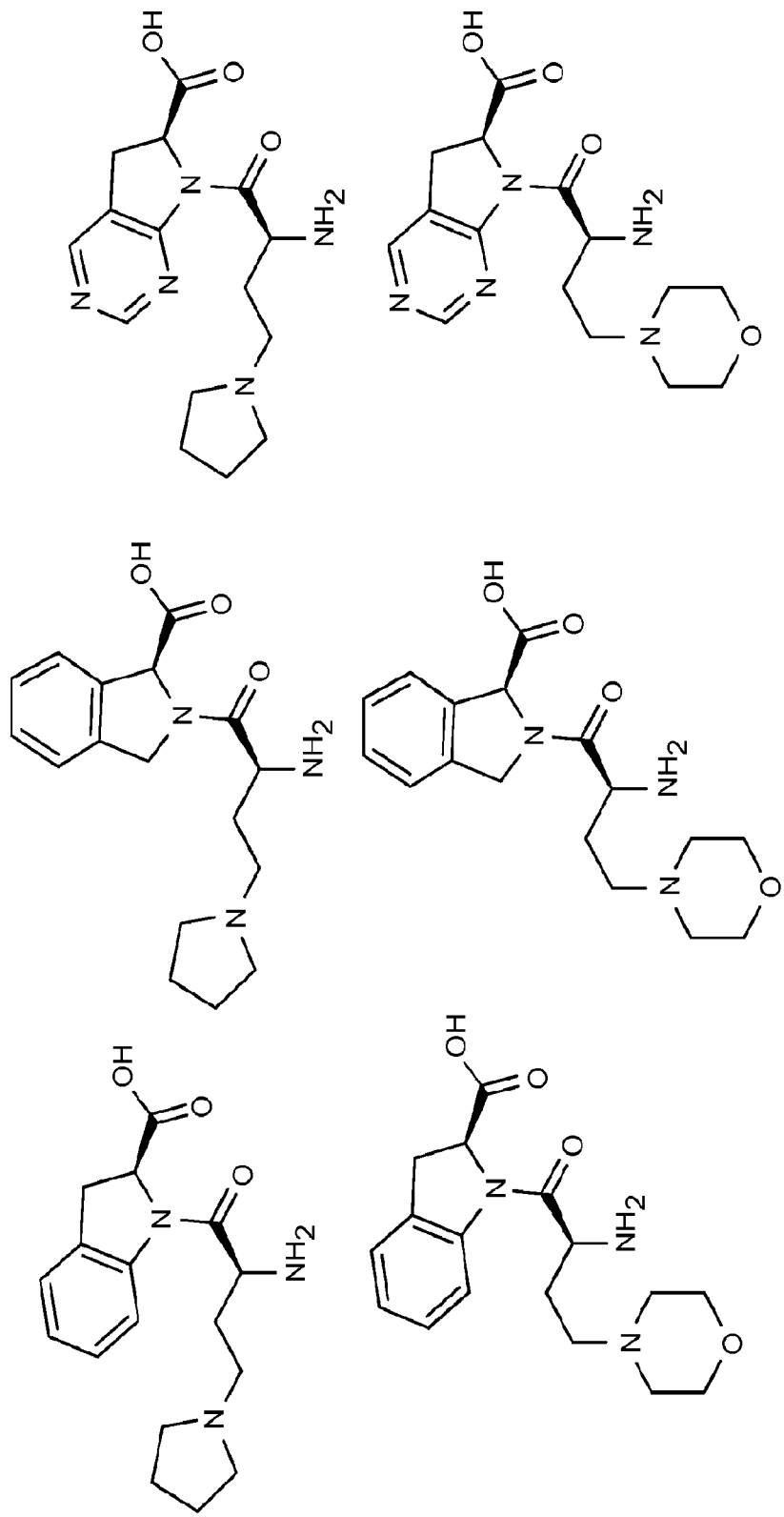
Figure 3:
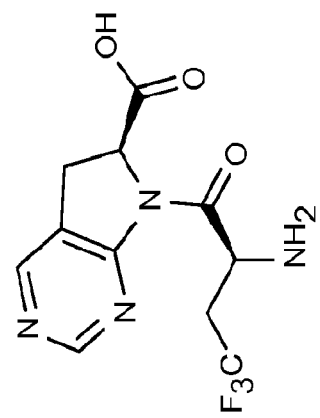
Figure 3:
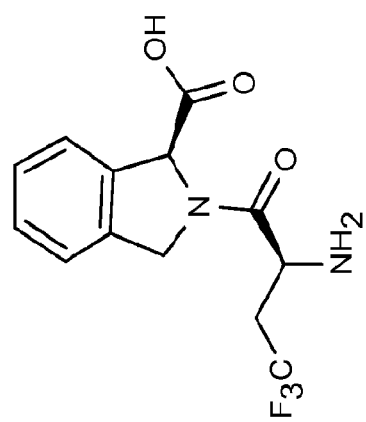
Figure 3:
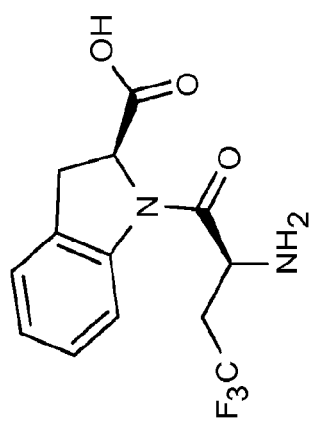

R* in Scheme 6 represents the C(R$^1$)(R$^2$)(R$^{11}$)portion of formula (III). R$^{21-23}$ in Scheme 6 represents any substitution pattern set encompassed by the definitions of R$^{21}$, R$^{22}$, and R$^{23}$ provided herein. In certain embodiments, the left hand fragment include one or two unnatural amino acids. Typically, 5-10 reactions steps are involved in the synthesis of unnatural analogues of the proline and α-substituted L-glycine amino acid starting materials used in step 1. Substituted beta-hydroxy amino acids can be prepared by Peterson's Aldol approach. Amidation using peptide coupling agents, e.g., HBTU, HATU, BOP or pyBOP, can be used for assembly of the left-hand side dipeptides constituted by unnatural amino acids. Exemplary left hand fragments are delineated in FIG. 3.

A. Synthesis of NRX-4001 & 4006:

Scheme 7

-continued

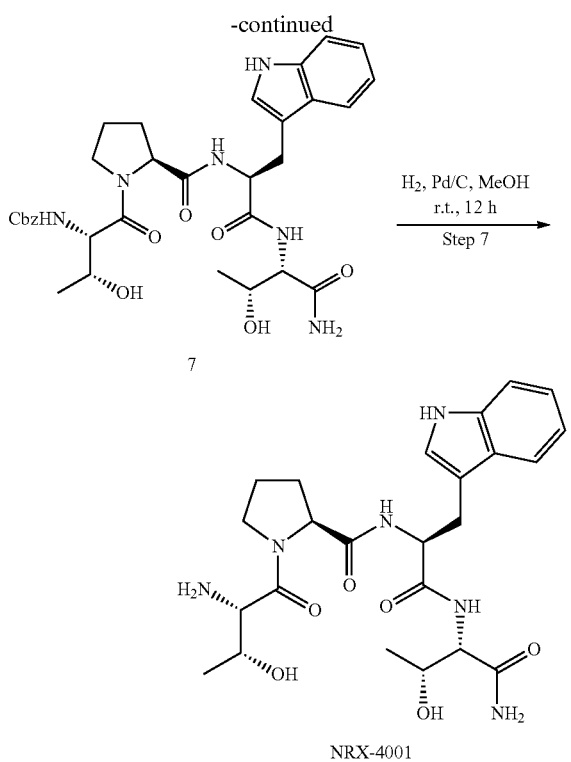

Synthesis of (S)-2-((tert-butoxycarbonyl)amino)-3-(1H-indol-3-yl)propanoic acid (2)

To a stirred solution of compound 1 (30 g, 147 mmol) in THF:$H_2O$ (1:1, 180 mL), sodium bicarbonate (24.7 g, 294 mmol) and di-tertiary butyl dicarbonate (35.2 g, 161 mmol) were added at 10-15° C. and the reaction mixture was allowed to stir at room temperature for 12 h. After completion of the reaction as indicated by TLC, the reaction mixture was concentrated under reduced pressure to obtain a residue and the residue was treated with MTBE and acidified to pH 2-3 using 1N HCl. The precipitated solid was stirred for 1 h in MTBE and filtered. The filtered solid was washed by stirring in water for 1 h, filtered, and dried to afford compound 2 (35.0 g, 79%).

MS (ESI) m/z 305 $[M+1]^+$.

Synthesis of tert-butyl ((S)-1-(((2S,3R)-1-amino-3-hydroxy-1-oxobutan-2-yl)amino)-3-(1H-indol-3-yl)-1-oxopropan-2-yl)carbamate (4)

To a stirred solution of compound 2 (5 g, 16.4 mmol) in DCM (50 mL), HATU (9.36 g, 24.6 mmol) and diisopropylethylamine (10 mL, 49.26 mmol) were added. The solution was stirred at rt for 35 min to generate the activated ester to which compound 3 (1.92 g, 16.4 mmol) was added and stirred at room temperature for 12 h. The progress of the reaction was monitored by TLC & LCMS. After complete consumption of starting material, the reaction was quenched with water and extracted with 10% methanol in DCM. The organic layers were washed with sodium bicarbonate solution and brine, dried over anhydrous $Na_2SO_4$ and concentrated under reduced pressure to obtain a crude residue, which was purified by column chromatography to afford compound 4 (5.2 g, 78%).

MS (ESI) m/z 405 $[M+1]^+$.

Synthesis of (2S,3R)-2-((S)-2-amino-3-(1H-indol-3-yl)propanamido)-3-hydroxybutanamide (5)

To a stirred solution of compound 4 (5.2 g, 12.8 mmol) in DCM (25 mL), TFA (25 mL) was added at 0° C. and the reaction mixture was stirred at rt for 2 h. The progress of the reaction was monitored by TLC & LCMS. After complete consumption of compound 4, the solvent was removed under reduced pressure to obtain a crude residue. The residue was dissolved in water and extracted with ethyl acetate. The aqueous layer was neutralized with saturated sodium bicarbonate solution and concentrated under reduced pressure to obtain a crude residue, which was purified by flash column chromatography to afford compound 5 (2.8 g, 71%).

MS (ESI) m/z 305 $[M+1]^+$.

Synthesis of (S)-tert-butyl 2-(((S)-1-(((2S,3R)-1-amino-3-hydroxy-1-oxobutan-2-yl)amino)-3-(1H-indol-3-yl)-1-oxopropan-2-yl)carbamoyl)pyrrolidine-1-carboxylate (6)

To a stirred solution of compound B (0.5 g, 2.32 mmol) in DCM (20 mL), HATU (1.32 g, 3.48 mmol) and diisopropylethylamine (1.21 mL, 6.96 mmol) were added. The solution was stirred at room temperature for 35 min to generate the activated ester to which compound 5 (0.77 g, 2.55 mmol) was added and stirred at room temperature for 12 h. The progress of the reaction was monitored by TLC & LCMS. After complete consumption of starting material, the reaction was quenched with water and extracted with DCM. The organic layer was washed with sodium bicarbonate solution and brine, dried over anhydrous $Na_2SO_4$ and concentrated under reduced pressure to obtain a crude residue, which was purified by column chromatography to afford compound 6 (0.71 g, 63%).

MS (ESI) m/z: 402 $[M-BOC]^+$.

Synthesis of (S)—N—((S)-1-(((2S,3R)-1-amino-3-hydroxy-1-oxobutan-2-yl)amino)-3-(1H-indol-3-yl)-1-oxopropan-2-yl)pyrrolidine-2-carboxamide (NRX-4006)

To a stirred solution of compound 6 (0.71 g, 1.41 mmol) in dioxane (5 mL), 4 M dioxane: HCl (8 mL) was added at 0° C. and the reaction mixture was stirred at rt for 3 h. The progress of the reaction was monitored by TLC & LCMS. After complete consumption of compound 6, the solvent was removed under reduced pressure to obtain a crude residue, which was purified by Prep HPLC to obtain NRX-4006 (0.1 g, 17.5%) as an off-white solid.

$^1$H NMR (400 MHz, DMSO-$d_6$) δ: 10.83 (s, 1H), 8.34-8.24 (m, 2H), 7.80 (d, J=8.6 Hz, 1H), 7.57 (d, J=7.9 Hz, 1H), 7.31 (d, J=8.0 Hz, 1H), 7.13 (d, J=7.4 Hz, 2H), 7.15-7.13 (m, 1H), 6.99-6.85 (m, 1H), 4.63 (td, J=8.3, 4.6 Hz, 1H), 4.17-3.97 (m, 2H), 3.59 (dd, J=8.6, 5.2 Hz, 1H), 3.18 (dd, J=14.7, 4.8 Hz, 1H), 3.04 (dd, J=14.7, 8.6 Hz, 1H), 2.82-2.75 (m, 1H), 2.59-2.57 (m, 1H), 1.85-1.91 (m, 1H), 1.61-1.29 (m, 3H), 1.00 (d, J=6.3 Hz, 3H).

HPLC purity: 96.6%

LCMS Calculated for $C_{20}H_{22}N_5O_4$: 401.47; Observed: 402.25 $[M+1]^+$.

Synthesis of benzyl ((2S,3R)-1-((S)-2-(((S)-1-(((2S,3R)-1-amino-3-hydroxy-1-oxobutan-2-yl)amino)-3-(1H-indol-3-yl)-1-oxopropan-2-yl)carbamoyl)pyrrolidin-1-yl)-3-hydroxy-1-oxobutan-2-yl)carbamate (7)

To a stirred solution of compound D (0.63 g, 2.48 mmol) in DCM (40 mL), HATU (1.41 g, 3.72 mmol) and diisopropylethylamine (1.28 mL, 7.44 mmol) were added. The solution was stirred at room temperature for 30 min to which NRX-4006 (1 g, 2.48 mmol) was added and stirred at room temperature for 12 h. The progress of the reaction was monitored by TLC & LCMS. After complete consumption of starting material, the reaction was quenched with water and extracted with DCM. The organic layers were washed with brine, dried over anhydrous $Na_2SO_4$ and concentrated under reduced pressure to obtain a crude residue, which was purified by column chromatography to afford compound 7 (0.65 g, 42%).

MS (ESI) m/z: 637 [M+1]$^+$.

Synthesis of (S)—N—((S)-1-(((2S,3R)-1-amino-3-hydroxy-1-oxobutan-2-yl)amino)-3-(1H-indol-3-yl)-1-oxopropan-2-yl)-1-((2S,3R)-2-amino-3-hydroxybutanoyl)pyrrolidine-2-carboxamide (NRX-4001)

To a stirred solution of compound 7 (0.650 g, 1.05 mmol) in methanol (20 mL), 10% palladium-carbon (0.08 g) was added and the reaction mixture was stirred under hydrogen atmosphere at bladder pressure at room temperature for 12 h. The progress of the reaction was monitored by TLC. After complete consumption of starting material, the reaction mixture was filtered through a pad of celite and filtrate was concentrated under reduced pressure to obtain a crude residue, which was purified by Prep HPLC (Basic method) to afford compound NRX-4001 (0.480 g, 91%) as an off-white solid.

$^1$H NMR (400 MHz, DMSO-$d_6$) δ: 10.88-10.80 (m, 1H), 8.33 (s, 3H), 8.08-7.99 (m, 1H), 7.57 (dd, J=15.8, 7.9 Hz, 2H), 7.31 (d, J=8.1 Hz, 1H), 7.17-6.92 (m, 4H), 4.65-4.60 (m, 1H), 4.58-4.44 (m, 2H), 4.34 (d, J=8.0 Hz, 1H), 4.05-3.99 (m, 2H), 3.58 (d, J=18.7 Hz, 3H), 3.24-3.12 (m, 1H), 3.11-2.95 (m, 1H), 2.48-2.43 (m, 1H), 1.97 (s, 1H), 1.77-1.64 (m, 3H), 1.08-0.98 (m, 6H).

HPLC purity: 94.1%

LCMS Calculated for $C_{24}H_{34}N_6O_6$: 502.57; Observed: 503.55 [M+1]$^+$.

B. Synthesis of NRX-4002:

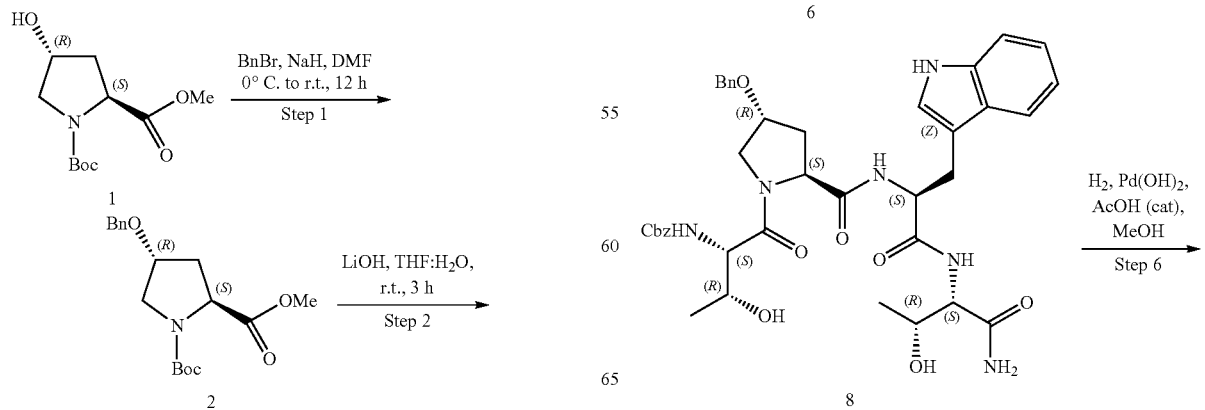

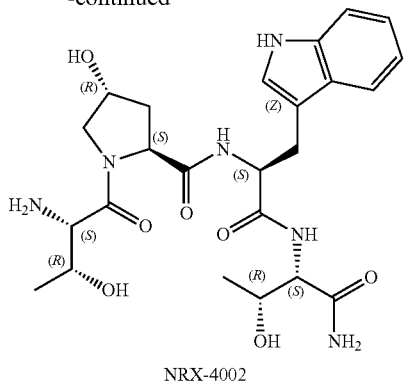

NRX-4002

Synthesis of 1-(tert-butyl)-2-methyl-(2S,4R)-4-(benzyloxy)pyrrolidine-1,2-dicarboxylate (2)

To a stirred solution of compound 1 (2.65 g, 10.80 mmol) in DMF (75 mL), sodium hydride (0.570 g, 23.75 mmol) was added at 0° C. and stirred for 10 min. The reaction mixture was treated with benzyl bromide (1.39 mL, 11.69 mmol) in DMF (10 mL) and stirred at room temperature for 16 h. The reaction mixture was concentrated under reduced pressure and the residue was treated with water and extracted with ethyl acetate. The organic layers were washed with brine, separated, dried over sodium sulphate and concentrated under reduced pressure to afford compound 2 (3.45 g, 96%).
MS (ESI) m/z 336 [M+1]$^+$.

Synthesis of (2S,4R)-4-(benzyloxy)-1-(tert-butoxycarbonyl)pyrrolidine-2-carboxylic acid (3)

To a solution of compound 2 (3.45 g, 10.29 mmol) in THF:H$_2$O (60 mL, 2:1) lithium hydroxide monohydrate (1.29 g, 30.87 mmol) was added and the reaction mixture was stirred at room temperature for 3 h. After completion of the reaction as indicated by TLC the reaction mixture was concentrated under reduced pressure, acidified with 1N hydrochloric acid and extracted with ethyl acetate. The organic layers were separated, washed with brine, dried over Na$_2$SO$_4$ and concentrated under reduced pressure to obtain the crude residue. The residue was purified by trituration with pentene to afford compound 3 (3.21 g, 97%).
MS (ESI) m/z 322 [M+1]$^+$.

Synthesis of tert-butyl-(2S,4R)-2-(((S)-1-(((2S,3R)-1-amino-3-hydroxy-1-oxobutan-2-yl)amino)-3-(1H-indol-3-yl)-1-oxopropan-2-yl)carbamoyl)-4-(benzyloxy)pyrrolidine-1-carboxylate (5)

To a stirred solution of compound 3 (1 g, 3.11 mmol) in DCM (20 mL), HATU (1.7 g, 4.6 mmol) and diisopropylethylamine (1.6 mL, 9.33 mmol) were added. The solution was stirred at rt for 1 h to generate the activated ester and treated with compound 4 (0.947 g, 3.11 mmol) and stirred at room temperature for 12 h. The progress of the reaction was monitored by TLC & LCMS. After complete consumption of starting material, the reaction was quenched with water and extracted with DCM. The organic layers were washed with sodium bicarbonate solution and brine, dried over anhydrous Na$_2$SO$_4$ and concentrated under reduced pressure to obtain a crude residue, which was purified by column chromatography to afford compound 5 (1.23 g, 65%).
LCMS: 508 (M−Boc)$^+$.

Synthesis of (2S,4R)—N—((S)-1-(((2S,3R)-1-amino-3-hydroxy-1-oxobutan-2-yl)amino)-3-(1H-indol-3-yl)-1-oxopropan-2-yl)-4-(benzyloxy)pyrrolidine-2-carboxamide (6)

To a stirred solution of compound 5 (1.23 g, 2.02 mmol) in dioxane (5 mL), 4 M HCl in dioxane (12 mL) was added at 0° C. and the reaction mixture was stirred at room temperature for 3 h. The progress of the reaction was monitored by TLC & LCMS. After complete consumption of compound 5, the solvent was removed under reduced pressure to obtain a crude residue, which was purified by trituration with DCM to afford compound 6 (1 g, 90%).
MS (ESI) m/z 508 [M+1]$^+$.

Synthesis of benzyl ((2S,3R)-1-((2S,4R)-2-(((S)-1-(((2S,3R)-1-amino-3-hydroxy-1-oxobutan-2-yl)amino)-3-(1H-indol-3-yl)-1-oxopropan-2-yl)carbamoyl)-4-(benzyloxy)pyrrolidin-1-yl)-3-hydroxy-1-oxobutan-2-yl)carbamate (8)

To a stirred solution of compound 7 in DCM (30 mL), HATU (1.1 g, 2.94 mmol) and diisopropylethylamine (1 mL, 5.88 mmol) were added. The solution was stirred at room temperature for 1 h to generate the activated ester to which compound 6 (1 g, 1.96 mmol) was added and stirred at room temperature for 12 h. The progress of the reaction was monitored by TLC & LCMS. After complete consumption of starting material, the reaction was quenched with water and extracted with DCM. The organic layers were washed with sodium bicarbonate solution and brine, dried over anhydrous Na$_2$SO$_4$ and concentrated under reduced pressure to obtain a crude residue, which was purified by column chromatography to afford compound 8 (0.950 g, 65%).
MS (ESI) m/z: 743 (M+1)$^+$.

Synthesis of (2S,4R)—N—((S)-1-(((2S,3R)-1-amino-3-hydroxy-1-oxobutan-2-yl)amino)-3-(1H-indol-3-yl)-1-oxopropan-2-yl)-1-((2S,3R)-2-amino-3-hydroxybutanoyl)-4-hydroxypyrrolidine-2-carboxamide (NRX-4002)

To a stirred solution of compound 8 (0.55 g, 0.74 mmol) in methanol (40 mL), 20% palladium hydroxide (0.06 g) and acetic acid (0.1 mL) were added and the reaction mixture was stirred under hydrogen atmosphere at bladder pressure at room temperature for 12 h. The progress of the reaction was monitored by TLC. After complete consumption of starting material, the reaction mixture was filtered through a pad of celite and the filtrate was concentrated under reduced pressure to obtain a crude residue, which was purified by Prep HPLC (Basic method) to afford compound NRX-4002. Data for two different batches is a follows:
Batch-I:
Yield: 0.02 g as an off-white solid; $^1$H NMR (400 MHz, DMSO-d$_6$) δ: 10.88-10.78 (m, 1H), 8.35 (s, 2H), 8.16 (t, J=6.8 Hz, 1H), 7.63-7.43 (m, 2H), 7.32 (d, J=8.0 Hz, 1H), 7.26-7.13 (m, 1H), 7.17.03 (m, 5H), 4.65-4.60 (m, 1H), 4.5-4.44 (m, 2H), 4.24-4.11 (m, 1H), 4.16-3.98 (m, 2H), 3.75-3.33 (m, 3H), 3.27-3.06 (m, 1H), 3.09-2.90 (m, 1H), 2.02-1.91 (m, 1H), 1.73-1.53 (m, 1H), 1.16-0.88 (m, 6H); HPLC purity: 91.48%; LCMS Calculated for $C_{24}H_{34}N_6O_2$: 518.57; Observed: 519.45 $[M+1]^+$.

Batch-II:

Yield: 0.04 g as an off-white solid; $^1$H NMR (400 MHz, DMSO-$d_6$) δ: $^1$H NMR (400 MHz, DMSO-$d_6$) δ: 10.87-10.76 (m, 1H), 8.32 (s, 2H), 8.10 (d, J=7.5 Hz, 1H), 7.63-7.43 (m, 2H), 7.32 (d, J=8.0 Hz, 1H), 7.24-6.92 (m, 6H), 4.65-4.60 (m, 1H), 4.56-4.33 (m, 3H), 4.24-4.11 (m, 1H), 4.11-4.04 (m, 3H), 3.70-3.54 (m, 1H), 3.52-3.29 (m, 2H), 3.27-3.19 (m, 1H), 3.18 (dd, J=14.9, 4.8 Hz, 1H), 3.10-3.05 (m, 1H), 1.96 (dd, J=13.2, 8.0 Hz, 1H), 1.71-1.56 (m, 1H), 1.13-0.91 (m, 6H); HPLC purity: 93.7%; LCMS Calculated for $C_{24}H_{34}N_6O_7$: 518.57; Observed: 519.45 $[M+1]^+$.

C. Synthesis of NRX-4007:

Scheme 9

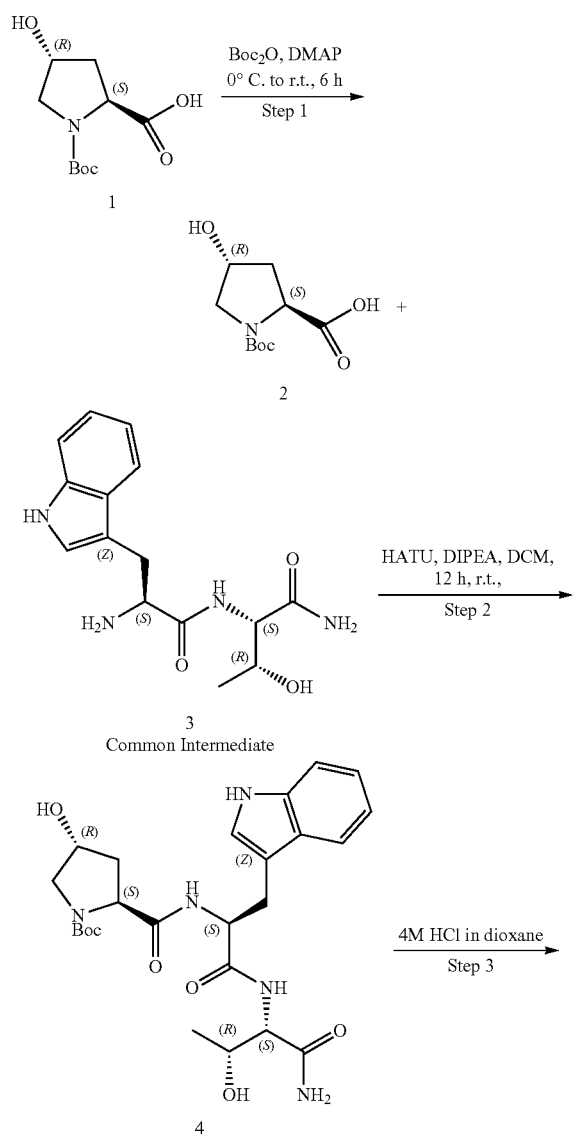

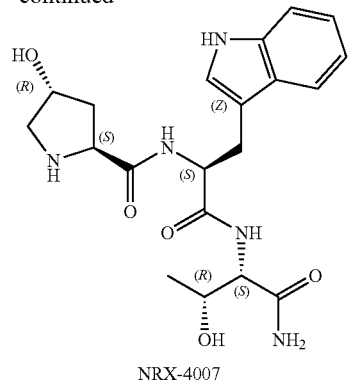

NRX-4007

Synthesis of (2S,4R)-1-(tert-butoxycarbonyl)-4-hydroxypyrrolidine-2-carboxylic acid (2)

To a stirred solution of compound 1 (1.2 g, 7.35 mmol) in dichloromethane (50 mL), N,N-dimethylaminopyridine (0.898 g, 7.35 mmol) followed by di-tertiary butyl dicarbonate (3.2 g, 14.70 mmol) were added and the reaction mixture was allowed to stir at room temperature for 6 h. The reaction mixture was quenched with water and the compound was extracted in ethyl acetate. The organic layers were washed with 0.5 M HCl and brine, separated, dried over sodium sulphate and concentrated under reduced pressure. The residue was purified by silica gel column chromatography using 1-2% methanol in dichloromethane as eluent to afford compound 2 (1.75 g, 92%).

MS (ESI) m/z 232 $[M+1]^+$.

Synthesis of (2S,4R)-tert-butyl 2-(((S)-1-(((2S,3R)-1-amino-3-hydroxy-1-oxobutan-2-yl)amino)-3-(1H-indol-3-yl)-1-oxopropan-2-yl)carbamoyl)-4-hydroxypyrrolidine-1-carboxylate(4)

To a stirred solution of compound 2 (1.5 g, 6.49 mmol) in DCM (30 mL), HATU (3.7 g, 9.73 mmol) and diisopropylethylamine (3.4 mL, 19.47 mmol) were added. The solution was stirred at room temperature for 1 h to form the activated ester and treated with compound 3 (2.1 g, 7.14 mmol) and stirred for 12 h. The progress of the reaction was monitored by TLC & LCMS. After complete consumption of starting material, the reaction was quenched with 1N HCl solution and extracted with DCM. The organic layer was washed with sodium bicarbonate solution and brine, dried over anhydrous $Na_2SO_4$ and concentrated under reduced pressure to obtain a crude residue, which was purified by column chromatography to afford compound 4 (2.15 g, 59%).

MS (ESI) m/z 418.2 $[M-Boc]^+$.

Synthesis of (2S,4R)—N—((S)-1-(((2S,3R)-1-amino-3-hydroxy-1-oxobutan-2-yl)amino)-3-(1H-indol-3-yl)-1-oxopropan-2-yl)-4-hydroxypyrrolidine-2-carboxamide (NRX-4007)

To a stirred solution of compound 4 (2.15 g, 4.15 mmol) in dioxane (10 mL), 4 M HCl in dioxane (20 mL) was added at 0° C. and the reaction mixture was stirred at rt for 2 h. The progress of the reaction was monitored by TLC & LCMS. After complete consumption of compound 4, the solvent was removed under reduced pressure to obtain a crude residue, which was purified by Prep HPLC (Basic method) to obtain compound NRX-4007 (0.125 g, 7.2%) as an off-white solid.

$^1$H NMR (400 MHz, DMSO-d$_6$) δ: 10.80 (d, J=2.5 Hz, 1H), 8.12 (d, J=8.1 Hz, 1H), 7.82 (d, J=8.6 Hz, 1H), 7.52 (d, J=7.9 Hz, 1H), 7.30 (d, J=8.0 Hz, 1H), 7.21-6.89 (m, 5H), 4.62-4.58 (m, 1H), 4.13 (dd, J=8.6, 3.6 Hz, 1H), 4.06-3.89 (m, 2H), 3.62 (t, J=8.1 Hz, 1H), 3.16 (dd, J=14.6, 4.8 Hz, 1H), 3.04 (dd, J=14.7, 8.2 Hz, 1H), 2.62-2.50 (m, 1H), 2.31 (dd, J=11.6, 3.8 Hz, 1H), 1.82-1.78 (m, 1H), 1.40-1.37 (m, 1H), 1.00 (d, J=6.3 Hz, 3H).

HPLC purity: 91.2%

LCMS Calculated for C$_{20}$H$_{22}$N$_5$O$_5$: 417.47; Observed: 418.40 [M+1]$^+$.

D. Synthesis of NRX-4003 and O-Acetyl Tripeptide:

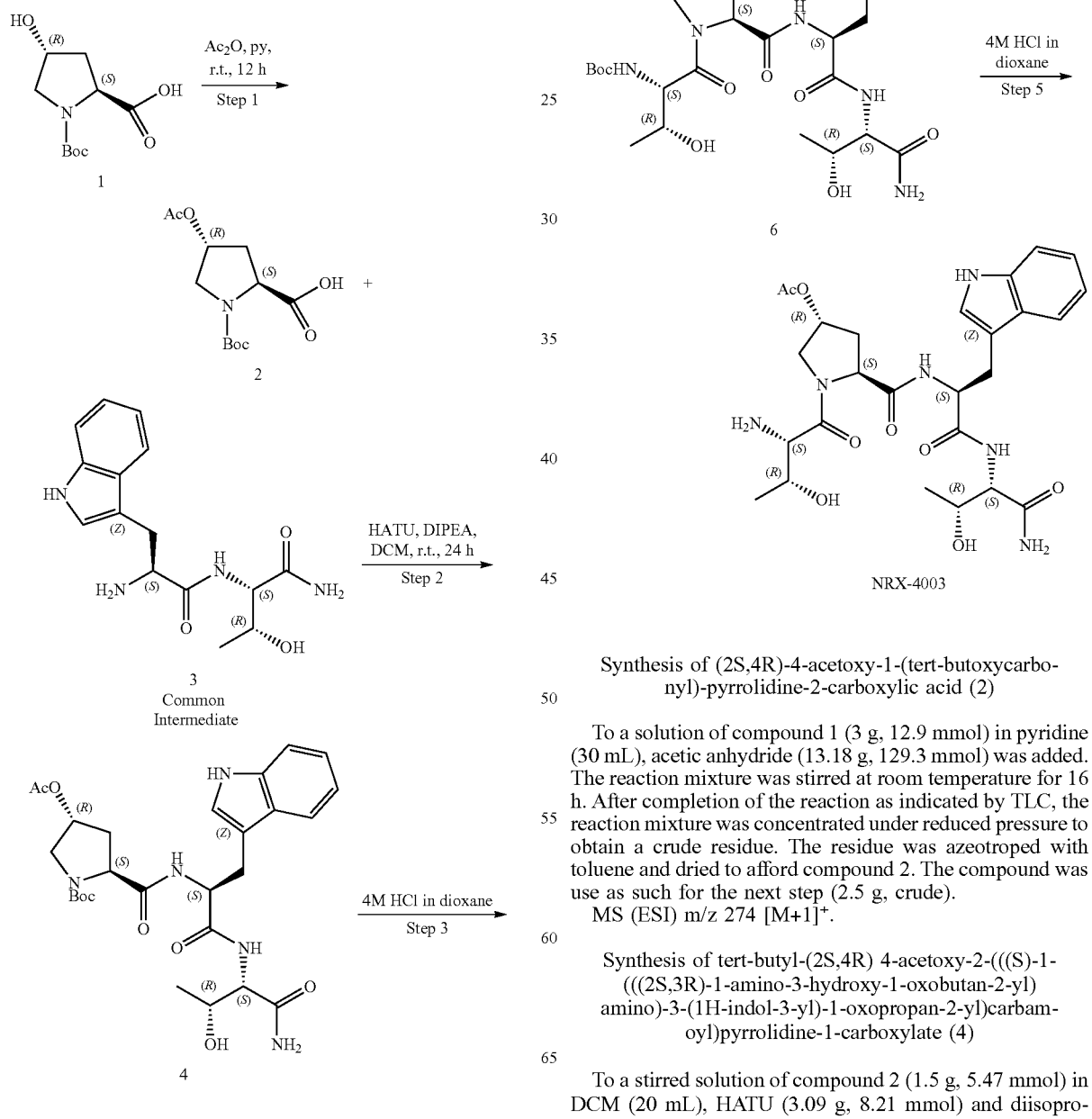

Synthesis of (2S,4R)-4-acetoxy-1-(tert-butoxycarbonyl)-pyrrolidine-2-carboxylic acid (2)

To a solution of compound 1 (3 g, 12.9 mmol) in pyridine (30 mL), acetic anhydride (13.18 g, 129.3 mmol) was added. The reaction mixture was stirred at room temperature for 16 h. After completion of the reaction as indicated by TLC, the reaction mixture was concentrated under reduced pressure to obtain a crude residue. The residue was azeotroped with toluene and dried to afford compound 2. The compound was use as such for the next step (2.5 g, crude).

MS (ESI) m/z 274 [M+1]$^+$.

Synthesis of tert-butyl-(2S,4R) 4-acetoxy-2-(((S)-1-(((2S,3R)-1-amino-3-hydroxy-1-oxobutan-2-yl)amino)-3-(1H-indol-3-yl)-1-oxopropan-2-yl)carbamoyl)pyrrolidine-1-carboxylate (4)

To a stirred solution of compound 2 (1.5 g, 5.47 mmol) in DCM (20 mL), HATU (3.09 g, 8.21 mmol) and diisopropylethylamine (2.85 mL, 16.4 mmol) were added. The solution was stirred at room temperature for 1 h to generate the activated ester and treated with compound 3 (1.83 g, 6.02 mmol) and stirred at room temperature for 12 h. The progress of the reaction was monitored by TLC & LCMS. After complete consumption of starting material, the reaction was quenched with 1N HCl solution and extracted with DCM. The organic layers were washed with saturated sodium bicarbonate solution and brine, dried over anhydrous $Na_2SO_4$ and concentrated under reduced pressure to obtain a crude residue, which was purified by column chromatography to afford compound 4 (2.25 g, 73%).

MS (ESI) m/z 450 [M−Boc]+.

Synthesis of (3R,5S)-5-(((S)-1-(((2S,3R)-1-amino-3-hydroxy-1-oxobutan-2-yl)amino)-3-(1H-indol-3-yl)-1-oxopropan-2-yl)carbamoyl)pyrrolidin-3-yl acetate (O-acetyl tripeptide) (NRX-4013)

To a stirred solution of compound 4 (2.2 g, 3.93 mmol) in dioxane (5 mL), 4 M HCl in dioxane (20 mL) was added at 0° C. and the reaction mixture was stirred at rt for 2 h. The progress of the reaction was monitored by TLC & LCMS. After complete consumption of compound 2, the solvent was removed under reduced pressure to obtain a crude residue, which was purified by Prep HPLC (Basic method) to afford O-acetyl tripeptide NRX-4013 (1.65 g, 91.6%) as an off-white solid.

$^1$H NMR (400 MHz, DMSO-$d_6$) δ: 10.81 (d, J=2.3 Hz, 1H), 8.21 (s, 1H), 8.11 (d, J=8.1 Hz, 1H), 7.83 (d, J=8.6 Hz, 1H), 7.53 (d, J=7.9 Hz, 1H), 7.30 (d, J=8.0 Hz, 1H), 7.18-6.90 (m, 5H), 4.84 (t, J=4.7 Hz, 1H), 4.64 (td, J=8.1, 4.9 Hz, 1H), 4.14 (dd, J=8.6, 3.7 Hz, 1H), 4.07-3.96 (m, 1H), 3.70-3.62 (m, 1H), 3.18 (dd, J=14.5, 4.8 Hz, 1H), 3.04 (dd, J=14.6, 8.1 Hz, 1H), 2.75 (d, J=12.8 Hz, 1H), 2.62-2.53 (m, 1H), 2.42-2.39 (m, 2H), 1.95 (s, 3H), 1.65-1.58 (m, 1H), 1.04 (dd, J=27.1, 6.5 Hz, 4H).

HPLC purity: 96.14%

LCMS Calculated for $C_{22}H_{29}N_5O_6$: 459.50; Observed: 461[M+1]+.

Synthesis of (3R,5S)-5-(((S)-1-(((2S,3R)-1-amino-3-hydroxy-1-oxobutan-2-yl)amino)-3-(1H-indol-3-yl)-1-oxopropan-2-yl)carbamoyl)-1-((2S,3R)-2-((tert-butoxycarbonyl)amino)-3-hydroxybutanoyl) pyrrolidin-3-yl acetate (6)

To a stirred solution of compound 5 (0.76 g, 3.47 mmol) in DCM (50 mL), HATU (1.98 g, 5.21 mmol) and diisopropylethylamine (1.79 g, 16.4 mmol) were added. The solution was stirred at rt for 1 h to generate the activated ester to which O-acetyl tripeptide NRX-4013 (1.6 g, 13.9 mmol) in DCM was added and stirred at rt for 12 h. The progress of the reaction was monitored by TLC & LCMS. After complete consumption of starting material, the reaction was quenched with 1N HCl solution and extracted with DCM. The organic layers were washed with sodium bicarbonate solution and brine, dried over anhydrous $Na_2SO_4$ and concentrated under reduced pressure to obtain a crude residue, which was purified by column chromatography to afford compound 6 (1.5 g, 65%).

MS (ESI) m/z 561 [M−Boc]+.

Synthesis of (3R,5S)-5-(((S)-1-(((2S,3R)-1-amino-3-hydroxy-1-oxobutan-2-yl)amino)-3-(1H-indol-3-yl)-1-oxopropan-2-yl)carbamoyl)-1-((2S,3R)-2-amino-3-hydroxybutanoyl) pyrrolidin-3-yl acetate (NRX-4003)

To a stirred solution of compound 6 (1.0 g, 1.51 mmol) in dioxane (4 mL), 4 M HCl in dioxane (10 mL) was added at 0° C. and the reaction mixture was stirred at room temperature for 2 h. The progress of the reaction was monitored by TLC & LCMS. After complete consumption of compound 6, the solvent was removed under reduced pressure to obtain a crude residue, which was purified by Prep HPLC (Basic method) to obtain NRX-400 (0.8 g, 94.3%) as an off-white solid.

$^1$H NMR (400 MHz, DMSO-$d_6$) δ: 10.82 (d, J=19.1 Hz, 1H), 8.30 (s, 2H), 8.23 (d, J=7.5 Hz, 1H), 7.64-7.49 (m, 2H), 7.32 (d, J=8.1 Hz, 1H), 7.23 (s, 1H), 7.16 (s, 2H), 7.13-6.92 (m, 4H), 5.15 (s, 1H), 4.78-4.60 (m, 2H), 4.10-3.98 (m, 2H), 3.87-3.71 (m, 2H), 3.63 (t, J=6.3 Hz, 1H), 3.39 (d, J=6.4 Hz, 1H), 3.21-2.98 (m, 4H), 3.01 (dd, J=15.8, 9.3 Hz, 1H), 2.18 (dd, J=14.6, 8.1 Hz, 1H), 2.00 (s, 2H), 1.92 (d, J=22.3 Hz, 1H), 1.09 (d, J=6.2 Hz, 2H), 0.99 (dd, J=24.2, 6.4 Hz, 5H).

Hplc Purity: 97.2%

LCMS Calculated for $C_{26}H_{36}N_6O_8$: 560.61; Observed: 561.55[M+1]+.

E. Synthesis of NRX-4004 & 4008:

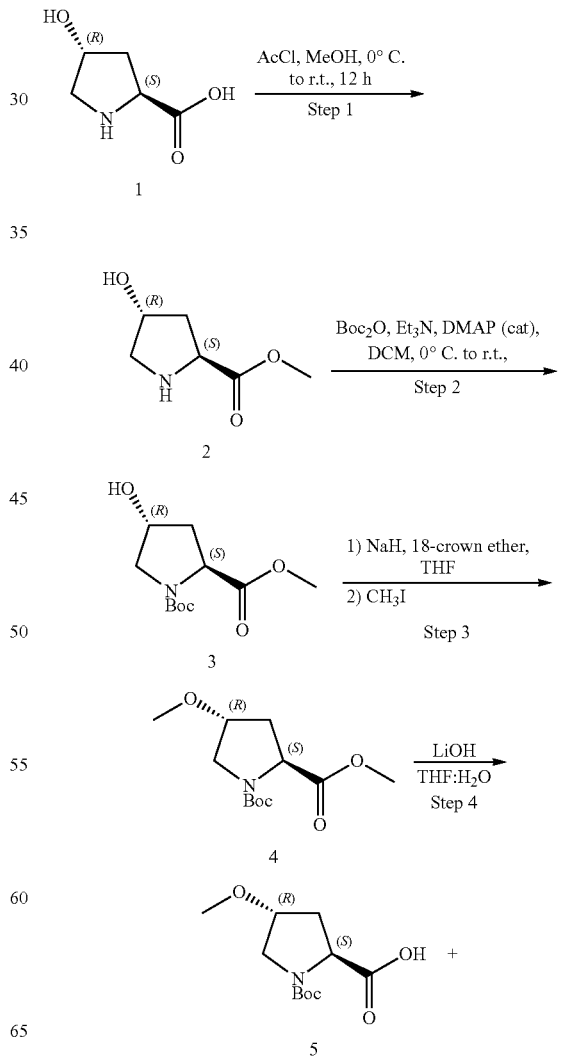

Scheme 11

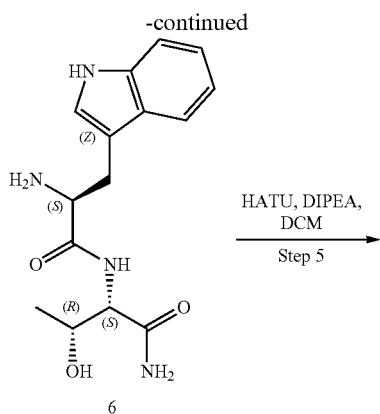

6

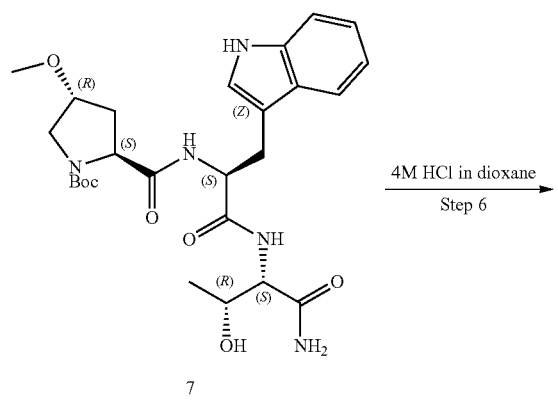

7

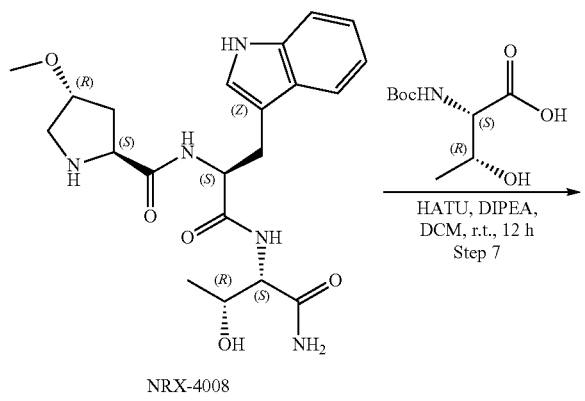

NRX-4008

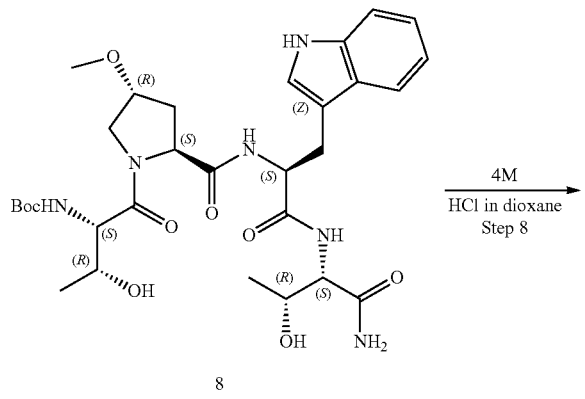

8

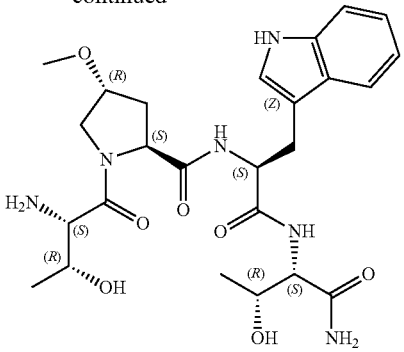

NRX-4004

Synthesis of (2S,4R)-methyl 4-hydroxypyrrolidine-2-carboxylate (2)

To a stirred solution of compound 1 (20 g, 152.6 mmol) in methanol (200 mL) acetyl chloride (23.93 g, 305.3 mmol) was added over a period of 30 min at 0° C. and the reaction mixture was stirred at room temperature for 16 h. The reaction mixture was concentrated under reduced pressure. The residue was washed with ether and purified by silica gel column chromatography using 10% methanol in dichloromethane as eluent to afford compound 2 (25.1 g, crude).

MS (ESI) m/z 146 [M+1]$^+$.

Synthesis of (2S,4R)-1-tert-butyl 2-methyl 4-hydroxypyrrolidine-1,2-dicarboxylate (3)

To a stirred solution of compound 2 (26 g, 180.5 mmol) in dichloromethane (400 mL), N,N-dimethylaminopyridine (1.10 g, 9.02 mmol), triethylamine (50 mL, 361.1 mmol) followed by di-tertiary butyl dicarbonate (58 mL, 252.7 mmol) were added and the reaction mixture was allowed to stir at room temperature for 12 h. After completion of the reaction as indicated by TLC, the residue was taken in ether. The precipitated solid was filtered and washed with ether. The ether layer was concentrated under reduced pressure to obtain a residue The residue was dissolved in DCM and washed with sodium bicarbonate solution. The organic layer was separated and dried over sodium sulphate and concentrated under reduced pressure. The residue was purified by silica gel column chromatography using 1-2% methanol in dichloromethane as eluent to afford compound 3 as white solid (30.1 g, 67.8%).

MS (ESI) m/z 246[M+1]$^+$.

Synthesis of (2S,4R)-1-tert-butyl 2-methyl 4-methoxypyrrolidine-1,2-dicarboxylate (4)

To a stirred solution of compound 3 (5 g, 20.49 mmol) in THF (50 mL), sodium hydride (0.9 g, 22.53 mmol, 60%) was added portion wise over a period of 30 min. The reaction mixture was treated with methyl iodide (6.38 mL, 102.4 mmol) and 18-crown-6 (3.24 g, 12.29 mmol) and stirred at room temperature for 6 h. The reaction completion was monitored by TLC. After complete consumption of starting material, the reaction was quenched with 1N HCl solution and extracted with ethyl acetate. The organic layers were separated, washed with saturated sodium bicarbonate solution and brine, dried over Na$_2$SO$_4$ and concentrated under reduced pressure to obtain a crude residue, which was purified by column chromatography to afford compound 4 (5 g, 90%).

MS (ESI) m/z 260[M+1]$^+$.

Synthesis of (2S,4R)-1-(tert-butoxycarbonyl)-4-methoxypyrrolidine-2-carboxylic acid (5)

To a solution of compound 4 (5 g, 19.3 mmol) in THF:water (35 mL, 6:1) lithium hydroxide monohydrate (1.22 g, 29.06 mmol) was added and the reaction mixture was stirred at room temperature for 2 h. The reaction completion was monitored by TLC. The reaction mixture was concentrated under reduced pressure, acidified with 1N hydrochloric acid and extracted with 5% methanol in DCM. The organic layer was separated, washed with brine, dried over $Na_2SO_4$ and concentrated under reduced pressure to obtain crude residue of compound 5. The compound was used as such for the next step without further purification (4.5 g, crude).

MS (ESI) m/z 246[M+1]$^+$.

Synthesis of (2S,4R)-tert-butyl 2-(((S)-1-(((2S,3R)-1-amino-3-hydroxy-1-oxobutan-2-yl)amino)-3-(1H-indol-3-yl)-1-oxopropan-2-yl)carbamoyl)-4-methoxypyrrolidine-1-carboxylate(7)

To a stirred solution of compound 5 (0.5 g, 2.04 mmol) in DCM (20 mL), HATU (1.16 g, 3.06 mmol) and diisopropylethylamine (1.05 g, 6.12 mmol) were added. The solution was stirred at rt for 1 h and treated with compound 6 (0.682 g, 2.24 mmol) and stirred at same temperature for 12 h. The progress of the reaction was monitored by TLC & LCMS. After complete consumption of starting material, the reaction was quenched with 1N HCl solution and extracted with DCM. The organic layer was washed with sodium bicarbonate solution and brine, dried over anhydrous $Na_2SO_4$ and concentrated under reduced pressure to obtain a crude residue, which was purified by column chromatography to afford compound 7 (0.6 g, 53%).

MS (ESI) m/z 432 (M–Boc)$^+$.

Synthesis of (2S,4R)—N—((S)-1-(((2S,3R)-1-amino-3-hydroxy-1-oxobutan-2-yl)amino)-3-(1H-indol-3-yl)-1-oxopropan-2-yl)-4-methoxypyrrolidine-2-carboxamide (NRX-4008)

To a stirred solution of compound 7 (0.45 g, 0.847 mmol) in dioxane (3 mL), 4 M HCl in dioxane (5 mL) was added at 0° C. and the reaction mixture was stirred at rt for 2 h. The progress of the reaction was monitored by TLC & LCMS. After complete consumption of compound 7, the solvent was removed under reduced pressure to obtain a crude residue, which was purified by Prep HPLC (Basic method) to obtain compound NRX-4008 (0.12 g, 32.8%) as an off-white solid.

$^1$H NMR (400 MHz, DMSO-d$_6$) δ: 10.83 (s, 1H), 8.13 (d, J=8.9 Hz, 1H), 7.86 (d, J=8.6 Hz, 1H), 7.53 (d, J=7.9 Hz, 1H), 7.30 (d, J=7.9 Hz, 1H), 7.23-6.99 (m, 4H), 6.94 (t, J=7.3 Hz, 1H), 5.34 (s, 1H), 5.04 (s, 2H), 4.63 (q, J=6.9 Hz, 1H), 4.13 (dd, J=8.5, 3.6 Hz, 1H), 4.05-4.10 (m, 1H), 3.62-3.55 (m, 2H), 3.23-2.99 (m, 5H), 2.76 (d, J=13.1 Hz, 1H), 1.93 (dd, J=13.5, 8.3 Hz, 1H), 1.43-1.39 (m, 1H), 1.00 (d, J=6.2 Hz, 3H).

HPLC purity: 95%

LCMS Calculated for $C_{21}H_{29}N_5O_5$: 431.49; Observed: 432.13[M+1]$^+$.

Synthesis of tert-butyl ((2S,3R)-1-02S,4R)-2-(((S)-1-(((2S,3R)-1-amino-3-hydroxy-1-oxobutan-2-yl)amino)-3-(1H-indol-3-yl)-1-oxopropan-2-yl)carbamoyl)-4-methoxypyrrolidin-1-yl)-3-hydroxy-1-oxobutan-2-yl)carbamate (8)

To a stirred solution of compound (2S,3R)-2-((tert-butoxycarbonyl)amino)-3-hydroxybutanoic acid (0.5 g, 2.32 mmol) in DMF (10 mL), HATU (1.32 g, 3.48 mmol) and diisopropylethylamine (1.61 mL, 9.28 mmol) were added. The solution was stirred at rt for 1 h to which NRX-4008 (1 g, 2.32 mmol) was added and stirred at rt for 12 h. The progress of the reaction was monitored by TLC & LCMS. After complete consumption of starting material, the reaction was quenched with 1N HCl solution and extracted with DCM. The organic layer was washed with sodium bicarbonate solution and brine, dried over anhydrous $Na_2SO_4$ and concentrated under reduced pressure to obtain a crude residue, which was purified by column chromatography to afford compound 8 (1.10 g, 75%).

LCMS: 533 (M–Boc)$^+$.

Synthesis of (2S,4R)—N—((S)-1-(((2S,3R)-1-amino-3-hydroxy-1-oxobutan-2-yl)amino)-3-(1H-indol-3-yl)-1-oxopropan-2-yl)-1-((2S,3R)-2-amino-3-hydroxybutanoyl)-4-methoxypyrrolidine-2-carboxamide (NRX-4004)

To a stirred solution of compound 8 (1 g, 1.58 mmol) in dioxane (5 mL), 4 M HCl in dioxane (10 mL) was added at 0° C. and the reaction mixture was stirred at room temperature for 2 h. The progress of the reaction was monitored by TLC & LCMS. After complete consumption of compound 8, the solvent was removed under reduced pressure to obtain a crude residue, which was purified by Prep HPLC (Basic method) to obtain compound NRX-4004 (0.12 g, 14.2%) as an off-white solid.

$^1$H NMR (400 MHz, DMSO-d$_6$) δ: 10.84 (d, J=14.2 Hz, 1H), 8.34 (s, 2H), 8.19 (d, J=7.4 Hz, 1H), 7.68-7.47 (m, 2H), 7.32 (d, J=8.0 Hz, 1H), 7.22 (d, J=2.4 Hz, 1H), 7.19-6.92 (m, 4H), 4.58-4.39 (m, 1H), 4.34 (t, J=8.0 Hz, 1H), 4.10-4.04 (m, 2H), 3.85 (s, 1H), 3.77 (d, J=11.4 Hz, 1H), 3.72-3.43 (m, 3H), 3.28-2.93 (m, 5H), 2.11 (p, J=9.0, 8.1 Hz, 1H), 1.76-1.72 (m, 1H), 1.18-0.88 (m, 6H).

HPLC purity: 96.5%

LCMS Calculated for $C_{25}H_{36}N_6O_7$: 532.60; Observed: 533.5[M+1]$^+$.

F. Synthesis of NRX-4010:

Scheme 12

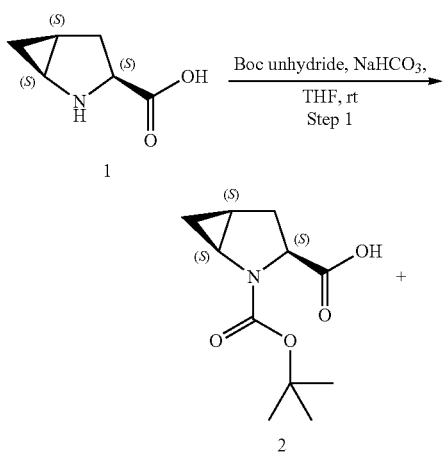

-continued

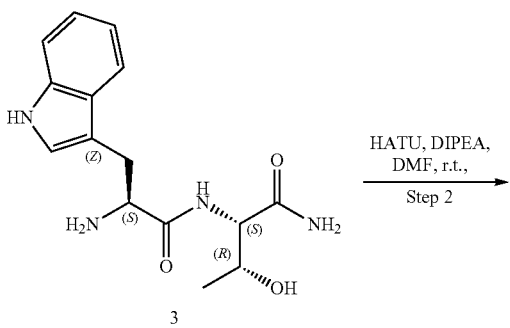

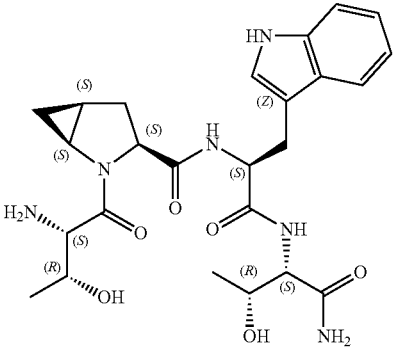

NRX-4010

Synthesis of (1S,3S,5S)-2-(tert-butoxycarbonyl)-2-azabicyclo[3.1.0]hexane-3-carboxylic acid (2)

To a stirred solution of compound 1 (0.9 g, 3.73 mmol) in aqueous solution of sodium bicarbonate (0.894 g, 4.10 mmol), di-tert-butyl-dicarbonate (0.941 g, 11.2 mmol) in THF (25 mL) was added drop wise at 0° C. The reaction mixture was allowed to stir at room temperature for 15 h. The reaction mixture was neutralized with 3N hydrochloric acid to pH 2 and extracted with ethyl acetate. The organic layers was separated, dried over sodium sulphate and concentrated under reduced pressure to afford compound 2 (1.20 g, 94%).

MS (ESI) m/z 228 [M+1]$^+$.

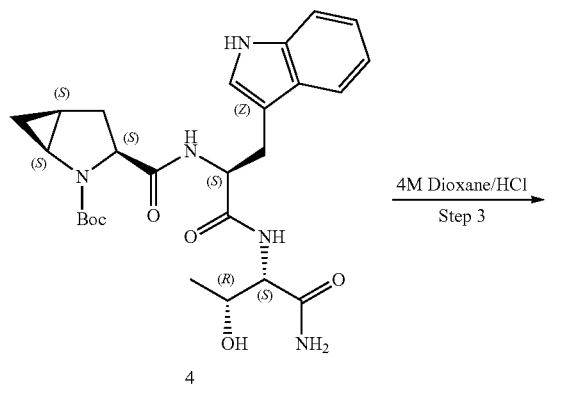

Synthesis of (1S,3S,5S)-tert-butyl 3-(((S)-1-(((2S,3R)-1-amino-3-hydroxy-1-oxobutan-2-yl)amino)-3-(1H-indol-3-yl)-1-oxopropan-2-yl)carbamoyl)-2-azabicyclo[3.1.0]hexane-2-carboxylate (4)

To a stirred solution of compound 2 (1.5 g, 4.39 mmol) in DCM (20 mL), HATU (2.50 g, 6.58 mmol) and diisopropylethylamine (2.29 mL, 13.1 mmol) were added. The solution was stirred at room temperature for 1 h to which compound 3 (1.46 g, 4.83 mmol) was stirring was continued for 12 h. The progress of the reaction was monitored by TLC & LCMS. After complete consumption of starting material, the reaction was quenched with 1N HCl solution and extracted with DCM. The organic layers were washed with sodium bicarbonate solution and brine, dried over anhydrous Na$_2$SO$_4$ and concentrated under reduced pressure to obtain a crude residue, which was purified by column chromatography to afford compound 4 (1.25 g, 55.5%).

MS (ESI) m/z 414 [M−Boc]$^+$.

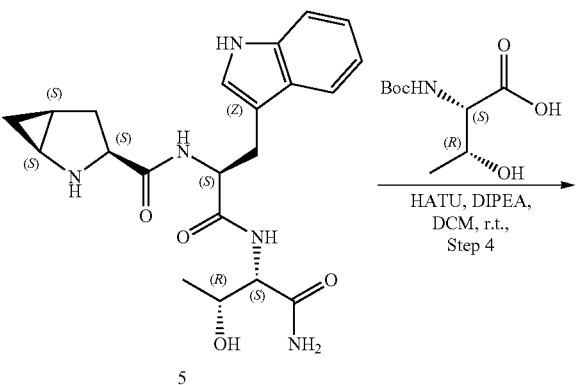

Synthesis of (1S,3S,5S)—N—((S)-1-(((2S,3R)-1-amino-3-hydroxy-1-oxobutan-2-yl)amino)-3-(1H-indol-3-yl)-1-oxopropan-2-yl)-2-azabicyclo[3.1.0]hexane-3-carboxamide (5)

To a stirred solution of compound 4 (1 g, 1.94 mmol) in dioxane (5 mL), 4 M HCl in dioxane (10 mL) was added at 0° C. and the reaction mixture was stirred at room temperature for 2 h. The progress of the reaction was monitored by TLC & LCMS. After complete consumption of compound 4, the solvent was removed under reduced pressure to obtain a crude residue, which was purified by trituration with hexane to obtain compound 5 (0.8 g, 99.3%).

MS (ESI) m/z 414[M+1]$^+$.

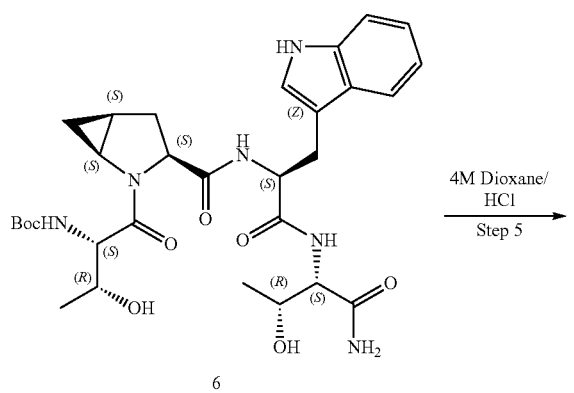

Synthesis of tert-butyl ((2S,3R)-1-41S,3S,5S)-3-(((S)-1-(((2S,3R)-1-amino-3-hydroxy-1-oxobutan-2-yl)amino)-3-(1H-indol-3-yl)-1-oxopropan-2-yl)carbamoyl)-2-azabicyclo[3.1.0]hexan-2-yl)-3-hydroxy-1-oxobutan-2-yl)carbamate (6)

To a stirred solution of (2S,3R)-2-((tert-butoxycarbonyl)amino)-3-hydroxybutanoic acid (0.466 g, 2.13 mmol) in DCM (20 mL), HATU (1.10 g, 2.90 mmol) and diisopropylethylamine (1.01 mL, 5.81 mmol) were added. The solution was stirred at room temperature for 1 h to which compound 5 (0.8 g, 1.93 mmol) was added and stirring was continued for 12 h. The progress of the reaction was monitored by TLC & LCMS. After complete consumption of starting material, the reaction was quenched with 1N HCl solution and extracted with DCM. The organic layers were washed with sodium bicarbonate solution and brine, dried over anhydrous Na$_2$SO$_4$ and concentrated under reduced pressure to obtain a crude residue, which was purified by column chromatography to afford compound 6 (1.05 g, 88.9%).

MS (ESI) m/z 515 [M−Boc]$^+$.

Synthesis of (1S,3S,5S)—N—((S)-1-(((2S,3R)-1-amino-3-hydroxy-1-oxobutan-2-yl)amino)-3-(1H-indol-3-yl)-1-oxopropan-2-yl)-2-((2S,3R)-2-amino-3-hydroxybutanoyl)-2-azabicyclo[3.1.0]hexane-3-carboxamide (NRX-4010)

To a stirred solution of compound 6 (1 g, 1.62 mmol) in dioxane (5 mL), 4 M HCl in dioxane (10 mL) was added at 0° C. and the reaction mixture was stirred at room temperature for 2 h. The progress of the reaction was monitored by TLC & LCMS. After complete consumption of compound 6, the solvent was removed under reduced pressure to obtain a crude residue, which was purified by Prep HPLC (Basic method) to obtain NRX-4010 (0.16 g, 19.1%) as a white solid.

$^1$H NMR (400 MHz, DMSO-d$_6$) δ: 10.85 (d, J=2.4 Hz, 1H), 8.32 (s, 2H), 8.14 (d, J=7.4 Hz, 1H), 7.54 (t, J=7.4 Hz, 2H), 7.31 (d, J=8.1 Hz, 1H), 7.21 (d, J=2.4 Hz, 1H), 7.15-6.92 (m, 4H), 4.72 (dd, J=11.4, 3.5 Hz, 1H), 4.54-4.50 (m, 1H), 4.1-4.04 (m, 2H), 3.81 (p, J=6.3 Hz, 1H), 3.69 (dd, J=6.6, 4.3 Hz, 2H), 3.14 (dd, J=15.0, 5.1 Hz, 1H), 2.99 (dd, J=15.0, 9.1 Hz, 1H), 2.44-2.42 (m, 1H), 1.84 (dd, J=13.6, 3.5 Hz, 1H), 1.68-1.56 (m, 1H), 1.18 (d, J=6.3 Hz, 3H), 0.97 (d, J=6.3 Hz, 3H), 0.76-0.65 (m, 1H), 0.63-0.59 (m, 1H).

HPLC purity: 97.68%

LCMS Calculated for C$_{25}$H$_{34}$N$_6$O$_6$: 514.25; Observed: 515.15[M+1]$^+$.

G. Synthesis of NRX-4012:

Scheme 13

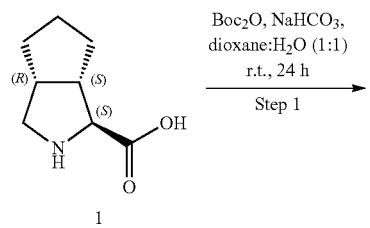

Boc$_2$O, NaHCO$_3$,
dioxane:H$_2$O (1:1)
r.t., 24 h
Step 1

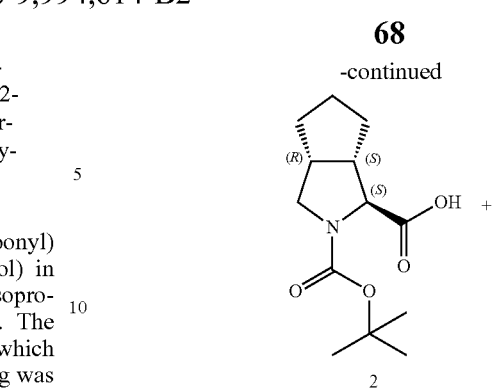

HATU, DIPEA,
DMF, r.t.,
Step 2

4M Dioxne•HCl
Step 3

BocHN
HATU, DIPEA,
DCM, r.t., 24 h
Step 4

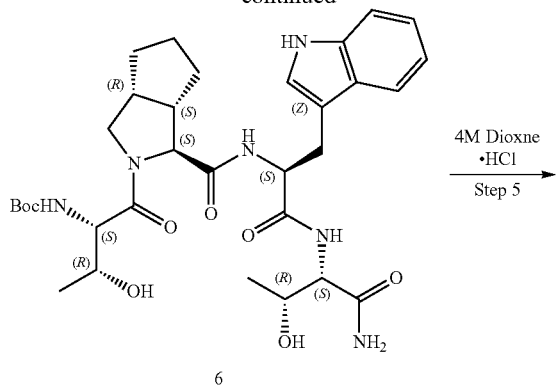

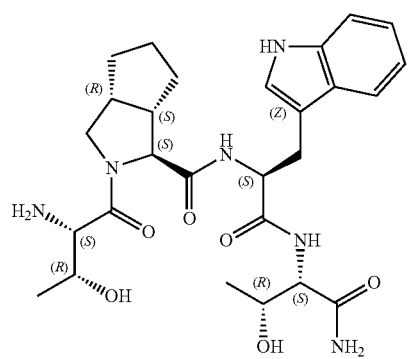

NRX-4012

Synthesis of (1S,3aR,6aS)-2-(tert-butoxycarbonyl) octahydrocyclopenta[c]pyrrole-1-carboxylic acid (2)

To a stirred solution of compound 1 (1.1 g, 7.09 mmol) and sodium bicarbonate (1.18 g, 14.1 mmol) in water (20 mL), di-tertiary butyl dicarbonate (2.25 g, 10.6 mmol) in dioxane (20 mL) was added and the reaction mixture was allowed to stir at room temperature for 12 h. After completion of the reaction as indicated by TLC, the reaction mixture was quenched with water and extracted with ethyl acetate. The aqueous layer was acidified by using 1N HCl to pH 2 and extracted with ethyl acetate. The organic layers were washed with brine, dried over anhydrous $Na_2SO_4$ and concentrated under reduced pressure to obtain a crude residue, which was purified by column chromatography to afford compound 2 (1.3 g, 72%).

MS (ESI) m/z 256 $[M+1]^+$

Synthesis of (1S,3aR,6aS)-tert-butyl 1-(((S)-1-(((2S,3R)-1-amino-3-hydroxy-1-oxobutan-2-yl)amino)-3-(1H-indol-3-yl)-1-oxopropan-2-yl)carbamoyl)hexahydrocyclopenta[c]pyrrole-2(1H)-carboxylate(4)

To a stirred solution of compound 2 (1.3 g, 5.07 mmol) in DCM (20 mL), HATU (2.89 g, 7.61 mmol) and diisopropylethylamine (2.65 mL, 15.2 mmol) were added. The solution was stirred at room temperature for 35 min, followed by compound 3 (1.54 g, 5.07 mmol and stirred at room temperature for 12 h. The progress of the reaction was monitored by TLC & LCMS. After complete consumption of starting material, the reaction was quenched with water and extracted with DCM. The organic layers were washed with brine, dried over anhydrous $Na_2SO_4$ and concentrated under reduced pressure to obtain a crude residue, which was purified by column chromatography to afford compound 4 (2.3 g, 83%).

LCMS: 442 $(M-Boc)^+$.

Synthesis of (1S,3aR,6aS)—N—((S)-1-(((2S,3R)-1-amino-3-hydroxy-1-oxobutan-2-yl)amino)-3-(1H-indol-3-yl)-1-oxopropan-2-yl)octahydrocyclopenta[c]pyrrole-1-carboxamide (5)

To a stirred solution of compound 4 (2.2 g, 4.06 mmol) in dioxane (5 mL), 4M HCl in dioxane (10 mL) was added at 0° C. and the reaction mixture was stirred at rt for 3 h. The progress of the reaction was monitored by TLC & LCMS. After complete consumption of compound 4, the solvent was removed under reduced pressure to obtain a crude residue, which was purified by repeated washing with DCM to afford compound 5 (1.65 g, 92%).

MS (ESI) m/z 442 $[M+1]^+$.

Synthesis of tert-butyl ((2S,3R)-1-41S,3aR,6aS)-1-(((S)-1-(((2S,3R)-1-amino-3-hydroxy-1-oxobutan-2-yl)amino)-3-(1H-indol-3-yl)-1-oxopropan-2-yl)carbamoyl)hexahydrocyclopenta[c]pyrrol-2(1H)-yl)-3-hydroxy-1-oxobutan-2-yl)carbamate (6)

To a stirred solution of (2S,3R)-2-((tert-butoxycarbonyl)amino)-3-hydroxybutanoic acid (1.6 g, 3.62 mmol) in DCM (20 mL), HATU (2.06 g, 5.44 mmol) and diisopropylethylamine (1.40 g, 10.8 mmol) were added. The solution was stirred at room temperature for 35 min followed by compound 5 (0.79 g, 3.62 mmol) was added and stirred at rt for 12 h. The progress of the reaction was monitored by TLC & LCMS. After complete consumption of starting material, the reaction was quenched with water and extracted with DCM. The organic layers were washed with sodium bicarbonate solution and brine, dried over anhydrous $Na_2SO_4$ and concentrated under reduced pressure to obtain a crude residue, which was purified by column chromatography to afford compound 6 (1.8 g, 77.5%).

MS (ESI) m/z: 543 $[M-Boc]^+$.

Synthesis of (1S,3aR,6aS)—N—((S)-1-(((2S,3R)-1-amino-3-hydroxy-1-oxobutan-2-yl)amino)-3-(1H-indol-3-yl)-1-oxopropan-2-yl)-2-((2S,3R)-2-amino-3-hydroxybutanoyl)octahydrocyclopenta[c]pyrrole-1-carboxamide (NRX-4012)

To a stirred solution of compound 6 (0.65 g, 1.01 mmol) in dioxane (5 mL), 4 M HCl in dioxane (10 mL) was added at 0° C. and the reaction mixture was stirred at rt for 3 h.

The progress of the reaction was monitored by TLC & LCMS. After complete consumption of compound 6, the solvent was removed under reduced pressure to obtain a crude residue, which was purified by Prep HPLC (Basic method) to obtain compound NRX-4012 (0.19 g, 35%) as an off-white solid.

$^1$H NMR (400 MHz, DMSO-$d_6$) δ: 10.88-10.81 (m, 1H), 8.36 (s, 2H), 8.17 (d, J=7.3 Hz, 1H), 7.61-7.51 (m, 2H), 7.31

(d, J=8.1 Hz, 1H), 7.20 (d, J=2.4 Hz, 1H), 7.17-6.92 (m, 5H), 4.51 (td, J=8.2, 5.0 Hz, 1H), 4.22-4.09 (m, 1H), 4.09-3.98 (m, 2H), 3.73-3.38 (m, 3H), 3.31-3.13 (m, 1H), 3.11-2.97 (m, 1H), 1.85-1.33 (m, 6H), 1.10-0.94 (m, 6H).

HPLC purity: 95.3%

LCMS Calculated for $C_{27}H_{38}N_6O_6$: 542.64; Observed: 543.55 $[M+1]^+$.

Example 4—Synthesis of Compounds of Formula (V)

A. Synthesis of NRX-1001 & 1002:

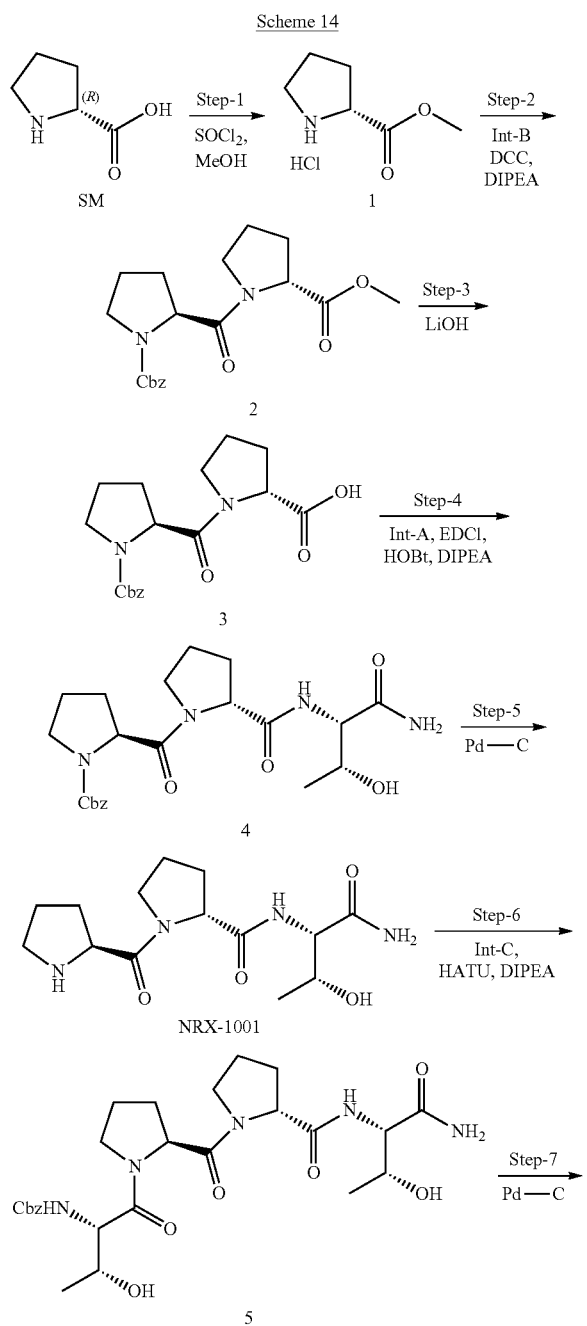

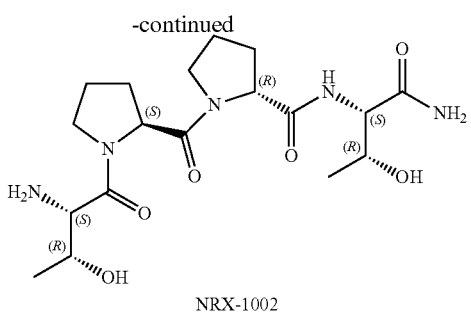

NRX-1002

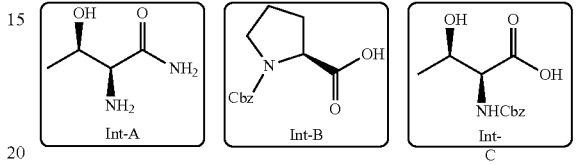

Synthesis of Methyl D-Prolinate Hydrochloride (1)

To a stirred solution of D-proline (SM) (20 g, 173.9 mmol) in methanol (200 mL) was added thionyl chloride (16 mL, 208.4 mmol) drop wise at 0° C. under argon atmosphere. The reaction mixture was allowed to stir at 80° C. for 8 h. After consumption of the starting material (by TLC), reaction mixture was brought to RT and volatiles were evaporated under reduced pressure. Obtained residue was triturated with ether to afford compound 1 (21.5 g, 75%) as thick syrup.

$^1$H-NMR: (500 MHz, DMSO-$d_6$): δ 9.10 (s, 1H), 4.34-4.24 (m, 1H), 3.75 (s, 3H), 3.20-3.16 (m, 2H), 2.27-2.21 (m, 2H), 2.01-1.87 (m, 2H).

Synthesis of benzyl (S)-2-((R)-2-(methoxycarbonyl)pyrrolidine-1-carbonyl)pyrrolidine-1-carboxylate (2)

To a stirring solution of compound 1 (1 g, 6.06 mmol) in DCM (50 mL) were added and DIPEA (3.2 ml, 18.18 mmol), DCC (1.8 g, 9.09 mmol) and Int-B (1.88 g, 7.27 mmol) at 0° C. under argon atmosphere. The reaction mixture was brought to RT and stirred for 16 h. After consumption of the starting material (by TLC), the reaction mixture was diluted with water (20 mL) and extracted with DCM (3×50 mL). Combined organic layers were dried over anhydrous $Na_2SO_4$ and concentrated under reduced pressure to afford crude compound which was purified by column chromatography by eluting with 2% MeOH/DCM to obtain compound 2 (1 g, 47%) as thick syrup.

$^1$H-NMR: (500 MHz, DMSO-$d_6$): δ 7.37-7.28 (m, 5H), 5.11-5.00 (m, 2H), 4.57-4.51 (m, 1H), 4.27-4.23 (m, 1H), 3.65 (s, 3H), 3.47-3.36 (m, 4H), 2.21-2.08 (m, 2H), 1.95-1.70 (m, 4H), 1.27-1.09 (m, 2H).

LCMS (m/z): 361.4 $[M^++1]$

Synthesis of ((benzyloxy)carbonyl)-L-prolyl-D-proline (3)

To a stirring solution of compound 2 (1 g, 2.7 mmol) in THF:$H_2O$ (10 mL, 1:1) was added LiOH (232 mg, 5.5 mmol) at 0° C. The reaction mixture was brought to RT and stirred for 18 h. After consumption of the starting material (by TLC), volatiles were evaporated under reduced pressure. The residue was diluted with water (20 mL), pH was adjusted to 2 with citric acid and extracted with EtOAc (2×30 mL). Combined organic layer was dried over $Na_2SO_4$ and concentrated to afford compound 3 (800 mg, 83%) as sticky solid.

$^1$H-NMR: (500 MHz, DMSO-$d_6$): δ 12.45 (br s, 1H), 7.31-7.27 (m, 5H), 5.12-5.00 (m, 2H), 4.25-4.17 (m, 2H), 3.46-3.17 (m, 4H), 2.19-2.08 (m, 2H), 1.85-1.72 (m, 6H).

LCMS (m/z): 347.4 [M$^+$+1]

Synthesis of benzyl (S)-2-((R)-2-(((2S,3R)-1-amino-3-hydroxy-1-oxobutan-2-yl)carbamoyl)pyrrolidine-1-carbonyl)pyrrolidine-1-carboxylate (4)

To a stirring solution of compound 3 (700 mg, 2.01 mmol) in DCM (15 mL) was added DIPEA (1.1 mL, 6.05 mmol), EDCI (577 mg, 3.02 mmol) and HOBt (408 mg, 3.02 mmol) at 0° C. under argon atmosphere. The reaction mixture was stirred at RT for 10 minutes. Then Int-A (285 g, 2.4 mmol) in DMF (10 mL) was added at 0° C. and allowed to stir at RT for 18 h. The reaction mixture was brought to RT and stirred for 16 h. After consumption of the starting material (by TLC), the reaction mixture was diluted with water (10 mL) and extracted with DCM (3×20 mL). Combined organic layers were dried over anhydrous $Na_2SO_4$ and concentrated under reduced pressure to afford crude compound which was purified by column chromatography by eluting with 2% MeOH/DCM to obtain compound 4 (630 mg, 70%) as off white solid.

$^1$H-NMR: (500 MHz, DMSO-$d_6$): δ 8.01-7.95 (dd, J=23.0, 8.5 Hz, 1H), 7.41-7.28 (m, 5H), 5.12-4.99 (m, 2H), 4.90-4.81 (m, 2H), 4.59-4.45 (m, 2H), 4.18-4.06 (m, 2H), 3.52-3.38 (m, 4H), 2.01-1.67 (m, 9H), 1.04-1.00 (m, 3H).

LCMS (m/z): 447.5 [M$^+$+1]

Synthesis of (R)-1-(L-prolyl)-N-((2S,3R)-1-amino-3-hydroxy-1-oxobutan-2-yl)pyrrolidine-2-carboxamide (NRX-1001)

To a stirring solution of compound 4 (570 mg, 1.27 mmol) in methanol (10 mL) was added 50% wet 10% Pd/C (150 mg) at RT and stirred for 12 h under $H_2$ atmosphere. After consumption of the starting material (by TLC), the reaction mixture was filtered through a pad of celite, filtrate was concentrated under reduced pressure and dried under vacuum to afford NRX-1001 (300 mg, 75%) an off white solid.

$^1$H-NMR: (400 MHz, $D_2O$): δ 4.61-4.57 (m, 1H), 4.46-4.39 (m, 2H), 4.10-4.07 (m, 1H), 3.85-3.70 (m, 2H), 3.19-3.13 (m, 1H), 2.97-2.91 (m, 1H), 2.43-2.30 (m, 2H), 2.17-2.02 (m, 3H), 1.95-1.78 (m, 3H), 1.27-1.30 (m, 3H).

LCMS (ESI): m/z 313.3 [M$^+$+1]
UPLC: 95.36%

Synthesis of benzyl ((2S,3R)-1-((S)-2-((R)-2-(((2S, 3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (5)

To a stirring solution of NRX-1001 (200 mg, 0.64 mmol) in DCM (10 mL) was added DIPEA (0.35 mL, 1.92 mmol), HATU (243 mg, 0.64 mmol) and Int C (194 mg, 0.76 mmol) and at 0° C. under argon atmosphere. The reaction mixture was brought to RT and stirred for 18 h. After consumption of the starting material (by TLC), the reaction mixture was diluted with water (10 mL) and extracted with 10% MeOH/DCM (3×20 mL). Combined organic layers were dried over anhydrous $Na_2SO_4$ and concentrated under reduced pressure to afford crude compound which was purified by column chromatography by eluting with 3% MeOH/DCM to obtain compound 5 (260 mg, 74%) as an off white solid.

$^1$H-NMR: (400 MHz, $CD_3OD$): δ 7.35-7.29 (m, 5H), 5.08 (s, 2H), 4.95-4.93 (m, 1H), 4.54-4.52 (m, 1H), 4.36-4.30 (m, 2H), 4.21-4.20 (m, 1H), 3.98-3.94 (m, 2H), 3.76-3.67 (m, 2H), 3.64-3.54 (m, 1H), 2.10-2.05 (m, 2H), 1.38-1.35 (m, 6H), 1.28-1.26 (m, 3H), 1.17-1.14 (m, 3H).

LCMS (m/z): 548.6 [M$^+$+1]

Synthesis of (R)-1-(L-threonyl-L-prolyl)-N-((2S, 3R)-1-amino-3-hydroxy-1-oxobutan-2-yl)pyrrolidine-2-carboxamide (NRX-1002)

To a stirring solution of compound 5 (260 mg, 0.47 mmol) in methanol (5 mL) was added 50% wet 10% Pd/C (100 mg) at RT and stirred for 2 h under $H_2$ atmosphere. After consumption of the starting material (by TLC), the reaction mixture was filtered through a pad of celite and the filtrate was dried over anhydrous $Na_2SO_4$ and concentrated under reduced pressure to afford crude compound which was purified by column chromatography by eluting with 1% aq.$NH_3$ in 15% MeOH/DCM to obtain NRX-1002 (80 mg, 40%) as a white solid.

$^1$H-NMR: (400 MHz, $D_2O$): δ 4.64-4.55 (m, 2H), 4.41-4.26 (m, 2H), 3.99-3.59 (m, 6H), 2.56-2.27 (m, 2H), 2.22-2.16 (m, 6H), 1.30-1.22 (m, 6H).

LCMS (ESI): m/z 414.5 [M$^+$+1]
UPLC 94.94%

B. Synthesis of NRX-1015 & 1016:

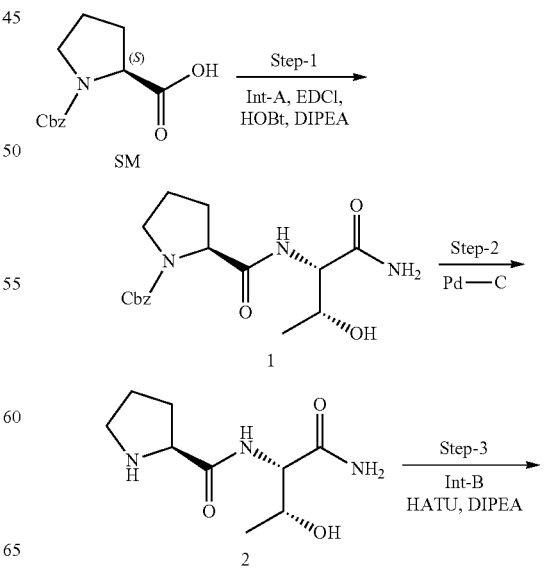

Scheme 15

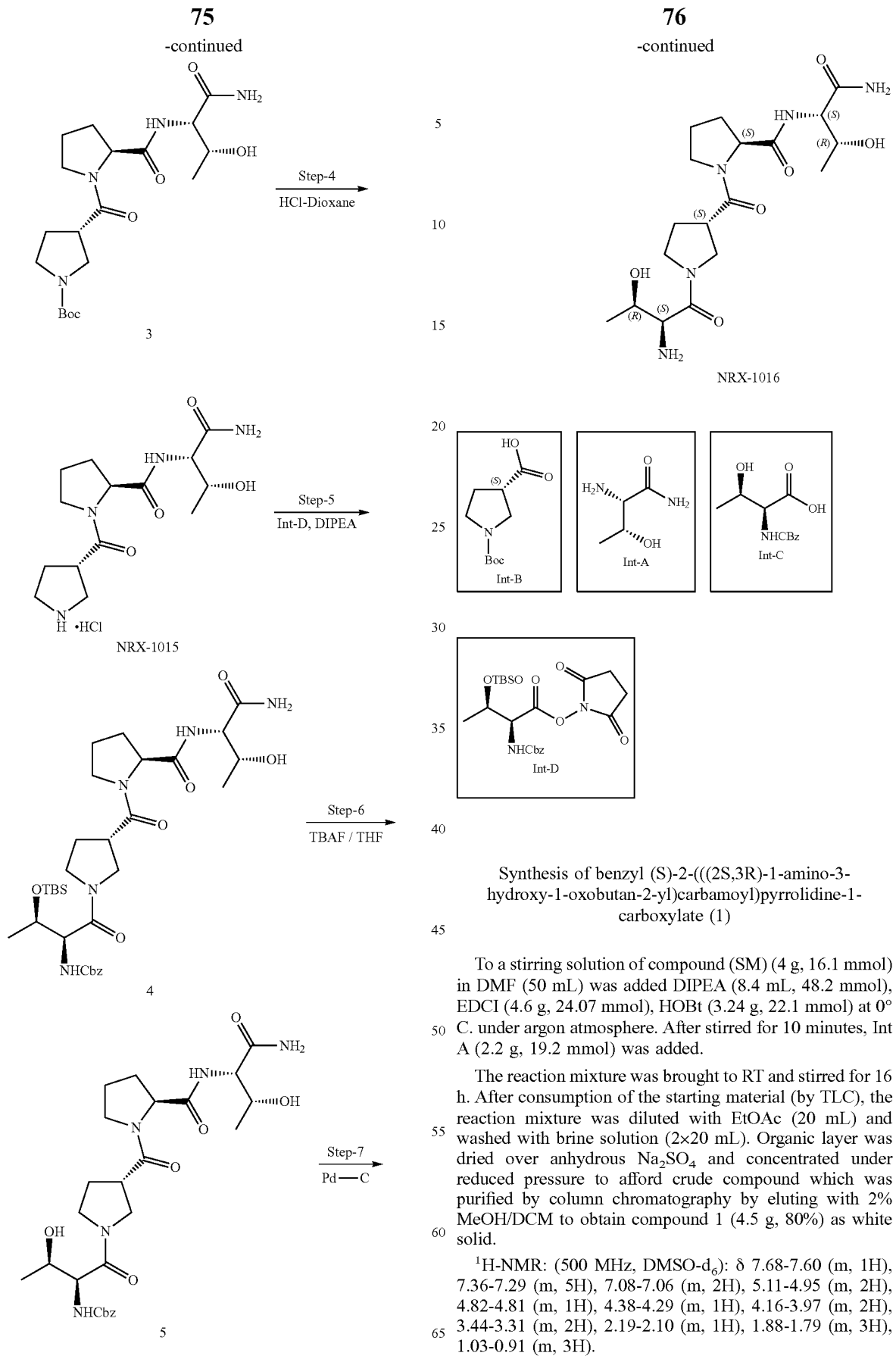

Synthesis of benzyl (S)-2-(((2S,3R)-1-amino-3-hydroxy-1-oxobutan-2-yl)carbamoyl)pyrrolidine-1-carboxylate (1)

To a stirring solution of compound (SM) (4 g, 16.1 mmol) in DMF (50 mL) was added DIPEA (8.4 mL, 48.2 mmol), EDCI (4.6 g, 24.07 mmol), HOBt (3.24 g, 22.1 mmol) at 0° C. under argon atmosphere. After stirred for 10 minutes, Int A (2.2 g, 19.2 mmol) was added.

The reaction mixture was brought to RT and stirred for 16 h. After consumption of the starting material (by TLC), the reaction mixture was diluted with EtOAc (20 mL) and washed with brine solution (2×20 mL). Organic layer was dried over anhydrous $Na_2SO_4$ and concentrated under reduced pressure to afford crude compound which was purified by column chromatography by eluting with 2% MeOH/DCM to obtain compound 1 (4.5 g, 80%) as white solid.

$^1$H-NMR: (500 MHz, DMSO-$d_6$): δ 7.68-7.60 (m, 1H), 7.36-7.29 (m, 5H), 7.08-7.06 (m, 2H), 5.11-4.95 (m, 2H), 4.82-4.81 (m, 1H), 4.38-4.29 (m, 1H), 4.16-3.97 (m, 2H), 3.44-3.31 (m, 2H), 2.19-2.10 (m, 1H), 1.88-1.79 (m, 3H), 1.03-0.91 (m, 3H).

LCMS (m/z): 350.3 [M$^+$+1]

Synthesis of (S)—N-((2S,3R)-1-amino-3-hydroxy-1-oxobutan-2-yl)pyrrolidine-2-carboxamide (2)

To a stirring solution of compound 1 (2.3 g, 6.5 mmol) in methanol (50 mL) was added 50% wet 10% Pd/C (800 mg) at RT and stirred for 2 h under $H_2$ atmosphere. After consumption of the starting material (by TLC), the reaction mixture was filtered through a pad of celite and the filtrate was washed with pentane (10 mL) and $Et_2O$ (10 mL). Obtained filtrate was concentrated under reduced pressure and dried under vacuum to afford compound 2 (1.2 g, 85%) as semi solid.

$^1$H-NMR: (500 MHz, DMSO-$d_6$): δ 8.10 (d, J=9.0 Hz, 1H), 7.20-7.16 (m, 2H), 4.91 (d, J=4.5 Hz, 1H), 4.07-4.02 (m, 2H), 3.59-3.56 (m, 1H), 2.92-2.87 (m, 2H), 2.78-2.73 (m, 1H), 1.97-1.91 (m, 1H), 1.70-1.57 (m, 3H), 1.00-0.95 (m, 3H).

LCMS (ESI): m/z 216.0 [M$^+$+1]

Synthesis of tert-butyl (S)-3-((S)-2-(((2S,3R)-1-amino-3-hydroxy-1-oxobutan-2-yl)carbamoyl)pyrrolidine-1-carbonyl)pyrrolidine-1-carboxylate (3)

To a stirring solution of compound 2 (125 mg, 0.58 mmol) in DMF (1.5 mL) was added DIPEA (0.3 mL, 1.74 mmol), HATU (220 mg, 0.58 mmol) and Int B (124 mg, 0.58 mmol) at 0° C. under argon atmosphere. The reaction mixture was brought to RT and stirred for 16 h. After consumption of the starting material (by TLC), the reaction mixture was diluted with water (10 mL) and extracted with 5% MeOH/DCM (2×50 mL). Combined organic layers were dried over anhydrous $Na_2SO_4$ and concentrated under reduced pressure to afford crude compound which was purified by column chromatography by eluting with 5% MeOH/DCM to obtain compound 3 (160 mg, 66%) as sticky material.

$^1$H-NMR: (500 MHz, DMSO-$d_6$): δ 7.54-7.47 (m, 1H), 7.06 (s, 2H), 4.91-4.80 (m, 2H), 4.16-3.98 (m, 2H), 3.62-3.42 (m, 3H), 3.36-3.32 (m, 1H), 3.16-3.13 (m, 2H), 3.08-3.01 (m, 1H), 2.06-2.04 (m, 2H), 1.89-1.78 (m, 4H), 1.39 (s, 9H), 1.04-1.01 (m, 3H).

LCMS (m/z): 411.3 [M$^+$−1]

Synthesis of (S)—N-((2S,3R)-1-amino-3-hydroxy-1-oxobutan-2-yl)-1-((S)-pyrrolidine-3-carbonyl)pyrrolidine-2-carboxamide (NRX-1015)

To a solution of compound 3 (630 mg, 1.53 mmol) in DCM (5 mL) was added 4N HCl in dioxane (1.1 mL, 4.59 mmol) at 0° C. under argon atmosphere. The reaction mixture was allowed to stir at RT for 4 h. After consumption of the starting material (by TLC), volatiles were evaporated under reduced pressure. Obtained crude was triturated with methyl tertiary-butyl ether (2×10 mL) and dried under vacuum to afford NRX-1015 (532 mg, 95%) as an off white solid.

$^1$H-NMR: (400 MHz, $D_2O$): δ 4.59-4.56 (m, 1H), 4.39-4.36 (m, 1H), 4.34-4.32 (m, 1H), 3.83-3.78 (m, 2H), 3.68-3.64 (m, 1H), 3.61-3.56 (m, 2H), 3.54-3.46 (m, 2H), 2.54-2.37 (m, 2H), 2.23-2.03 (m, 4H), 1.30 (t, J=6.0 Hz, 3H).

LCMS (ESI): m/z 313.5 [M$^+$+1]

UPLC: 94.13%

Synthesis of benzyl ((2S,3R)-1-((S)-3-((S)-2-(((2S,3R)-1-amino-3-hydroxy-1-oxobutan-2-yl)carbamoyl)pyrrolidine-1-carbonyl)pyrrolidin-1-yl)-3-((tert-butyldimethylsilyl)oxy)-1-oxobutan-2-yl)carbamate (5)

To a stirring solution of NRX-1015 (300 mg, 0.86 mmol) in DMF (3 mL) was added DIPEA (0.45 mL, 2.58 mmol) and Int D (479 mg, 1.03 mmol) at 0° C. under argon atmosphere. The reaction mixture was brought to RT and stirred for 4 h. After consumption of the starting material (by TLC), the reaction mixture was diluted with water (5 mL) and extracted with EtOAc (2×10 mL). Combined organic layers were dried over anhydrous $Na_2SO_4$ and concentrated under reduced pressure to afford crude compound which was purified by column chromatography by eluting with 3% MeOH/DCM to obtain compound 5 (400 mg, 70%) as sticky liquid.

$^1$H-NMR: (500 MHz, DMSO-$d_6$): δ 7.94-7.89 (m, 1H), 7.56-7.50 (m, 1H), 7.34-7.26 (m, 5H), 7.06 (s, 2H), 4.79 (s, 2H), 4.69-4.65 (m, 1H), 4.40-4.38 (m, 1H), 4.26-4.22 (m, 2H), 4.07-4.03 (m, 2H), 3.93-3.87 (m, 1H), 3.66-3.86 (m, 2H), 3.39-3.34 (m, 3H), 3.19-3.09 (m, 1H), 2.23-2.07 (m, 2H), 1.94-1.79 (m, 4H), 1.08-1.02 (m, 6H), 0.81 (s, 9H), 0.06-0.01 (m, 6H).

LCMS (ESI): m/z 662.8 [M$^+$+1]

Synthesis of benzyl ((2S,3R)-1-((S)-3-((S)-2-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (6)

To a stirring solution of compound 5 (400 mg, 0.61 mmol) in THF (2 mL) was added TBAF (189 mg, 0.72 mmol) at 0° C. under argon atmosphere. The reaction mixture was brought to RT and stirred for 4 h. After consumption of the starting material (by TLC), the reaction mixture was diluted with water (5 mL) and extracted with 10% MeOH/DCM (2×10 mL). Combined organic layers were dried over anhydrous $Na_2SO_4$ and concentrated under reduced pressure to afford crude compound which was purified by column chromatography by eluting with 4% MeOH/DCM to obtain compound 6 (200 mg, 60%) as off white solid.

$^1$H-NMR: (400 MHz, $D_2O$): δ 7.44 (s, 5H), 5.15 (s, 2H), 4.52-4.48 (m, 1H), 4.37-4.28 (m, 2H), 4.09-3.97 (m, 1H), 3.76-3.46 (m, 8H), 2.34-2.32 (m, 2H), 2.05-1.92 (m, 4H), 0.97-0.93 (m, 6H).

LCMS (ESI): m/z 548.6 [M$^+$+1]

Synthesis of (S)-1-((S)-1-(L-threonyl)pyrrolidine-3-carbonyl)-N-((2S,3R)-1-amino-3-hydroxy-1-oxobutan-2-yl)pyrrolidine-2-carboxamide (NRX-1016)

To a stirring solution of compound 6 (700 mg, 1.28 mmol) in methanol (10 mL) was added 50% wet 10% Pd/C (300 mg) at RT and stirred for 4 h under $H_2$ atmosphere. After consumption of the starting material (by TLC), the reaction mixture was filtered through a pad of celite and the filtrate was washed with pentane (10 mL) and $Et_2O$ (10 mL). Obtained filtrate was concentrated under reduced pressure to afford crude compound which was purified by column chromatography by eluting with 15% MeOH/DCM+1 mL aq.$NH_3$ to obtain NRX-1016 (250 mg, 47%) as an off white solid.

¹H-NMR: (400 MHz, D₂O): δ 4.89-4.85 (m, 1H), 4.58-4.55 (m, 1H), 4.42-4.33 (m, 2H), 4.02-3.97 (m, 1H), 3.86-3.53 (m, 7H), 2.45-2.33 (m, 2H), 2.22-2.01 (m, 4H), 1.30-1.26 (m, 6H).

LCMS (ESI): m/z 414.5 [M+$^+$1]

UPLC: 95.15%

C. Synthesis of NRX-1005 & 1006:

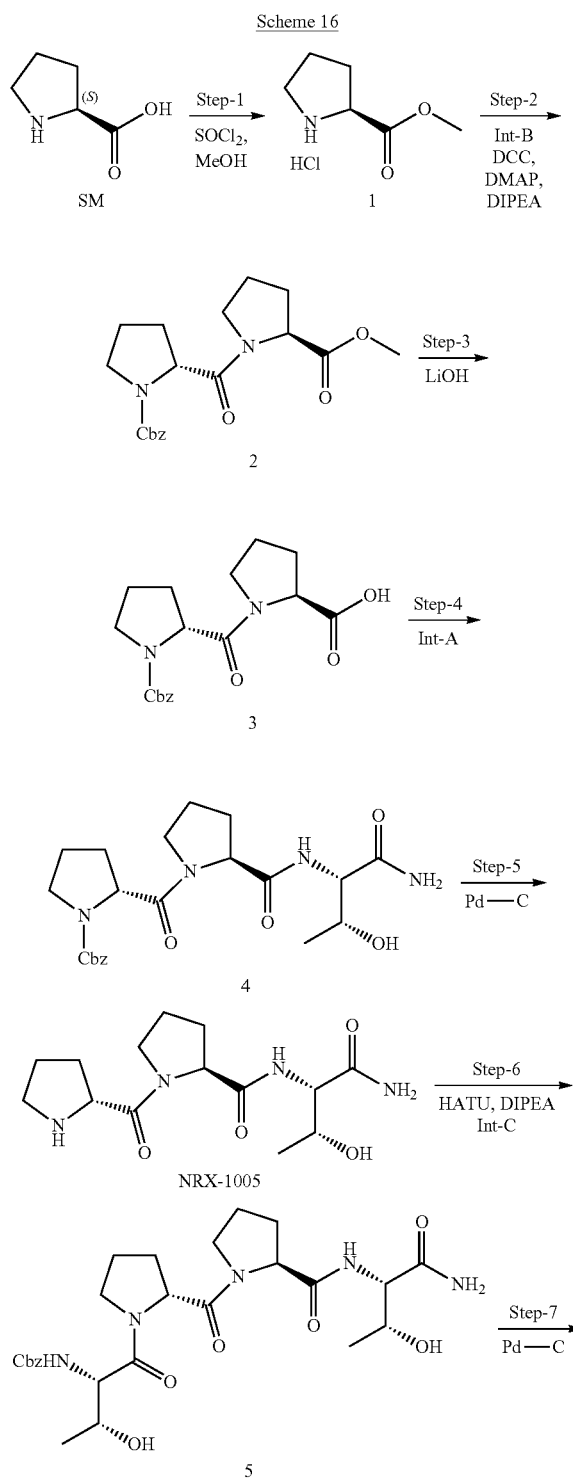

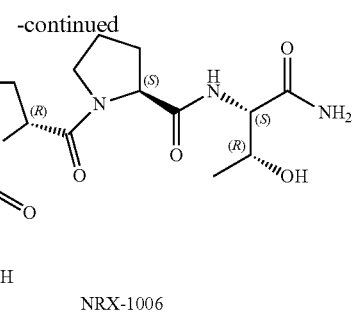

Synthesis of methyl L-prolinate (1)

To a stirred solution of L-proline (SM) (25 g, 217.3 mmol) in methanol (10 mL) was added thionyl chloride (19 mL, 260.8 mmol) drop wise at 0° C. under argon atmosphere. The reaction mixture was allowed to stir at 70° C. for 16 h. After consumption of the starting material (by TLC), reaction mixture was brought to RT and volatiles were evaporated under reduced pressure to afford compound 1 (35 g, 98%) as yellow color syrup.

¹H-NMR: (500 MHz, DMSO-d₆): δ 9.09 (s, 1H), 4.35-4.24 (m, 1H), 3.75 (s, 3H), 3.21-3.16 (m, 2H), 2.28-2.21 (m, 2H), 2.01-1.88 (m, 2H).

LCMS (m/z): 130.1 [M$^+$+1]

Synthesis of benzyl (R)-2-((S)-2-(methoxycarbonyl)pyrrolidine-1-carbonyl)pyrrolidine-1-carboxylate (2)

To a stirring solution of compound 1 (5 g, 20.07 mmol) in DCM (50 mL) were added Int B (4.98 g, 30.1 mmol), DCC (6.21 g, 30.1 mmol) and DMPP (245 mg, 2.01 mmol) at 0° C. under argon atmosphere. The reaction mixture was stirred at RT for 10 minutes. Then DIPEA (6.97 mL, 40.1 mmol) was added at 0° C. and allowed to stir at RT for 16 h. After consumption of the starting material (by TLC), the reaction mixture was diluted with water (20 mL) and extracted with DCM (3×50 mL). Combined organic layers were dried over anhydrous Na₂SO₄ and concentrated under reduced pressure to afford crude compound which was purified by column chromatography by eluting with 50% EtOAc/n-hexane to obtain compound 2 (5 g, 69%) as brown solid.

¹H-NMR: (500 MHz, DMSO-d₆): δ 7.53-7.27 (m, 5H), 5.10-5.00 (m, 1H), 4.56-4.52 (m, 1H), 4.26-4.24 (m, 1H), 3.72-3.69 (m, 1H), 3.64 (s, 3H), 3.46-3.36 (m, 4H), 2.20-2.09 (m, 2H), 1.95-1.82 (m, 6H).

LCMS (m/z): 361.3 [M$^+$+1]

Synthesis of ((benzyloxy)carbonyl)-D-prolyl-L-proline (3)

To a stirring solution of compound 2 (400 mg, 1.11 mmol) in THF:H$_2$O (10 mL, 1:1) was added LiOH.H$_2$O (140 mg, 3.33 mmol) at 0° C. The reaction mixture was brought to RT and stirred for 16 h. After consumption of the starting material (by TLC), volatiles were evaporated under reduced pressure, washed with 1N HCl and extracted with DCM (2×20 mL). Combined organic layer was dried over Na$_2$SO$_4$ and concentrated to afford compound 3 (240 mg, 63%) as white color sticky solid.

$^1$H-NMR: (500 MHz, DMSO-d$_6$): δ 12.82 (br s, 1H), 7.36-7.26 (m, 5H), 5.12-5.01 (m, 2H), 4.24-4.15 (m, 2H), 3.42-3.16 (m, 4H), 2.19-2.08 (m, 6H), 1.60-1.52 (m, 2H).

LCMS (m/z): 347.3 [M$^+$+1]

Synthesis of benzyl (R)-2-((S)-2-(((2S,3R)-1-amino-3-hydroxy-1-oxobutan-2-yl)carbamoyl)pyrrolidine-1-carbonyl)pyrrolidine-1-carboxylate (4)

To a stirring solution of compound 3 (3 g, 8.6 mmol) in DMF (15 mL) was added Int A (1.22 g, 10.4 mmol), EDCI (2.48 g, 12.9 mmol), HOBt (1.75 g, 12.9 mmol) and DIPEA (4.65 mL, 25.8 mmol) at 0° C. under argon atmosphere. The reaction mixture was brought to RT and stirred for 16 h. After consumption of the starting material (by TLC), the reaction mixture was diluted with water (15 mL) and extracted with DCM (3×50 mL). Combined organic layers were dried over anhydrous Na$_2$SO$_4$ and concentrated under reduced pressure to afford crude compound which was purified by column chromatography by eluting with 50% EtOAc/hexane to obtain compound 4 (2.9 g, 75%) as off white sticky solid.

$^1$H-NMR: (400 MHz, DMSO-d$_6$): δ 7.91-7.88 (dd, J=13.6, 8.8 Hz, 0.5H), 7.39-7.27 (m, 5H), 5.19-5.01 (m, 2H), 5.12-5.03 (m, 1H), 4.97-4.83 (m, 2H), 4.68-4.51 (m, 1H), 4.36-4.26 (m, 1H), 4.14-3.94 (m, 1.5H), 3.89-3.82 (m, 1H), 3.56-3.53 (m, 0.5H), 3.45-3.37 (m, 3H), 3.24-3.20 (m, 0.5H), 1.98-1.67 (m, 8H), 1.04-1.00 (m, 3H).

LCMS (m/z): 447.6 [M$^+$+1]

Synthesis of (S)-1-(D-prolyl)-N-((2S,3R)-1-amino-3-hydroxy-1-oxobutan-2-yl)pyrrolidine-2-carboxamide (NRX-1005)

To a stirring solution of compound 4 (700 mg, 1.56 mmol) in methanol (10 mL) was added 50% wet 10% Pd/C (100 mg) at RT and stirred for 16 h under H$_2$ atmosphere. After consumption of the starting material (by TLC), the reaction mixture was filtered through a pad of celite and the filtrate was washed with pentane (10 mL) and Et$_2$O (10 mL). Obtained filtrate was concentrated under reduced pressure and dried under vacuum to afford NRX-1005 (400 mg, 81%) as white color solid.

$^1$H-NMR: (500 MHz, D$_2$O): δ 4.55-4.52 (m, 1H), 4.37-4.30 (m, 2H), 4.09-4.06 (m, 1H), 3.83-3.78 (m, 1H), 3.71-3.62 (m, 1H), 3.16-3.11 (m, 1H), 2.94-2.89 (m, 1H), 2.40-2.27 (m, 2H), 2.10-2.01 (m, 3H), 1.94-1.76 (m, 3H), 1.28 (t, J=5.2 Hz, 3H).

LCMS (ESI): m/z 313.3 [M$^+$+1]
UPLC: 99.67%

Synthesis of benzyl ((2S,3R)-1-((R)-2-((S)-2-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (5)

To a stirring solution of NRX-1005 (400 mg, 1.28 mmol) in DMF (8 mL) was added HATU (487 mg, 1.28 mmol) and Int C (356 mg, 1.41 mmol) and DIPEA (0.44 mL, 2.56 mmol) at 0° C. under argon atmosphere. The reaction mixture was brought to RT and stirred for 16 h. After consumption of the starting material (by TLC), the reaction mixture was diluted with water (10 mL) and extracted with DCM (2×20 mL) and 10% MeOH/DCM (2×20 mL). Combined organic layers were dried over anhydrous Na$_2$SO$_4$ and concentrated under reduced pressure to afford crude compound which was purified by column chromatography by eluting with 7% MeOH/DCM to obtain compound 5 (250 mg, 35%) as brown sticky solid.

$^1$H-NMR: (400 MHz, D$_2$O): δ 7.53-7.51 (m, 5H), 5.27-5.19 (m, 2H), 4.57-4.51 (m, 2H), 4.43-4.29 (m, 2H), 4.24-4.18 (m, 1H), 4.13-4.05 (m, 1H), 3.85-3.77 (m, 3H), 3.63-3.57 (m, 1H), 2.44-2.41 (m, 2H), 2.17-2.01 (m, 6H), 1.28-1.26 (m, 6H).

LCMS (m/z): 548.6 [M$^+$+1]

Synthesis of (S)-1-(L-threonyl-D-prolyl)-N-((2S,3R)-1-amino-3-hydroxy-1-oxobutan-2-yl)pyrrolidine-2-carboxamide (NRX-1006)

To a stirring solution of compound 5 (250 mg, 0.45 mmol) in methanol (10 mL) was added 50% wet 10% Pd/C (80 mg) at RT and stirred for 16 h under H$_2$ atmosphere. After consumption of the starting material (by TLC), the reaction mixture was filtered through a pad of celite and the filtrate was washed with pentane (10 mL) and Et$_2$O (10 mL). Organic layer was dried over anhydrous Na$_2$SO$_4$ and concentrated under reduced pressure to afford crude compound which was purified by column chromatography by eluting with 15% MeOH/DCM+1 mL aq.NH$_3$ to obtain to afford NRX-1006 (65 mg, 34%) as white color solid.

$^1$H-NMR: (400 MHz, D$_2$O): δ 4.55-4.53 (m, 1H), 4.40-4.37 (m, 2H), 4.06-3.95 (m, 2H), 3.89-3.72 (m, 4H), 3.62-3.61 (m, 1H), 2.42-2.35 (m, 2H), 2.15-1.98 (m, 6H), 1.28-1.26 (m, 6H).

LCMS (ESI): m/z 414.5 [M$^+$+1]
UPLC: 95.41%

D. Synthesis of NRX-1009 & 1010:

Scheme 17

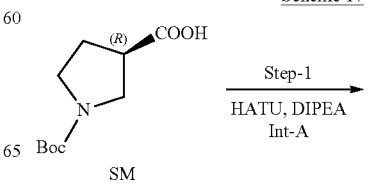

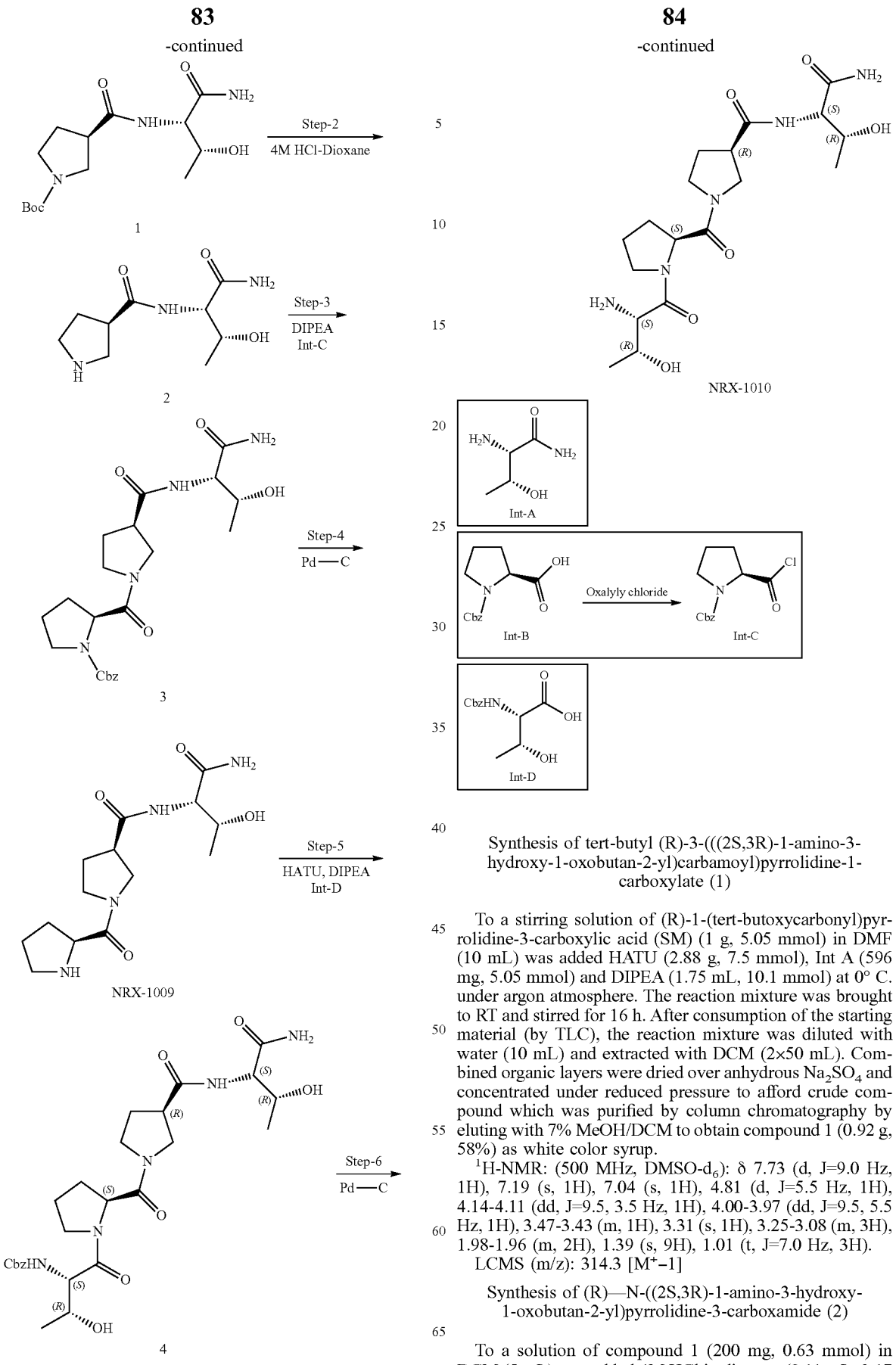

Synthesis of tert-butyl (R)-3-(((2S,3R)-1-amino-3-hydroxy-1-oxobutan-2-yl)carbamoyl)pyrrolidine-1-carboxylate (1)

To a stirring solution of (R)-1-(tert-butoxycarbonyl)pyrrolidine-3-carboxylic acid (SM) (1 g, 5.05 mmol) in DMF (10 mL) was added HATU (2.88 g, 7.5 mmol), Int A (596 mg, 5.05 mmol) and DIPEA (1.75 mL, 10.1 mmol) at 0° C. under argon atmosphere. The reaction mixture was brought to RT and stirred for 16 h. After consumption of the starting material (by TLC), the reaction mixture was diluted with water (10 mL) and extracted with DCM (2×50 mL). Combined organic layers were dried over anhydrous $Na_2SO_4$ and concentrated under reduced pressure to afford crude compound which was purified by column chromatography by eluting with 7% MeOH/DCM to obtain compound 1 (0.92 g, 58%) as white color syrup.

$^1$H-NMR: (500 MHz, DMSO-$d_6$): δ 7.73 (d, J=9.0 Hz, 1H), 7.19 (s, 1H), 7.04 (s, 1H), 4.81 (d, J=5.5 Hz, 1H), 4.14-4.11 (dd, J=9.5, 3.5 Hz, 1H), 4.00-3.97 (dd, J=9.5, 5.5 Hz, 1H), 3.47-3.43 (m, 1H), 3.31 (s, 1H), 3.25-3.08 (m, 3H), 1.98-1.96 (m, 2H), 1.39 (s, 9H), 1.01 (t, J=7.0 Hz, 3H).
LCMS (m/z): 314.3 [M$^+$−1]

Synthesis of (R)—N-((2S,3R)-1-amino-3-hydroxy-1-oxobutan-2-yl)pyrrolidine-3-carboxamide (2)

To a solution of compound 1 (200 mg, 0.63 mmol) in DCM (5 mL) was added 4M HCl in dioxane (0.11 mL, 3.17 mmol) at 0° C. under argon atmosphere. The reaction mixture was allowed to stir at RT for 4 h. After consumption of the starting material (by TLC), volatiles were evaporated under reduced pressure. Obtained crude was washed with hexanes (2×10 mL) and dried under vacuum to afford compound 2 (130 mg, 81%) as white color solid.

$^1$H-NMR: (400 MHz, D$_2$O): δ 4.38-4.21 (m, 2H), 3.60-4.48 (m, 2H), 3.47-3.37 (m, 3H), 2.48-2.38 (m, 1H), 2.31-2.16 (m, 1H), 1.26 (t, J=6.4 Hz, 3H).

LCMS (ESI): m/z 216.0 [M$^+$+1]

Synthesis of benzyl (S)-2-((R)-3-(((2S,3R)-1-amino-3-hydroxy-1-oxobutan-2-yl)carbamoyl)pyrrolidine-1-carbonyl)pyrrolidine-1-carboxylate (3)

To a stirring solution of Int C (4.2 g, 15.7 mmol) in DMF (15 mL) was added DIPEA (3.17 mL, 18.2 mmol) and compound 2 (2.3 g, 9.1 mmol) at 0° C. under argon atmosphere. The reaction mixture was brought to RT and stirred for 16 h. After consumption of the starting material (by TLC), the reaction mixture was diluted with water (10 mL) and extracted with DCM (2×50 mL) and 10% MeOH/DCM. Combined organic layers were dried over anhydrous Na$_2$SO$_4$ and concentrated under reduced pressure to afford crude compound which was purified by column chromatography by eluting with 7% MeOH/DCM to obtain compound 3 (1.1 g, 27%) as brown color solid.

$^1$H-NMR: (400 MHz, D$_2$O): δ 7.56-7.41 (m, 5H), 5.23-5.17 (m, 1H), 5.07-5.04 (m, 1H), 4.64-4.61 (m, 1H), 4.42-4.27 (m, 2H), 3.85-3.72 (m, 1H), 3.63-3.58 (m, 2H), 3.54-3.40 (m, 2H), 3.35-3.25 (m, 1H), 2.39-2.29 (m, 1H), 2.18-1.90 (m, 3H), 1.42-1.39 (m, 3H), 1.30-1.24 (m, 3H).

LCMS (m/z): 447.4 [M$^+$+1]

Synthesis of (R)-1-(L-prolyl)-N-((2S,3R)-1-amino-3-hydroxy-1-oxobutan-2-yl)pyrrolidine-3-carboxamide (NRX-1009)

To a stirring solution of compound 3 (1.1 g, 2.46 mmol) in methanol (10 mL) was added 50% wet 10% Pd/C (200 mg) at RT and stirred for 16 h under H$_2$ atmosphere. After consumption of the starting material (by TLC), the reaction mixture was filtered through a pad of celite and the filtrate was washed with pentane (10 mL) and Et$_2$O (10 mL). Obtained filtrate was concentrated under reduced pressure and dried under vacuum to afford NRX-1009 (605 mg, 78%) as white color solid.

$^1$H-NMR: (400 MHz, D$_2$O): δ 4.3-4.33 (m, 1H), 4.28-4.25 (m, 1H), 4.20-4.17 (m, 1H), 3.81-3.24 (m, 6H), 3.09-3.05 (m, 1H), 2.39-2.08 (m, 3H), 2.05-1.79 (m, 3H), 1.26-1.23 (m, 3H).

LCMS (ESI): m/z 313.5 [M$^+$+1]
HPLC: 98.64%

Synthesis of benzyl ((2S,3R)-1-((S)-2-((R)-3-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (4)

To a stirring solution of NRX-1009 (200 mg, 0.64 mmol) in DMF (3 mL) was added HATU (244 mg, 0.64 mmol), Int D (178 mg, 0.7 mmol) and DIPEA (0.22 mL, 1.28 mmol) at 0° C. under argon atmosphere. The reaction mixture was brought to RT and stirred for 16 h. After consumption of the starting material (by TLC), the reaction mixture was diluted with water (10 mL) and extracted with 10% MeOH/DCM (2×20 mL). Combined organic layers were dried over anhydrous Na$_2$SO$_4$ and concentrated under reduced pressure to afford crude compound which was purified by column chromatography by eluting with 7% MeOH/DCM to obtain compound 4 (190 mg, 54%) as brown solid.

$^1$H-NMR: (400 MHz, D$_2$O): δ 7.50-7.48 (m, 5H), 5.26-5.18 (m, 2H), 4.71-4.67 (m, 1H), 4.43-4.29 (m, 3H), 4.13-4.09 (m, 1H), 3.80-3.75 (m, 2H), 3.62-3.59 (m, 2H), 3.48-3.44 (m, 3H), 3.36-3.24 (m, 1H), 2.43-2.38 (m, 1H), 2.32-2.25 (m, 1H), 2.13 (s, 1H), 2.14-1.95 (m, 2H), 1.41-1.31 (m, 3H), 1.29-1.25 (m, 3H).

LCMS (m/z): 548.5 [M$^+$+1]

Synthesis of (R)-1-(L-threonyl-L-prolyl)-N-((2S,3R)-1-amino-3-hydroxy-1-oxobutan-2-yl)pyrrolidine-3-carboxamide (NRX-1010)

To a stirring solution of compound 4 (185 mg, 0.33 mmol) in methanol (5 mL) was added 50% wet 10% Pd/C (90 mg) at RT and stirred for 16 h under H$_2$ atmosphere. After consumption of the starting material (by TLC), the reaction mixture was filtered through a pad of celite and the filtrate was washed with pentane (10 mL) and Et$_2$O (10 mL). Organic layer was dried over anhydrous Na$_2$SO$_4$ and concentrated under reduced pressure to afford crude compound which was purified by column chromatography by eluting with 1% aq.NH$_3$ in 10% MeOH/DCM to obtain to afford NRX-1010 (55 mg, 39%) as off white solid.

$^1$H-NMR: (400 MHz, D$_2$O): δ 4.81-4.70 (m, 1H), 4.40-4.37 (m, 1H), 4.31-4.28 (m, 1H), 3.99-3.33 (m, 9H), 4.45-34.25 (m, 3H), 2.18-2.04 (m, 2H), 2.02-1.89 (m, 1H), 1.33-1.26 (m, 6H).

LCMS (ESI): m/z 414.6 [M$^+$+1]
UPLC: 98.16%

E. Synthesis of NRX-1003 & 1004:

Scheme 18

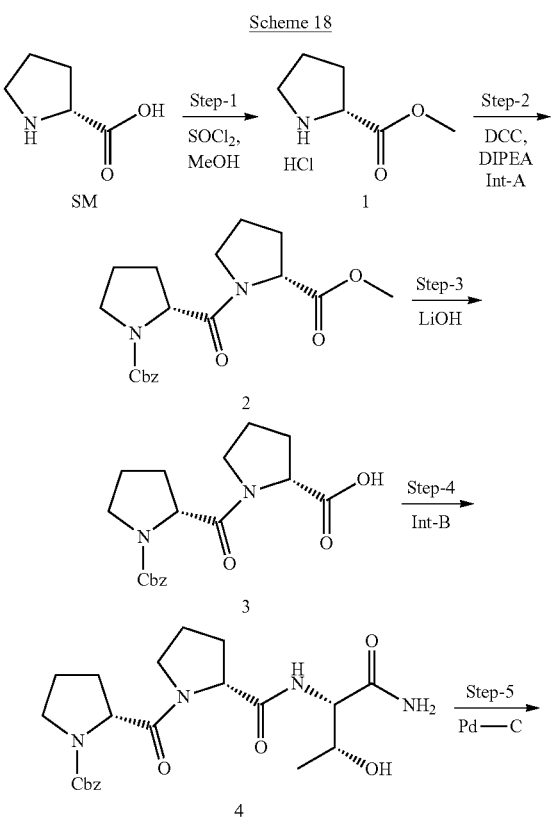

-continued

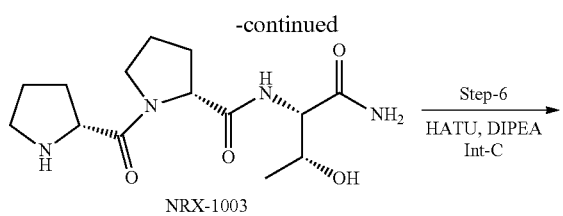

NRX-1003

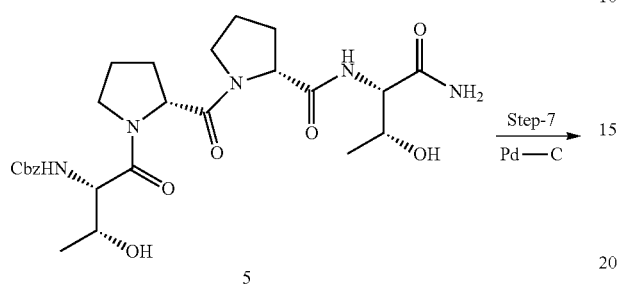

5

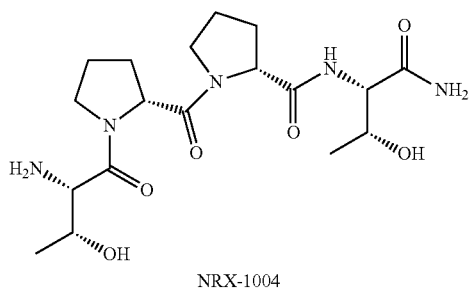

NRX-1004

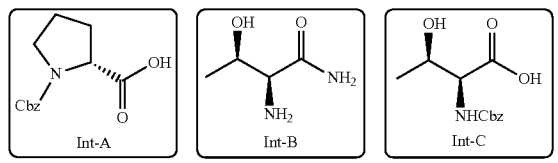

Synthesis of methyl D-prolinate hydrochloride (1)

To a stirred suspension of D-proline (SM) (10 g, 86.9 mmol) in methanol (100 mL) was added thionyl chloride (7.6 mL, 104.3 mmol) drop wise at 0° C. under nitrogen atmosphere. The reaction mixture was heated to reflux for 16 h. After consumption of the starting material (by TLC), reaction mixture was brought to RT, volatiles were concentrated under vacuum and the crude was triturated with n-hexane to afford compound 1 as hydrochloride salt (10.5 g, 93%) as brown syrup.

$^1$H-NMR: (400 MHz, DMSO-$d_6$): δ 10.32-10.14 (d, 1H), 9.05-8.74 (d, 1H), 3.97-3.78 (m, 1H), 3.75 (s, 3H), 3.21-3.16 (m, 2H), 2.30-2.21 (m, 1H), 1.99-1.87 (m, 3H).

LCMS (m/z): 144.2 [M$^+$+1]

Synthesis of benzyl (R)-2-((R)-2-(methoxycarbonyl)pyrrolidine-1-carbonyl)pyrrolidine-1-carboxylate (2)

To a stirring solution of compound 1 (5 g, 38.4 mmol) in DCM (50 mL) were added DIPEA (20 mL, 115.2 mmol), DCC (11.9 g, 57.6 mmol) and Int-A (11.5 g, 46.1 mmol) at 0° C. under nitrogen atmosphere. The reaction mixture was brought to RT and stirred for 16 h. After consumption of the starting material (by TLC), brought to RT and filtered through cotton bed. The reaction was diluted with water (50 mL) and extracted with CH$_2$Cl$_2$ (3×30 mL). The organic layer was dried over Na$_2$SO$_4$ and concentrated under reduced pressure to afford crude compound which was purified by column chromatography by eluting with 20% EtOAC/n-hexane to obtain compound 2 (6.1 g, 44%) as syrup.

$^1$H-NMR: (500 MHz, D$_2$O): δ 7.34-7.25 (m, 5H), 5.04 (s, 2H), 4.88-3.86 (m, 1H), 4.54-4.52 (m, 1H), 3.62 (s, 3H), 3.44-3.34 (m, 4H), 1.93-1.78 (m, 8H).

LCMS (ESI): m/z 144.1 [(M$^+$+1)-Boc]

Synthesis of ((benzyloxy)carbonyl)-D-prolyl-D-proline (3)

To a stirring solution of compound 2 (6.1 g, 16.9 mmol) in THF:H$_2$O (60 mL, 1:1) were added lithium hydroxide (1.77 g, 42.3 mmol) at 0° C. The reaction mixture was brought to RT and stirred for 16 h. After consumption of the starting material (by TLC), the reaction was extracted with DCM (3×30 mL). The combined organic layers were dried over Na$_2$SO$_4$ and concentrated to obtain crude compound which was washed with hexane to afford compound 3 (3.2 g, crude) as an off white solid.

$^1$H-NMR: (500 MHz, D$_2$O): δ 7.48-7.40 (m, 5H), 5.18 (s, 2H), 4.66-3.64 (m, 1H), 4.13-4.11 (m, 1H), 3.57-3.45 (m, 4H), 2.12-1.90 (m, 8H).

LCMS (ESI): m/z 242.2 [M$^+$+1];

Synthesis of benzyl (R)-2-((R)-2-(((2S,3R)-1-amino-3-hydroxy-1-oxobutan-2-yl)carbamoyl)pyrrolidine-1-carbonyl)pyrrolidine-1-carboxylate (4)

To a stirring solution of compound 3 (3 g, 8.6 mmol) in DCM (30 mL) were added, DIPEA (4.6 mL, 25.8 mmol), EDCI.HCl (2.47 g, 12.9 mmol) and HOBt (6.7 mL, 38.4 mmol) at 0° C. under nitrogen atmosphere. A solution of Int-B (1.2 g, 10.3 mmol) in DMF (10 mL) was added to the reaction mixture and allowed to stir at RT for 16 h. After consumption of the starting material (by TLC), the reaction mixture was diluted with water (50 mL) and extracted with DCM (3×30 mL). Separated organic layer was dried over anhydrous Na$_2$SO$_4$ and concentrated under reduced pressure to afford crude compound which was purified by column chromatography by eluting with 5% MeOH-DCM to obtain compound 4 (3 g, 77%) as an off white solid.

$^1$H-NMR: (500 MHz, DMSO-$d_6$): δ 7.81-7.80 (d, 1H), 7.37-7.26 (m, 5H), 5.09-5.00 (m, 2H), 4.91-4.82 (m, 2H), 4.54-4.42 (m, 2H), 4.14 (s, 1H), 3.97-3.96 (m, 1H), 3.53-3.36 (m, 4H), 2.19-2.15 (m, 1H), 1.98-1.90 (m, 1H), 1.85-1.76 (m, 6H), 1.64-1.58 (m, 1H), 1.05-1.01 (m, 3H).

LCMS (ESI): m/z 242.2 [M$^+$+1];

Synthesis of (R)-1-(D-prolyl)-N-((2S,3R)-1-amino-3-hydroxy-1-oxobutan-2-yl)pyrrolidine-2-carboxamide (NRX-1003)

To a stirring solution of compound 4 (1 g, 2.2 mmol) in methanol (20 mL) was added 50% wet 10% Pd/C (400 mg) at RT and stirred for 16 h under H$_2$ atmosphere. After consumption of the starting material (by TLC), the reaction mixture was filtered through a pad of celite and the pad was washed with methanol (50 mL). Obtained filtrate was concentrated under reduced pressure to afford NRX-1003 (550 mg, 78%) as white solid.

¹H-NMR: (400 MHz, D₂O): δ 4.67-4.59 (m, 1H), 4.43-4.37 (m, 2H), 4.10-4.08 (m, 1H), 3.82-3.78 (m, 1H), 3.71-3.65 (m, 1H), 3.13-3.09 (m, 1H), 2.93-2.91 (m, 1H), 2.43-2.32 (m, 2H), 2.15-1.99 (m, 3H), 1.91-1.79 (m, 3H), 1.26-1.24 (m, 3H).
LCMS (ESI): m/z 258.9 [M⁺]

Synthesis of benzyl ((2S,3R)-1-((R)-2-((R)-2-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (5)

To a stirring solution of NRX-1003 (600 mg, 1.98 mmol) in DCM (6 mL) were added DIPEA (1 mL, 5.7 mmol), HATU (730 mg, 1.98 mmol) and Int C (583 mg, 2.3 mmol) at 0° C. under nitrogen atmosphere. The reaction mixture was brought to RT and stirred for 16 h. After consumption of the starting material (by TLC), the reaction mixture was diluted with water (15 mL) and extracted with 15% MeOH-DCM solvent mixture (3×20 mL). Separated organic layer was dried over anhydrous Na₂SO₄ and concentrated under reduced pressure to afford crude compound which was purified by column chromatography by eluting with 5% MeOH-DCM to obtain compound 5 (510 mg, 51%) as white solid.
¹H-NMR: (500 MHz, D₂O): δ 7.48 (s, 5H), 5.19 (s, 2H), 4.59-4.57 (m, 2H), 4.51-4.41 (m, 2H), 4.17-4.15 (m, 2H), 3.78-3.70 (m, 4H), 2.13-1.96 (m, 4H), 1.51-1.32 (m, 4H), 1.24-1.22 (m, 6H).
LCMS (ESI): m/z 477.4 [M⁺+1]

Synthesis of (R)-1-(L-threonyl-D-prolyl)-N-((2S,3R)-1-amino-3-hydroxy-1-oxobutan-2-yl)pyrrolidine-2-carboxamide (NRX-1004)

To a stirring solution of compound 5 (500 mg, 0.91 mmol) in methanol (5 mL) was added 50% wet 10% Pd/C (500 mg) at RT under nitrogen atmosphere. The reaction mixture was stirred RT for 16 h under H₂ atmosphere. After consumption of the starting material (by TLC), the reaction mixture was filtered through a pad of celite and the pad was washed with MeOH (20 mL). Obtained filtrate was concentrated under reduced pressure to afford crude compound which was purified by column chromatography by eluting with 15% MeOH-DCM to obtain NRX-1004 (75 mg, 20%) as white solid. The racemic was separated by chiral HPLC purification.
¹H-NMR: (400 MHz, D₂O): δ 4.31-4.28 (m, 2H), 4.12-4.06 (m, 1H), 4.00-3.94 (m, 3H), 3.64 (s, 2H), 3.59-3.52 (m, 1H), 3.41-3.34 (m, 1H), 2.02-1.93 (m, 4H), 1.30 (d, J=5.6 Hz, 3H),
1.23 (d, J=6.4 Hz, 3H)
LCMS (ESI): m/z 343.4 [M⁺+1];
HPLC: 96.77%

F. Synthesis of NRX-1011 & 1012:

Scheme 19

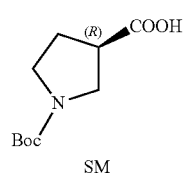

SM

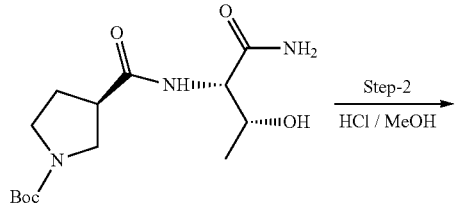

1

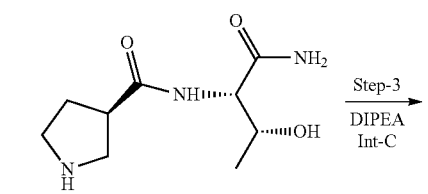

2

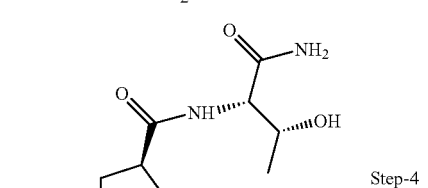

3

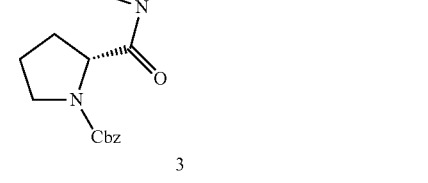

NRX-1011

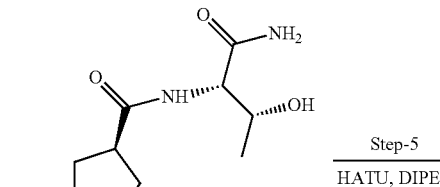

4

-continued

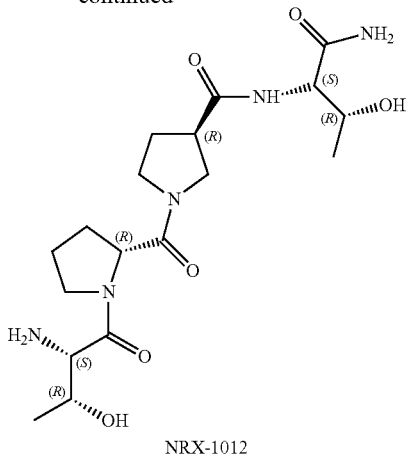

NRX-1012

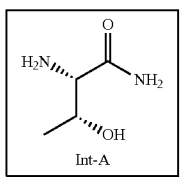

Int-A

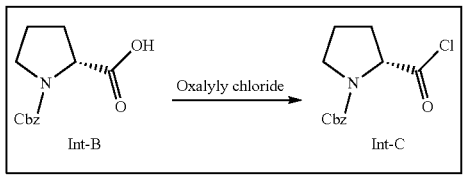

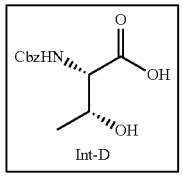

Int-D

Synthesis of tert-butyl (R)-3-(((2S,3R)-1-amino-3-hydroxy-1-oxobutan-2-yl)carbamoyl)pyrrolidine-1-carboxylate (1)

To a stirring solution of (R)-1-(tert-butoxycarbonyl)pyrrolidine-3-carboxylic acid (SM) (1 g, 5.05 mmol) in DMF (10 mL) was added HATU (2.88 g, 7.5 mmol), Int A (596 mg, 5.05 mmol) and DIPEA (1.75 mL, 10.1 mmol) at 0° C. under argon atmosphere. The reaction mixture was brought to RT and stirred for 16 h. After consumption of the starting material (by TLC), the reaction mixture was diluted with water (10 mL) and extracted with DCM (2×50 mL). Combined organic layers were dried over anhydrous $Na_2SO_4$ and concentrated under reduced pressure to afford crude compound which was purified by column chromatography by eluting with 7% MeOH/DCM to obtain compound 1 (0.92 g, 58%) as white color syrup.

$^1$H-NMR: (500 MHz, DMSO-$d_6$): δ 7.73 (d, J=9.0 Hz, 1H), 7.19 (s, 1H), 7.04 (s, 1H), 4.81 (d, J=5.5 Hz, 1H), 4.14-4.11 (dd, J=9.5, 3.5 Hz, 1H), 4.00-3.97 (dd, J=9.5, 5.5 Hz, 1H), 3.47-3.43 (m, 1H), 3.31 (s, 1H), 3.25-3.08 (m, 3H), 1.98-1.96 (m, 2H), 1.39 (s, 9H), 1.01 (t, J=7.0 Hz, 3H).

LCMS (m/z): 314.3 [M$^+$–1]

Synthesis of (R)—N-((2S,3R)-1-amino-3-hydroxy-1-oxobutan-2-yl)pyrrolidine-3-carboxamide (2)

To a solution of compound 1 (200 mg, 0.63 mmol) in DCM (5 mL) was added 4M HCl in dioxane (0.11 mL, 3.17 mmol) at 0° C. under argon atmosphere. The reaction mixture was allowed to stir at RT for 4 h. After consumption of the starting material (by TLC), volatiles were evaporated under reduced pressure. Obtained crude was washed with hexanes (2×10 mL) and dried under vacuum to afford compound 2 (130 mg, 81%) as white color solid.

$^1$H-NMR: (400 MHz, $D_2O$): δ 4.38-4.21 (m, 2H), 3.60-4.48 (m, 2H), 3.47-3.37 (m, 3H), 2.48-2.38 (m, 1H), 2.31-2.16 (m, 1H), 1.26 (t, J=6.4 Hz, 3H).

LCMS (ESI): m/z 216.0 [M$^+$+1]

Synthesis of benzyl (R)-2-((R)-3-(((2S,3R)-1-amino-3-hydroxy-1-oxobutan-2-yl)carbamoyl)pyrrolidine-1-carbonyl)pyrrolidine-1-carboxylate (3)

To a stirring solution of compound 2 (950 mg, 3.77 mmol) in DMF (5 mL) was added Int C (1.71 g, 6.42 mmol) and DIPEA (1.31 mL, 7.55 mmol) and at 0° C. under argon atmosphere. The reaction mixture was brought to RT and stirred for 16 h. After consumption of the starting material (by TLC), the reaction mixture was diluted with water (5 mL) and extracted with 10% MeOH/DCM (2×10 mL). Combined organic layers were dried over anhydrous $Na_2SO_4$ and concentrated under reduced pressure to afford crude compound which was purified by column chromatography by eluting with 6% MeOH/DCM to obtain compound 3 (510 mg, 30%) as brown color solid.

$^1$H-NMR: (500 MHz, $D_2O$): δ 7.51-7.40 (m, 5H), 5.18 (s, 2H), 4.64-4.60 (m, 1H), 4.36-4.27 (m, 2H), 3.80-3.72 (m, 3H), 3.76-3.45 (m, 4H), 2.37-2.31 (m, 3H), 2.06-1.96 (m, 3H), 1.32-1.25 (m, 3H).

LCMS (m/z): 447.7 [M$^+$+1]

Synthesis of (R)-1-(D-prolyl)-N-((2S,3R)-1-amino-3-hydroxy-1-oxobutan-2-yl)pyrrolidine-3-carboxamide (NRX-1011)

To a stirring solution of compound 3 (500 mg, 1.12 mmol) in methanol (10 mL) was added 50% wet 10% Pd/C (200 mg) at RT and stirred for 16 h under $H_2$ atmosphere. After consumption of the starting material (by TLC), the reaction mixture was filtered through a pad of celite and the filtrate was washed with pentane (5 mL) and DCM (5 mL). Obtained filtrate was concentrated under reduced pressure and dried under vacuum to afford NRX-1011 (250 mg, 71%) as off white color solid.

$^1$H-NMR: (400 MHz, $D_2O$): δ 4.47-4.40 (m, 1H), 4.36-4.34 (m, 1H), 4.30-4.24 (m, 1H), 3.91-3.55 (m, 4H), 3.48-3.26 (m, 3H), 2.51-2.48 (m, 1H), 2.41-2.23 (m, 2H), 2.17-2.01 (m, 3H), 1.27-1.25 (m, 3H).

LCMS (ESI): m/z 313.5 [M$^+$+1]
UPLC: 94.51%

Synthesis of benzyl ((2S,3R)-1-((R)-2-((R)-3-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (4)

To a stirring solution of NRX-1011 (240 mg, 0.76 mmol) in DMF (3 mL) was added HATU (292 mg, 0.76 mmol), Int D (214 mg, 0.84 mmol) and DIPEA (0.26 mL, 1.53 mmol) at 0° C. under argon atmosphere. The reaction mixture was brought to RT and stirred for 16 h. After consumption of the starting material (by TLC), the reaction mixture was diluted with water (5 mL) and extracted with 10% MeOH/DCM (2×10 mL). Combined organic layers were dried over anhydrous Na$_2$SO$_4$ and concentrated under reduced pressure to afford crude compound which was purified by column chromatography by eluting with 7% MeOH/DCM to obtain compound 4 (235 mg, 55%) as white solid.

$^1$H-NMR: (500 MHz, D$_2$O): δ 7.56-7.46 (m, 5H), 5.20 (s, 2H), 4.51-4.49 (m, 1H), 4.37-4.27 (m, 1H), 4.12-3.96 (m, 2H), 3.78-3.73 (m, 3H), 3.64-3.55 (m, 2H), 3.36-3.22 (m, 3H), 2.34-2.28 (m, 2H), 2.06-1.92 (m, 4H), 1.32-1.25 (m, 6H).

LCMS (m/z): 548.5 [M$^+$+1]

Synthesis of (R)-1-(L-threonyl-D-prolyl)-N-((2S,3R)-1-amino-3-hydroxy-1-oxobutan-2-yl)pyrrolidine-3-carboxamide (NRX-1012)

To a stirring solution of compound 4 (230 mg, 0.42 mmol) in methanol (10 mL) was added 50% wet 10% Pd/C (100 mg) at RT and stirred for 16 h under H$_2$ atmosphere. After consumption of the starting material (by TLC), the reaction mixture was filtered through a pad of celite and the filtrate was washed with pentane (10 mL) and Et$_2$O (10 mL). Organic layer was dried over anhydrous Na$_2$SO$_4$ and concentrated under reduced pressure to afford crude compound which was purified by column chromatography by eluting with 7% MeOH/DCM to obtain to afford NRX-1012 (65 mg, 37%) as off brown color sticky solid.

$^1$H-NMR: (400 MHz, D$_2$O): δ 4.36-4.33 (m, 1H), 4.28-4.26 (m, 1H), 3.99-3.90 (m, 2H), 3.80-3.70 (m, 4H), 3.63-3.54 (m, 2H), 3.44-3.29 (m, 2H), 2.37-2.24 (m, 2H), 2.16-1.92 (m, 4H), 1.25-1.22 (m, 6H).

LCMS (ESI): m/z 414.4 [M$^+$+1]

UPLC: 95.06%

G. Synthesis of NRX-1017 & 1018:

Scheme 20

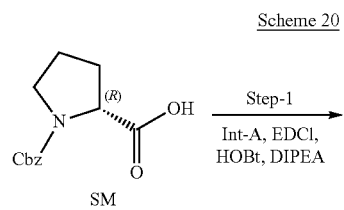

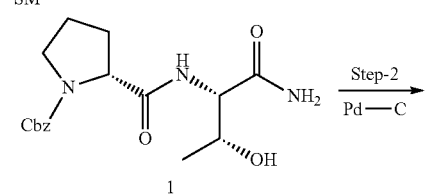

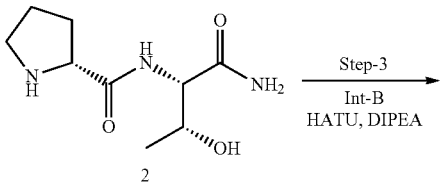

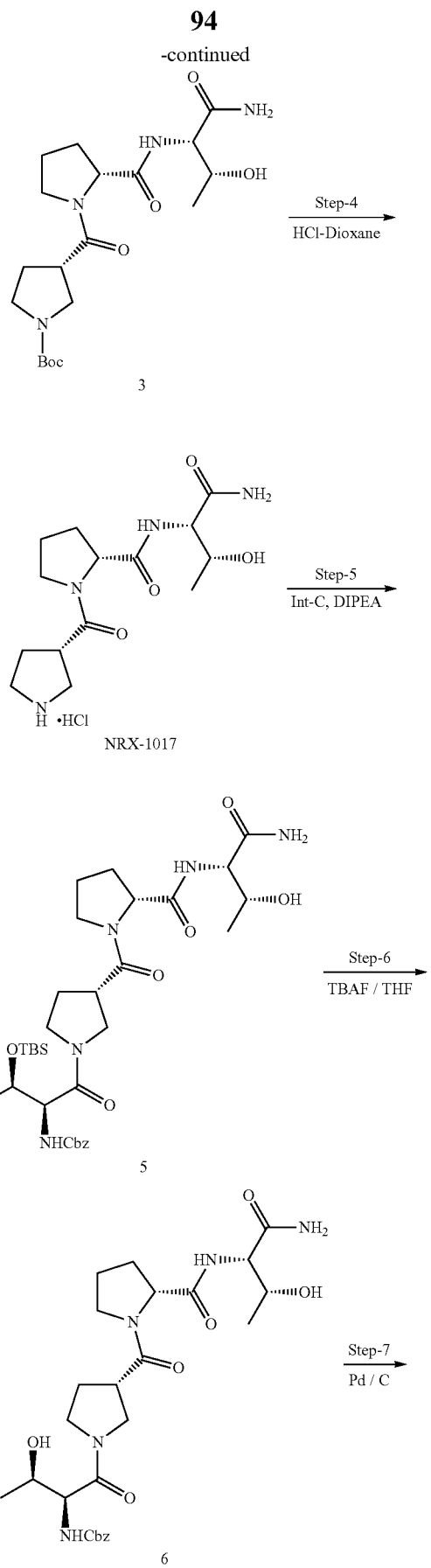

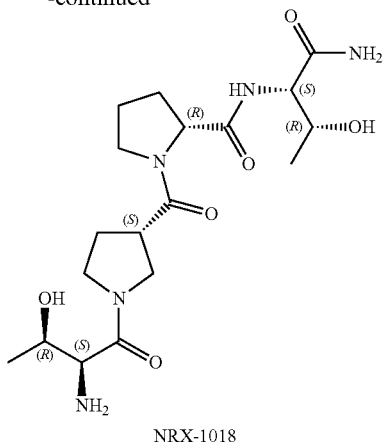

NRX-1018

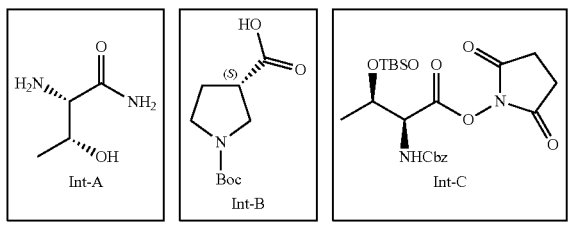

Int-A, Int-B, Int-C

Synthesis of benzyl (R)-2-(((2S,3R)-1-amino-3-hydroxy-1-oxobutan-2-yl)carbamoyl)pyrrolidine-1-carboxylate (1)

To a stirring solution of compound (SM) (15 g, 60.1 mmol) in DMF (100 mL) was added EDCI (17.2 g, 90.1 mmol), HOBt (13.8 g, 90.1 mmol) and DIPEA (33.2 mL, 180.2 mmol) at 0° C. under argon atmosphere. After stirred for 10 minutes, Int A (8.5 g, 72.1 mmol) was added. The reaction mixture was brought to RT and stirred for 16 h. After consumption of the starting material (by TLC), the reaction mixture was diluted with water (20 mL) and extracted with 10% MeOH/DCM (2×20 mL). Organic layer was dried over anhydrous $Na_2SO_4$ and concentrated under reduced pressure to afford crude compound which was purified by column chromatography by eluting with 3% MeOH/DCM to obtain product as thick syrup. This was further triturated with TBTE to obtain compound 1 (10 g, 47%) as an off white solid.

$^1$H-NMR: (500 MHz, DMSO-$d_6$): δ 7.86-7.70 (m, 1H), 7.36-7.23 (m, 5H), 7.12-7.06 (m, 2H), 5.09-5.03 (m, 2H), 4.96-4.83 (m, 1H), 4.41-4.36 (m, 1H), 4.19-3.99 (m, 2H), 3.43-3.30 (m, 2H), 2.18-2.10 (m, 1H), 1.84-1.79 (m, 3H), 1.01-0.96 (m, 3H).

LCMS (m/z): 350.4 [M$^+$+1]

Synthesis of (R)—N-((2S,3R)-1-amino-3-hydroxy-1-oxobutan-2-yl)pyrrolidine-2-carboxamide (2)

To a stirring solution of compound 1 (10 g, 28.6 mmol) in methanol (100 mL) was added 50% wet 10% Pd/C (3.5 g) at RT and stirred for 5 h under $H_2$ atmosphere. After consumption of the starting material (by TLC), the reaction mixture was filtered through a pad of celite and the filtrate was concentrated under reduced pressure. Obtained crude was triturated with $Et_2O$ and dried under vacuum to afford compound 2 (4.5 g, 73%) as an off white solid.

$^1$H-NMR: (400 MHz, DMSO-$d_6$): δ 8.05 (d, J=8.0 Hz, 1H), 7.14 (s, 1H), 7.02 (s, 1H), 4.91 (s, 1H), 4.07-4.00 (m, 2H), 3.60-3.58 (m, 1H), 2.90-2.75 (m, 3H), 1.98-1.89 (m, 1H), 1.72-1.56 (m, 3H), 1.00-0.98 (m, 3H).

LCMS (ESI): m/z 216.1 [M$^+$+1]

Synthesis of tert-butyl (S)-3-((R)-2-(((2S,3R)-1-amino-3-hydroxy-1-oxobutan-2-yl)carbamoyl)pyrrolidine-1-carbonyl)pyrrolidine-1-carboxylate (3)

To a stirring solution of compound 2 (2 g, 9.3 mmol) in DMF (15 mL) was added HATU (3.53 g, 9.3 mmol), MITA (5.2 mL, 27.9 mmol) and Int B (1.99 g, 9.3 mmol) at 0° C. under argon atmosphere. The reaction mixture was brought to RT and stirred for 16 h. After consumption of the starting material (by TLC), the reaction mixture was diluted with water (5 mL) and extracted with 10% MeOH/DCM (2×30 mL). Combined organic layers were dried over anhydrous $Na_2SO_4$ and concentrated under reduced pressure to afford crude compound which was purified by column chromatography by eluting with 5% MeOH/DCM to obtain compound 3 (1.7 g, 44%) as an off white solid.

$^1$H-NMR: (500 MHz, DMSO-$d_6$): δ 7.83-7.76 (m, 1H), 7.10-7.02 (m, 2H), 4.44-4.42 (m, 1H), 4.16-4.14 (m, 1H), 4.02-3.98 (m, 1H), 3.62-3.58 (m, 2H), 3.45-3.38 (m, 2H), 3.36-3.17 (m, 4H), 1.96-1.75 (m, 6H), 1.39 (s, 9H), 1.03-1.00 (m, 3H).

LCMS (m/z): 411.3 [M$^+$−1]

Synthesis of (R)—N-((2S,3R)-1-amino-3-hydroxy-1-oxobutan-2-yl)-1-((S)-pyrrolidine-3-carbonyl)pyrrolidine-2-carboxamide (NRX-1017)

To a solution of compound 3 (1 g, 2.42 mmol) in DCM (10 mL) was added 4M HCl in dioxane (1.8 mL, 7.28 mmol) at 0° C. under argon atmosphere. The reaction mixture was allowed to stir at RT for 4 h. After consumption of the starting material (by TLC), volatiles were evaporated under reduced pressure. Obtained crude was triturated with pentane (2×10 mL) and dried under vacuum to afford NRX-1017 (750 mg, 88%) as an off white solid.

$^1$H-NMR: (400 MHz, $D_2O$): δ 4.60-4.56 (m, 1H), 4.42-4.35 (m, 2H), 3.80-3.73 (m, 2H), 3.66-3.57 (m, 2H), 3.52-3.41 (m, 3H), 2.53-2.35 (m, 2H), 2.19-1.98 (m, 4H), 1.26-1.23 (m, 3H).

LCMS (ESI): m/z 313.1 [M$^+$+1]
UPLC: 92.22%

Synthesis of benzyl ((2S,3R)-1-((S)-3-((R)-2-(((2S,3R)-1-amino-3-hydroxy-1-oxobutan-2-yl)carbamoyl)pyrrolidine-1-carbonyl)pyrrolidin-1-yl)-3-((tert-butyldimethylsilyl)oxy)-1-oxobutan-2-yl)carbamate (5)

To a stirring solution of NRX-1017 (650 mg, 1.86 mmol) in DMF (10 mL) was added DIPEA (1.03 mL, 5.61 mmol) and Int C (1.03 g, 2.24 mmol) at 0° C. under argon atmosphere. The reaction mixture was brought to RT and stirred for 16 h. After consumption of the starting material (by TLC), the reaction mixture was diluted with water (5 mL) and extracted with 10% MeOH/DCM (2×10 mL). Combined organic layers were dried over anhydrous $Na_2SO_4$ and concentrated under reduced pressure to afford crude compound which was purified by column chromatography by eluting with 5% MeOH/DCM to obtain compound 5 (850 mg, 69%) as an off white solid.

$^1$H-NMR: (400 MHz, CD$_3$OD): δ 7.38-7.29 (m, 5H), 5.09 (s, 2H), 4.52-4.47 (m, 1H), 4.43-4.36 (m, 2H), 4.22-4.18 (m, 1H), 4.15-4.11 (m, 1H), 3.76-3.68 (m, 4H), 3.58-3.46 (m, 2H), 3.44-3.32 (m, 1H), 2.31-1.90 (m, 6H), 1.20-1.16 (m, 6H), 0.87 (s, 9H), 0.07-0.04 (m, 6H).

LCMS (ESI): m/z 662.8 [M$^+$+1]

Synthesis of benzyl ((2S,3R)-1-((S)-3-((R)-2-(((2S, 3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (6)

To a stirring solution of compound 5 (850 mg, 1.28 mmol) in THF (10 mL) was added TBAF (1M in THF) (402 mg, 1.54 mmol) at 0° C. under argon atmosphere. The reaction mixture was brought to RT and stirred for 5 h. After consumption of the starting material (by TLC), the reaction mixture was diluted with water (10 mL) and extracted with 10% MeOH/DCM (2×10 mL). Combined organic layers were dried over anhydrous Na$_2$SO$_4$ and concentrated under reduced pressure to afford crude compound which was purified by column chromatography by eluting with 2% MeOH/DCM to obtain compound 6 (550 mg, 78%) as white solid.

$^1$H-NMR: (500 MHz, CD$_3$OD): δ 7.37-7.29 (m, 5H), 5.12 (s, 2H), 4.49 (s, 1H), 4.49-4.33 (m, 2H), 4.20-4.18 (m, 1H), 4.04-3.91 (m, 2H), 3.82-3.72 (m, 2H), 3.66-3.56 (m, 1H), 3.53-3.49 (m, 2H), 3.42-3.37 (m, 1H), 2.30-2.11 (m, 4H), 2.06-2.00 (m, 2H), 1.21-1.16 (m, 6H).

LCMS (ESI): m/z 548.6 [M$^+$+1]

Synthesis of (R)-1-((S)-1-(L-threonyl)pyrrolidine-3-carbonyl)-N-((2S,3R)-1-amino-3-hydroxy-1-oxobutan-2-yl)pyrrolidine-2-carboxamide (NRX-1018)

To a stirring solution of compound 6 (550 mg, 1.01 mmol) in methanol (10 mL) was added 50% wet 10% Pd/C (180 mg) at RT and stirred for 4 h under H$_2$ atmosphere. After consumption of the starting material (by TLC), the reaction mixture was filtered through a pad of celite and the filtrate was concentrated under reduced pressure. Obtained crude was triturated with pentane and dried under vacuum to afford NRX-1018 (250 mg, 60%) as white solid.

$^1$H-NMR: (400 MHz, D$_2$O): δ 4.58-4.54 (m, 1H), 4.42-4.37 (m, 2H), 3.99-3.71 (m, 7H), 3.69-3.49 (m, 2H), 2.45-2.331 (m, 2H), 2.17-1.99 (m, 4H), 1.26-1.22 (m, 6H).

LCMS (ESI): m/z 414.4 [M$^+$+1]

HPLC: 99.56%

H. Synthesis of NRX-1019 & 1020:

Scheme 21

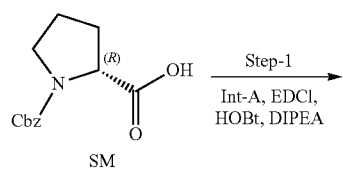

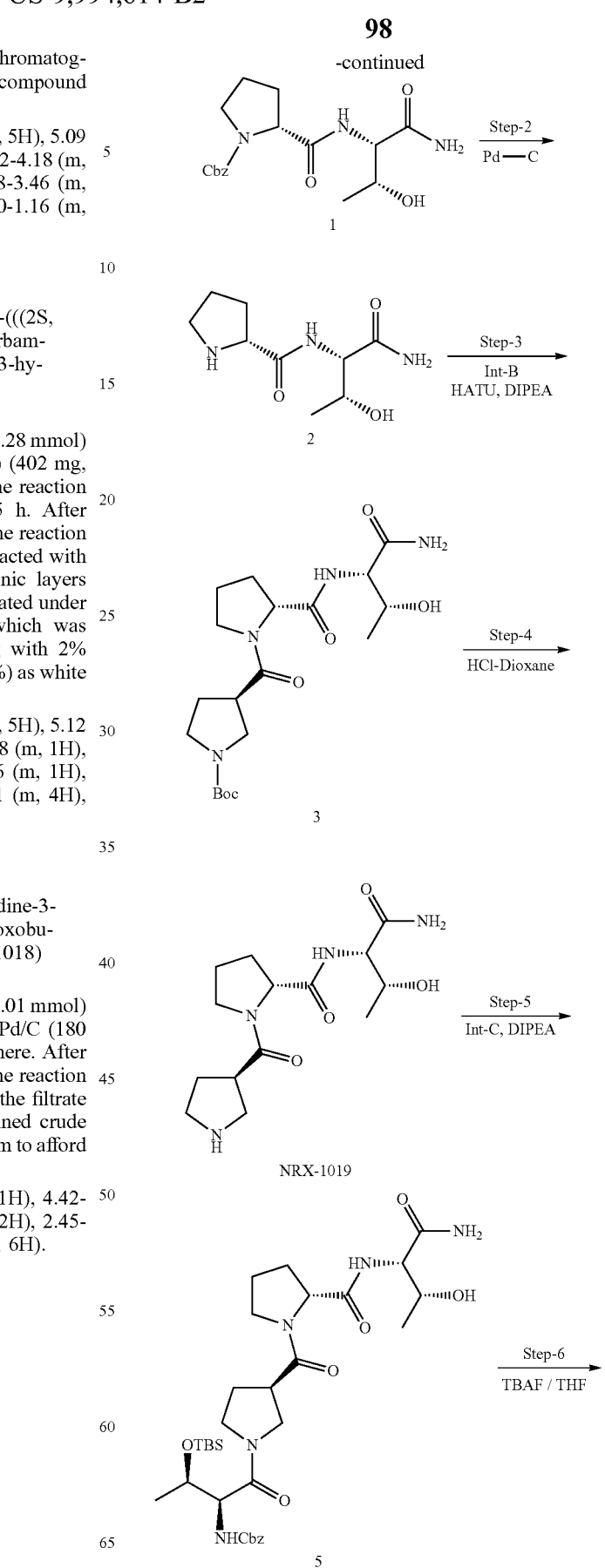

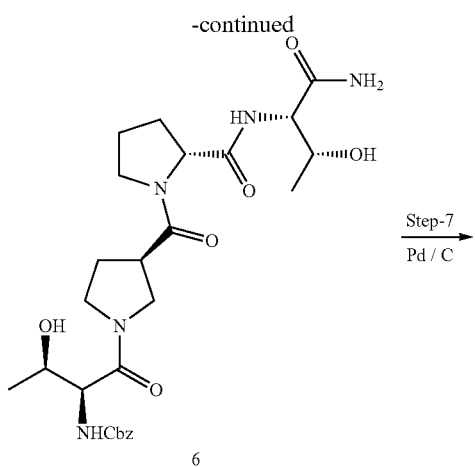

6

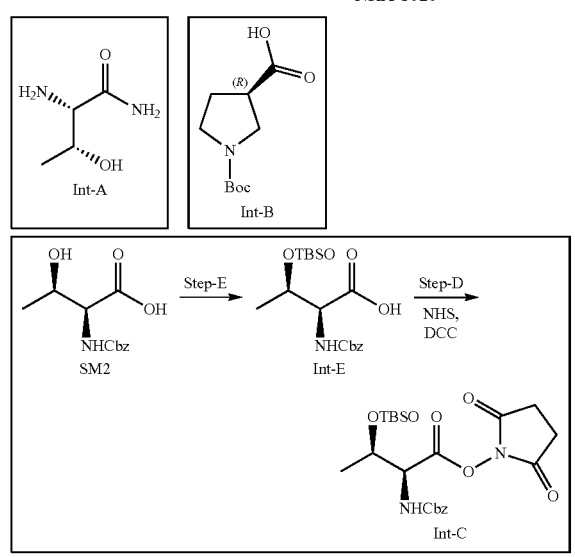

NRX-1020

Synthesis of benzyl (R)-2-(((2S,3R)-1-amino-3-hydroxy-1-oxobutan-2-yl)carbamoyl)pyrrolidine-1-carboxylate (1)

To a stirring solution of compound (SM) (15 g, 60.1 mmol) in DMF (100 mL) was added EDCI (17.2 g, 90.1 mmol), HOBt (13.8 g, 90.1 mmol) and DIPEA (33.2 mL, 180.2 mmol) at 0° C. under argon atmosphere. After stirred for 10 minutes, Int A (8.5 g, 72.1 mmol) was added. The reaction mixture was brought to RT and stirred for 16 h. After consumption of the starting material (by TLC), the reaction mixture was diluted with water (20 mL) and extracted with 10% MeOH/DCM (2×20 mL). Organic layer was dried over anhydrous $Na_2SO_4$ and concentrated under reduced pressure to afford crude compound which was purified by column chromatography by eluting with 3% MeOH/DCM to obtain product as thick syrup. This was further triturated with TBTE to obtain compound 1 (10 g, 47%) as an off white solid.

$^1$H-NMR: (500 MHz, DMSO-$d_6$): δ 7.86-7.70 (m, 1H), 7.36-7.23 (m, 5H), 7.12-7.06 (m, 2H), 5.09-5.03 (m, 2H), 4.96-4.83 (m, 1H), 4.41-4.36 (m, 1H), 4.19-3.99 (m, 2H), 3.43-3.30 (m, 2H), 2.18-2.10 (m, 1H), 1.84-1.79 (m, 3H), 1.01-0.96 (m, 3H).

LCMS (m/z): 350.4 [M++1]

Synthesis of (R)—N-((2S,3R)-1-amino-3-hydroxy-1-oxobutan-2-yl)pyrrolidine-2-carboxamide (2)

To a stirring solution of compound 1 (10 g, 28.6 mmol) in methanol (100 mL) was added 50% wet 10% Pd/C (3.5 g) at RT and stirred for 5 h under $H_2$ atmosphere. After consumption of the starting material (by TLC), the reaction mixture was filtered through a pad of celite and the filtrate was concentrated under reduced pressure. Obtained crude was triturated with $Et_2O$ and dried under vacuum to afford compound 2 (4.5 g, 73%) as an off white solid.

$^1$H-NMR: (400 MHz, DMSO-$d_6$): δ 8.05 (d, J=8.0 Hz, 1H), 7.14 (s, 1H), 7.02 (s, 1H), 4.91 (s, 1H), 4.07-4.00 (m, 2H), 3.60-3.58 (m, 1H), 2.90-2.75 (m, 3H), 1.98-1.89 (m, 1H), 1.72-1.56 (m, 3H), 1.00-0.98 (m, 3H).

LCMS (ESI): m/z 216.1 [M$^+$+1]

Synthesis of tert-butyl (R)-3-((R)-2-(((2S,3R)-1-amino-3-hydroxy-1-oxobutan-2-yl)carbamoyl)pyrrolidine-1-carbonyl)pyrrolidine-1-carboxylate (3)

To a stirring solution of compound 2 (1 g, 4.65 mmol) in DMF (15 mL) was added HATU (1.76 g, 4.65 mmol), DIPEA (2.5 mL, 13.9 mmol) and Int B (1 g, 4.65 mmol) at 0° C. under argon atmosphere. The reaction mixture was brought to RT and stirred for 16 h. After consumption of the starting material (by TLC), the reaction mixture was diluted with water (5 mL) and extracted with 10% MeOH/DCM (2×20 mL). Combined organic layers were dried over anhydrous $Na_2SO_4$ and concentrated under reduced pressure to afford crude compound which was purified by column chromatography by eluting with 5% MeOH/DCM to obtain compound 3 (1 g, 57%) as an off white solid.

$^1$H-NMR: (500 MHz, DMSO-$d_6$): δ 7.94-7.84 (m, 1H), 7.13-7.10 (m, 2H), 4.44-4.42 (m, 1H), 4.15-4.00 (m, 2H), 3.62-3.58 (m, 2H), 3.47-3.33 (m, 2H), 3.31-3.05 (m, 4H), 1.98-1.78 (m, 6H), 1.39 (s, 9H), 1.09-1.01 (m, 3H).

Synthesis of (R)—N-((2S,3R)-1-amino-3-hydroxy-1-oxobutan-2-yl)-1-((R)-pyrrolidine-3-carbonyl)pyrrolidine-2-carboxamide (NRX-1019)

To a solution of compound 3 (1 g, 2.42 mmol) in DCM (10 mL) was added 4N HCl in dioxane (1.8 mL, 7.28 mmol)

at 0° C. under argon atmosphere. The reaction mixture was allowed to stir at RT for 3 h. After consumption of the starting material (by TLC), volatiles were evaporated under reduced pressure. Obtained crude was triturated with pentane (2×10 mL) and dried under vacuum to afford NRX-1019 (800 mg, 95%) as an off white solid.

$^{1}$H-NMR: (400 MHz, D$_{2}$O): δ 4.61-4.57 (m, 1H), 4.42-4.36 (m, 2H), 3.81-3.77 (m, 2H), 3.67-3.60 (m, 1H), 3.58-3.53 (m, 2H), 3.48-3.40 (m, 2H), 2.52-2.38 (m, 2H), 2.23-2.00 (m, 4H), 1.30-1.25 (m, 3H).

LCMS (ESI): m/z 313.3 [M$^{+}$+1]
UPLC: 99.49%

Synthesis of benzyl ((2S,3R)-1-((R)-3-((R)-2-(((2S,3R)-1-amino-3-hydroxy-1-oxobutan-2-yl)carbamoyl)pyrrolidine-1-carbonyl)pyrrolidin-1-yl)-3-((tert-butyldimethylsilyl)oxy)-1-oxobutan-2-yl)carbamate (5)

To a stirring solution of NRX-1019 (500 mg, 1.43 mmol) in DMF (5 mL) was added DIPEA (0.8 mL, 4.31 mmol) and Int C (799 mg, 1.72 mmol) at 0° C. under argon atmosphere. The reaction mixture was brought to RT and stirred for 5 h. After consumption of the starting material (by TLC), the reaction mixture was diluted with water (5 mL) and extracted with 10% MeOH/DCM (2×10 mL). Combined organic layers were dried over anhydrous Na$_{2}$SO$_{4}$ and concentrated under reduced pressure to afford crude compound which was purified by column chromatography by eluting with 2% MeOH/DCM to obtain compound 5 (700 mg, 73%) as an off white solid.

$^{1}$H-NMR: (500 MHz, DMSO-d$_{6}$): δ 7.93-7.83 (m, 1H), 7.34-7.25 (m, 5H), 7.05 (s, 2H), 4.91 (s, 2H), 4.73-4.69 (m, 1H), 4.46-4.42 (m, 1H), 4.24-4.15 (m, 2H), 4.05-4.01 (m, 2H), 3.83-3.49 (m, 4H), 2.21-1.79 (m, 6H), 1.33-1.23 (m, 4H), 1.08-1.01 (m, 6H), 0.85 (s, 9H), 0.03-0.00 (m, 6H).

LCMS (ESI): m/z 662.8 [M$^{+}$+1]

Synthesis of benzyl ((2S,3R)-1-((R)-3-((R)-2-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (6)

To a stirring solution of compound 5 (700 mg, 1.05 mmol) in THF (10 mL) was added TBAF (1M in THF) (331 mg, 1.27 mmol) at 0° C. under argon atmosphere. The reaction mixture was brought to RT and stirred for 5 h. After consumption of the starting material (by TLC), the reaction mixture was diluted with water (10 mL) and extracted with 10% MeOH/DCM (2×10 mL). Combined organic layers were dried over anhydrous Na$_{2}$SO$_{4}$ and concentrated under reduced pressure to afford crude compound which was purified by column chromatography by eluting with 7% MeOH/DCM to obtain compound 6 (430 mg, 74%) as an off white solid.

$^{1}$H-NMR: (400 MHz, D$_{2}$O): δ 7.47-7.45 (m, 5H), 5.18 (s, 2H), 4.55-4.53 (m, 1H), 4.42-4.33 (m, 3H), 4.12-4.10 (m, 2H), 3.78-3.58 (m, 6H), 2.41-2.35 (m, 2H), 2.18-1.95 (m, 4H), 1.30-1.22 (m, 6H).

LCMS (ESI): m/z 548.6 [M$^{+}$+1]

Synthesis of (R)-1-((R)-1-(L-threonyl)pyrrolidine-3-carbonyl)-N-((2S,3R)-1-amino-3-hydroxy-1-oxobutan-2-yl)pyrrolidine-2-carboxamide (NRX-1020)

To a stirring solution of compound 6 (230 mg, 0.42 mmol) in methanol (10 mL) was added 50% wet 10% Pd/C (70 mg) at RT and stirred for 4 h under H$_{2}$ atmosphere. After consumption of the starting material (by TLC), the reaction mixture was filtered through a pad of celite and the filtrate was concentrated under reduced pressure. Obtained crude was triturated with pentane and dried under vacuum to afford NRX-1020 (105 mg, 60%) as white solid.

$^{1}$H-NMR: (400 MHz, D$_{2}$O): δ 4.58-4.55 (m, 1H), 4.40-4.35 (m, 2H), 4.13-4.06 (m, 1H), 3.91-3.84 (m, 1H), 3.81-3.75 (m, 4H), 3.68-3.50 (m, 3H), 2.41-2.30 (m, 2H), 2.22-1.94 (m, 4H), 1.31-1.22 (m, 6H).

LCMS (ESI): m/z 414.4 [M$^{+}$+1]
HPLC: 99.84%

Synthesis of N-((benzyloxy)carbonyl)-O-(tert-butyldimethylsilyl)-L-threonine (Int-E)

To a stirring solution of ((benzyloxy)carbonyl)-L-threonine (SM2) (5 g, 19.7 mmol) in DCM (50 mL) were added imidazole (4 g, 59.2 mmol), DMAP (241 mg, 1.97 mmol) and TBS-Cl (5.9 g, 39.5 mmol) at 0° C. under argon atmosphere. The reaction mixture was brought to RT and stirred for 18 h. After consumption of the starting material (by TLC), the reaction mixture was diluted with water (10 mL) and extracted with DCM (2×20 mL). Organic layer was dried over anhydrous Na$_{2}$SO$_{4}$ and concentrated under reduced pressure to afford crude compound which was purified by column chromatography by eluting with 2% MeOH/DCM to obtain compound Int-E (4.1 g, 57%) as an off white solid.

$^{1}$H-NMR: (500 MHz, CDCl$_{3}$): δ 7.37-7.25 (m, 5H), 5.51 (d, J=8.0 Hz, 1H), 5.13 (s, 2H), 4.47 (d, J=5.0 Hz, 1H), 4.33 (d, J=8.0 Hz, 1H), 1.20 (d, J=5.0 Hz, 3H), 0.86 (s, 9H), 0.80 (s, 6H).

LCMS (m/z): 368.4 [M$^{+}$+1]

Synthesis of 2,5-dioxopyrrolidin-1-yl N-((benzyloxy)carbonyl)-O-(tert-butyldimethylsilyl)-L-threoninate (Int-C)

To a stirring solution of compound Int-E (4.1 g, 11.1 mmol) in THF (40 mL) were added DCC (2.76 g, 13.3 mmol) and NHS (1.41 g, 12.2 mmol) at 0° C. under argon atmosphere. The reaction mixture was brought to RT and stirred for 3 h. After consumption of the starting material (by TLC), the reaction mixture was diluted with water (10 mL) and extracted with Et$_{2}$O (2×20 mL). Organic layer was dried over anhydrous Na$_{2}$SO$_{4}$ and concentrated under reduced pressure to afford crude compound which was purified by column chromatography by eluting with 3% MeOH/DCM to obtain Int-C (4.5 g, 86%) as semi solid.

$^{1}$H-NMR: (500 MHz, DMSO-d$_{6}$): δ 7.76 (d, J=9.0 Hz, 1H), 7.37-7.32 (m, 5H), 5.07 (s, 2H), 4.52-4.49 (dd, J=9.0, 4.5 Hz, 1H), 4.22 (t, J=5.5 Hz, 1H), 2.81 (s, 4H), 1.22 (d, J=5.5 Hz, 3H), 0.82 (s, 9H), 0.48 (s, 6H).

LCMS (m/z): 465.5 [M++1]

I. Synthesis of NRX-1021 & 1022:

Scheme 22

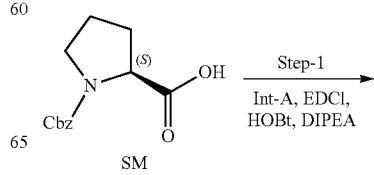

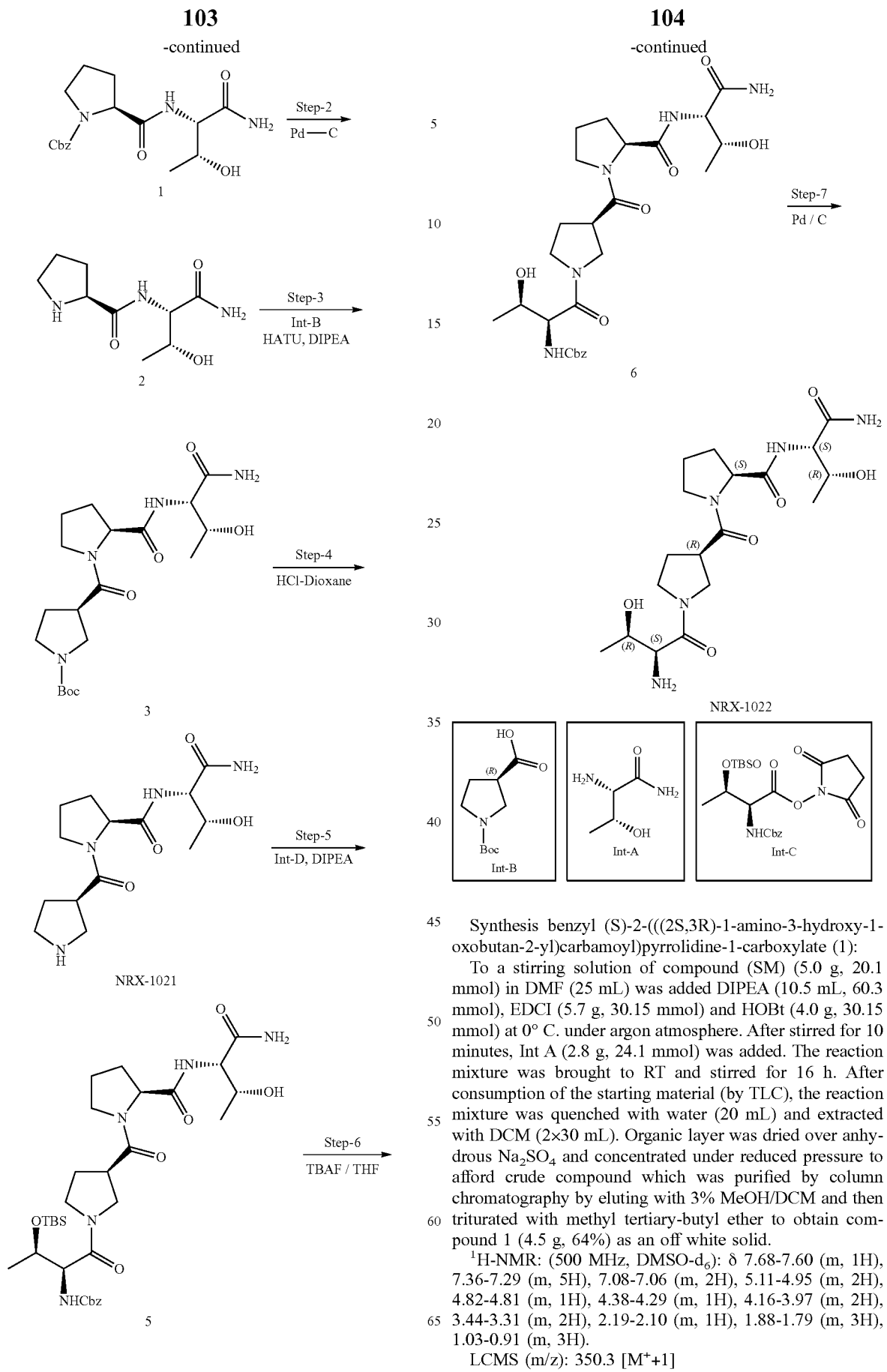

Synthesis benzyl (S)-2-(((2S,3R)-1-amino-3-hydroxy-1-oxobutan-2-yl)carbamoyl)pyrrolidine-1-carboxylate (1):

To a stirring solution of compound (SM) (5.0 g, 20.1 mmol) in DMF (25 mL) was added DIPEA (10.5 mL, 60.3 mmol), EDCI (5.7 g, 30.15 mmol) and HOBt (4.0 g, 30.15 mmol) at 0° C. under argon atmosphere. After stirred for 10 minutes, Int A (2.8 g, 24.1 mmol) was added. The reaction mixture was brought to RT and stirred for 16 h. After consumption of the starting material (by TLC), the reaction mixture was quenched with water (20 mL) and extracted with DCM (2×30 mL). Organic layer was dried over anhydrous $Na_2SO_4$ and concentrated under reduced pressure to afford crude compound which was purified by column chromatography by eluting with 3% MeOH/DCM and then triturated with methyl tertiary-butyl ether to obtain compound 1 (4.5 g, 64%) as an off white solid.

$^1$H-NMR: (500 MHz, DMSO-$d_6$): δ 7.68-7.60 (m, 1H), 7.36-7.29 (m, 5H), 7.08-7.06 (m, 2H), 5.11-4.95 (m, 2H), 4.82-4.81 (m, 1H), 4.38-4.29 (m, 1H), 4.16-3.97 (m, 2H), 3.44-3.31 (m, 2H), 2.19-2.10 (m, 1H), 1.88-1.79 (m, 3H), 1.03-0.91 (m, 3H).

LCMS (m/z): 350.3 [M$^+$+1]

Synthesis of (S)—N-((2S,3R)-1-amino-3-hydroxy-1-oxobutan-2-yl)pyrrolidine-2-carboxamide (2)

To a stirring solution of compound 1 (3.0 g, 8.59 mmol) in methanol (50 mL) was added 50% wet 10% Pd/C (1.0 g) at RT and stirred for 4 h under $H_2$ atmosphere. After consumption of the starting material (by TLC), the reaction mixture was filtered through a pad of celite and the filtrate was washed with pentane (10 mL) and $Et_2O$ (10 mL). Obtained filtrate was concentrated under reduced pressure and dried under vacuum to afford compound 2 (1.6 g, 88%) as sticky solid.

$^1$H-NMR: (500 MHz, DMSO-$d_6$): δ 8.10 (d, J=9.0 Hz, 1H), 7.20-7.16 (m, 2H), 4.91 (d, J=4.5 Hz, 1H), 4.07-4.02 (m, 2H), 3.59-3.56 (m, 1H), 2.92-2.87 (m, 2H), 2.78-2.73 (m, 1H), 1.97-1.91 (m, 1H), 1.70-1.57 (m, 3H), 1.00-0.95 (m, 3H).

LCMS (ESI): m/z 216.0 [M$^+$+1]

Synthesis of tert-butyl (R)-3-((S)-2-(((2S,3R)-1-amino-3-hydroxy-1-oxobutan-2-yl)carbamoyl)pyrrolidine-1-carbonyl)pyrrolidine-1-carboxylate (3)

To a stirring solution of compound 2 (800 mg, 3.71 mmol) in DMF (5 mL) was added DIPEA (2.0 mL, 11.1 mmol), HATU (1.4 g, 3.71 mmol) and Int B (879 mg, 4.08 mmol) at 0° C. under argon atmosphere. The reaction mixture was brought to RT and stirred for 16 h. After consumption of the starting material (by TLC), the reaction mixture was quenched with water (10 mL) and extracted with DCM (2×30 mL). Combined organic layers were dried over anhydrous $Na_2SO_4$ and concentrated under reduced pressure to afford crude compound 3 (900 mg, 60%) as sticky material, which was taken to next step without any further purification.

LCMS (m/z): 413.3 [M$^+$+1]

Synthesis of (S)—N-((2S,3R)-1-amino-3-hydroxy-1-oxobutan-2-yl)-1-((R)-pyrrolidine-3-carbonyl) pyrrolidine-2-carboxamide (NRX-1021)

To a solution of compound 3 (900 mg, 2.18 mmol) in DCM (5 mL) was added 4M HCl in dioxane (0.23 mL, 6.54 mmol) at 0° C. under argon atmosphere. The reaction mixture was allowed to stir at RT for 6 h. After consumption of the starting material (by TLC), volatiles were evaporated under reduced pressure. Obtained crude was triturated with methyl tertiary-butyl ether (2×10 mL) and dried under vacuum to afford NRX-1021 (540 mg, 71%) as sticky solid.

$^1$H-NMR: (400 MHz, $D_2O$): δ 4.58-4.55 (m, 1H), 4.40-4.27 (m, 2H), 3.80-3.76 (m, 2H), 3.68-3.54 (m, 3H), 3.49-3.41 (m, 2H), 2.55-2.33 (m, 2H), 2.22-2.03 (m, 4H), 1.30 (t, J=6.4 Hz, 3H).

LCMS (ESI): m/z 313.7[M$^+$+1]
UPLC: 93.42%

Synthesis of benzyl ((2S,3R)-1-((R)-3-((S)-2-(((2S,3R)-1-amino-3-hydroxy-1-oxobutan-2-yl)carbamoyl)pyrrolidine-1-carbonyl)pyrrolidin-1-yl)-3-((tert-butyldimethylsilypoxy)-1-oxobutan-2-yl)carbamate (5)

To a stirring solution of NRX-1021 (500 mg, 1.43 mmol) in DMF (2 mL) was added DIPEA (0.8 mL, 4.31 mmol) and Int D (799 mg, 1.71 mmol) at 0° C. under argon atmosphere. The reaction mixture was brought to RT and stirred for 2 h. After consumption of the starting material (by TLC), the reaction mixture was diluted with water (5 mL) and extracted with CM (2×10 mL). Combined organic layers were dried over anhydrous $Na_2SO_4$ and concentrated under reduced pressure to afford crude compound which was purified by column chromatography by eluting with 3% MeOH/DCM to obtain compound 5 (600 mg, 63%) as sticky compound.

$^1$H-NMR: (500 MHz, DMSO-$d_6$): δ 7.89-7.86 (m, 1H), 7.34-7.23 (m, 5H), 7.07-6.99 (m, 3H), 5.00 (s, 2H), 4.88-4.84 (m, 1H), 4.40-4.38 (m, 1H), 4.27-4.15 (m, 1H), 4.02-3.99 (m, 3H), 3.82-3.80 (m, 1H), 3.67-3.54 (m, 3H), 3.49-3.40 (m, 2H), 3.37-3.27 (m, 1H), 2.16-1.90 (m, 4H), 1.78 (br s, 1H), 1.23 (s, 1H), 1.09-0.97 (m, 6H), 0.85-0.81 (s, 9H), 0.02-0.02 (m, 6H).

LCMS (ESI): m/z 662.8 [M$^+$+1]

Synthesis of benzyl ((2S,3R)-1-((R)-3-((S)-2-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (6)

To a stirring solution of compound 5 (600 mg, 0.91 mmol) in THF (6 mL) was added TBAF (284 mg, 1.09 mmol) at 0° C. under argon atmosphere. The reaction mixture was brought to RT and stirred for 4 h. After consumption of the starting material (by TLC), the reaction mixture was diluted with water (5 mL) and extracted with DCM (2×10 mL). Combined organic layers were dried over anhydrous $Na_2SO_4$ and concentrated under reduced pressure to afford crude compound which was purified by column chromatography by eluting with 5% MeOH/DCM to obtain compound 6 (320 mg, 64%) as sticky compound.

$^1$H-NMR: (500 MHz, DMSO-$d_6$): δ 7.88-7.86 (m, 1H), 7.35-7.31 (m, 5H), 7.13-7.04 (m, 3H), 5.05-4.99 (m, 2H), 4.88-4.85 (m, 1H), 4.73-4.70 (m, 1H), 4.39-4.37 (m, 1H), 4.17-4.15 (m, 1H), 4.04-4.02 (m, 3H), 3.82-3.79 (m, 1H), 3.64-3.56 (m, 3H), 3.39-3.37 (m, 2H), 3.17-3.14 (m, 1H), 2.06-1.78 (m, 4H), 1.56 (br s, 1H), 1.33-1.23 (m, 1H), 1.04-0.92 (m, 6H).

LCMS (ESI): m/z 548.6 [M$^+$+1]

Synthesis of benzyl ((2S,3R)-1-((R)-3-((S)-2-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (NRX-1022)

To a stirring solution of compound 6 (320 mg, 0.58 mmol) in methanol (5 mL) was added 50% wet 10% Pd/C (100 mg) at RT and stirred for 12 h under $H_2$ atmosphere. After consumption of the starting material (by TLC), the reaction mixture was filtered through a pad of celite and the filtrate was washed with pentane (10 mL) and $Et_2O$ (10 mL). Obtained filtrate was concentrated under reduced pressure to afford crude compound which was triturated with methyl tertiary-butyl ether (2×10 mL) and dried under vacuum to afford NRX-1022 (210 mg, 87%) as an off white solid.

¹H-NMR: (400 MHz, D₂O): δ 4.58-4.52 (m, 1H), 4.35-4.26 (m, 2H), 3.99-3.49 (m, 9H), 2.43-2.32 (m, 2H), 2.24-2.00 (m, 4H), 1.28-1.22 (m, 6H).

LCMS (ESI): m/z 414.4 [M⁺+1]

UPLC: 95.12%

J. Synthesis of NRX-1007 & 1008:

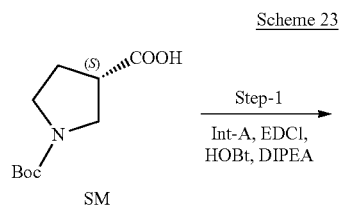
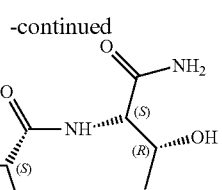

Synthesis of tert-butyl (S)-3-(((2S,3R)-1-amino-3-hydroxy-1-oxobutan-2-yl)carbamoyl)pyrrolidine-1-carboxylate (1)

To a stirring solution of (S)-1-(tert-butoxycarbonyl)pyrrolidine-3-carboxylic acid (SM) (5.0 g, 25.2 mmol) in DMF (30 mL) was added DIPEA (13.1 mL, 75.7 mmol), HATU (10.5 g, 27.7 mmol) and Int A (2.9 g, 25.2 mmol) at 0° C. under argon atmosphere. The reaction mixture was brought to RT and stirred for 16 h. After consumption of the starting material (by TLC), the reaction mixture was quenched with water (20 mL) and extracted with DCM (2×30 mL). Organic layer was dried over anhydrous Na$_2$SO$_4$ and concentrated under reduced pressure to afford crude compound which was purified by column chromatography by eluting with 4% MeOH/DCM to obtain compound 1 (4.7 g, 59%) as white solid.

$^1$H-NMR: (400 MHz, D$_2$O): δ 4.35 (d, J=4.0 Hz, 1H), 4.33-4.27 (m, 1H), 3.62-3.37 (m, 4H), 3.31-3.24 (m, 1H), 2.31-2.23 (m, 1H), 2.13-2.04 (m, 1H), 1.48 (s, 9H), 1.24 (d, J=2.4 Hz, 3H).

LCMS (m/z): 314.3 [M$^+$−1]

Synthesis of (S)—N-((2S,3R)-1-amino-3-hydroxy-1-oxobutan-2-yl)pyrrolidine-3-carboxamide (2)

To a solution of compound 1 (1.5 g, 4.76 mmol) in DCM (25 mL) was added 4M HCl in dioxane (3.6 mL, 14.2 mmol) at 0° C. under argon atmosphere. The reaction mixture was allowed to stir at RT for 4 h. After consumption of the starting material (by TLC), volatiles were evaporated under reduced pressure and dried under vacuum to afford compound 2.HCl salt (1.2 g) as white solid.

$^1$H-NMR: (500 MHz, D$_2$O): δ 4.37-4.29 (m, 2H), 3.60-3.57 (m, 2H), 3.49-3.42 (m, 3H), 2.49-2.42 (m, 1H), 2.27-2.18 (m, 1H), 1.26 (d, J=6.5 Hz, 3H).

LCMS (ESI): m/z 314.5 [M$^+$+1]

Synthesis of benzyl (S)-2-((S)-3-(((2S,3R)-1-amino-3-hydroxy-1-oxobutan-2-yl)carbamoyl)pyrrolidine-1-carbonyl)pyrrolidine-1-carboxylate (3)

To a stirring solution of compound 2 (800 mg, 3.18 mmol) in DCM:H$_2$O (16 mL, 1:1) was added Na$_2$CO$_3$ (844 mg, 7.97 mmol) and Int-C(1 g, 3.81 mmol) at 0° C. under argon atmosphere. The reaction mixture was stirred at RT for 2 h. After consumption of the starting material (by TLC), the reaction mixture was extracted with DCM (2×30 mL). Organic layer was dried over anhydrous Na$_2$SO$_4$ and concentrated under reduced pressure to afford crude compound which was purified by column chromatography by eluting with 4% MeOH/DCM to obtain compound 3 (540 mg, 38%) as an off white solid.

$^1$H-NMR: (400 MHz, DMSO-d$_6$): δ 7.85-7.75 (m, 1H), 7.33-7.24 (m, 5H), 7.05 (s, 1H), 5.10-5.00 (m, 2H), 4.92-4.89 (m, 1H), 4.84-4.82 (m, 1H), 4.51-4.44 (m, 1H), 4.18-4.13 (m, 1H), 4.03-4.01 (m, 1H), 3.59-3.54 (m, 2H), 3.53-3.36 (m, 3H), 3.26-3.19 (m, 1H), 3.12-3.05 (m, 1H), 2.20-2.11 (m, 2H), 1.93-1.80 (m, 4H), 1.03 (d, J=6.4 Hz, 3H).

LCMS (ESI): m/z 447.6 [M$^+$+1]

Synthesis of (S)-1-(L-prolyl)-N-((2S,3R)-1-amino-3-hydroxy-1-oxobutan-2-yl)pyrrolidine-3-carboxamide (NRX-1007)

To a stirring solution of compound 3 (520 mg, 1.16 mmol) in methanol (15 mL) was added 50% wet 10% Pd/C (200 mg) at RT and stirred for 1 h under H$_2$ atmosphere. After consumption of the starting material (by TLC), the reaction mixture was filtered through a pad of celite and washed with methanol (10 mL). Obtained filtrate was concentrated under reduced pressure to afford crude compound which was triturated with Et$_2$O and dried under vacuum to afford NRX-1007 (310 mg, 85%) as white solid.

$^1$H-NMR: (400 MHz, D$_2$O): δ 4.36-4.27 (m, 2H), 4.04-3.98 (m, 1H), 3.89-3.51 (m, 4H), 3.45-3.29 (m, 1H), 3.15-3.11 (m, 1H), 2.95-2.88 (m, 1H), 2.43-2.08 (m, 3H), 1.88-1.74 (m, 3H), 1.30-1.25 (d, J=6.4 Hz, 3H).

LCMS (ESI): m/z 313.5 [M$^+$+1]

HPLC: 98.51%

Synthesis of benzyl ((2S,3R)-1-((S)-2-((S)-3-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (5)

To a stirring solution of NRX-1007 (230 mg, 0.73 mmol) in DMF (5 mL) was added DIPEA (0.4 mL, 2.21 mmol), HATU (308 mg, 0.81 mmol) and Int D (223 mg, 0.88 mmol) at 0° C. under argon atmosphere. The reaction mixture was brought to RT and stirred for 3 h. After consumption of the starting material (by TLC), the reaction mixture was quenched with water (5 mL) and extracted with DCM (2×20 mL). Combined organic layers were dried over anhydrous Na$_2$SO$_4$ and concentrated under reduced pressure to afford crude compound which was purified by column chromatography by eluting with 6% MeOH/DCM to obtain crude compound 5 (210 mg, crude) as white solid, which was taken to next step without any further purification.

LCMS (m/z): 548.6 [M$^+$+1]

Synthesis of (S)-1-(L-threonyl-L-prolyl)-N-((2S,3R)-1-amino-3-hydroxy-1-oxobutan-2-yl)pyrrolidine-3-carboxamide (NRX-1008)

To a stirring solution of compound 5 (200 mg, 0.36 mmol) in methanol (10 mL) was added 50% wet 10% Pd/C (50 mg) at RT and stirred for 2 h under H$_2$ atmosphere. After consumption of the starting material (by TLC), the reaction mixture was filtered through a pad of celite and washed with methanol (10 mL). Obtained filtrate was concentrated under reduced pressure to afford crude compound which was triturated with Et$_2$O (2×10 mL) and dried under vacuum to afford NRX-1008 (48 mg, 31%) as white solid.

$^1$H-NMR: (400 MHz, D$_2$O): δ 4.80-4.70 (m, 1H), 4.40-4.28 (m, 2H), 4.17-4.13 (m, 2H), 4.03-3.86 (m, 2H), 3.82-3.55 (m, 4H), 3.52-3.33 (m, 1H), 2.44-2.24 (m, 2H), 2.18-2.02 (m, 3H), 1.99-1.90 (m, 1H), 1.41 (d, J=5.6 Hz, 3H), 1.28 (d, J=6.4 Hz, 3H).

LCMS (ESI): m/z 414.4 [M$^+$+1]

HPLC: 94.67%

K. Synthesis of NRX-1013 & 1014:

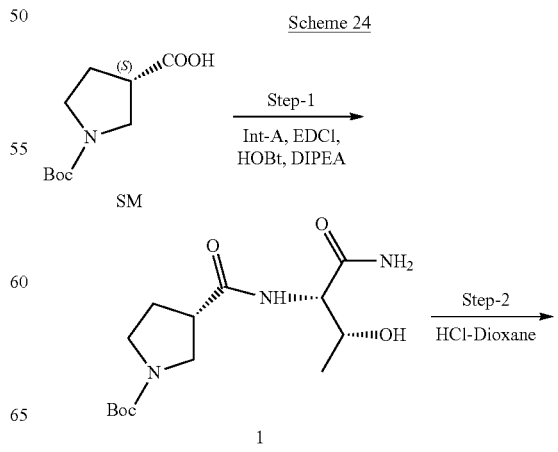

Scheme 24

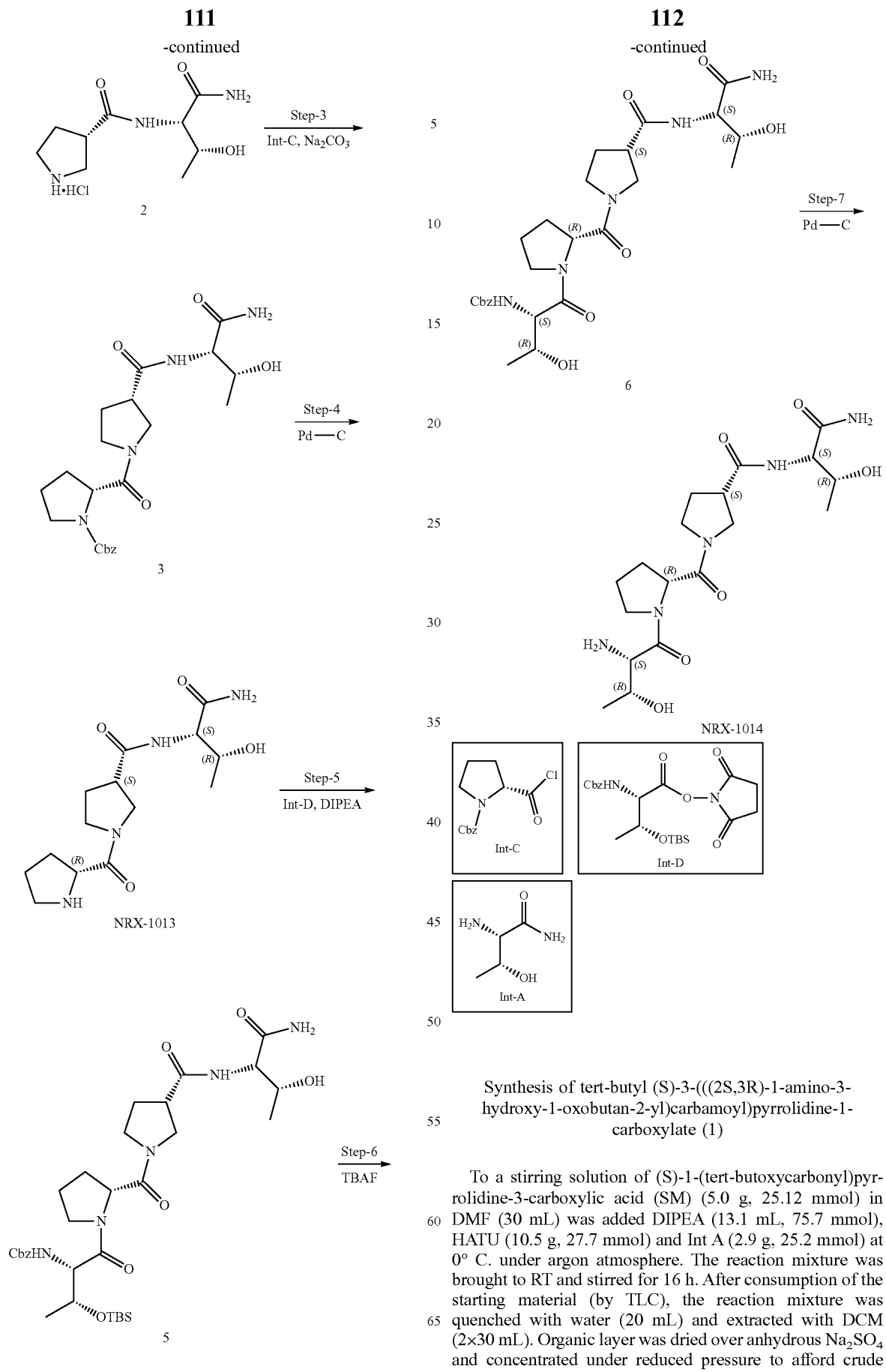

Synthesis of tert-butyl (S)-3-(((2S,3R)-1-amino-3-hydroxy-1-oxobutan-2-yl)carbamoyl)pyrrolidine-1-carboxylate (1)

To a stirring solution of (S)-1-(tert-butoxycarbonyl)pyrrolidine-3-carboxylic acid (SM) (5.0 g, 25.12 mmol) in DMF (30 mL) was added DIPEA (13.1 mL, 75.7 mmol), HATU (10.5 g, 27.7 mmol) and Int A (2.9 g, 25.2 mmol) at 0° C. under argon atmosphere. The reaction mixture was brought to RT and stirred for 16 h. After consumption of the starting material (by TLC), the reaction mixture was quenched with water (20 mL) and extracted with DCM (2×30 mL). Organic layer was dried over anhydrous $Na_2SO_4$ and concentrated under reduced pressure to afford crude compound which was purified by column chromatography by eluting with 4% MeOH/DCM to obtain compound 1 (4.7 g, 59%) as white solid.

$^1$H-NMR: (400 MHz, D$_2$O): δ 4.35 (d, J=4.0 Hz, 1H), 4.33-4.27 (m, 1H), 3.62-3.37 (m, 4H), 3.31-3.24 (m, 1H), 2.31-2.23 (m, 1H), 2.13-2.04 (m, 1H), 1.48 (s, 9H), 1.24 (d, J=2.4 Hz, 3H).

LCMS (m/z): 314.3 [M$^+$−1]

Synthesis of (S)—N-((2S,3R)-1-amino-3-hydroxy-1-oxobutan-2-yl)pyrrolidine-3-carboxamide (2)

To a solution of compound 1 (3.5 g, 11.1 mmol) in DCM (35 mL) was added 4M HCl in dioxane (0.83 mL, 3.33 mmol) at 0° C. under argon atmosphere. The reaction mixture was allowed to stir at RT for 2 h. After consumption of the starting material (by TLC), volatiles were evaporated under reduced pressure. Crude material was triturated with Et$_2$O dried under vacuum to afford compound 2.HCl salt (3.1 g) as white solid.

$^1$H-NMR: (400 MHz, D$_2$O): δ 4.35-4.29 (m, 2H), 3.67-3.57 (m, 4H), 3.44-3.41 (m, 1H), 2.51-2.38 (m, 1H), 2.28-2.16 (m, 1H), 1.26 (d, J=6.4 Hz, 3H).

LCMS (ESI): m/z 215.3 [M$^+$+1]

Synthesis of benzyl (R)-2-((S)-3-(((2S,3R)-1-amino-3-hydroxy-1-oxobutan-2-yl)carbamoyl)pyrrolidine-1-carbonyl)pyrrolidine-1-carboxylate (3)

To a stirring solution of compound 2.HCl salt (1.5 g, 5.97 mmol) in DCM:H$_2$O (30 mL, 1:1) was added Na$_2$CO$_3$ (1.5 g, 14.9 mmol) and Int-C(1.9 g, 7.16 mmol) at 0° C. under argon atmosphere. The reaction mixture was stirred at RT for 2 h. After consumption of the starting material (by TLC), the reaction mixture was extracted with DCM (2×30 mL). Organic layer was dried over anhydrous Na$_2$SO$_4$ and concentrated under reduced pressure to afford crude compound which was purified by column chromatography by eluting with 5% MeOH/DCM to obtain compound 3 (1.1 g, 42%) as an off white solid.

$^1$H-NMR: (500 MHz, DMSO-d$_6$): δ 7.79-7.76 (m, 1H), 7.38-7.26 (m, 5H), 7.06 (s, 1H), 5.09-5.00 (m, 2H), 4.94-4.91 (m, 1H), 4.84-4.82 (m, 1H), 4.45-4.41 (m, 1H), 4.15-4.13 (m, 1H), 4.04-4.01 (m, 1H), 3.69-3.66 (m, 1H), 3.49-3.41 (m, 2H), 3.31-3.21 (m, 2H), 3.07-2.97 (m, 2H), 2.19-2.12 (m, 2H), 1.89-1.80 (m, 4H), 1.04-1.01 (d, 3H).

LCMS (ESI): m/z 447.5 [M$^+$+1]

Synthesis of (S)-1-(D-prolyl)-N-((2S,3R)-1-amino-3-hydroxy-1-oxobutan-2-yl)pyrrolidine-3-carboxamide (NRX-1013)

To a stirring solution of compound 3 (1.1 g, 2.46 mmol) in methanol (25 mL) was added 50% wet 10% Pd/C (300 mg) at RT and stirred for 1 h under H$_2$ atmosphere. After consumption of the starting material (by TLC), the reaction mixture was filtered through a pad of celite and washed with methanol (10 mL). Obtained filtrate was concentrated under reduced pressure. Crude material was triturated with Et$_2$O and dried under vacuum to afford crude compound which was triturated with Et$_2$O and dried under vacuum to afford NRX-1013 (620 mg, 80%) as white solid.

$^1$H-NMR: (400 MHz, D$_2$O): δ 4.37-4.29 (m, 2H), 3.93-3.88 (m, 1H), 3.76-3.60 (m, 3H), 3.42-3.30 (m, 2H), 3.11-3.06 (m, 1H), 2.86-2.81 (m, 1H), 2.40-2.12 (m, 3H), 1.85-1.69 (m, 3H), 1.25 (d, J=6.4 Hz, 3H).

LCMS (ESI): m/z 313.3 [M$^+$+1]
HPLC: 99.56%

Synthesis of benzyl ((2S,3R)-1-((R)-2-((S)-3-(((2S,3R)-1-amino-3-hydroxy-1-oxobutan-2-yl)carbamoyl)pyrrolidine-1-carbonyl)pyrrolidin-1-yl)-3-((tert-butyldimethylsilyl)oxy)-1-oxobutan-2-yl)carbamate (5)

To a stirring solution of NRX-1013 (300 mg, 0.96 mmol) in DMF (5 mL) was added DIPEA (0.4 mL, 1.93 mmol) and Int D (535 mg, 1.15 mmol) at 0° C. under argon atmosphere. The reaction mixture was brought to RT and stirred for 2 h. After consumption of the starting material (by TLC), the reaction mixture was quenched with water (5 mL) and extracted with DCM (2×20 mL). Combined organic layers were dried over anhydrous Na$_2$SO$_4$ and concentrated under reduced pressure to afford crude compound 5 (710 mg, crude), which was taken to next step without any further purification.

LCMS (m/z): 662.3 [M$^+$+1]

Synthesis of benzyl ((2S,3R)-1-((R)-2-((S)-3-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (6)

To a stirring solution of crude compound 5 (710 mg, 1.07 mmol) in THF (10 mL) was added TBAF (336 mg, 1.29 mmol) at 0° C. under argon atmosphere. The reaction mixture was brought to RT and stirred for 4 h. After consumption of the starting material (by TLC), the reaction mixture was diluted with water (5 mL) and extracted with DCM (2×10 mL). Combined organic layers were dried over anhydrous Na$_2$SO$_4$ and concentrated under reduced pressure to afford crude compound 6 (230 mg, crude) as sticky compound, which was taken to next step without any further purification.

LCMS (ESI): m/z 548.6 [M$^+$+1]

Synthesis of (S)-1-(L-threonyl-D-prolyl)-N-((2S,3R)-1-amino-3-hydroxy-1-oxobutan-2-yl)pyrrolidine-3-carboxamide (NRX-1014)

To a stirring solution of compound 6 (230 mg, 0.42 mmol) in methanol (15 mL) was added 50% wet 10% Pd/C (100 mg) at RT and stirred for 2 h under H$_2$ atmosphere. After consumption of the starting material (by TLC), the reaction mixture was filtered through a pad of celite and washed with methanol (10 mL). Obtained filtrate was concentrated under reduced pressure to afford NRX-1014 (53 mg, 30%) as an off white sticky solid.

$^1$H-NMR: (400 MHz, D$_2$O): δ 4.80-4.70 (m, 2H), 4.41-4.30 (m, 2H), 4.03-4.00 (m, 1H), 3.89-3.71 (m, 5H), 3.63-3.58 (m, 1H), 3.36-3.33 (m, 1H), 2.45-2.32 (m, 2H), 2.15-1.94 (m, 4H), 1.28-1.25 (m, 6H).

LCMS (ESI): m/z 414.4 [M$^+$+1]
HPLC: 95.75%

L. Synthesis of NRX-1027 & 1028:

Scheme 25

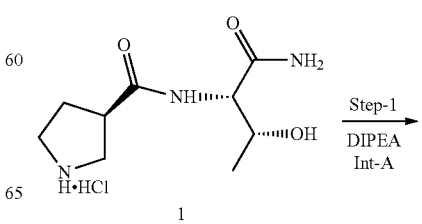

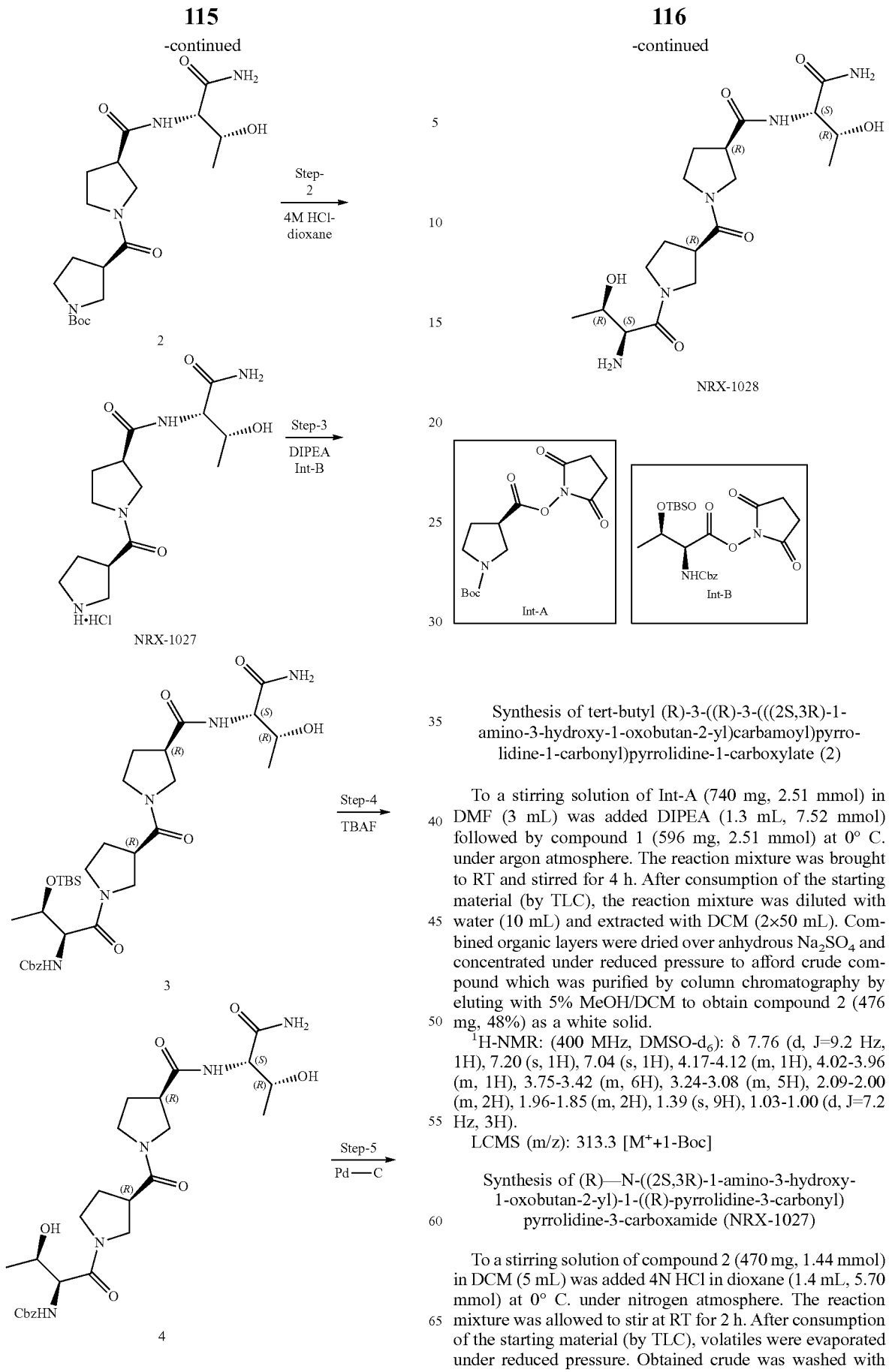

Synthesis of tert-butyl (R)-3-((R)-3-(((2S,3R)-1-amino-3-hydroxy-1-oxobutan-2-yl)carbamoyl)pyrrolidine-1-carbonyl)pyrrolidine-1-carboxylate (2)

To a stirring solution of Int-A (740 mg, 2.51 mmol) in DMF (3 mL) was added DIPEA (1.3 mL, 7.52 mmol) followed by compound 1 (596 mg, 2.51 mmol) at 0° C. under argon atmosphere. The reaction mixture was brought to RT and stirred for 4 h. After consumption of the starting material (by TLC), the reaction mixture was diluted with water (10 mL) and extracted with DCM (2×50 mL). Combined organic layers were dried over anhydrous $Na_2SO_4$ and concentrated under reduced pressure to afford crude compound which was purified by column chromatography by eluting with 5% MeOH/DCM to obtain compound 2 (476 mg, 48%) as a white solid.

$^1$H-NMR: (400 MHz, DMSO-$d_6$): δ 7.76 (d, J=9.2 Hz, 1H), 7.20 (s, 1H), 7.04 (s, 1H), 4.17-4.12 (m, 1H), 4.02-3.96 (m, 1H), 3.75-3.42 (m, 6H), 3.24-3.08 (m, 5H), 2.09-2.00 (m, 2H), 1.96-1.85 (m, 2H), 1.39 (s, 9H), 1.03-1.00 (d, J=7.2 Hz, 3H).

LCMS (m/z): 313.3 [M$^+$+1-Boc]

Synthesis of (R)—N-((2S,3R)-1-amino-3-hydroxy-1-oxobutan-2-yl)-1-((R)-pyrrolidine-3-carbonyl)pyrrolidine-3-carboxamide (NRX-1027)

To a stirring solution of compound 2 (470 mg, 1.44 mmol) in DCM (5 mL) was added 4N HCl in dioxane (1.4 mL, 5.70 mmol) at 0° C. under nitrogen atmosphere. The reaction mixture was allowed to stir at RT for 2 h. After consumption of the starting material (by TLC), volatiles were evaporated under reduced pressure. Obtained crude was washed with pentane (2×10 mL) and dried under vacuum to afford NRX-1027.HCl salt (402 mg, crude) as a white solid.

$^1$H-NMR: (400 MHz, D$_2$O): δ 4.35-4.33 (m, 1H), 4.29-4.24 (m, 1H), 3.92-3.30 (m, 10H), 2.48-2.10 (m, 4H), 1.27-1.24 (m, 3H).

LCMS (ESI): m/z 313.5 [M$^+$+1]

HPLC: 98.64%

Synthesis of benzyl ((2S,3R)-1-((R)-3-((R)-3-(((2S, 3R)-1-amino-3-hydroxy-1-oxobutan-2-yl)carbamoyl)pyrrolidine-1-carbonyl)pyrrolidin-1-yl)-3-((tert-butyldimethylsilypoxy)-1-oxobutan-2-yl)carbamate (3)

To a stirring solution of NRX-1027.HCl salt (150 mg, 0.43 mmol) in DMF (3 mL) were added DIPEA (0.22 mL, 1.29 mmol) and Int-B (239 mg, 0.52 mmol) and at 0° C. under nitrogen atmosphere. The reaction mixture was brought to RT and stirred for 16 h. After consumption of the starting material (by TLC), the reaction mixture was diluted with water (10 mL) and extracted with DCM (2×20 mL). Combined organic layers were dried over anhydrous Na$_2$SO$_4$ and concentrated under reduced pressure to afford crude compound which was purified by column chromatography by eluting with 8% MeOH/DCM to obtain compound 3 (205 mg, 72%) as a brown solid.

$^1$H-NMR: (400 MHz, DMSO-d$_6$): δ 7.81-7.76 (m, 1H), 7.35-7.29 (m, 5H), 7.20 (s, 1H), 7.05-6.99 (m, 2H), 5.00 (s, 2H), 4.83-4.81 (m, 1H), 4.26-4.22 (m, 1H), 4.16-4.12 (m, 1H), 4.01-3.99 (m, 2H), 3.71-3.47 (m, 7H), 3.30-3.10 (m, 3H), 2.07-1.84 (m, 4H), 1.27-1.22 (m, 3H), 1.03-1.00 (m, 3H), 0.81 (s, 9H), 0.03-0.00 (m, 6H).

LCMS (m/z): 662.8 [M$^+$+1]

Synthesis of benzyl ((2S,3R)-1-((R)-3-((R)-3-(((2S, 3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (4)

To a stirring solution of compound 3 (470 mg, 0.72 mmol) in THF (5 mL) was added TBAF (1M in THF) (0.86 mL, 0.86 mmol) at 0° C. under nitrogen atmosphere. The reaction mixture was brought to RT and stirred for 6 h. After consumption of the starting material (by TLC), the reaction mixture was diluted with water (5 mL) and extracted with DCM (2×10 mL). Combined organic layers were dried over anhydrous Na$_2$SO$_4$ and concentrated under reduced pressure to afford compound 4 (395 mg, crude) as a brown compound, which was taken to next step without any further purification.

LCMS (ESI): m/z 548.5 [M$^+$+1]

Synthesis of (R)-1-((R)-1-(L-threonyl)pyrrolidine-3-carbonyl)-N-((2S,3R)-1-amino-3-hydroxy-1-oxobutan-2-yl)pyrrolidine-3-carboxamide (NRX-1028)

To a stirring solution of crude compound 5 (390 mg, 0.71 mmol) in methanol (5 mL) was added 50% wet 10% Pd/C (150 mg) at RT and stirred for 4 h under H$_2$ atmosphere. After consumption of the starting material (by TLC), the reaction mixture was filtered through a pad of celite and the filtrate was concentrated under reduced pressure to afford crude compound which was purified by column chromatography by eluting with 15% MeOH/DCM+2 mL aq.NH$_3$ to obtain to afford NRX-1028 (35 mg, 12%) as a white solid.

$^1$H-NMR: (400 MHz, D$_2$O): δ 4.37-4.35 (m, 1H), 4.29-4.25 (m, 1H), 3.98-3.85 (m, 2H), 3.84-3.32 (m, 10H), 2.38-2.05 (m, 4H), 1.27-1.22 (m, 6H).

LCMS (ESI): m/z 414.4 [M$^+$+1]

UPLC: 94.07%

M. Synthesis of NRX-1025 & 1026:

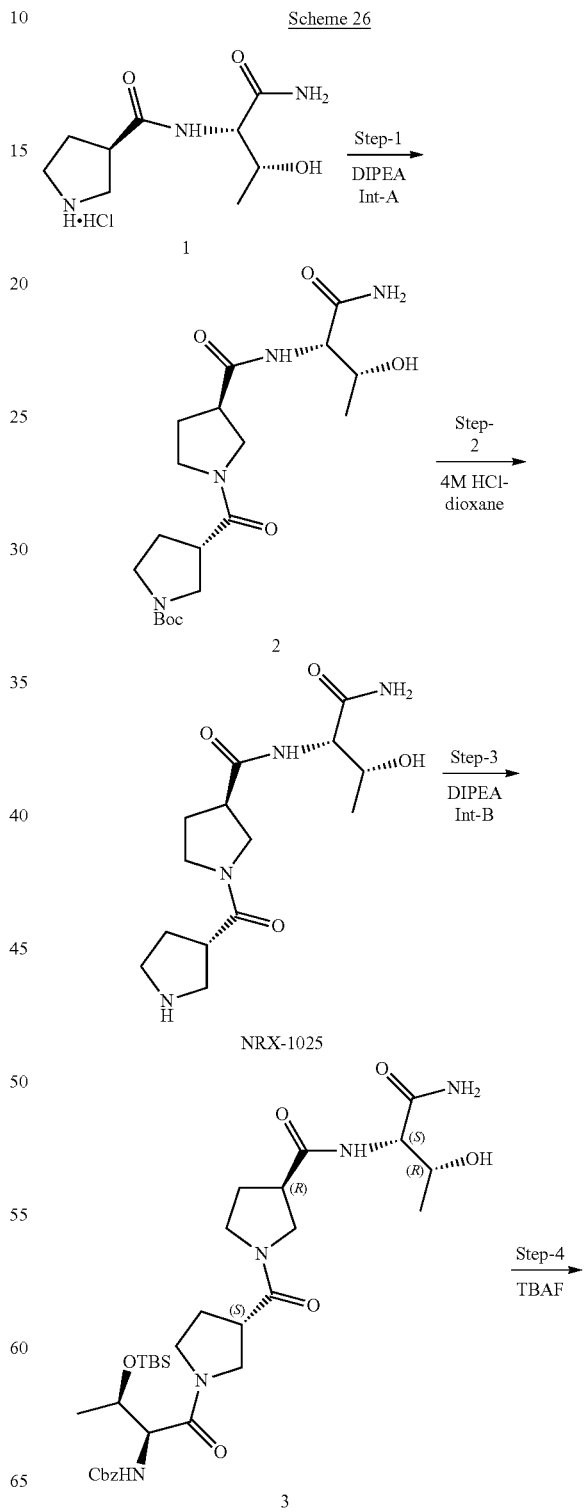

Scheme 26

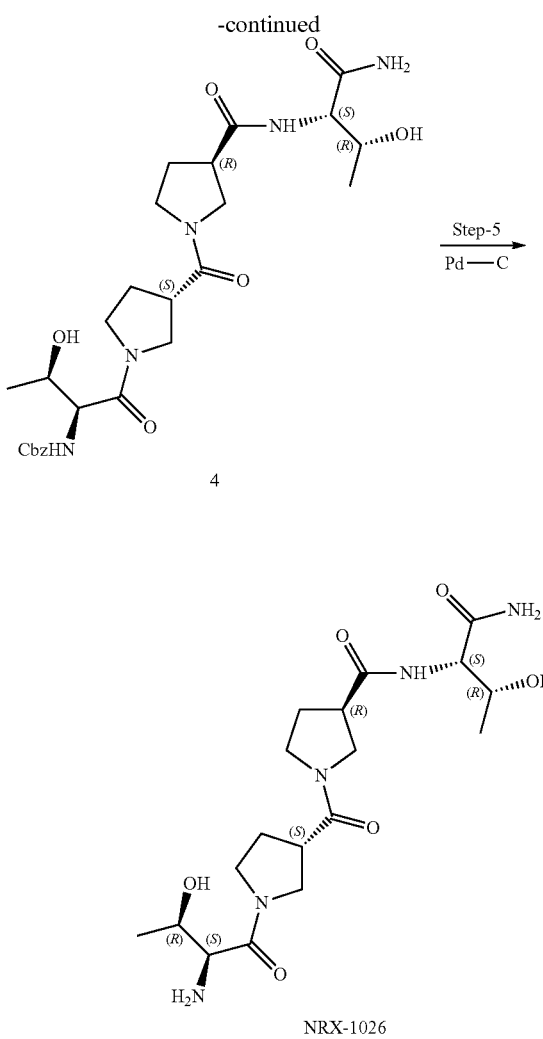

4

NRX-1026

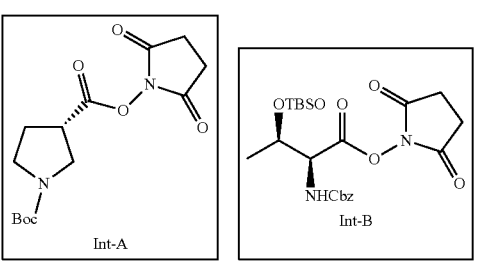

Int-A    Int-B

Synthesis of tert-butyl (S)-3-((R)-3-(((2S,3R)-1-amino-3-hydroxy-1-oxobutan-2-yl)carbamoyl)pyrrolidine-1-carbonyl)pyrrolidine-1-carboxylate (2)

To a stirring solution of Int-A (1.6 g, 5.12 mmol) in DMF (6 mL) was added DIPEA (2.6 mL, 15.4 mmol) followed by compound 1 (1.3 g, 5.12 mmol) at 0° C. under argon atmosphere. The reaction mixture was brought to RT and stirred for 16 h. After consumption of the starting material (by TLC), the reaction mixture was diluted with water (10 mL) and extracted with DCM (2×50 mL) and 10% MeOH/DCM. Combined organic layers were dried over anhydrous Na$_2$SO$_4$ and concentrated under reduced pressure to afford crude compound which was purified by column chromatography by eluting with 8% MeOH/DCM to obtain compound 2 (720 mg, 34%) as a brown solid.

$^1$H-NMR: (500 MHz, DMSO-d$_6$): δ 7.77 (d, J=9.0 Hz, 1H), 7.20 (s, 1H), 7.04 (s, 1H), 4.15-4.13 (m, 1H), 4.01-3.98 (m, 1H), 3.65-3.41 (m, 4H), 3.35-3.32 (m, 1H), 3.30-3.10 (m, 6H), 2.09-2.01 (m, 2H), 1.96-1.88 (m, 2H), 1.39 (s, 9H), 1.25 (d, J=8.5 Hz, 3H).

LCMS (m/z): 313.3 [M$^+$+1-Boc]

Synthesis of (R)—N-((2S,3R)-1-amino-3-hydroxy-1-oxobutan-2-yl)-1-((S)-pyrrolidine-3-carbonyl)pyrrolidine-3-carboxamide (NRX-1025)

To a stirring solution of compound 2 (600 mg, 1.45 mmol) in DCM (5 mL) was added 4M HCl in dioxane (1.8 mL, 7.28 mmol) at 0° C. under nitrogen atmosphere. The reaction mixture was allowed to stir at RT for 4 h. After consumption of the starting material (by TLC), volatiles were evaporated under reduced pressure. Obtained crude was washed with pentane (2×10 mL) and dried under vacuum to afford NRX-1025.HCl salt (350 mg, 69%) as a white solid.

$^1$H-NMR: (400 MHz, D$_2$O): δ 4.34-4.30 (m, 1H), 4.29-4.23 (m, 1H), 3.90-3.30 (m, 10H), 2.49-2.10 (m, 4H), 1.47-1.24 (m, 3H).

LCMS (ESI): m/z 313.3 [M$^+$+1]

HPLC: 91.72%

Synthesis of benzyl ((2S,3R)-1-((S)-3-((R)-3-(((2S,3R)-1-amino-3-hydroxy-1-oxobutan-2-yl)carbamoyl)pyrrolidine-1-carbonyl)pyrrolidin-1-yl)-3-((tert-butyldimethylsilypoxy)-1-oxobutan-2-yl)carbamate (3)

To a stirring solution of NRX-1025.HCl salt (400 mg, 1.14 mmol) in DMF (6 mL) were added DIPEA (0.59 mL, 3.44 mmol) and Int-B (639 mg, 1.37 mmol) at 0° C. under nitrogen atmosphere. The reaction mixture was brought to RT and stirred for 16 h. After consumption of the starting material (by TLC), the reaction mixture was diluted with water (10 mL) and extracted with 10% MeOH/DCM (2×20 mL). Combined organic layers were dried over anhydrous Na$_2$SO$_4$ and concentrated under reduced pressure to afford crude compound which was purified by column chromatography by eluting with 7% MeOH/DCM to obtain compound 3 (390 mg, 51%) as brown solid.

$^1$H-NMR: (400 MHz, DMSO-d$_6$): δ 7.80-7.74 (m, 1H), 7.36-7.29 (m, 5H), 7.18 (s, 1H), 7.10-7.04 (m, 2H), 5.00 (s, 2H), 4.84-4.82 (m, 1H), 4.24-4.21 (m, 1H), 4.18-4.16 (m, 1H), 4.03-3.97 (m, 2H), 3.88-3.77 (m, 1H), 3.42-3.23 (m, 6H), 3.19-3.08 (m, 3H), 2.07-2.04 (m, 2H), 1.96-1.82 (m, 2H), 1.08-1.01 (m, 6H), 0.79 (s, 9H), 0.01-0.02 (d, 6H).

LCMS (m/z): 662.8 [M$^+$+1]

Synthesis of benzyl ((2S,3R)-1-((S)-3-((R)-3-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (4)

To a stirring solution of compound 3 (385 mg, 0.58 mmol) in THF (5 mL) was added TBAF (1M in THF) (0.69 mL, 0.69 mmol) at 0° C. under nitrogen atmosphere. The reaction mixture was brought to RT and stirred for 6 h. After consumption of the starting material (by TLC), the reaction mixture was diluted with water (5 mL) and extracted with DCM (2×10 mL) and 10% MeOH/DCM (2×10 mL). Combined organic layers were dried over anhydrous $Na_2SO_4$ and concentrated under reduced pressure to afford crude compound which was purified by column chromatography by eluting with 7% MeOH/DCM to obtain compound 4 (270 mg, 85%) as white color compound.

$^1$H-NMR: (400 MHz, DMSO-$d_6$): δ 7.81-7.76 (m, 1H), 7.38-7.29 (m, 5H), 7.20 (s, 1H), 7.11-7.05 (m, 2H), 5.06-4.99 (m, 2H), 4.84-4.82 (m, 1H), 4.74-4.70 (m, 1H), 4.22-4.12 (m, 2H), 4.01-3.97 (m, 1H), 3.88-3.77 (m, 2H), 3.64-3.38 (m, 6H), 3.31-3.09 (m, 3H), 2.07-1.82 (m, 4H), 1.05-1.00 (m, 6H).

LCMS (ESI): m/z 548.5 [M$^+$+1]

Synthesis of (R)-1-((S)-1-(L-threonyl)pyrrolidine-3-carbonyl)-N-((2S,3R)-1-amino-3-hydroxy-1-oxobutan-2-yl)pyrrolidine-3-carboxamide (NRX-1026)

To a stirring solution of compound 4 (260 mg, 0.47 mmol) in methanol (5 mL) was added 50% wet 10% Pd/C (100 mg) at RT and stirred for 4 h under $H_2$ atmosphere. After consumption of the starting material (by TLC), the reaction mixture was filtered through a pad of celite and the filtrate was concentrated under reduced pressure to afford crude compound which was purified by column chromatography by eluting with 15% MeOH/DCM+2 mL aq.$NH_3$ to obtain to afford NRX-1026 (65 mg, 33%) as white solid.

$^1$H-NMR: (400 MHz, $D_2O$): δ 4.36-4.34 (m, 1H), 4.31-4.25 (m, 1H), 3.99-3.87 (m, 2H), 3.84-3.31 (m, 10H), 2.38-2.00 (m, 4H), 1.27-1.22 (m, 6H).

LCMS (ESI): m/z 414.5 [M$^+$+1]

UPLC: 99.84%

N. Synthesis of NRX-1029 & 1030:

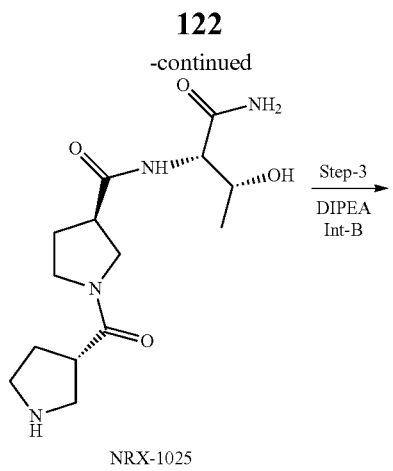

NRX-1025

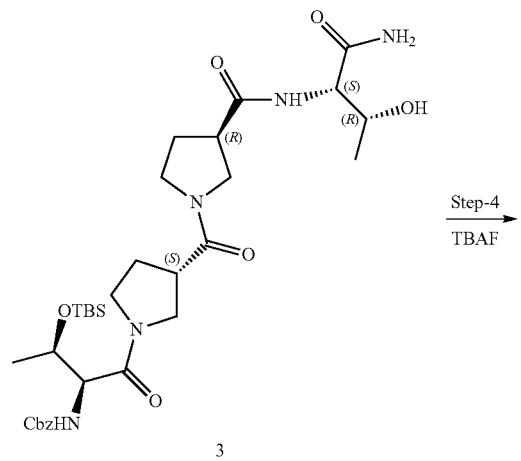

Scheme 27

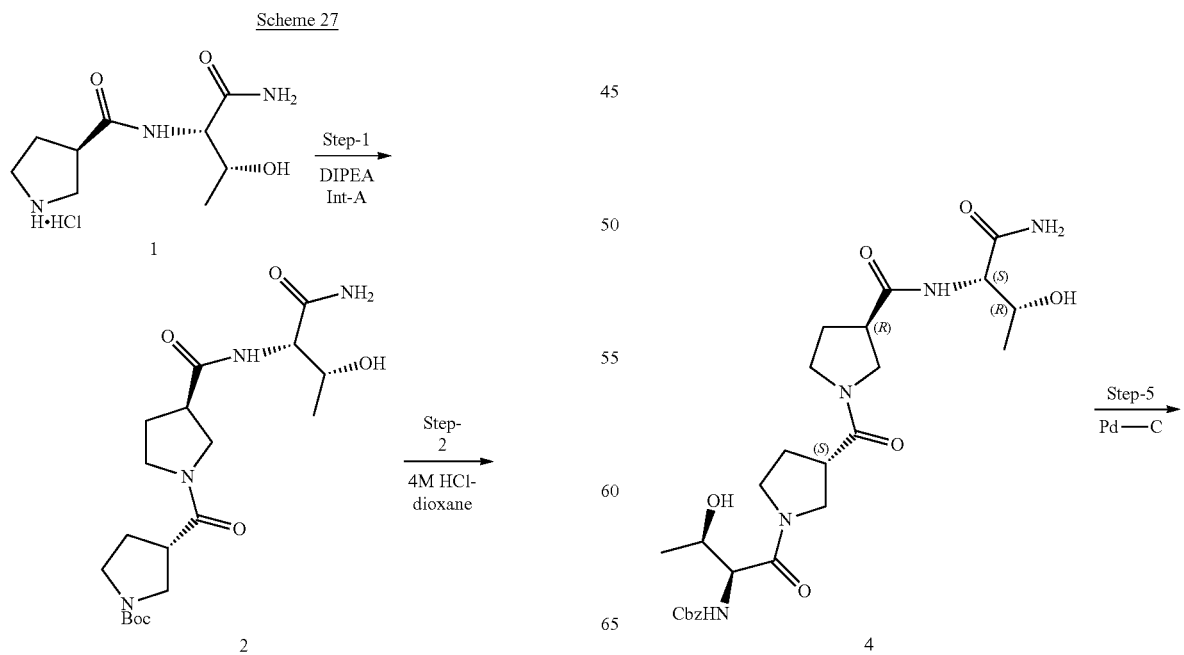

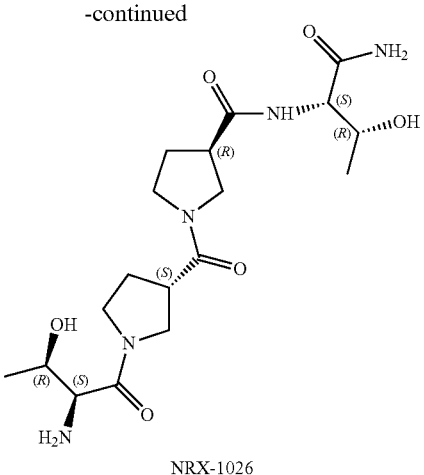

NRX-1026

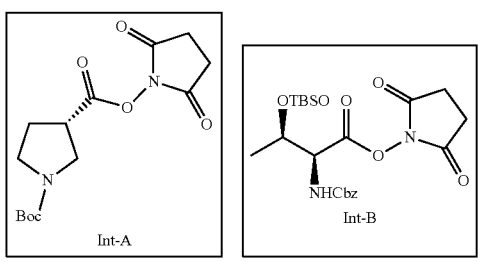

Int-A    Int-B

Synthesis of tert-butyl (R)-3-((S)-3-(((2S,3R)-1-amino-3-hydroxy-1-oxobutan-2-yl)carbamoyl)pyrrolidine-1-carbonyl)pyrrolidine-1-carboxylate (2)

To a stirring solution of compound 1 (1.3 g, 5.17 mmol) in DMF (5 mL) was added DIPEA (2.8 mL, 15.5 mmol) and Int-A (1.9 g, 6.21 mmol) at 0° C. under argon atmosphere. The reaction mixture was brought to RT and stirred for 4 h. After consumption of the starting material (by TLC), the reaction mixture was quenched with water (5 mL) and extracted with DCM (2×20 mL). Combined organic layers were dried over anhydrous $Na_2SO_4$ and concentrated under reduced pressure to afford crude compound which was purified by column chromatography by eluting 5% MeOH/DCM to obtain compound 2 (750 mg, 35%) as off white solid.

$^1$H-NMR: (400 MHz, DMSO-$d_6$): δ 7.76 (d, J=8.8 Hz, 1H), 7.20 (s, 1H), 7.04 (s, 1H), 4.82 (t, J=5.6 Hz, 1H), 4.14-4.10 (m, 1H), 4.04-3.98 (m, 1H), 3.70-3.33 (m, 6H), 3.27-3.11 (m, 4H), 2.18-1.84 (m, 4H), 1.39 (s, 9H), 1.01 (d, J=6.4 Hz, 3H).

LCMS (m/z): 411.3 [M$^+$−1]

Synthesis of (S)—N-((2S,3R)-1-amino-3-hydroxy-1-oxobutan-2-yl)-1-((R)-pyrrolidine-3-carbonyl)pyrrolidine-3-carboxamide (NRX-1029)

To a solution of compound 2 (400 mg, 0.97 mmol) in DCM (2 mL) was added 4M HCl in dioxane (0.7 mL, 2.91 mmol) at 0° C. under argon atmosphere. The reaction mixture was allowed to stir at RT for 4 h. After consumption of the starting material (by TLC), volatiles were evaporated under reduced pressure. Crude material was triturated with $Et_2O$ dried under vacuum to afford NRX-1029.HCl salt (220 mg) as off white solid.

$^1$H-NMR: (400 MHz, $D_2O$): δ 4.39-4.31 (m, 2H), 3.89-3.62 (m, 4H), 3.45-3.24 (m, 3H), 3.21-3.06 (m, 3H), 2.43-2.11 (m, 3H), 2.02-1.93 (m, 1H), 1.28 (d, J=6.4 Hz, 3H).

LCMS (ESI): m/z 313.5 [M$^+$+1]

Synthesis of benzyl ((2S,3R)-1-((R)-3-((S)-3-(((2S,3R)-1-amino-3-hydroxy-1-oxobutan-2-yl)carbamoyl)pyrrolidine-1-carbonyl)pyrrolidin-1-yl)-3-((tert-butyldimethylsilyl)oxy)-1-oxobutan-2-yl)carbamate (3)

To a stirring solution of NRX-1029.HCl salt (220 mg, 0.65 mmol) in DMF (5 mL) was added DIPEA (0.2 mL, 1.26 mmol) and Int-B (351 mg, 0.75 mmol) at 0° C. under argon atmosphere. The reaction mixture was brought to RT and stirred for 16 h. After consumption of the starting material (by TLC), the reaction mixture was quenched with water (5 mL) and extracted with DCM (2×20 mL). Combined organic layers were dried over anhydrous $Na_2SO_4$ and concentrated under reduced pressure to afford crude compound which was purified by column chromatography by eluting 5% MeOH/DCM to obtain compound 3 (200 mg, 47%) as sticky solid.

$^1$H-NMR: (500 MHz, DMSO-$d_6$): δ 7.82-7.76 (m, 1H), 7.37-7.30 (m, 5H), 7.21 (s, 1H), 7.05-6.95 (m, 2H), 5.00 (s, 2H), 4.83 (m, 1H), 4.26-4.22 (m, 1H), 4.14-4.12 (m, 1H), 4.04-4.01 (m, 2H), 3.60-3.34 (m, 6H), 3.31-3.21 (m, 2H), 3.17-3.12 (m, 2H), 2.12-1.86 (m, 4H), 1.09-1.02 (m, 6H), 0.81 (s, 9H), 0.02 (s, 3H), −0.00 (s, 3H).

LCMS (m/z): 411.3 [M$^+$−1]

Synthesis of benzyl ((2S,3R)-1-((R)-3-((S)-3-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (4)

To a stirring solution of compound 3 (200 mg, 0.31 mmol) in THF (2 mL) was added TBAF (94 mg, 0.37 mmol) at 0° C. under argon atmosphere. The reaction mixture was brought to RT and stirred for 4 h. After consumption of the starting material (by TLC), volatiles were evaporated to obtain crude compound which was purified by column chromatography by eluting 5% MeOH/DCM to obtain crude compound 4 (170 mg) as an off white solid.

$^1$H-NMR: (500 MHz, DMSO-$d_6$): δ 7.81-7.79 (m, 1H), 7.35-7.31 (m, 5H), 7.21 (s, 1H), 7.13-7.05 (m, 2H), 5.05-4.98 (m, 2H), 4.83-4.81 (m, 1H), 4.73-4.71 (m, 1H), 4.22-4.13 (m, 2H), 4.04-4.01 (m, 1H), 3.85-3.83 (m, 1H), 3.74-3.48 (m, 6H), 3.31-3.25 (m, 2H), 3.16-3.11 (m, 2H), 2.12-2.01 (m, 3H), 1.90-1.83 (m, 1H), 1.06-1.04 (m, 6H).

LCMS (ESI): m/z 662.3 [M$^+$+1]

Synthesis of (S)-1-((R)-1-(L-threonyl)pyrrolidine-3-carbonyl)-N-((2S,3R)-1-amino-3-hydroxy-1-oxobutan-2-yl)pyrrolidine-3-carboxamide (NRX-1030)

To a stirring solution of crude compound 4 (170 mg, 0.31 mmol) in methanol (5 mL) was added 50% wet 10% Pd/C (75 mg) at RT and stirred for 3 h under $H_2$ atmosphere. After consumption of the starting material (by TLC), the reaction mixture was filtered through a pad of celite and washed with methanol (10 mL). Obtained filtrate was concentrated under reduced pressure to afford NRX-1030 (52 mg, 45%) as a sticky compound.

¹H-NMR: (400 MHz, D₂O): δ 4.39-4.29 (m, 2H), 4.04-4.01 (m, 1H), 3.90-3.33 (m, 11H), 2.42-2.08 (m, 4H), 1.29-1.26 (m, 6H).
LCMS (ESI): m/z 414.4 [M⁺+1]
LCMS: 99.83%

O. Synthesis of NRX-1023 & 1024:

Scheme 28

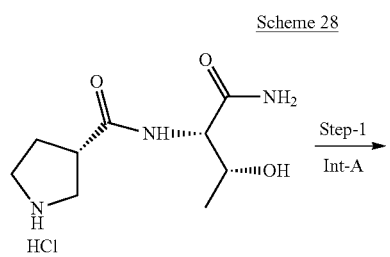

1 · HCl

Step-1
Int-A

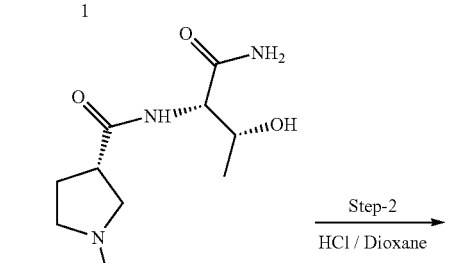

2 (Boc)

Step-2
HCl / Dioxane

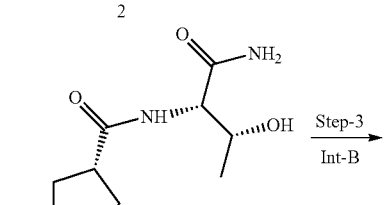

NRX-1025

Step-3
Int-B

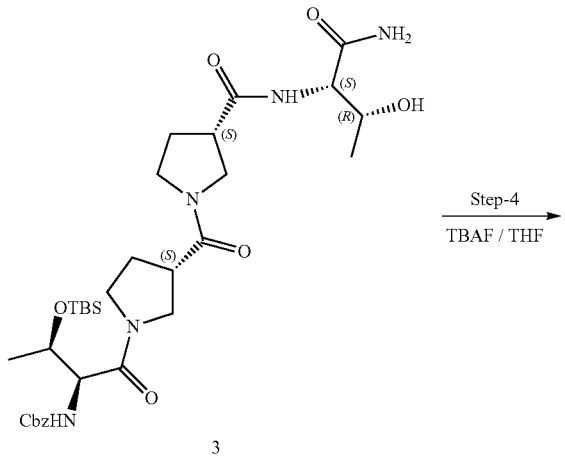

3

Step-4
TBAF / THF

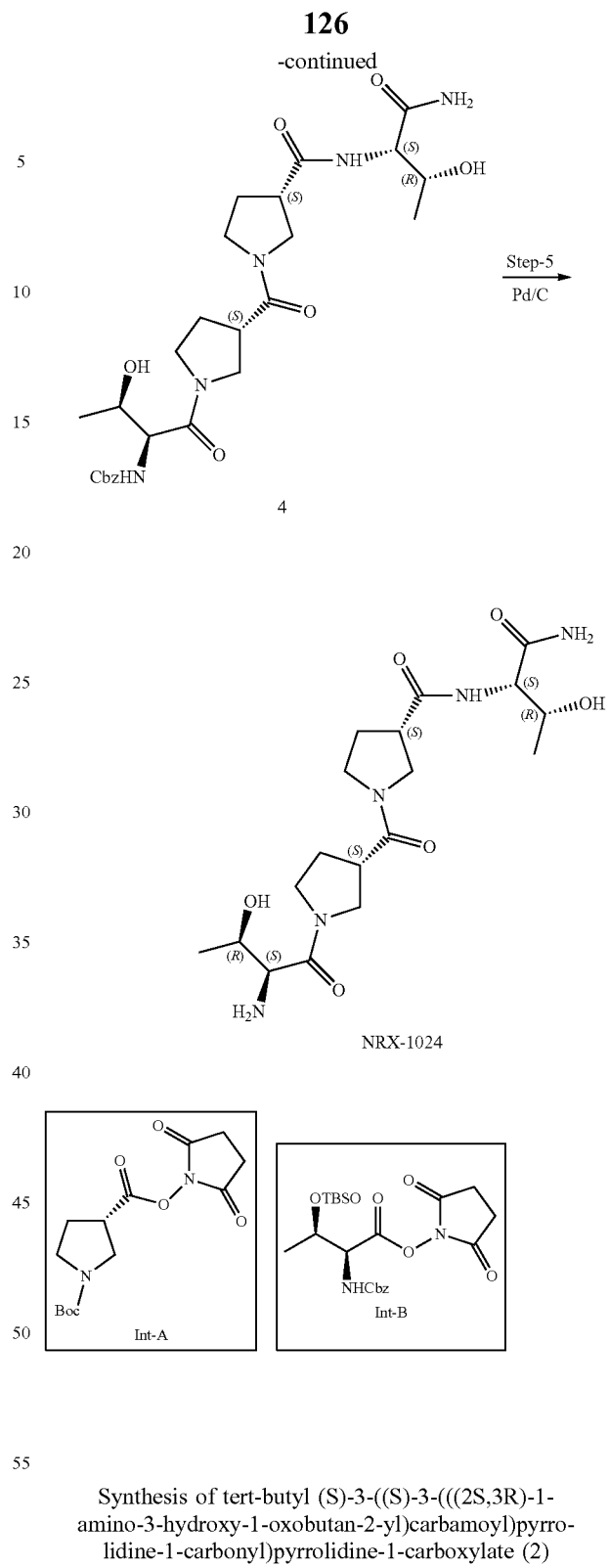

Synthesis of tert-butyl (S)-3-((S)-3-(((2S,3R)-1-amino-3-hydroxy-1-oxobutan-2-yl)carbamoyl)pyrrolidine-1-carbonyl)pyrrolidine-1-carboxylate (2)

To a stirring solution of compound 1 (595 mg, 2.37 mmol) in DMF (4 mL) was added DIPEA (1.3 mL, 7.11 mmol) and Int-A (740 mg, 2.37 mmol) at 0° C. under argon atmosphere. The reaction mixture was brought to RT and stirred for 4 h. After consumption of the starting material (by TLC), the reaction mixture was quenched with water (5 mL) and extracted with DCM (2×20 mL). Combined organic layers were dried over anhydrous $Na_2SO_4$ and concentrated under reduced pressure to afford crude compound which was purified by column chromatography by eluting 2% MeOH/DCM to obtain compound 2 (350 mg, 35%) as thick syrup.

$^1$H-NMR: (400 MHz, DMSO-$d_6$): δ 7.78 (d, J=8.8 Hz, 1H), 7.21 (s, 2H), 4.83 (t, J=5.6 Hz, 1H), 4.15-4.10 (m, 1H), 4.02 (br s, 1H), 3.72-3.50 (m, 2H), 3.49-3.40 (m, 2H), 3.37-3.33 (m, 2H), 3.28-3.07 (m, 4H), 2.17-1.85 (m, 4H), 1.39 (s, 9H), 1.02 (d, J=6.4 Hz, 3H).

LCMS (m/z): 411.3 [M$^+$−1]

Synthesis of (S)—N-((2S,3R)-1-amino-3-hydroxy-1-oxobutan-2-yl)-1-((S)-pyrrolidine-3-carbonyl)pyrrolidine-3-carboxamide (NRX-1023)

To a solution of compound 2 (350 mg, 0.84 mmol) in DCM (2 mL) was added 4M HCl in dioxane (0.6 mL, 2.54 mmol) at 0° C. under argon atmosphere. The reaction mixture was allowed to stir at RT for 2 h. After consumption of the starting material (by TLC), volatiles were evaporated under reduced pressure. Crude material was triturated with $Et_2O$ dried under vacuum to afford NRX-1023.HCl salt (330 mg) as off white solid.

$^1$H-NMR: (400 MHz, $D_2O$): δ 4.37-4.28 (m, 2H), 3.90-3.18 (m, 10H), 2.41-2.01 (m, 4H), 1.25 (d, J=6.4 Hz, 3H).

LCMS (ESI): m/z 313.5 [M$^+$+1]

Synthesis of benzyl ((2S,3R)-1-((S)-3-((S)-3-(((2S,3R)-1-amino-3-hydroxy-1-oxobutan-2-yl)carbamoyl)pyrrolidine-1-carbonyl)pyrrolidin-1-yl)-3-((tert-butyldimethylsilypoxy)-1-oxobutan-2-yl)carbamate (3)

To a stirring solution of NRX-1023.HCl salt (700 mg, 2.01 mmol) in DMF (10 mL) was added DIPEA (0.7 mL, 4.02 mmol) and Int-B (1.1 g, 2.41 mmol) at 0° C. under argon atmosphere. The reaction mixture was brought to RT and stirred for 16 h. After consumption of the starting material (by TLC), the reaction mixture was quenched with water (5 mL) and extracted with 10% MeOH/DCM (2×20 mL). Combined organic layers were dried over anhydrous $Na_2SO_4$ and concentrated under reduced pressure to afford crude compound which was purified by column chromatography by eluting 2% MeOH/DCM to obtain compound 3 (700 mg, 53%) as an off white solid.

LCMS (m/z): 662.3 [M$^+$−1]

Synthesis of benzyl ((2S,3R)-1-((S)-3-((S)-3-(((2S,3R)-1-amino-3-hydroxy-1-oxobutan-2-yl)carbamoyl)pyrrolidine-1-carbonyl)pyrrolidin-1-yl)-3-hydroxy-1-oxobutan-2-yl)carbamate (4)

To a stirring solution of compound 3 (500 mg, 1.08 mmol) in THF (5 mL) was added TBAF (501 mg, 1.91 mmol) at 0° C. under argon atmosphere. The reaction mixture was brought to RT and stirred for 4 h. After consumption of the starting material (by TLC), volatiles were evaporated to obtain crude compound which was purified by column chromatography by eluting 6% MeOH/DCM to obtain compound 4 (300 mg, 51%) as an off white solid.

LCMS (ESI): m/z 548.6 [M$^+$+1]

Synthesis of (S)-1-((S)-1-(L-threonyl)pyrrolidine-3-carbonyl)-N-((2S,3R)-1-amino-3-hydroxy-1-oxobutan-2-yl)pyrrolidine-3-carboxamide (NRX-1024)

To a stirring solution of compound 4 (300 mg, 0.54 mmol) in methanol (10 mL) was added 50% wet 10% Pd/C (100 mg) at RT and stirred for 16 h under $H_2$ atmosphere. After consumption of the starting material (by TLC), the reaction mixture was filtered through a pad of celite and washed with methanol (10 mL). Obtained filtrate was concentrated under reduced pressure to afford NRX-1024 (90 mg, 39%) as an off white solid.

$^1$H-NMR: (400 MHz, $D_2O$): δ 4.36-4.27 (m, 2H), 4.02-3.91 (m, 1H), 3.91-3.29 (m, 11H), 2.40-2.02 (m, 4H), 1.24-1.22 (m, 6H).

LCMS (ESI): m/z 414.5 [M$^+$+1]
LCMS: 93.08%

Example 5—Biological Data

I. In Vitro [$^3$H]MK-801 Potentiation Assay: Overview

Rat Cortical Membrane Preparation

Crude synaptic membranes were prepared using rat telencephalon (frontal cortex and hippocampus tissue) from male Sprague-Dawley rats and extensively washed using procedures modified from the Moskal et al. 2001 Review; The use of antibody engineering to create novel drugs that target N-methyl-D-aspartate receptors, *Current Drug Targets*, 2(3):331-45. Briefly, tissue that had been stored at −80° C. was homogenized in ice cold 10 mM Tris (pH7.4 at 4° C.) using a Brinkman Polytron and then pelleted by centrifugation at 51,500 g for 20 min. The resulting supernatant was discarded and the membranes were homogenized and washed an additional 3×. Pellets were then resuspended in 5 mM EDTA/15 mM Tris (pH7.4) and incubated for 1 hr at 37° C. The membrane suspensions were then pelleted by centrifugation at 51,500 g for 20 min and stored at −80° C. overnight. The pellets were resuspended in 10 mM Tris HCl (pH7.4 at 4° C.) and homogenized and washed an additional 7 times and frozen at 80° C. until assay.

Assay

Functional glycine site agonist effects were measured using an a [$^3$H]MK-801 potentiation assay (see Urwyler S, Floersheim P, Roy B L, Koller M. *J Med Chem.* (2009) 52(16):5093-107). Briefly, 300 µg of membrane extract protein were preincubated for 15 minutes at 25° C. in the presence of a saturating concentration of glutamate (50 µM) and varying concentrations of GLYX-13. Following the addition of 0.3 mCi of [$^3$H]MK-801 (Amersham, 22.5 Ci/mmol), reactions were incubated for an additional 15 minutes (non-equilibrium conditions). Bound and free [$^3$H]MK-801 were separated via rapid filtration using a Brandel apparatus. Zero levels were determined in the absence of any glycine ligand in the presence of 30 µM dichlorokyneurenic acid. The % maximal [$^3$H]MK-801 binding was calculated relative to stimulation measured in the presence of 1 mM glycine and 50 μM glutamate. Binding curves were fitted using GraphPad software.

For compounds with relatively low activity (e.g., GLYX-13), the identification and elimination of background glycine levels can have a significant effect on the interpretation of this assay. The origin of aberrantly high background glycine, or bioactive plastic leachates that act like glycine, can stem rom either the water itself, the LC/MS grade water filter used, or a result of time-dependent leaching from plasticware (including storage tubes, beakers, pipette tips). As such, determination of background glycine levels that may be present in the assay solutions is performed prior to any preclinical assay. Absolute background percentages are calculated.

To minimize the effect of high background, a full glycine dose response is run in the presence and absence of 5.7 dichlorokyneurenic acid to determine the absolute zero background glycine levels. The measured background in this assay is preferably not greater than 5-10%.

II. In Vitro [$^3$H]MK-801 Potentiation Assay: Preparation of Rat Cortical Membranes Solutions Utilized:
2 L of 10 mM Tris HCl (pH7.4 at 4° C.)
1 L 5 mM EDTA/15 mM Tris (pH7.4)
1 L 10 mM Tris Acetate (pH7.4 at 4° C.)
Reagents Utilized:
Trizma Base
3 L Reagent grade H$_2$O
EDTA
2N HCl
Glacial acetic acid
Materials Utilized:
Rat whole brains (8 max)
Polytron homogenizer
JA 20.1 rotor centrifuge tubes
50 ml conical tubes
20 ml pipette tips
10 ml pipette tips
5 ml pipette tips
Experimental Design
One Day Prior:
  Prepare 1 L of 10 mM Tris HCl (pH7.4 at 4° C.)
    1.2112 g Trizma Base (FW 121.14) to 1 L milliQ H$_2$O
    Add 2N HCl until pH is 7.4 at 4° C. (~4 ml HCl needed)
  Store at 4° C. overnight and use cold
  Make 1 L of 15 mM Tris HCl/5 mM EDTA (pH7.4 at room temp)
    1.8168 g Trizma Base (FW 121.14)
    1.4612 g EDTA, anhydrous (MW 292.24) to 1 L MilliQ H$_2$O
    Add 2N HCl until pH is 7.4 at 4° C.
  Store at room temperature overnight
Day 1:
  Cool centrifuge and JA 20.1 rotor to 4° C. before starting the membrane isolation.
  Turn on the 37° C. water bath and put 5 mM EDTA/15 mM Tris (pH7.4) at 37° C.
  Cool Polytron homogenizer by putting in 50 ml conical tube with reagent grade H$_2$O on ice. Place JA 20.1 centrifuge tubes on ice at 4° C. to cool before adding rat cortical dissections (2/brain being homogenized with a maximum of 16 tubes). In addition, cool to 4° C. the 50 ml tubes that will be used to homogenize rat brains (1/brain being homogenized for a maximum of 8 tubes) and the 10 mM Tris HCl (pH7.4 at 4° C.) to be used in the isolation.

Remove the previously dissected and frozen rat telencephalon (frontal cortex and hippocampus tissue from male Sprague-Dawley rats; 8 max) from the −80° C. freezer and place on ice. Add 24 ml of 10 mM Tris HCl (pH7.4 at 4° C.) to each of these 50 ml conical tubes and keep them on ice. Homogenize on setting 3.5 of the Polytron homogenizer until the tissue is completely suspended. Add 12 ml to each of two JA 20.1 centrifuge tubes, also on ice. Centrifuge at 51,500×g for 30 min at 4° C. Clean the Polytron homogenizer by running the homogenizer in MilliQ water and wiping clean with a Kimwipe. Keep the homogenizer cold between homogenizations by putting it in 50 ml conical tube with reagent grade H$_2$O on ice.

After the 30 min centrifugation step pour off the supernatant leaving the cell pellet. Add 3 ml of 10 mM Tris HCl (pH7.4 at 4° C.) and resuspend the membranes by homogenization for 30 seconds on setting 3.5 of the Polytron homogenizer, or until completely resuspended. Once the membranes are resuspended add an additional 9 ml of 10 mM Tris HCl (7.4 at 4 C) for a total volume of 12 ml. Again, centrifuge at 51,500×g for 30 min at 4° C. Clean the Polytron homogenizer as before and repeat 3 times for a total of 4 wash steps.

After the final wash step, to the cell pellet, add 3 ml of 5 mM EDTA/15 mM Tris (pH7.4) previously incubated at 37° C. and resuspend by homogenization on setting 3.5 of the Polytron homogenizer. Add an additional 9 ml of 5 mM EDTA/15 mM Tris (pH7.4 at 37° C.) for a total volume of 12 ml. Cover the JA 20.1 centrifuge tubes with parafilm and incubate the samples in a 37° C. water bath for 1 hour (Note: be careful to ensure that the water level does not cover the top of the centrifuge tubes). Remove the parafilm from the centrifuge tubes and then centrifuge them at 51,500×g for 30 min at 4° C. Pour off the supernatant. Cover the JA 20.1 centrifuge tubes with parafilm and quick freeze the rat cortical pellet by immersing the centrifuge tube containing the pellet in liquid nitrogen until completely frozen. Store the membrane extract at −80° C.

Prepare 1 L of 10 mM Tris HCl (pH7.4 at 4° C.)
    1.2112 g Trizma Base (FW 121.14) to 1 L reagent grade H$_2$O
    Add 2N HCl until pH is 7.4 at 4° C. (~4 ml HCl needed)
  Store at 4° C. overnight for use on Day 2.
Day 2:
  Prepare 1 L of 10 mM Tris Acetate (pH7.4 at Room Temperature)
    1.2112 g Trizma Base (FW 121.14) to 1 L reagent grade H$_2$O
    Add glacial acetic acid until pH is 7.4 at room temperature
  Cool centrifuge to 4° C. to allow it to reach temperature before starting the membrane preparation and put the JA 20.1 rotor in the centrifuge. Cool Polytron homogenizer by putting in 50 ml conical tube with reagent grade H$_2$O on ice. Put the 10 mM Tris HCl (pH 0.4 at 4° C.) stored at 4° on ice to keep cool.
  Remove the frozen membrane extracts made on day one from the −80° C. freezer and put on ice. Add 3 ml of 10 mM Tris HCl (pH7.4 at 4° C.) and homogenize on setting 3.5 of the Polytron homogenizer until the pellet is completely in suspension. Once the membranes are resuspended add an additional 9 ml of 10 mM Tris HCl (pH7.4 at 4 C) for a total volume of 12 ml. Centrifuge at 51,500×g for 30 min at 4° C. Clean the Polytron homogenizer by running the homogenizer in MilliQ water and wiping clean with a Kimwipe. Keep the homogenizer cold by putting it in 50 ml conical tube with reagent grade $H_2O$ on ice. Repeat 6 times for a total of 7 wash steps.

After the seventh wash step in Tris HCl, add 3 ml of 10 mM Tris Acetate to each sample and homogenize until completely resuspended. Pool the samples in a 50 ml conical tube and quantify the protein levels using the BCA assay.

Once protein levels are quantified, aliquot 5 mg of rat cortical membrane extracts into 50 ml conical tubes and label them with the volume, protein concentration, date, and your name. Store these aliquots at −80° C. until use in the Brandel Assay.

III. in vitro [$^3$H]MK-801 Potentiation Assay: Brandel Rapid Filtration

Solutions Utilized:
10 mM Tris Acetate (pH7.4 at room temp)
500 mM Glycine
10 mM Glutamate
30 mM DCK
100 mM 7CK
Reagents Utilized:
LC/MS grade MilliQ water
Trizma Base
glacial acetic acid
Materials Utilized:
Previously frozen, aliquoted, and tested rat cortical membrane preps
50 ml conical tubes
10 ml pipette tips
5 ml pipette tips
1.5 ml tubes
Stock Solutions (these can be made in advance):
500 mM Glycine in 10 mM TA

| Total Volume: 10 ml | Add |
|---|---|
| glycine | 0.375 g |
| 10 mM TA | to 10 ml |
| Store at 4° C. | |

10 mM Glutamate in 10 mM TA

| Total Volume: 10 ml | Add |
|---|---|
| L-glutamate | 0.0147 g |
| 10 mM TA | to 10 ml |
| pH to 7.4 using 10N NaOH | |
| Store at 4° C. | |

30 mM 5,7 dichlorokyneurenic acid (DCK) in DMSO

| Total Volume: 1 ml | Add |
|---|---|
| DCK | 0.0083 g |
| Dimethyl sulfoxide (DMSO) | 1.0 ml |
| Store at 4° C. | |

Experimental Design
Prepare 10 mM Tris Acetate (pH7.4 at 25° C.)

Add 1.2114 g Trizma Base/L of MilliQ LC/MS grade $H_2O$ and mix using a stir-rod. After mixing, pH the solution to pH7.4 using glacial acetic acid (requires ~500 µl glacial acetic acid/L solution). 1 L/run is used with an extra 2 L for the 24-channel harvester, and 2 L/run with an extra 4 L for the 48-channel harvester, stored at room temperature.

Prepare 0.3% Polyethyleneimine (PEI) in MilliQ $H_2O$

Add 3 ml of 50% polyethyleneimine solution to 500 ml of MilliQ $H_2O$ using a 10 ml syringe. Mix solution thoroughly with a stir-rod and store at room temperature until later use.

Prepare a 50× e Dilution Series

Prelabel 1.5 ml tubes for each of the drug dilution series and add 900 µl of 10 mM TA (pH7.4 @ room temp.) to each tube. Add 100 µl of the 500 mM glycine to the first tube ($10^{-3}$M) and continue the 1:10 dilution series until final dilution for that compound ($10^{-12}$M). Weigh out GLYX-13 for the drug dilution series (which will also range from $1\times10^{-3}$M to $1\times10^{-12}$M) and dilute to 50 mM with 10 mM TA (pH7.4). Pipette 40 µl of each dilution into the appropriate reaction vial The final concentration of DCK will be 30 µM in the reaction vial.

The final concentration of glutamate will be 50 µM in the reaction vial. For 12 runs, you will need 0.25 ml of 10 mM glutamate and 24.75 ml of 10 mM TA.

Presoak Filters in the 0.3% PEI Solution

Add the Membrane Extract

Prior to adding extract to a set of 24 reaction tubes, dilute the extract to a final volume of 23.4 ml with 10 mM TA and mix by vortexing for 1 minute, or until completely resuspended. When the filters have been in 0.3% PEI solution for at least 35 minutes, add 935 µl of the membrane extract to each tube (corresponding to 200 µg of rat cortical membrane extract protein in each reaction). Briefly vortex the membrane extract with the drug dilutions. Add [$^3$H] MK-801.

Add the [$^3$H] MK-801

Three minutes prior to the end of the first 15 minute incubation period, remove the stock vial of [$^3$H]MK-801 from the −20° C. freezer and add 7.8 µl [$^3$H]MK-801 (1 µCi/µl) to a 1.5 ml tube containing 642.2 µl 10 mM TA (26× Master Mix). Return the stock vial to the freezer. (Note: only open the [$^3$H]MK-801 in the designated place on the work bench and change your gloves after closing the stock vial). After returning the vial to the freezer mix the diluted [$^3$H]MK-801 by vortexing. Once the 15 minute incubation period has ended, add 25 µl to each of the 24 reaction tubes, and, finally, mix the solution by vortexing on setting 3.5. Filtering the samples through the Brandel harvester.

Add 5 ml Scintillant to Each Reaction Vial

Once the filters have been placed in the appropriate scintillation vial, add 5 ml scintillant to each vial, cap the vial, and, finally, ensure that the filter is at the bottom of the vial. Put the [$^3$H]MK-801 input vial in first, followed by each of the samples in order from left to right, and top to bottom, in the mini scintillation vial tube racks, for a total of 25 tubes in each run.

As a control, add 25 µl of the diluted [$^3$H]MK-801 stock solution directly to a scintillant vial. Add 5 ml scintillant, cap, and label the vial. This will assess the raw input to each reaction vial. Discard any pipette tips or waste [$^3$H]MK-801 in the appropriate radioactive solid waste container. After finishing, change your gloves to prevent any [$^3$H] contamination.

Scintillation Counting

Samples must wait at least 3 hours prior to quantitation in the scintillation counter. You can either wait three hours before starting the machine, or you can add at least 3 hrs worth of vials containing only scintillant (blanks) at the beginning. Use the appropriate settings on the scintillation counter to account for vial size (typically 7 ml mini-vials) and count time (typically 5 minutes).

IV. In Vitro [$^3$H]MK-801 Potentiation Assay: Results

Figure 5:
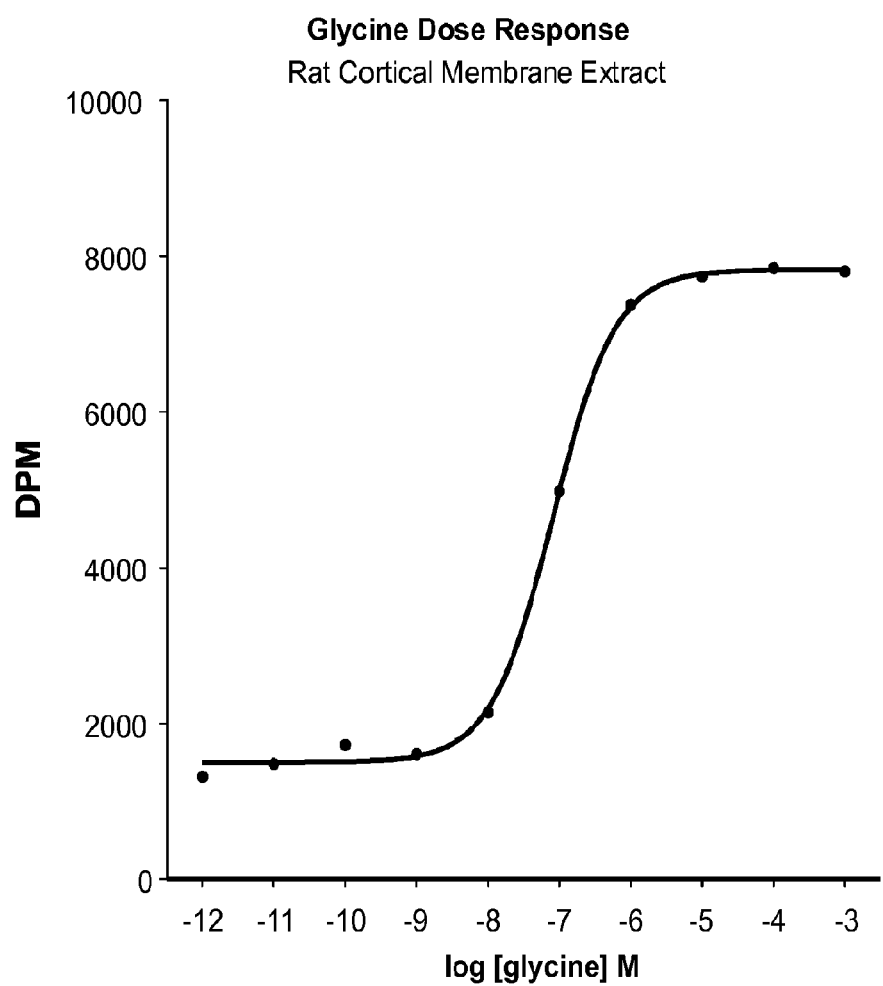
FIG. 5 shows the results of glycine dose response in the presence of 50 μM glutamate.
Figure 6:
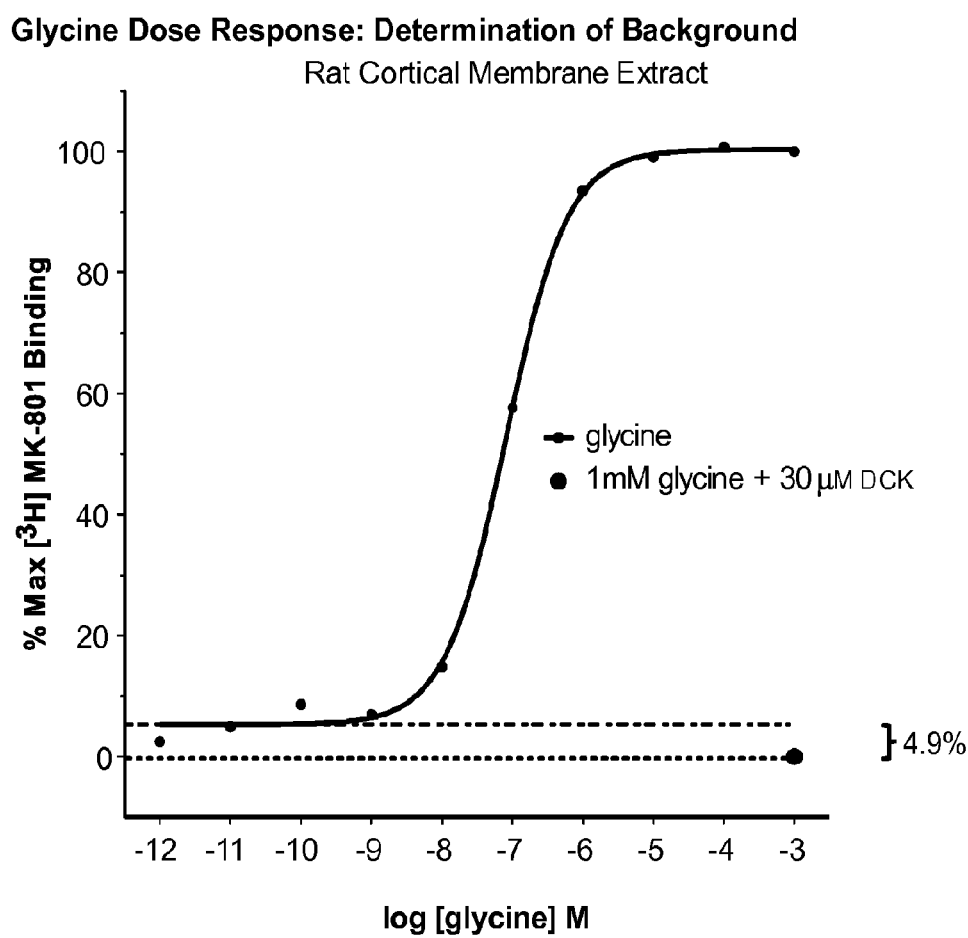
FIG. 6 shows a transformation of the glycine dose response to determine the absolute background.

A glycine dose response in the presence of 50 μM glutamate is shown as follows:

FIG. 5 shows that response to maximal glycine is typically 8000 dpm with background counts (in the absence of DCK) to 1500 dpm. Addition of 30 μM DCK to determine absolute background reduces these background counts to 1200 dpm which translates to 4.5% background. Transformation of the typical glycine dose response data experimental data produces is shown in FIG. 6.

GLYX-13 dose response performed using the [$^3$H]MK-801 assay as outlined in this protocol reproducibly produces a graph with efficacy (activity) and potency as depicted in FIG. 7.

Data obtained using the assay described above is shown in Table 2 using the compounds shown in Table 1.

TABLE 1

| Compound | Structure |
|---|---|
| A-1 | (structure) |
| A-2 | (structure) |
| A-3 | (structure) |
| A-4 | (structure) |
| A-5 | (structure) |

TABLE 2

| Cmpd. | NR2A Activity % max glycine | NR2A Potency logM | NR2B Activity % max glycine | NR2B Potency logM | NR2C Activity % max glycine | NR2C Potency logM | NR2D Activity % max glycine | NR2D Potency logM |
|---|---|---|---|---|---|---|---|---|
| A-3 | 58.25 | −10.76 | | | | | 35.17 | −13.68 |
| A-5 | not active | not active | 29.53 | −13.86 | 38.75 | −11.68 | 41.34 | −11.63 |

Exemplary compounds of formula (III) and (IV) and corresponding starting materials are also delineated in FIGS. 1-4.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:
1. A compound having formula (I):

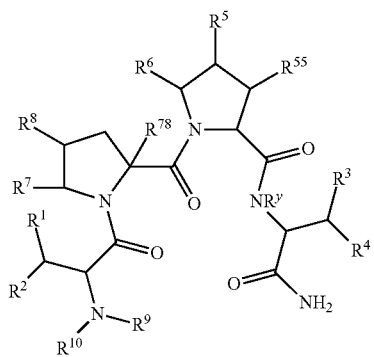

and pharmaceutically acceptable salts, thereof, wherein:
$R^1$, $R^2$, $R^3$, and $R^4$ are each independently selected from the group consisting of hydrogen; halogen; $C_{1-6}$alkyl; $C_{1-6}$ perfluoroalkyl; $C_{2-6}$alkenyl; $C_{2-6}$alkynyl; $C_{3-6}$cycloalkyl; phenyl; heteroaryl including from 5 to 6 ring atoms wherein 1, 2, or 3 of the ring atoms are independently selected from the group consisting of N, NH, N(C1-C3 alkyl), O, and S; —OR$^x$; —C(O)R$^x$; —CO$_2$(R$^x$); —C(O)N(R$^x$)$_2$; —C(NR$^x$)N(R$^x$)$_2$; —OC(O)R$^x$; —OCO$_2$R$^x$; —OC(O)N(R$^x$)$_2$; —N(R$^x$)$_2$; —NR$^x$C(O)R$^x$; —NR$^x$C(O)N(R$^x$)$_2$; —NR$^x$C(O)OR$^x$; and —NR$^x$C(NR$^x$)N(R$^x$)$_2$; wherein $C_{1-6}$alkyl is optionally substituted by one, two, or three substituents independently selected from the group consisting of halogen; hydroxyl; phenyl; heteroaryl including from 5 to 6 ring atoms wherein 1, 2, or 3 of the ring atoms are independently selected from the group consisting of N, NH, N(C1-C3 alkyl), O, and S; and N(R$^x$)$_2$;
$R^5$ and $R^6$ are independently selected from the group consisting of hydrogen; $C_1$-$C_6$ alkyl, optionally substituted by one, two or three substituents independently selected from the group consisting of halogen, hydroxyl, and N(R$^x$)$_2$; $C_{1-6}$ perfluoroalkyl; $C_1$-$C_6$ alkoxy, optionally substituted by one, two, or three substituents independently selected from the group consisting of halogen, hydroxyl, phenyl, and N(R$^x$)$_2$; and -Q-Ar, wherein Q is a bond or $C_1$-$C_6$ alkylene, optionally substituted by one, two or three independently selected halogens, and Ar is selected from the group consisting of phenyl and heteroaryl including from 5 to 6 ring atoms wherein 1, 2, or 3 of the ring atoms are independently selected from the group consisting of N, NH, N(C1-C3 alkyl), O, and S, wherein phenyl and heteroaryl are each optionally substituted by one, two, or three substituents independently selected from the group consisting of halogen, hydroxyl, phenyl, and N(R$^x$)$_2$; or
$R^5$ and $R^6$, together with the atoms to which they are attached, form a C3-C6 cycloalkyl or heterocyclyl including from 3 to 6 ring atoms wherein 1, 2, or 3 of the ring atoms are independently selected from the group consisting of N, NH, N(C1-C3 alkyl), O, and S; wherein the C3-C6 cycloalkyl and heterocyclyl are each optionally substituted by one, two, or three substituents independently selected from the group consisting of halogen, hydroxyl, phenyl, and N(R$^x$)$_2$;
$R^{55}$ is H, or $R^{55}$ and $R^5$, together with the atoms to which they are attached, form a C3-C6 cycloalkyl or heterocyclyl including from 3 to 6 ring atoms wherein 1, 2, or 3 of the ring atoms are independently selected from the group consisting of N, NH, N(C1-C3 alkyl), O, and S; wherein the C3-C6 cycloalkyl and heterocyclyl are each optionally substituted by one, two, or three substituents independently selected from the group consisting of halogen, hydroxyl, phenyl, and N(R$^x$)$_2$;
$R^7$ and $R^{78}$ are each independently selected from the group consisting of hydrogen; $C_1$-$C_6$ alkyl; $C_{1-6}$ perfluoroalkyl; $C_1$-$C_6$ alkoxy; $C_3$-$C_6$ cycloalkoxy; heteroaryl including from 5 to 6 ring atoms wherein 1, 2, or 3 of the ring atoms are independently selected from the group consisting of N, NH, N(C1-C3 alkyl), O, and S; heterocyclyl including from 3 to 6 ring atoms wherein 1, 2, or 3 of the ring atoms are independently selected from the group consisting of N, NH, N(C1-C3 alkyl), O, and S; and phenyl; wherein $C_1$-$C_6$ alkyl; $C_1$-$C_6$ alkoxy; $C_3$-$C_6$ cycloalkoxy; heteroaryl; heterocyclyl; phenyl are each optionally substituted by one, two, or three substituents independently selected from the group consisting of halogen; hydroxyl; phenyl; heteroaryl including from 5 to 6 ring atoms wherein 1, 2, or 3 of the ring atoms are independently selected from the group consisting of N, NH, N(C1-C3 alkyl), O, and S; and N(R$^x$)$_2$;
$R^8$ is selected from the group consisting of hydrogen; halogen; hydroxyl; $C_1$-$C_6$ alkyl; $C_{1-6}$ perfluoroalkyl; $C_1$-$C_6$ alkoxy; $C_3$-$C_6$ cycloalkoxy; heteroaryl including from 5 to 6 ring atoms wherein 1, 2, or 3 of the ring atoms are independently selected from the group consisting of N, NH, N(C1-C3 alkyl), O, and S; heterocyclyl including from 3 to 6 ring atoms wherein 1, 2, or 3 of the ring atoms are independently selected from the group consisting of N, NH, N(C1-C3 alkyl), O, and S; and phenyl; wherein $C_1$-$C_6$ alkyl; $C_1$-$C_6$ alkoxy; $C_3$-$C_6$ cycloalkoxy; heteroaryl; heterocyclyl; and phenyl are each optionally substituted by one, two, or three substituents independently selected from the group consisting of halogen, hydroxyl, phenyl, and N(R$^x$)$_2$; or
$R^7$ and $R^8$, together with the atoms to which they are attached, form C3-C6 cycloalkyl or heterocyclyl including from 3 to 6 ring atoms wherein 1, 2, or 3 of the ring atoms are independently selected from the group consisting of N, NH, N(C$_1$-C$_3$ alkyl), O, and S; wherein the C$_3$-C$_6$ cycloalkyl and heterocyclyl are each optionally substituted by one, two, or three substituents independently selected from the group consisting of halogen, hydroxyl, phenyl, and N(R$^x$)$_2$;

with the proviso that at least one of R$^7$, R$^{78}$, R$^5$, and R$^6$ is not H;

R$^9$ and R$^{10}$ are independently selected, for each occurrence, from the group consisting of hydrogen; C$_1$-C$_6$ alkyl, optionally substituted by one, two, or three substituents substituents independently selected from the group consisting of halogen, oxo, hydroxyl, phenyl, and heteroaryl including from 5 to 6 ring atoms wherein 1, 2, or 3 of the ring atoms are independently selected from the group consisting of N, NH, N(C$_1$-C$_3$ alkyl), O, and S; C$_{1-6}$ perfluoroalkyl; C$_{2-6}$alkenyl, optionally substituted by one, two, or three substituents substituents independently selected from the group consisting of halogen, oxo, and hydroxyl; C$_{2-6}$alkynyl, optionally substituted by one, two, or three substituents substituents independently selected from the group consisting of halogen, oxo, and hydroxyl; C$_{3-6}$cycloalkyl, optionally substituted by one, two, or three substituents substituents independently selected from the group consisting of C$_{1-6}$alkyl, C$_{1-6}$ perfluoroalkyl; halogen, oxo, and hydroxyl; phenyl, optionally substituted by one, two, or three substituents substituents independently selected from the group consisting of C$_{1-6}$alkyl; C$_{1-6}$ perfluoroalkyl; C$_{1-6}$alkoxy; halogen; hydroxyl; —C(O)R$^x$; —CO$_2$(R$^x$); —C(O)N(R$^x$)$_2$; —C(NR$^x$)N(R$^x$)$_2$; and —C(R$^x$)$_3$;

or R$^9$ and R$^{10}$, together with the nitrogen atom to which each is attached, form a heterocyclyl including from 3 to 6 ring atoms, which is optionally substituted by one, two, or three substituents substituents independently selected from the group consisting of C$_{1-6}$alkyl, C$_{1-6}$ perfluoroalkyl; halogen, oxo, and hydroxyl; wherein when R$^9$ and R$^{10}$ form a heterocyclyl including 6 ring atoms, the heterocyclyl optionally includes, in addition to the nitrogen atom attached to R$^9$ and R$^{10}$, a second ring heteroatom selected from the group consisting of N, NH, N(C1-C3 alkyl), O, and S;

R$^x$ is independently selected, for each occurrence, from the group consisting of hydrogen; halogen; acyl; C$_{1-6}$alkyl; C$_{1-6}$ perfluoroalkyl; and phenyl; and R$^y$ is hydrogen or C$_{1-3}$ alkyl.

2. A pharmaceutical composition, comprising:
a therapeutically effective amount of a compound of claim 1 and a pharmaceutically acceptable carrier.

3. The pharmaceutical composition of claim 2, wherein the composition is suitable for injection.

4. A method of treating a NMDA receptor modulated disease selected from autism in a patient in need thereof, comprising administering to the patient a pharmaceutically effective amount of a compound of claim 1.

5. A method of treating a NMDA receptor modulated condition selected from the group consisting of epilepsy, AIDS dementia, multiple system atrophy, progressive supranuclear palsy, Friedrich's ataxia, Down's syndrome, fragile X syndrome, tuberous sclerosis, olivio-ponto-cerebellar atrophy, cerebral palsy, drug-induced optic neuritis, peripheral neuropathy, myelopathy, ischemic retinopathy, diabetic retinopathy, glaucoma, cardiac arrest, behavior disorders, and impulse control disorders, in a patient in need thereof, comprising administering to the patient a pharmaceutically effective amount of a compound of claim 1.

6. A method of treating a NMDA receptor modulated condition selected from the group consisting of attention deficit disorder, ADHD, schizophrenia, depression, anxiety, amelioration of opiate, nicotine, and/or ethanol addiction, traumatic brain injury, spinal cord injury, post-traumatic stress syndrome, and Huntington's chorea, in a patient in need thereof, comprising administering to the patient a pharmaceutically effective amount of a compound of claim 1.

7. A method of treating a NMDA receptor modulated disease selected from Alzheimer's disease, or memory loss that accompanies early stage Alzheimer's disease in a patient in need thereof, comprising administering to the patient a pharmaceutically effective amount of a compound of claim 1.

8. A method of treating a NMDA receptor modulated disease selected from Huntington's disease, in a patient in need thereof, comprising administering to the patient a pharmaceutically effective amount of a compound of claim 1.

9. The method of claim 4, wherein the compound is administered intravenously, intraperitoneally, intranasally, orally, intramuscularly, or subcutaneously.

* * * * *